United States Patent
Huang et al.

(10) Patent No.: US 7,417,178 B2
(45) Date of Patent: Aug. 26, 2008

(54) EXPRESSION OF HUMAN MILK PROTEINS IN TRANSGENIC PLANTS

(75) Inventors: Ning Huang, Davis, CA (US); Raymond L. Rodriguez, Davis, CA (US); Frank E. Hagie, Sacramento, CA (US)

(73) Assignee: Ventria Bioscience, Sacramento, CA (US)

( * ) Notice: Subject to any disclaimer, the term of this patent is extended or adjusted under 35 U.S.C. 154(b) by 562 days.

(21) Appl. No.: 10/639,835

(22) Filed: Aug. 12, 2003

(65) Prior Publication Data

US 2004/0111766 A1    Jun. 10, 2004

Related U.S. Application Data

(63) Continuation-in-part of application No. 10/077,381, filed on Feb. 14, 2002, now Pat. No. 6,991,824, and a continuation-in-part of application No. 09/847,232, filed on May 2, 2001, now abandoned.

(60) Provisional application No. 60/201,182, filed on May 2, 2000, provisional application No. 60/266,920, filed on Feb. 6, 2001, provisional application No. 60/269,199, filed on Feb. 14, 2001.

(51) Int. Cl.
C12N 15/82 (2006.01)
A01H 5/00 (2006.01)
C07H 21/04 (2006.01)

(52) U.S. Cl. .................. 800/288; 800/287; 800/298; 800/320.2; 536/24.1

(58) Field of Classification Search .................. None
See application file for complete search history.

(56) References Cited

U.S. PATENT DOCUMENTS

| | | | |
|---|---|---|---|
| 4,977,137 A | 12/1990 | Nichols et al. | |
| 5,543,576 A | 8/1996 | van Ooijen et al. | |
| 5,571,896 A | 11/1996 | Conneely et al. | |
| 5,585,257 A | 12/1996 | De Baetselier et al. | |
| 5,618,712 A | 4/1997 | Slediewski et al. | |
| 5,714,474 A * | 2/1998 | Van Ooijen et al. | 514/44 |
| 5,767,377 A * | 6/1998 | Nakajima et al. | 800/279 |
| 5,850,016 A | 12/1998 | Jung et al. | |
| 5,955,316 A | 9/1999 | Conneely et al. | |
| 5,994,628 A | 11/1999 | Rodriguez | |
| 6,020,015 A | 2/2000 | Gaull | |
| 6,066,469 A | 5/2000 | Kruzel et al. | |
| 6,160,202 A | 12/2000 | Bustos et al. | |
| 6,270,827 B1 | 8/2001 | Gaull et al. | |
| 6,319,895 B1 | 11/2001 | Tomita et al. | |
| 6,455,687 B1 | 9/2002 | Kruzel et al. | |
| 6,528,297 B1 | 3/2003 | Yu et al. | |
| 6,569,831 B1 | 5/2003 | Legrand et al. | |
| 6,635,806 B1 | 10/2003 | Kriz et al. | |
| 2002/0192296 A1 | 12/2002 | Gaull et al. | |
| 2003/0056244 A1 * | 3/2003 | Huang et al. | 800/278 |
| 2003/0074700 A1 | 4/2003 | Huang et al. | |
| 2003/0229925 A1 | 12/2003 | Legrand et al. | |

FOREIGN PATENT DOCUMENTS

| | | |
|---|---|---|
| EP | 0 591 530 | 4/1994 |
| FR | 2 762 850 | 11/1998 |
| WO | WO 98/05788 | 2/1998 |
| WO | WO 98/10062 | 3/1998 |
| WO | WO 98/50543 | 11/1998 |
| WO | WO 98/59062 | 12/1998 |
| WO | WO 99/16890 * | 4/1999 |
| WO | WO 00/04146 | 1/2000 |
| WO | WO 01/83792 | 8/2001 |
| WO | WO 02/063975 A2 | 8/2002 |
| WO | WO 02/064750 | 8/2002 |
| WO | WO 02/064814 | 8/2002 |

OTHER PUBLICATIONS

Muth et al. The role of multiple binding sites in the activation of zein gene expression by Opaque-2. (1996) MGG, vol. 252, pp. 723-732.*

Jigani et al. Expression of synthetic human-lysozyme gene in *Saccharomyces cerevisiae*: use of a synthetic chicken-lysozyme signal sequence for secretion and processing. (1986) Gene, vol. 43, pp. 273-279.*

(Continued)

*Primary Examiner*—Anne Marie Grunberg
*Assistant Examiner*—Cathy Kingdon Worley
(74) *Attorney, Agent, or Firm*—Susan J. Myers Fitch; Peter J. Denlinger; Perkins Coie LLP

(57) ABSTRACT

The invention is directed to seed and seed extract compositions containing levels of a human milk protein between 3-40% or higher of the total protein weight of the soluble protein extractable from the seed. Also disclosed is a method of producing the seed with high levels of extractable human milk protein. The method includes transforming a monocotyledonous plant with a chimeric gene having a protein-coding sequence encoding a protein normally present in human milk under the control of a seed maturation-specific promoter. The method may further includes a leader DNA sequence encoding a monocot seed-specific transit sequence capable to target a linked milk protein to a storage body.

17 Claims, 38 Drawing Sheets

OTHER PUBLICATIONS

Arakawa, T. et al., "Improvements in Human Health through Production of Human Milk Proteins in Transgenic Food Plants," *Chemicals via Higher Plant Bioengineering*, pp. 149-159, 1999.

Bosch, D. et al., "A trout growth hormone is expressed, correctly folded and partially glycosylated in the leaves but not the seeds of transgenic plants," *Transgenic Research* 3:304-310, 1994.

Chong, D.K.X. et al., "Expression of the human milk protein β-casein in transgenic potato plants," *Transgenic Research* 6:289-296, 1997.

Lönnerdal, B., "Recombinant human milk proteins—an opportunity and a challenge," *Am. J.. Clin. Nutr.* 63:4, 621S-626S, 1996.

Qiu, J. et al., "Human milk lactoferrin inactivates two putative colonization factors expressed by *Haemophilus influenzae*," *Proc. Natl. Acad. Sci.* USA 95:12641-12646, 1998.

Horvath, H. et al., "The production of recombinant proteins in transgenic barley grains," *PNAS* 97:4, 1914-1919, 2000.

Lönnerdal, B. and Iyer S., "Lactoferrin: Molecular Structure and Biological Function", *Annual Reviews Nutr.* 15:93-110, 1995.

Salmon, V. et al., "Production of Human Lactoferrin in Transgenic Tobacco Plants", *Protein Expression and Purification* 13:127-135, 1998.

Chong, D. K. X. et al., Expression of full-length bioactive antimicrobial human lactoferrin in potato plants *Transgenic Research* 9:71-78, 2000.

Terashima, M. et al., "Production of functional human $\alpha_1$-antitrypsin by plant cell culture," *Appl. Microbiol Biotechnol.* 52:516-523, 1999.

Yang, D. et al., Expression of the REB transcriptional activator in rice grains improves the yield of recombinant proteins whose genes are controlled by a Reb-responsive promoter, *PNAS USA*, 98(20):11438-11443, 2001.

Huang, J. et al., "Expression of natural antimicrobial human lysozyme in rice grains", *Molecular Breeding* 10:83-94, 2002.

Yang, D. et al., "Expression and localization of human lysozyme in the endosperm of transgenic rice", *Planta*, 216(4):597-603, 2003.

Nandi, S. et al., "Expression of human lactoferrin in transgenic rice grains for the application in infant formula", *Plant Science*, 163(4):713-722, 2002.

International Search Report from PCT/US2004/026230.

Lohmann et al., *Cell* 105:793-803, 2001.

Russell DA and ME Fromm, (1997), "Tissue specific expression in transgenic maize of four endosperm promoters from maize and rice," *Transgenic Res* 6:157-168.

Genschik P, et al., (1994), "Structure and promoter activity of a stress and developmentally regulated polyubiquitin-encoding gene of *Nicotiana tabacum*," *Gene* 148:195-202.

McElroy DE, et al., (1990), "Isolation of an efficient actin promoter for use in rice transformation," *Plant Cell* 2:163-171.

Wang Y, et al., (1992), "Characterization of cis-acting elements regulating transcription from the promoter of a constitutively active rice actin gene," *Molec Cell Biol* 12(8):3399-3406.

Washida H, et al., (1999), "Identification of cis-regulatory elements required for endosperm expression of the rice storage protein glutelin gene GluB-1," *Plant Molec Biol* 40:1-12.

Cercós M, et al., (1999), "Hormonal regulation of a cysteine proteinase gene, EPB-1, in barley aleurone layers: cis and trans-acting elements involved in co-ordinated gene expression regulated by gibberellins and abscisic acid," *Plant Journal* 19(2):107-118.

Holdsworth MJ, et al., (1995), "The maize transcription factor Opaque-2 activates a wheat glutenin promoter in plant and yeast cells," *Plant Molec Biol* 29:711-720.

Schmidt RJ, et al., (1992), "Opaque-2 is a transcriptional activator that recognized a specific target site in 22-kD zein genes," *Plant Cell* 4:689-700.

Wu CY, et al., (1998), "The GCN4 motif in a rice glutelin gene is essential for endosperm-specific gene expression and is activated by Opaque-2 in transgenic rice plants," *Plant Journal* 14(6):673-683.

Mena MI, et al., (1998), "An endosperm-specific DOF protein from barley, highly conserved in wheat, binds to and activates transcription from the prolamin-box of a native B-hordeln promoter in barley endosperm," *Plant Journal* 16(1): 53-62.

Vicente-Carbajosa V, et al., (1998), "Barley BLZ1: a bZIP transcriptional activator that interacts with endosperm-specific gene promoters," *Plant Journal* 13(5):629-640.

Schwechheimer et al., *Funct Intergr Genomics* 1:35-43, 2000.

Izawa et al., *J. Mol. Biol.* 230:1131-1144, 1993.

Hao et al., *The J. of Biological Chemistry* 273(41):26847-26861, 1998.

Busch et al., *Science* 285:585-587, 1999.

Albani, D. et al., "The Wheat Transcriptional Activator SPA: A Speed-Specific bZIP Protein That Recognizes the GCN4-like Motif in the Bifactorial Endosperm Box of Prolamin Genes" *Plant Cell*, 9:171-184, 1997.

GenBank Accession No. AB021736 *Oryza sativa* gene for bZIP protein, complete cds.

GenBank Accession No. D11385 *Oryza sativa* mRNA for prolamin, complete cds.

GenBank Accession No. M29411 *Z. mays* DNA binding protein opaque-2 (O2) mRNA, complete cds.

GenBank Accession No. U82230 *Zea mays* endosperm-specific prolamin box ginding factor (PBF) mRNA, complete cds.

GenBank Accession No. X15544 *Xea mays* opaque-2 gene.

Muller, M. et al., Regulation of Storage Protein Synthesis in Cereal Seeds: Developmental and Nutritional Aspects, *J. Plant Physiol.*, 145:606-608, 1995.

Nakase, M. et al., "Characterization of a novel rice bZIP protein which binds to the α-globulin promoter," *Plant Mol Biol*, 33(3):513-522, 1997.

Vicente-Carbajosa, J. et al., "A maize zinc-finger protein binds the prolamin box in zein gene promoters and interacts with the basic leucine zipper transcriptional activator Opaque-2," *Proc. Natl. Acad. Sci., USA*, 94:7685-7690, 1997.

Higo, et al., *Biosci. Biotech. Biochem.* 57(9):1477-1481, 1993.

Huang, et al., *Biotechnology Progress*, 17(1):126-133, 2001.

Nakase, et al., *Gene*, 170(2):223-226, 1996.

Hwang, et al., *Plant Cell Reports*, 20(9):842-847, 2002.

\* cited by examiner

Sequence Range Egfactor: 4 to 165

```
                    10            20            30            40            50
Egfactor     AAC TCC GAC TCG GAG TGC CCC CTC TCC CAC GAC GGT TAC TGC CTC CAC GAC GGG
              N   S   D   S   E   C   P   L   S   H   D   G   Y   C   L   H   D   G>

3360          3370          3380          3390          3400
Native Gene  AAT GGT GAC TCT GAA TGT CCC CTG TCC CAC GAT GGG TAC TGC CTC CAT GAT GGT
              ||  |||  ||  ||  ||  |||  ||  |||  |||  ||  ||  |||  |||  |||  ||  ||  ||
Egfactor     AAC TCC GAC TCG GAG TGC CCC CTC TCC CAC GAC GGT TAC TGC CTC CAC GAC GGG 60            70            80            90           100           110
Egfactor     GTC TGC ATG TAC ATC GAG GCC CTC GAC AAG TAC GCC TGC AAC TGC GTC GTG GGC
              V   C   M   Y   I   E   A   L   D   K   Y   A   C   N   C   V   V   G>

3410          3420          3430          3440          3450
Native Gene  GTG TGC ATG TAT ATT GAA GCA TTG GAC AAG TAT GCA TGC AAC TGT GTT GTT GGC
              ||  |||  |||  ||  ||  ||  ||   |  |||  |||  ||  ||  |||  |||  ||  ||  |||
Egfactor     GTC TGC ATG TAC ATC GAG GCC CTC GAC AAG TAC GCC TGC AAC TGC GTC GTG GGC 120           130           140           150           160
Egfactor     TAC ATC GGC GAG CGG TGC CAG TAC CGC GAC CTC AAG TGG TGG GAG CTG CGC TGA
              Y   I   G   E   R   C   Q   Y   R   D   L   K   W   W   E   L   R   *>

3460          3470          3480          3490          3500
Native Gene  TAC ATC GGG GAG CGA TGT CAG TAC CGA GAC CTG AAG TGG TGG GAA CTG CGC
              |||  |||  ||  |||  ||  ||  |||  |||  ||  |||  ||  |||  |||  |||  ||  |||  |||
Egfactor     TAC ATC GGC GAG CGG TGC CAG TAC CGC GAC CTC AAG TGG TGG GAG CTG CGC TGA
```

Epidermal Growth Factor

Number of codons in mature peptide:   53
Number of codons changed:             27 (51%)
Number of nucleotides changed:        30 (19%)

Fig. 21

EXPRESSION OF HUMAN MILK PROTEINS IN TRANSGENIC PLANTS

This application is a continuation-in-part of U.S. patent application Ser. No. 10/077,381, filed Feb. 14, 2002, now issued as U.S. Pat. No. 6,991,824, which claims priority benefit to U.S. Provisional Application No. 60/269,199, filed Feb. 14, 2001. The Ser. No. 10/077,381 application is also a continuation-in-part of U.S. patent application Ser. No. 09/847,232, filed May 2, 2001, now abandoned, which claims the benefit of U.S. Provisional Application No. 60/266,920, filed Feb. 6, 2001, and U.S. Provisional Application No. 60/201,182, filed May 2, 2000, all of which are incorporated herein by reference.

FIELD OF THE INVENTION

The present invention relates to a seed and seed extract compositions containing levels of a human milk protein between 3-40% or higher of the total protein weight of the soluble protein extractable from the seed. Also disclosed is a method of producing the seed with high levels of extractable human milk protein.

REFERENCES

The following references are cited herein, and to the extent they may be pertinent to the practice of the invention, are incorporated herein by reference.

Alber and Kawasaki, *Mol. and Appl. Genet.*, 1:419-434, 1982.
Aniansson, G. et al., "Anti-Adhesive Activity Of Human Casein Against *Streptococcus Pneumoniae* And *Haemophilus Influenzae*," *Microb Pathog*, 8(5):315-323, 1990.
Arnold R. R. et al., *Infect Immun.*, 28:893-898, 1980.
Ausubel F. M. et al., *Current Protocols in Molecular Biology*, John Wiley & Sons, New York, N.Y., 1993.
Bhan, M. K. et al., *J Pediatr Gastroenterol Nutr*, 7:208-213, 1988.
Beatty, K., et al., "Kinetics of association of serine proteinases with native and oxidized alpha-1-proteinase inhibitor and alpha-1-antichymotrypsin," *J. Biol. Chem.*, 255:3931-3934, 1980.
Boesman-Finkelstein M. and Finkelstein R. A. *FEBS Letters*, 144:1-5, 1982.
Bradford M. *Analytical Biochem.*, 72:248-254, 1976.
Brandt, et al., *Carlsberg Res. Commun.*, 50:333-345, 1985.
Briggs, D, et al., *Malting And Brewing Science—Volume 1, Malt And Sweet Wort* (Chapman & Hall, New York, 2nd edition), 1981.
Briggs, D, *Malts And Malting* (Blackie Academic And Professional, New York), 1998.
Bullen J. J. et al., *Br. Med. J.*, 1:69-75, 1972.
Carrell, R. W. et al., "Structure and variation of human alpha-1-antitrypsin", *Nature*, 298:329-334, 1983.
Castañón M. J. et al., *Gene*, 66:223-234, 1988.
Chandan R. C., *J Dairy Sci*, 51:606-607, 1968.
Chong, D. K. and Langridge, W. H., *Transgenic Res*, 9:71-78, 2000.
Chowanadisai, W. and Lönnerdal, B., "Alpha-1-antitrypsin and antichymotrypsin in human milk: origin, concentrations, and stability", *Am. J. Clin. Nutr.*, 76(4):828-833, 2002.
Chrispeels K., *Ann. Rev. Plant Phys. Plant Mol. Biol.*, 42:21-53, 1991.
Christensen, A and Quail, P, "Ubiquitin promoter-based vectors for high-level expression of selectable and/or screenable marker genes in monocotyledonous plants, *Transgenic Research*, 5:213-218, 1996.
Clark et al., *J. Biol. Chem.*, 264:17544-17550, 1989.
Davidson L A, et al., "Persistence Of Human Milk Proteins In The Breast-Fed Infant", *Act Paediatr Scand*, 76(5):733-740, 1987.
Davidson, L. A., and Lönnerdal, B. "Fecal alpha-1-antitrypsin in breast-fed infants is derived from human milk and is not indicative of enteric protein loss", *Acta Paediatr Scand*, 79:137-141, 1990.
della-Cioppa et al., *Plant Physiol.*, 84:965-968, 1987.
Dellaporta S. L. et al., *Plant Mol. Biol. Rep.*, 1:19-21, 1983.
Depicker et al., *Mol. Appl. Genet.*, 1:561-573, 1982.
Dewey K. G. et al., *Pediatrics*, 89:1035-1041, 1992.
Dewey K. G. et al., *Am J Clin Nutr*, 57:140-145, 1993.
Dewey K. G. et al, J Pediatrics, 126:696-702, 1995.
Ditta et al., *Proc. Nat. Acad. Sci., U.S.A.*, 77:7347-7351, 1980.
Doncheck, J, *Malts And Malting*. In: *Kirk-Othmer Encyclopedia Of Chemical Technology* (John Wiley & Sons, New York, 4th edition), volume 15, pp. 947-962, 1995.
Edlund, A, et al., "Structure of the human κ-casein gene", *Gene*, 174:65-69, 1996.
Eley, E, *A Wandful World. Food Processing*, pp. 17-18, 1990.
Faure A. and Jollès P., et al., *Comptes Rendus Hebdomadaires des Seances de L Academie des Sciences. D: Sciences Naturelles*, 271:1916-1918, 1970.
Fujihara T. and Hayashi K., *Archives of Virology*, 140:1469-1472, 1995.
Gastañaduy, A. et al., *J Pediatr Gastroenterol Nutr*, 11:240-6, 1990.
Gelvin, S. B. et al., eds. *Plant Molecular Biology Manual*, 1990.
Gielen, et al., *EMBO J.* 3:835-846, 1984.
Goto, F et al., *Nature Biotech.*, 17:282-286, 1999.
Groenen, M A M and Van der Poel, J J, "Regulation of expression of milk protein genes: a review", *Livestock Prod Sci*, 38:61-78, 1994.
Grover M. et al., *Acta Paediatrica*, 86:315-316, 1997.
Hamosh, M, et al., "Protective Function Of Human Milk: The Fat Globule," *Semin Perinatol*, 23(3):242-249, 1999.
Harmsen M. C. et al., *Journal of Infectious Diseases*, 172: 380-388, 1995.
Hickenbottom, J W, *Sweeteners In Biscuits And Crackers. The Bakers Digest*, pp. 18-22, 1977.
Hickenbottom, J W, *AIB Research Department Technical Bulletin*, V(3), pp. 1-8, 1983.
Hickenbottom, J W, *Processing, Types, And Uses Of Barley Malt Extracts And Syrups. Cereal Foods World*, 41(10): 778-790, 1996.
Hickenbottom J W, *Malts In Baking. American Society Of Bakery Engineers*, Technical Bulletin #238, pp. 1010-1013, 1997.
Horvath H. et al., *Proc. Natl. Acad. Sci. USA*, 97:1914-1919, 2000.
Hough, J S, et al., *Malting And Brewing Science—Volume 2, Hopped Wort And Beer* (Chapman & Hall, New York, 2nd edition), 1982.
Huang N. et al., *Plant Mol. Biol.*, 23:737-747, 1993.
Huang N. et al., *J CAASS*, 1:73-86, 1990a.
Huang N. et al., *Plant Mol. Biol.*, 14:655-668, 1990b.
Huang, J., et al., "Expression and purification of functional human alpha-1-antitrypsin from cultured plant cells", *Biotechnol. Prog.*, 17:126-133, 2001.
Huang, J. et al., "Expression of natural antimicrobial human lysozyme in rice grains", *Molec Breeding*, 10:83-94, 2002.

Humphreys, D. P. and Glover, D. J. "Therapeutic antibody production technologies: molecules, applications, expression and purification," *Curr Opin Drug Discov Devel*, 4(2): 172-185, 2001.

Hwang, Y-S, et al., "Evaluation of expression cassettes in developing rice endosperm using an expression transient assay", *Plant Sci*, 161:1107-1116, 2001

Jensen L. G. et al., *Proc. Natl. Acad. Sci. USA*, 93:3487-3491, 1996.

Jigami Y. et al., *Gene*, 43:273-279, 1986.

Johnson, T. "Human alpha-1-proteinase inhibitor", *Methods Enzymol.*, 80:756-757, 1981.

Jollès P., *Lysozymes—Model Enzymes in Biochemistry and Biology*, Birkhäuser Verlag, Basel; Boston, 1996.

Jouanin et al., *Mol. Gen. Genet.*, 201:370-374, 1985.

Kortt A. A. et al., "Dimeric and trimeric antibodies: high avidity scFvs for cancer targeting," *Biomol Eng*, 18:95-108, 2001.

Kovar M. G. et al., *Pediatrics*, 74:615-638, 1984.

Kunz C. et al., *Clin. Perinatol.*, 26(2):307-333, 1999.

Lake, C, *From Strength To Strength. Flood Flavorings, Ingredients, Packaging And Processing*, pp. 55-57, 1988.

Langridge et al., *Planta*, 156:166-170, 1982.

Larrick, J. W. et al., "Production of antibodies in transgenic plants", *Res Immunol*, 149:603-608, 1998.

Lásztity, R. *The chemistry of cereal proteins*. CRC Press, Boca Raton, 1996.

Lee-Huang S. et al., *Proc. Natl. Acad. Sci. USA*, 96:2678-2681, 1999.

Lemaux, P J and Cho, M C, U.S. Pat. No. 6,235,529.

Lindberg, T. "Protease inhibitors in human milk", *Pediatr. Res.*, 13:969-972, 1979.

Lollike K. et al., *Leukemia*, 9:206-209, 1995.

Lönnerdal B., *Am L Clin Nutr*, 42:1299-1317, 1985.

Lönnerdal, B. "Recombinant milk proteins—an opportunity and a challenge", *Am. J. Clin. Nutr.*, 63:622S-626S, 1996.

Maga E. et al., *Transgenic Research*, 3:36-42, 1994.

Maga E. et al., *Journal of Dairy Science*, 78:2645-2652, 1995.

Maga E. et al., *J. of Food Protection*, 61:52-56, 1998.

Maniatis, et al., *Molecular Cloning: A Laboratory Manual*, 2nd Edition, 1989.

Marchylo, B A, et al., "Quantitative variation in high molecular weight glutenin subunit-7 in some Canadian wheats", *J Cereal Sci*, 15:29-37, 1992.

Matsumoto, A. et al., *Plant Mol Bio*, 27:1163-1172, 1995.

Maynard, J. and Georgiou, G, "Antibody engineering", *Annu Rev Biomed Eng*, 2:339-76, 2000.

McBride and Summerfelt, *Plant Mol. Biol.*, 14:269-276, 1990.

Mcgilligan, K M, et al., "Alpha-1-Antitrypsin Concentration In Human Milk," *Pediatr Res*, 22(3):268-270, 1987.

Mitra A. and Zhang Z., *Plant Physiol.*, 106:977-981, 1994.

Moe, T, et al., *Mashing Of Rice With Barley Malt Under Non-Conventional Process Conditions For Use In Food Processes. International Journal Of food Science And Technology* 29:635-649, 1995.

Moore, K, "Rice-Barley Malt Combo Improves Functionality And Nutrition Of Meats, Breads, And Baked Goods", *Food Product Development*, 12(5):74, 1978.

Moreira-Ludewig, R. and Healy, C., *J. Pharm. and Tox. Meth.*, 27:75-100, 1992.

Motil K. J., *Curr Opin Pediatr*, 12(5):469-476, 2000.

Murphy M S, "Growth Factors And The Gastrointestinal Tract", *Nutrition*, 14(10):771-774, 1998.

Nakajima H. et al., *Plant Cell Reports*, 16:674-679, 1997.

Newburg, D S, et al., "Role Of Human-Milk Lactadherin In Protection Against Symptomatic Rotavirus Infection", *Lancet*, 351(1910):1160-1164, 1998.

Newburg, D S, "Human Milk Glycoconjugates That Inhibit Pathogens", *Curr Med Chem*, 6(2):117-127, 1999.

NIH publication, American Academy of Allergy and Immunology Committee on adverse reaction to food and National Institute of Allergy and Infectious Diseases, NIH, Bethesda, 1984.

Peeters, K., et al., "Production of antibodies and antibody fragments in plants", *Vaccine*, 9:2756-2761, 2001.

Peterson J A, et al., "Glycoproteins Of The Human Milk Fat Globule In The Protection Of The Breast-Fed Infant Against Infections", *Bio Neonate*, 74(2):143-162, 1998.

Piper, D. W. and Fenton, B. H. "pH stability and activity curves of pepsin with special reference to their clinical importance", *Gut*, 6:506-508, 1965.

Prosser, C G, "Insulin-Like Growth Factors In Milk And Mammary Gland," *J Mammary Gland Bio Neoplasia*, (3): 297-306, 1996.

Raikhel N., *Plant Phys.*, 100:1627-1632, 1992.

Rey, M. W., "Complete nucleotide sequence of human mammary gland lactoferrin", *Nucleic Acid Res.*, 18(17):5288, 1990.

Romer et al., *Biochem. Biophys. Res Commun.*, 196:1414-1421, 1993.

Rudloff, S. and Lönnerdal, B. "Solubility and digestibility of milk proteins in infant formulas exposed to different heat treatments", *J. Pediatr. Gastroenterol. Nutr.*, 15:25-33, 1992.

Saarinen K. M. et al., *Adv Exp Med Biol*, 478:121-130, 2000.

Salmon V. et al., *Protein Expression and Purification*, 9:203-210, 1997.

Salmon, V. et al., *Protein Expr Purif*, 13:127-135, 1998.

Samaranayake Y. H. et al., *Apmis*, 105:875-883, 1997.

Sambrook J. et al., *Molecular Cloning: a Laboratory Manual* (Second Edition), Cold Spring arbor Press, Plainview, N.Y., 1989.

Satue-Gracia M. T. et al., *J Agric Food Chem*, 48(10):4984-4990, 2000.

Schütte H. and Kula M. R., *Biotechnology and Applied Biochemistry*, 12:599-620, 1990.

Sfat, M, et al., *Malts And Malting*. In: *Kirk-Othmer Encyclopedia Of Chemical Technology* (John Wiley & Sons, New York, 3rd edition), volume 14, pp. 810-823, 1981.

Shah et al., *Science*, 233:478-481, 1986.

Shin, K et al., "*PCR Cloning And Baculovirus Expression Of Human* Lactoperoxidase And Myeloperoxidase", *Biochem Biophys Res Commun*, 27(13):831-836, 2000.

Shugar D., *Biochim. Biophys. Acta*, 8:680-686, 1952.

Symbicon A B, "Human Milk Kappa-Casein And Inhibition Of *Helicobacter pylori* Adhesion To Human Gastric Mucosa", *J Pediatr Gastroenterol Nutr* 21(3):288-296, 1995.

Takai I. et al., *J. Chrom. B, Biomedical Applications*, 685:21-25, 1996.

Tsuchiya K. et al., *Applied Microbiology and Biotechnology*, 38:109-114, 1992.

Von Heijne et al., *Plant Mol. Biol. Rep.*, 9:104-126, 1991.

Wang C. S. and Kloer H. U., *Anal. Biochem.*, 139:224-227, 1984.

Wang C. et al., *Comp. Biochem. Physiol.*, 78B:575-580, 1984.

Ward P. P. et al., *Biotechnology*, 10:784-789, 1992.

Ye X. et al., *Science*, 287:303-305, 2000.

Yoshimura K. et al., *Biochem. Biophys Res Com*, 150:794-801, 1988.

BACKGROUND OF THE INVENTION

Milk proteins such as lactoferrin (LF), lysozyme (LZ), lactoperoxidase (LP), immunoglobulin-A (IgA), alpha-lactalbumin, beta-lactoglobulin, alpha-, beta- and kappa-caseins, serum albumin, lipase and others are known to have a number of nutritional and other beneficial effects, particularly for infants. Breast feeding of fresh human milk has traditionally been considered the best means to provide nutrition to an infant, especially during the first six months of life. Although all the physiological roles of human milk proteins have not yet been elucidated, evidence has been obtained that lysozyme, lactoferrin and other milk proteins can control the microflora in the gut of infants (Lönnerdal, 1985). Breast milk is a source of peptides, amino acids, and nitrogen and also contains casein and whey proteins, which are involved in the development of the immune response (e.g., immunoglobulins), together with other non-immunologic defense proteins (e.g., lactoferrin). Breast milk has additionally been suggested to contain many immune factors that compensate for the undeveloped defense mechanisms of the gut of infants (Saarinen K M et al., 2000). Several human milk proteins have been demonstrated to have beneficial physiologic effects in infants, particularly in the defense against infection and in the optimization of nutrient uptake.

However, many situations arise where the infant cannot be fed mother's milk and synthetic infant milk formulas are used in the place of breast feeding (Motil K J, 2000). Infant formulas and not standard cow's milk are used because (1) cow's milk has more than twice the protein of breast milk or infant formula and this protein may be hard for babies to digest; (2) the level of iron, zinc and vitamin C (which babies need in their diet) is low in cow's milk; and (3) the level of sodium level is three to four times that of breast milk and generally too high for infants less than a year old. A number of types of infant formulas which vary in caloric content, nutrient composition, digestibility, taste, and cost are available as an alternative to breast milk. Examples include standard cow milk-based formulas, soy protein formulas and formulas for premature infants or infants with special dietary needs due to allergies, etc. Considerable effort has been made to improve synthetic infant milk formulas in order to closely simulate mother's milk.

The protein and non-protein composition of the human milk and cow milk is described by Kunz et al., 1999. The relative concentrations of milk proteins vary between human and cows' milk. For example, lactoferrin and lysozyme are present in a relatively high amount in human milk but in only low or trace amounts in cow's milk.

In general, synthetic infant formula that has been prepared using cow's milk does not closely resemble the protein composition found in human milk. Accordingly, cow's milk based infant formula is typically supplemented with various human milk protein components. Typically, commercial infant formulas based on cow's milk contain approximately of 0.1 mg/mL lactoferrin whereas natural human breast milk contains an average concentration of 1.4 mg/mL. Soy-based infant formulas contain no added lactoferrin, lysozyme or other mammalian proteins.

Although addition of recombinant human milk proteins to infant milk or milk formula has been proposed, e.g., using transgenic cows or by addition of microbially produced human milk proteins to milk or milk formula, these approaches do not overcome the various problems of (i) allergies to cow's milk, (ii) the high cost of recombinant protein production and/or (iii) safety issues related to food products.

During the last several decades, improved infant formulas have become available that are safe and contain nutrient concentrations similar to, or higher than, breast milk. However, breast-fed infants still have a lower prevalence of infection than formula-fed infants and when they become ill, the duration of both diarrhea and upper respiratory infections is shorter than in formula-fed infants. (See, e.g., Kovar et al., 1984, and Dewey et al., 1995). In addition, it has been reported that breast-fed infants have a different growth pattern than formula-fed infants (Dewey et al., 1992; Dewey et al., 1993), and epidemiological studies show that they have a lower incidence of chronic diseases, such as diabetes and coronary heart disease.

It has been postulated that many of advantages to infants provided by mother's milk are effectuated through unique proteins present in breast milk, but not in baby formula (Lönnerdal, 1985). Human milk proteins are unique and even if the alternative protein sources used in infant formulas (e.g., skim milk, whey protein and soy isolates) mimic the amino acid concentration and ratio found in breast milk, the biological properties of human proteins cannot be readily copied.

Exemplary unique proteins present in human milk include lactoferrin and lysozyme. Lactoferrin is an iron-binding protein found in the granules of neutrophils which exerts an antimicrobial activity and lysozyme is a crystalline, basic protein present in saliva, tears, egg white, and many animal fluids, which functions as an antibacterial enzyme.

It is therefore desirable to provide transgenic plants that produce beneficial levels of proteins normally present in human milk, while largely avoiding costly recombinant protein production techniques and associated safety issues. More generally, it is desirable to provide a composition containing beneficial levels of proteins normally present in human milk that can be delivered by itself, as a nutraceutical or added to processed foods, for supplying one or more human milk proteins beneficial to human health.

SUMMARY OF THE INVENTION

In one aspect, the invention includes a mature, transgenic monocot seed that yields, by extracting ground seed with an aqueous medium, a total soluble protein fraction containing at least 3% by total protein weight of a human milk protein. The human milk protein(s) produced in the seed include lactoferrin, lysozyme, lactoferricin, lactadherin, kappa-casein, haptocorrin, lactoperoxidase, alpha-lactalbumin, beta-lactoglobulin, alpha-casein, beta-casein or alpha-1-antitrypsin. In a preferred embodiment, the human milk protein(s) is lysozyme, lactoferrin, alpha-1-antitrypsin, or kappa-casein. In a particularly preferred embodiment, the milk protein is lactoferrin or lysozyme. The seed may further yield two or more milk proteins. The seed is preferably a mature, transgenic rice or wheat seed.

The monocot seed preferably comprises a total soluble protein fraction of at least 3% by total protein weight of a human milk protein. In another embodiment, the total soluble protein fraction contains at least 5% by total protein weight of the human milk protein. In another embodiment, the total soluble protein fraction contains at least 10% by total protein weight of the human milk protein. In yet another embodiment, the total soluble protein fraction contains at least 20% by total protein weight of the human milk protein.

In another aspect, the invention includes a milk-protein composition comprising a total soluble protein fraction (i) obtained from a mature, transgenic, monocot seed by extracting a ground seed with an aqueous medium, and (ii) containing at least 3% by total protein weight of a human milk protein. The composition may be used in liquid or dried form as an additive for an ingestible food or feed. The composition may be used as a therapeutic agent for use in humans or animals. Alternatively, the composition may further be utilized as a starting material for purification of human milk proteins for therapeutic/pharmaceutical use in humans and animals.

The human milk protein(s) present in the composition may be lactoferrin, lysozyme, lactoferricin, lactadherin, kappa-casein, haptocorrin, lactoperoxidase, alpha-lactalbumin, beta-lactoglobulin, alpha-casein, beta-casein or alpha-1-antitrypsin. In a preferred embodiment, the human milk protein(s) is lysozyme, lactoferrin, alpha-1-antitrypsin, or kappa-casein. In a particularly preferred embodiment, the human milk protein(s) is lactoferrin or lysozyme.

In one embodiment, the composition contains at least 5% by total protein weight of a human milk protein. In another embodiment, the composition contains at least 10% by total protein weight of human milk protein. In yet another embodiment, the composition contains at least 20% of human milk protein by total protein weight.

In another aspect, the invention includes a method of producing a recombinant human milk protein in monocot plant seeds comprising (a) obtaining a monocot plant stably transformed with a chimeric gene having (i) a transcriptional regulatory region from a monocot gene having a seed maturation-specific promoter, (ii) operably linked to the transcriptional regulatory region, a leader DNA sequence encoding a monocot seed-specific transit sequence capable of targeting a linked polypeptide to an endosperm-cell organelle, and (iii) a protein-coding sequence encoding a protein normally present in human milk, (b) cultivating the plant under seed-maturation conditions, and (c) harvesting the seeds from the plant, wherein the human milk protein constitutes at least 3% of the total soluble protein contained in the harvested seeds.

Exemplary transcriptional regulatory regions in the chimeric gene may be the promoter of a gene selected from the group of rice glutelins, globulins, oryzins, and prolamines, barley hordeins, wheat gliadins, glutenins and purindolines, maize zeins and glutelins, oat glutelins, sorghum kafirins, millet pennisetins, and rye secalins genes. The leader sequence is likewise selected from rice glutelins, globulins, oryzins and prolamines, barley hordeins, wheat gliadins, glutenins and purindolines, maize zeins and glutelins, oat glutelins, sorghum kafirins, millet pennisetins, and rye secalins genes.

In a preferred embodiment, the transformed monocot plant is a rice plant, the transcriptional regulatory region in the chimeric gene is a rice glutelin Gt1 promoter, and the leader DNA sequence a rice glutelin Gt1 signal sequence capable of targeting a linked polypeptide to a protein storage body. An exemplary glutelin Gt1 promoter and glutelin Gt1 signal sequence are included within the sequence identified by SEQ ID NO:13.

In another preferred embodiment, the transformed monocot plant is a rice plant, the transcriptional regulatory region in the chimeric gene is a rice globulin Glb promoter, and the leader DNA sequence is a rice glutelin Gt1 signal sequence capable of targeting a linked polypeptide to a protein storage body. An exemplary globulin Glb promoter and glutelin Gt1 signal sequence are included within the sequence identified by SEQ ID NO:14.

In an embodiment, the transformed monocot plant further comprises a nucleic acid that encodes at least one transcription factor selected from the group consisting of Reb, O2 and PBF, and an active fragment thereof. In a preferred embodiment, the transcription factor is O2 and/or PBF.

The protein-coding sequence is a coding sequence for a human milk protein selected from lactoferrin, lysozyme, lactoferricin, lactadherin, kappa-casein, haptocorrin, lactoperoxidase, alpha-1-antitrypsin, and immunoglobulins. Preferably, the protein coding sequence is a codon-optimized sequence selected from SEQ ID NOS: 1, 3, and 7-12.

These and other objects and features of the invention will become more fully apparent when the following detailed description of the invention is read in conjunction with the accompanying drawings.

Extraction was conducted at room temperature for 1 h with shaking. Homogenate was centrifuged at 14,000 rpm for 15 min at 4° C. Protein supernatant was removed and diluted as needed for lysozyme turbidimetric activity assay. Extraction was repeated three times and standard deviation was shown as an error bar. Lysozyme yield was expressed as percentage of total soluble protein (% TSP).

Figure 8:
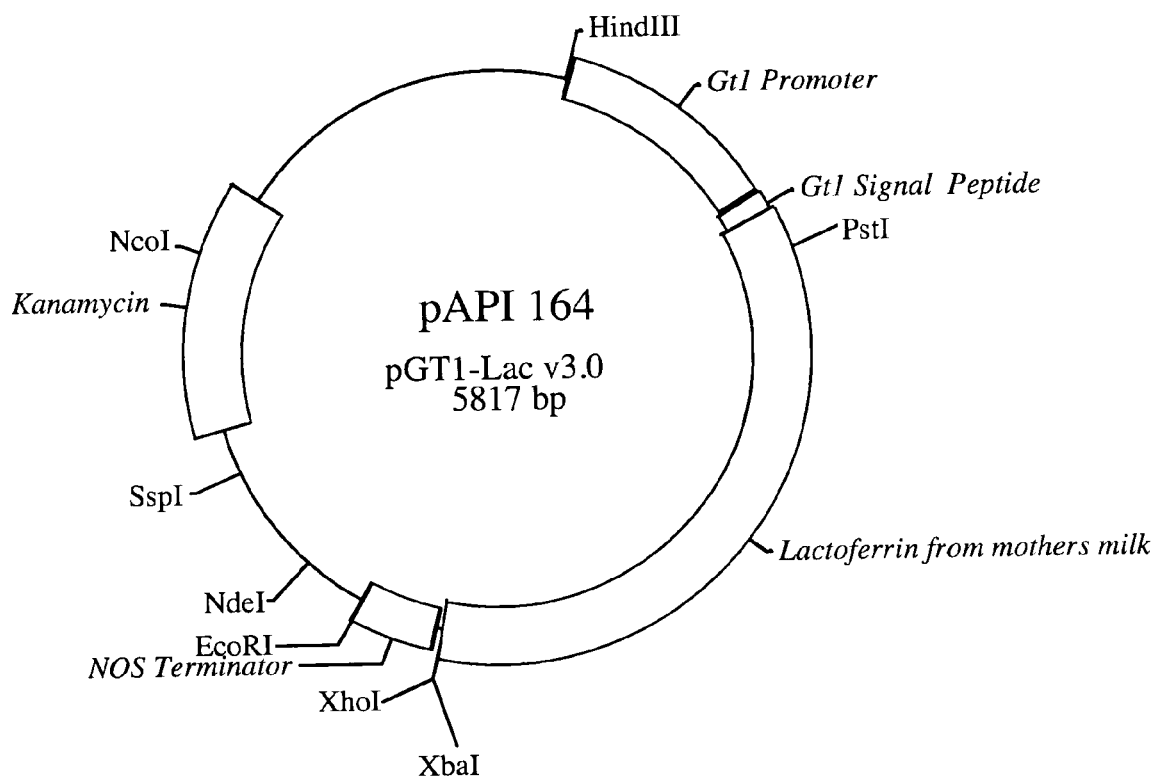

FIG. 8 is a restriction map of the pAPI164 plasmid that contains the human lactoferrin coding sequence under the control of a rice glutelin (Gt1) promoter, aGt1 signal peptide, and a nopaline synthase (Nos) terminator/polyadenylation site.

Figure 9:
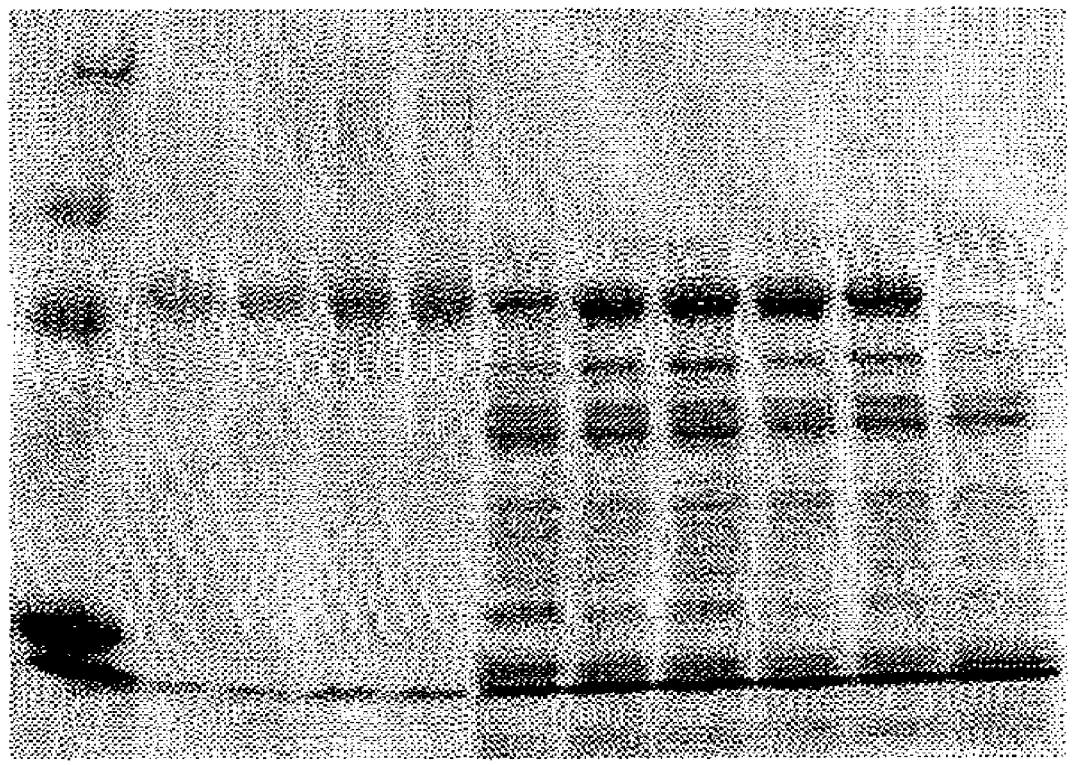

FIG. 9 shows the results of a SDS-PAGE analysis for human lactoferrin stained with Coomassie blue, where lane 1 is the molecular weight marker; lanes 2-5 are purified human derived lactoferrin (Sigma, USA); lanes 6-10 are single seed extracts from homozygous transgenic lines and lane 11 is a seed extract from non-transformed TP-309.

Figure 10:
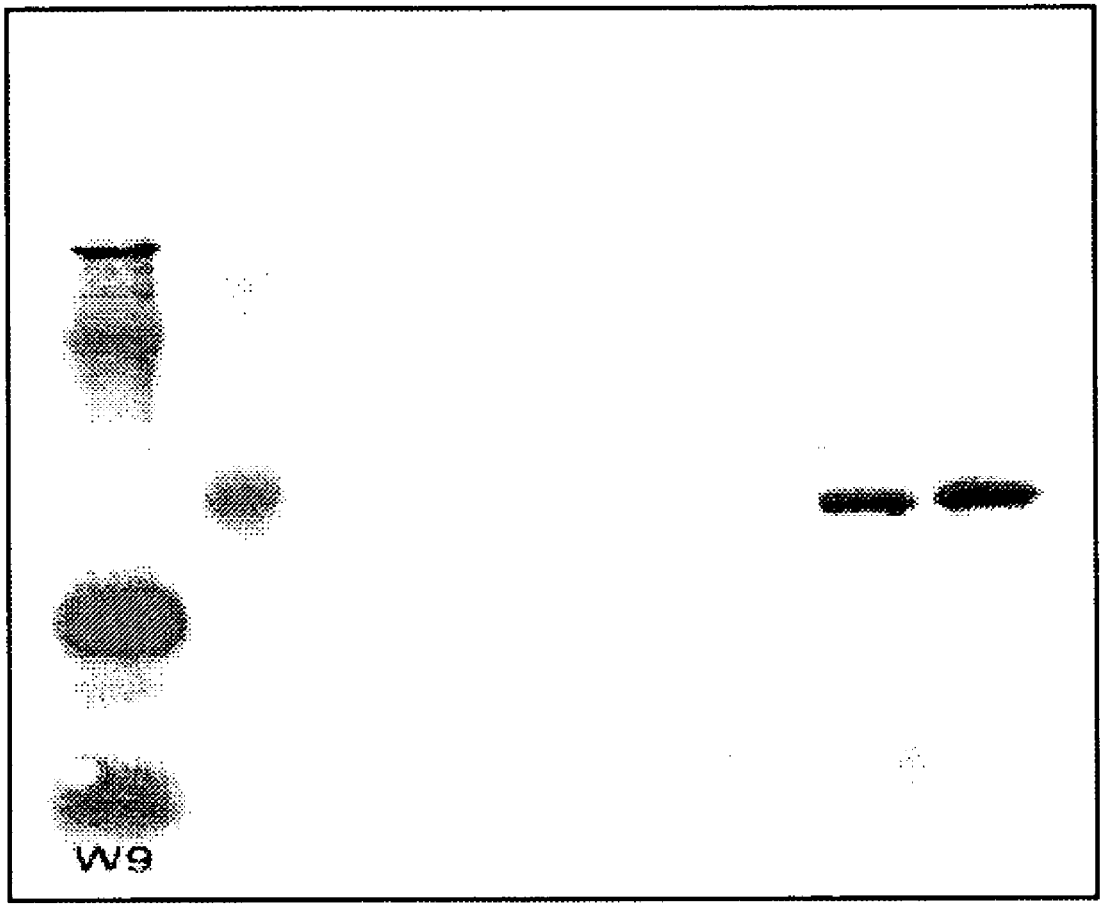

FIG. 10 shows the results of a Western blot analysis of various tissues of the transgenic rice plants, demonstrating the tissue specificity of rLF expression. Lane 1 is the molecular weight marker; lane 2 is human lactoferrin (Sigma, USA); lane 3 is an extract from leaf; lane 4 is an extract from sheath; lane 5 is an extract from root; lane 6 is an extract from seed and lane 7 is an extract from 5-day germinated seeds.

Figure 11:
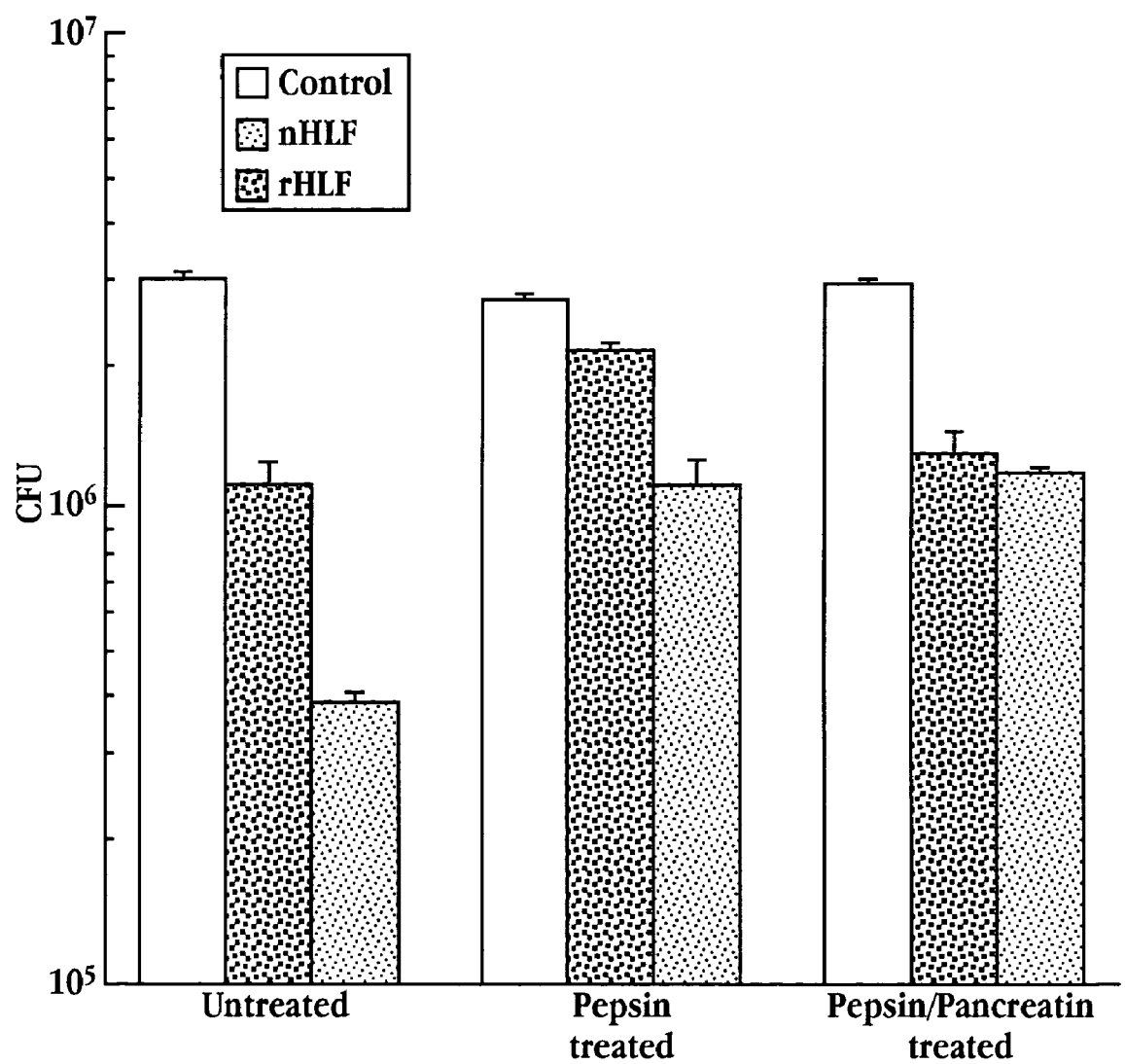

FIG. 11 is a bar diagram illustrating the bactericidal effect of native human lactoferrin ("nHLF") and purified recombinant human lactoferrin produced by transgenic rice ("rHLF") on growth of *E. coli* (EPEC) after pepsin/pancreatic treatment.

Figure 12:
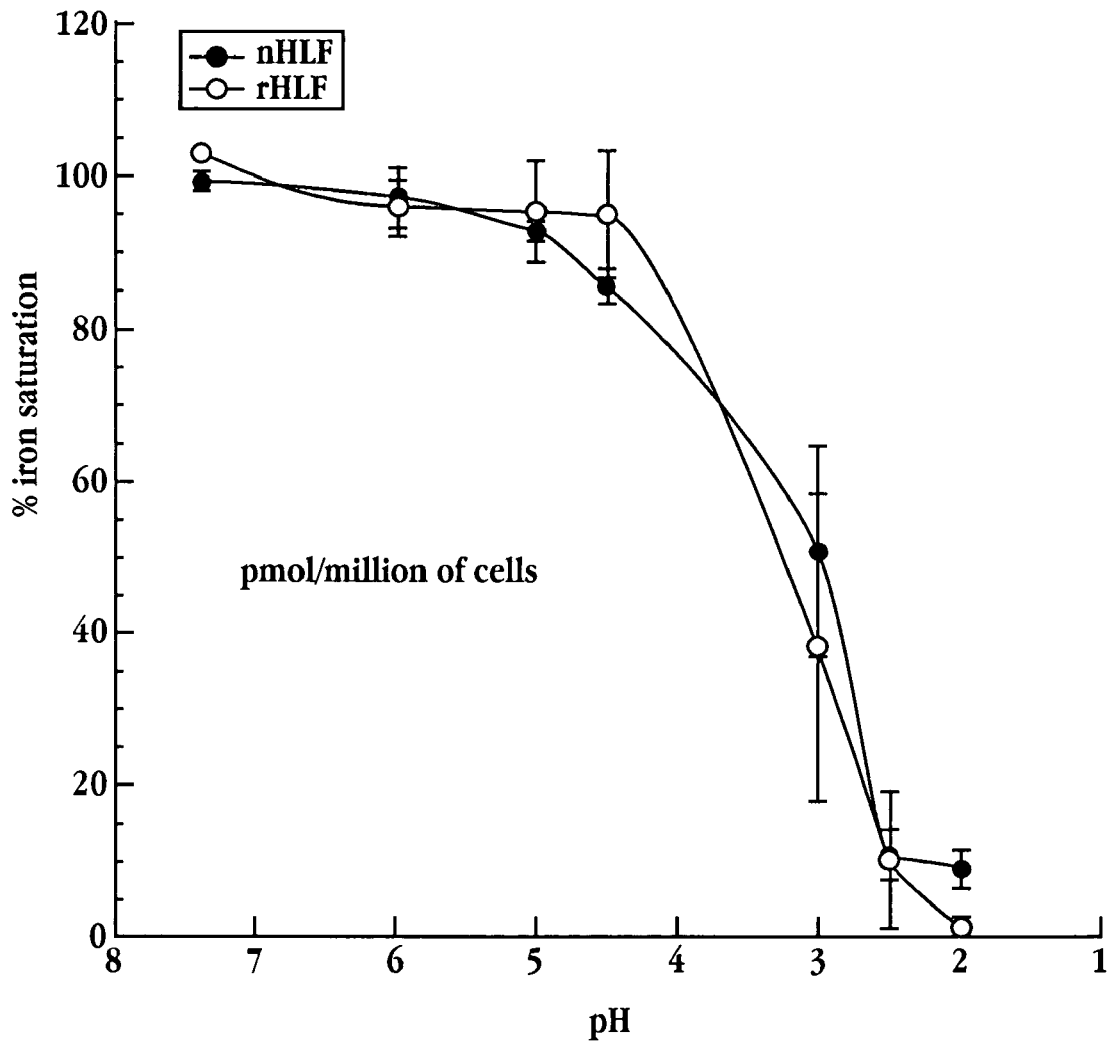

FIG. 12 is a graph illustrating pH-dependent iron release by native human lactoferrin ("nHLF") and purified recombinant human lactoferrin produced by transgenic rice seeds ("rHLF").

Figure 13A:
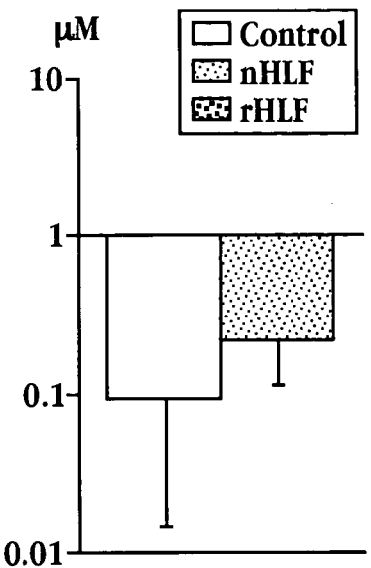
Figure 13B:
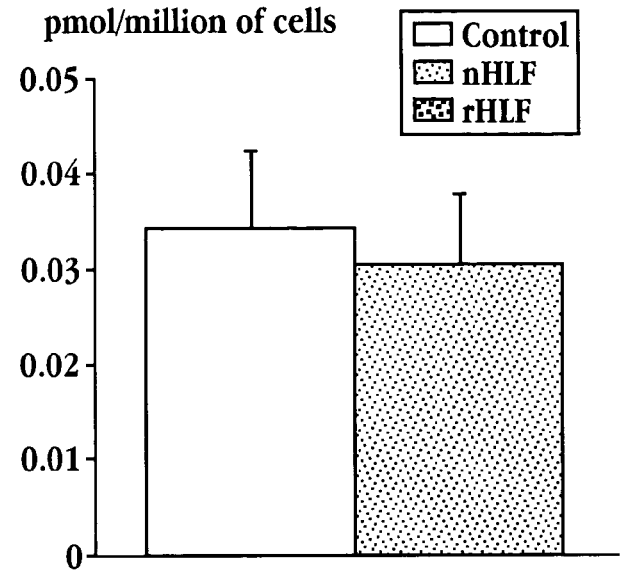
Figure 13C:
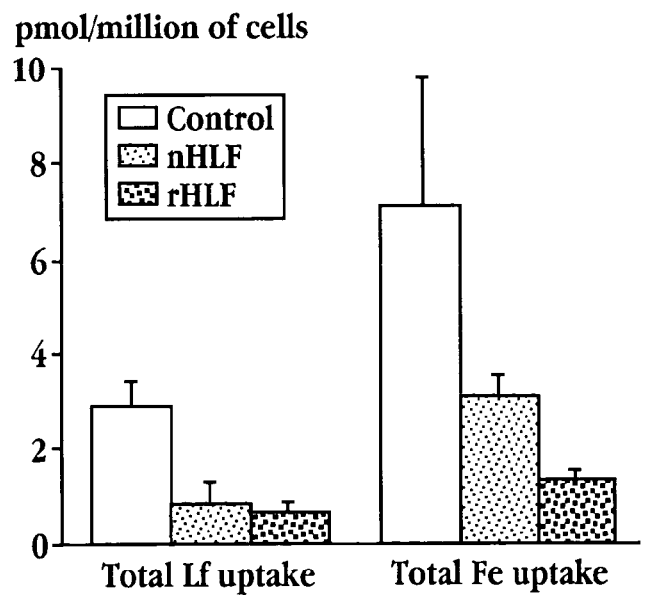
Figure 13D:
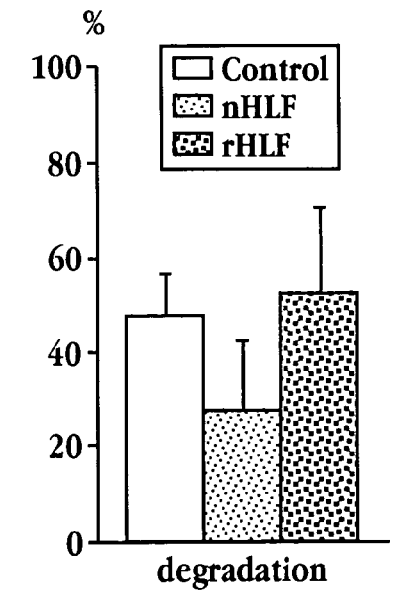

FIGS. 13A-13D show the binding and uptake of HLf to Caco-2 cells after in vitro digestion. FIG. 13A shows the determination of Dissociation constant. FIG. 13B shows the number of binding sites for HLf on Caco-2 cells. FIG. 13C shows the total uptake of HLf and Fe to Caco-2 cells within 24 h. FIG. 13D shows degradation of HLf after uptake into Caco cells determined by the amount of free $^{125}I$ in the cell fractions.

Figure 14:
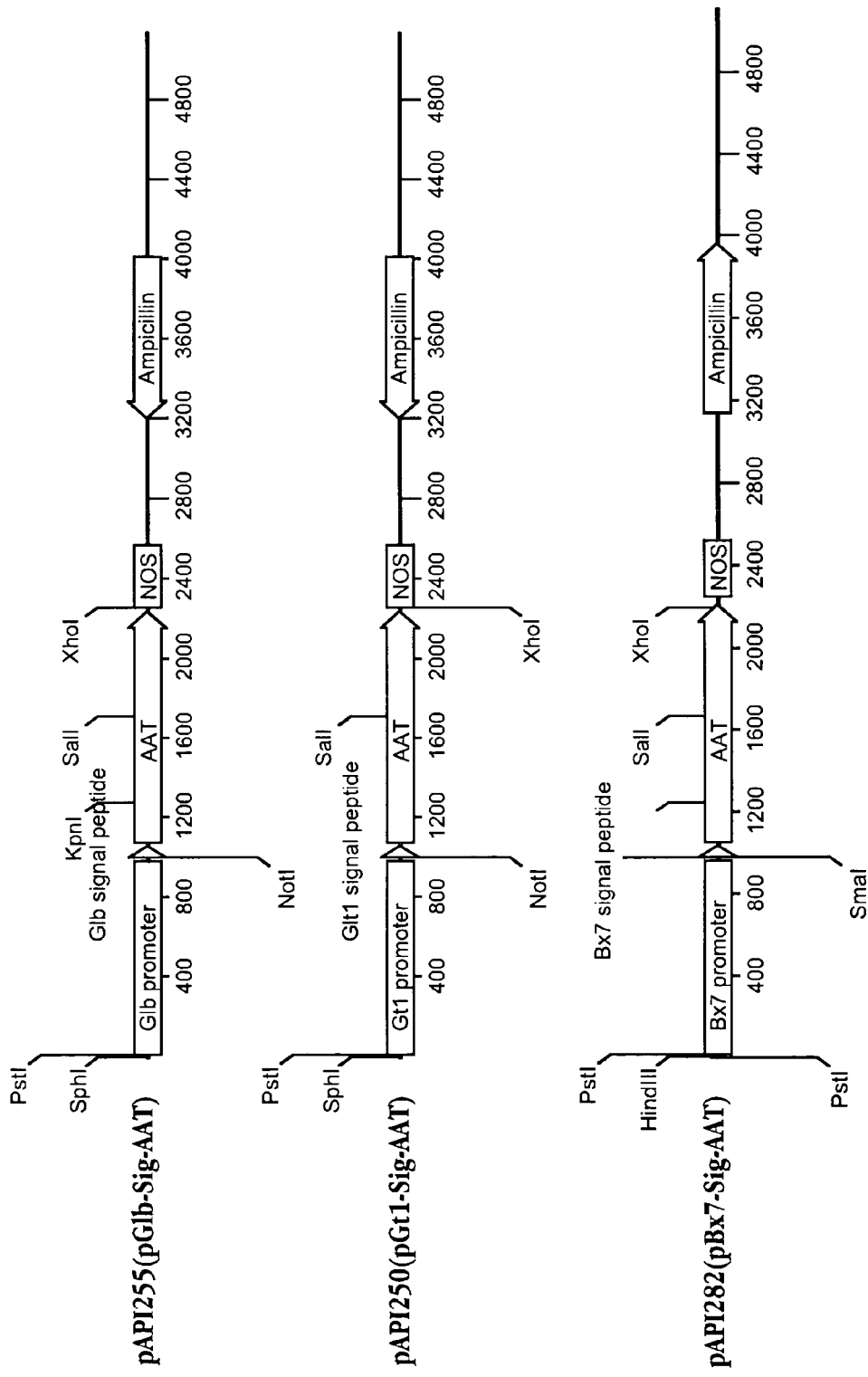

FIG. 14 shows three AAT plasmids: pAPI255 containing Glb promoter, Glb signal peptide, codon-optimized AAT gene, Nos terminator and ampicillin resistance gene; pAPI250 containing Gt1 promoter, Gt1 signal peptide, codon-optimized AAT gene, Nos terminator and ampicillin resistance gene; and pAPI282 containing Bx7 promoter, Bx7 signal peptide, codon-optimized AAT gene, Nos terminator and ampicillin resistance gene.

Figure 15:
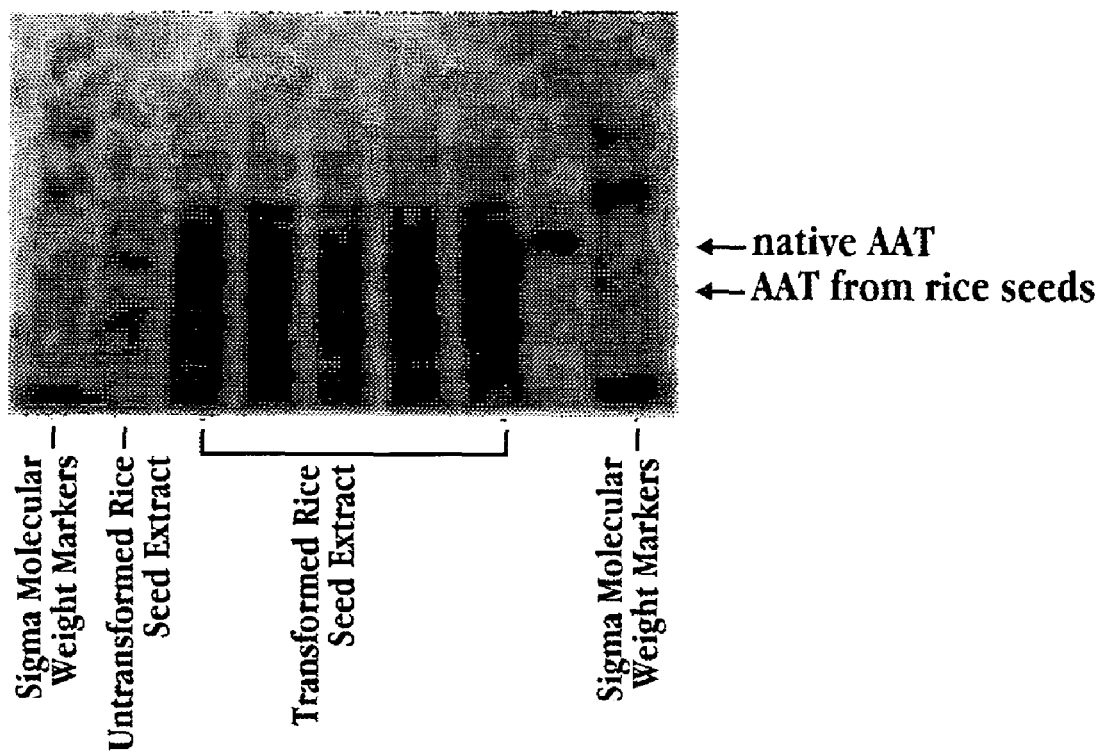

FIG. 15 shows Coomassie brilliant blue staining of aqueous phase extraction of transgenic rice cells expressing human MT. Both untransformed and transgenic rice grains were ground with PBS. The resulting extract was spun at 14,000 rpm at 4° C. for 10 min. Supernatant was collected and loaded onto a precast SDS-PAGE gel.

Figure 16:
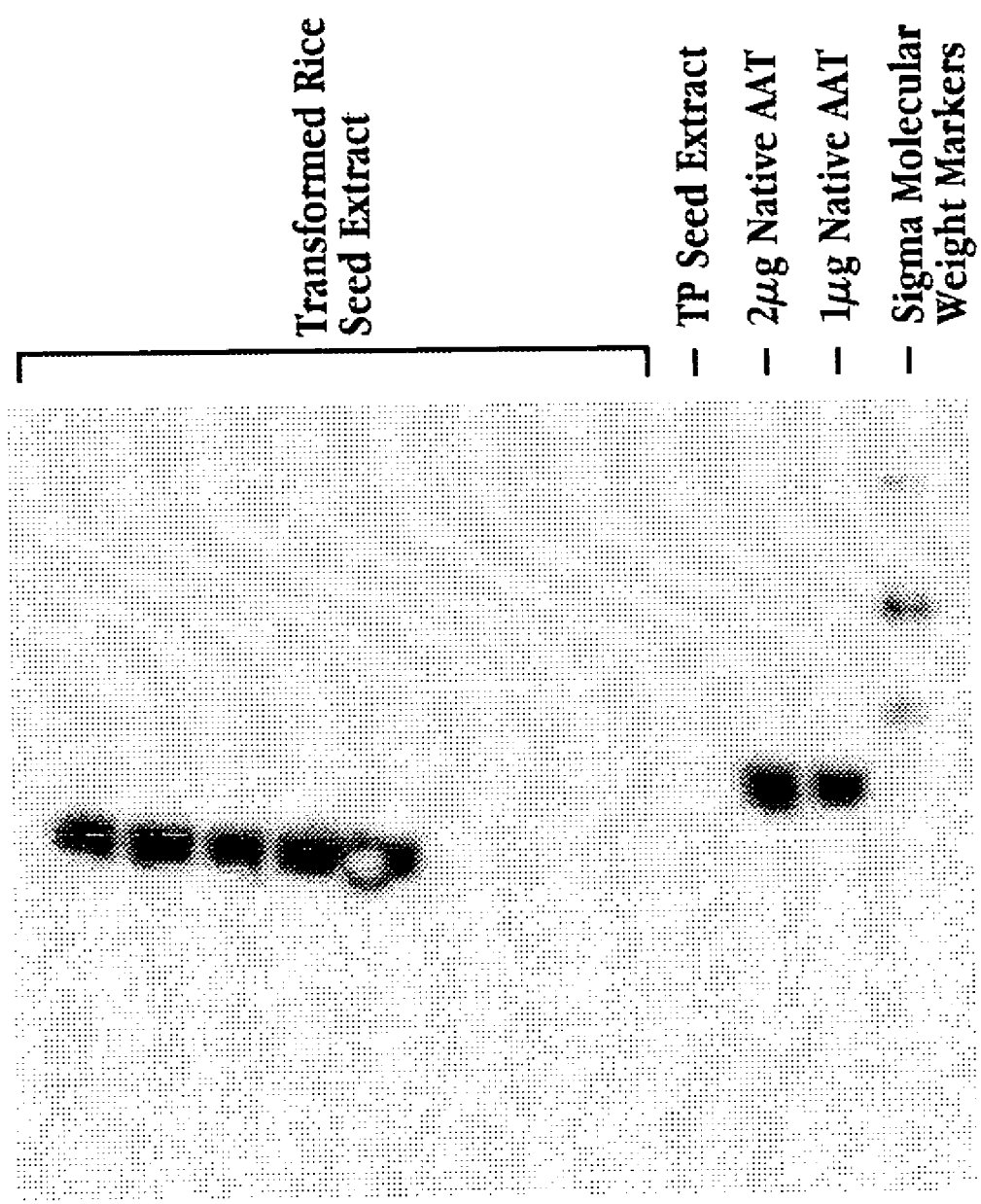

FIG. 16 shows Western blot analysis of recombinant human AAT from transgenic rice grains. The extract from transgenic rice grain was separated by SDS-PAGE gel and then blotted onto a filter. The identification of AAT in rice grain was carried out by anti-AAT antibody by Western analysis.

Figure 17A:
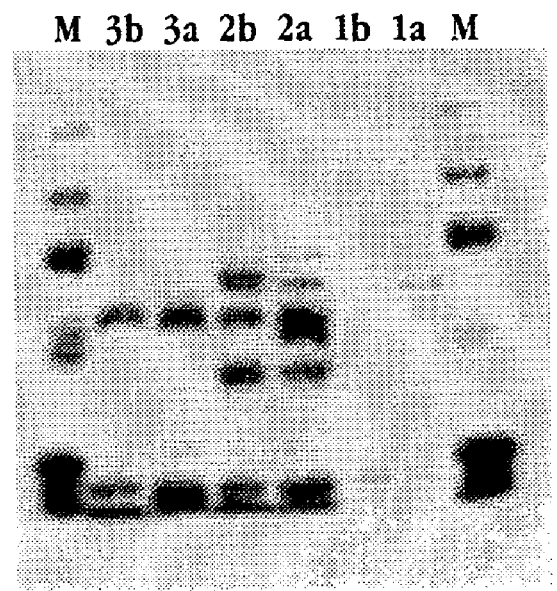
Figure 17B:
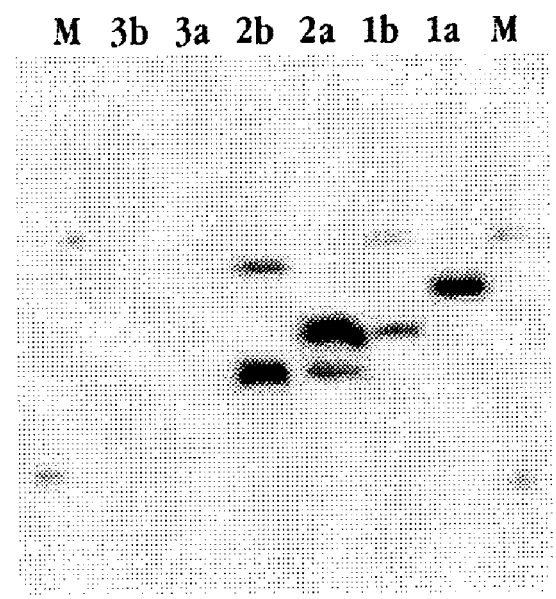

FIGS. 17A-17B show Coomassie staining (FIG. 17A) and western blot analysis (FIG. 17B) of protein from transgenic rice grains expressing AAT. The activity of rAAT was demonstrated by a band shift assay. AAT samples from different sources were incubated with equal moles of porcine pancreatic elastase (PPE) at 37° C. for 15 min. Negative control for band shift assay was prepared with the AAT samples incubated with equal volume of PPE added. Lane M is molecular weight markers. Lane 1a is purified AAT from human plasma. Lane 1b is purified AAT from human plasma+PPE. Lane 2a is protein extract containing AAT from transgenic rice seed; Lane 2b is protein extract containing AAT from transgenic rice seed+PPE. Lane 3a is untransformed seed extract. Lane 3b is untransformed seed extract+PPE. A shifted band was shown in lane 1b, 2b and 3b in FIG. 17A. The shifted band was confirmed to contain AAT entity by Western blot in FIG. 17B.

Figure 18A:
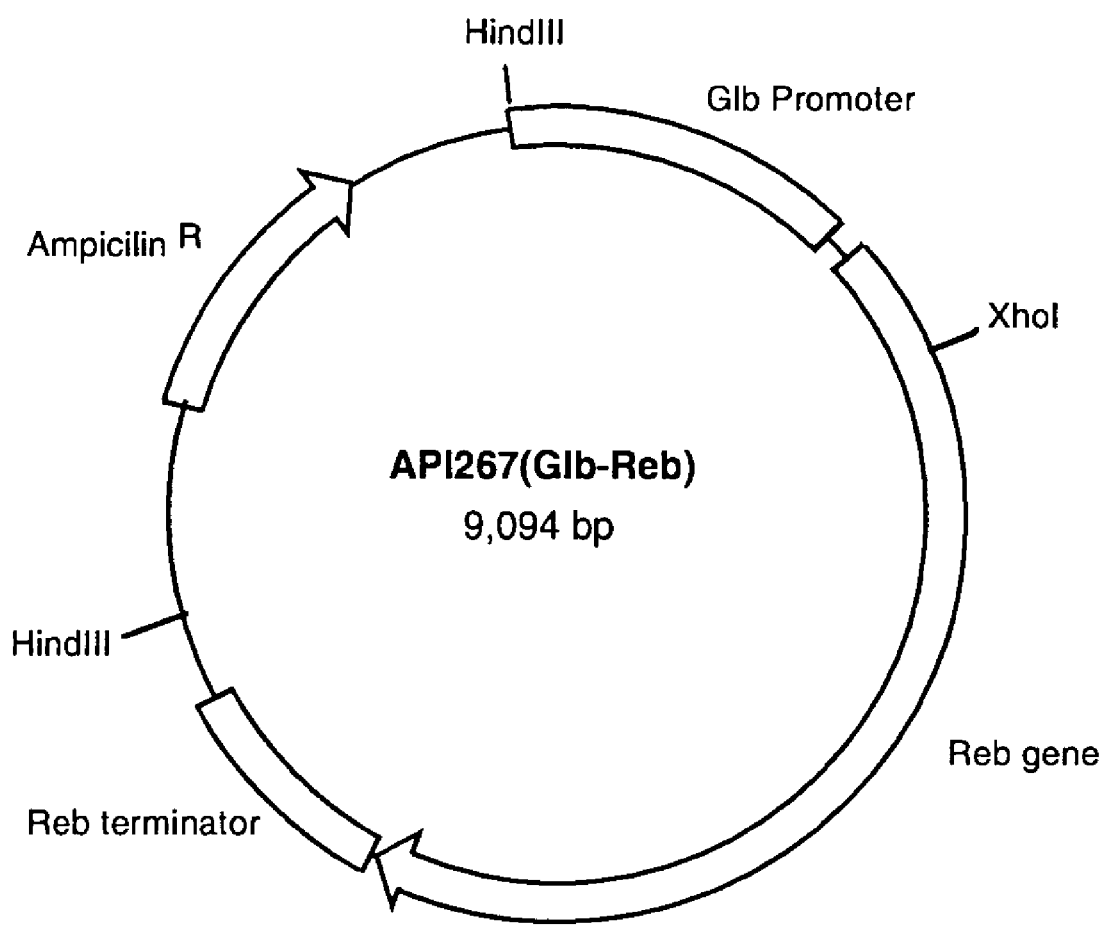
Figure 18B:
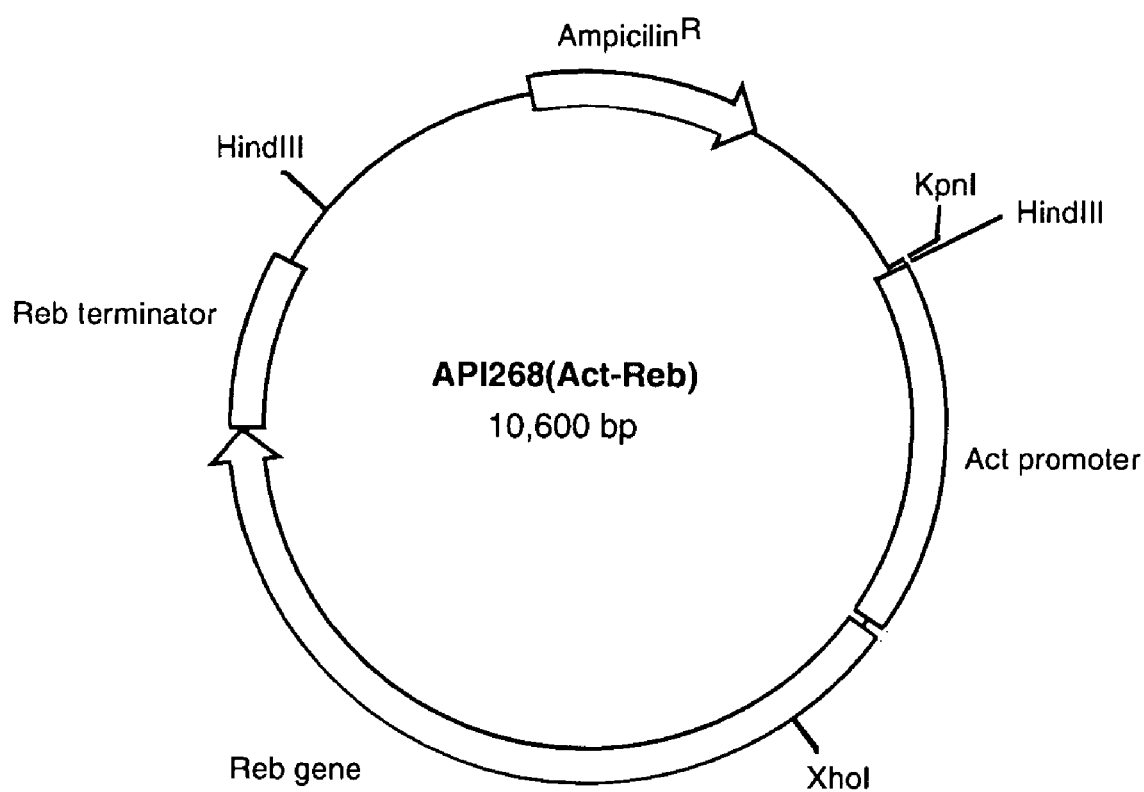
Figure 18C:
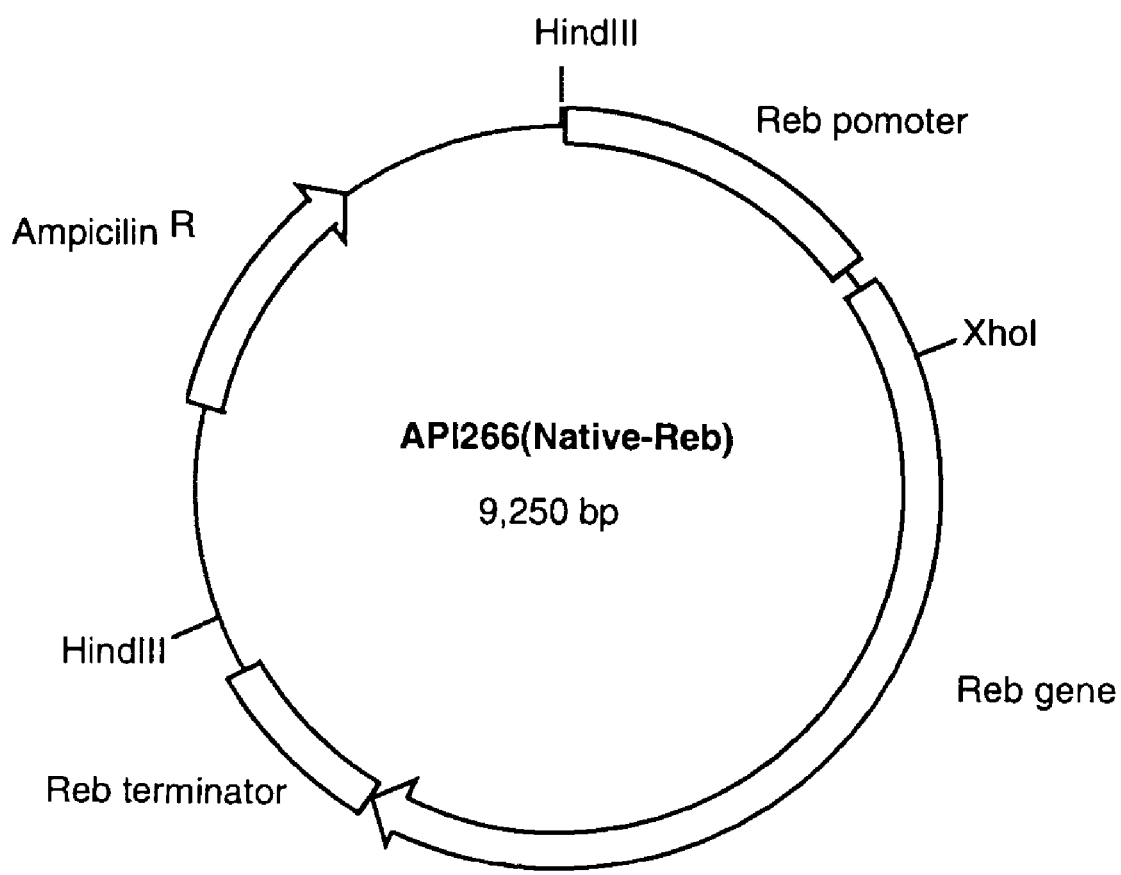

FIGS. 18A-18C are schematic representations of 3 plasmids containing the Reb coding sequence under the control of 3 different promoters. FIG. 18A shows the globulin promoter (Glb), with the Reb gene and the Reb terminator. FIG. 18B shows the actin promoter (Act), with the Reb gene and the Reb terminator. FIG. 18C shows the native Reb promoter, with the Reb gene and the Reb terminator.

Figure 19A:
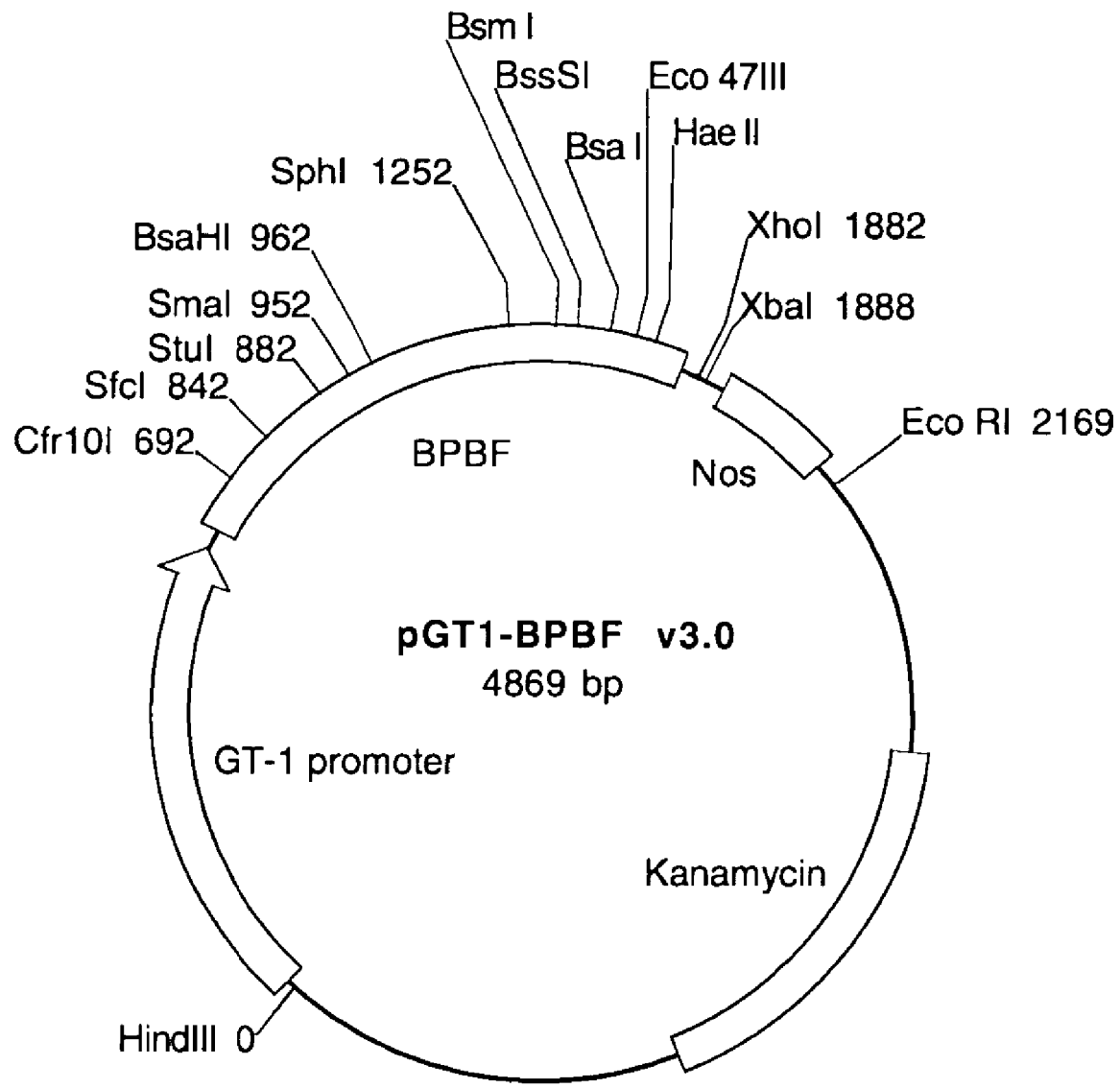
Figure 19B:
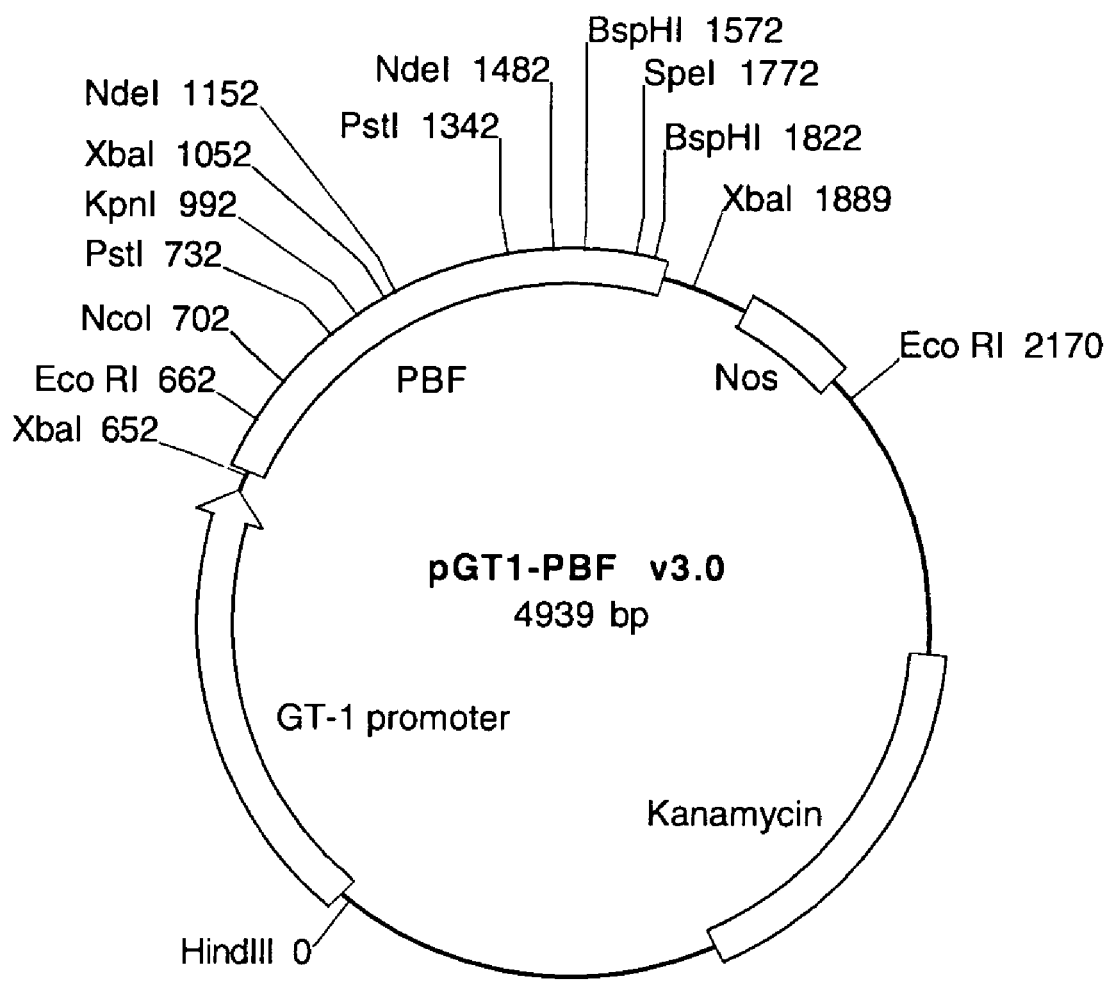

FIGS. 19A-19B are schematic depictions of two plasmids which contain different transcription factor coding sequences under the control of the rice endosperm-specific glutelin promoter (Gt-1). FIG. 19A shows plasmid pGT1-BPBF (API286) containing the Gt1 promoter, barley prolamin box binding factor (BPBF), Nos terminator and kanamycin resistance gene. FIG. 19B shows pGT1-PBF (API285) containing the Gt1 promoter, the maize prolamin box binding factor (PBF), Nos terminator and kanamycin resistance gene.

Figure 20:
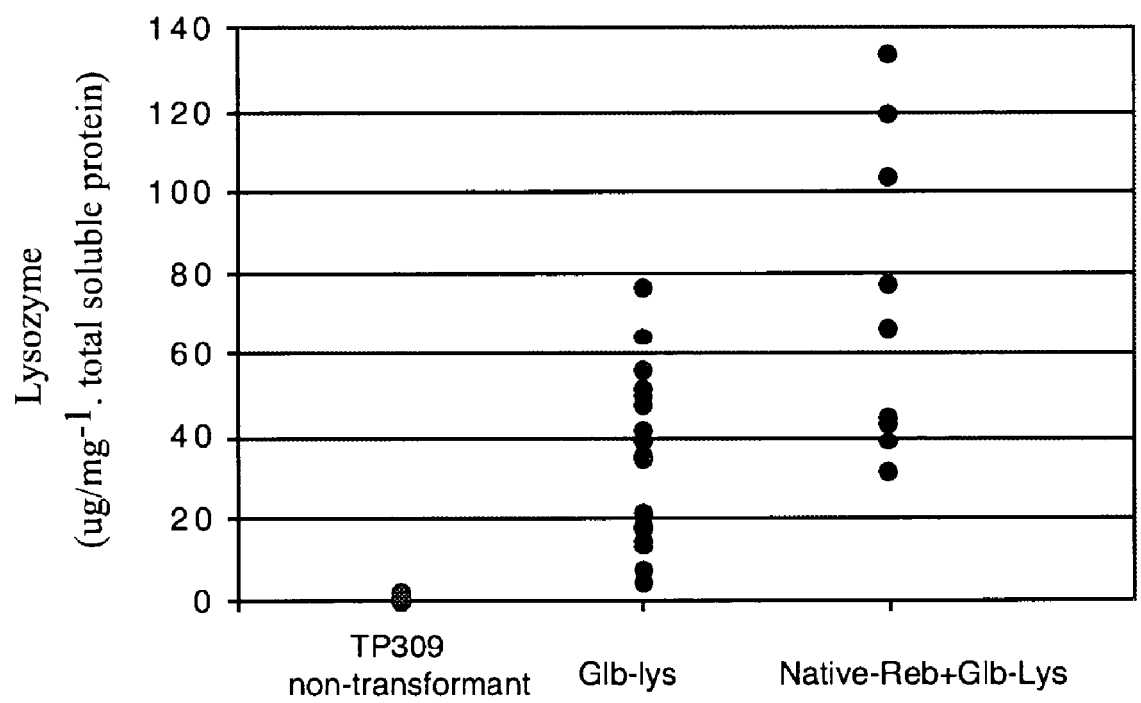

FIG. 20 illustrates the results of an analysis for the expression of recombinant human lysozyme in mature seed of $T_0$ transgenic plants derived from progenitor cells transformed with constructs containing the human lysozyme gene expressed under the control of the Glb promoter and the Reb gene expressed under the control of its own promoter ("Native-Reb"). Seeds of 30 plants containing the Reb and lysozyme genes and seeds from 17 plants containing only the lysozyme gene were analyzed for lysozyme, with twenty individual seeds of each plant analyzed.

FIG. 21 is a comparison of the codon-optimized epidermal growth factor sequence ("Egfactor"; SEQ ID NO: 36) with a native epidermal growth factor sequence ("Native Gene"; SEQ ID NO: 37), aligned to show 53 codons in the mature sequences, with 27 (51%) codon changes and 30 (19%) nucleotide changes.

Figure 22:
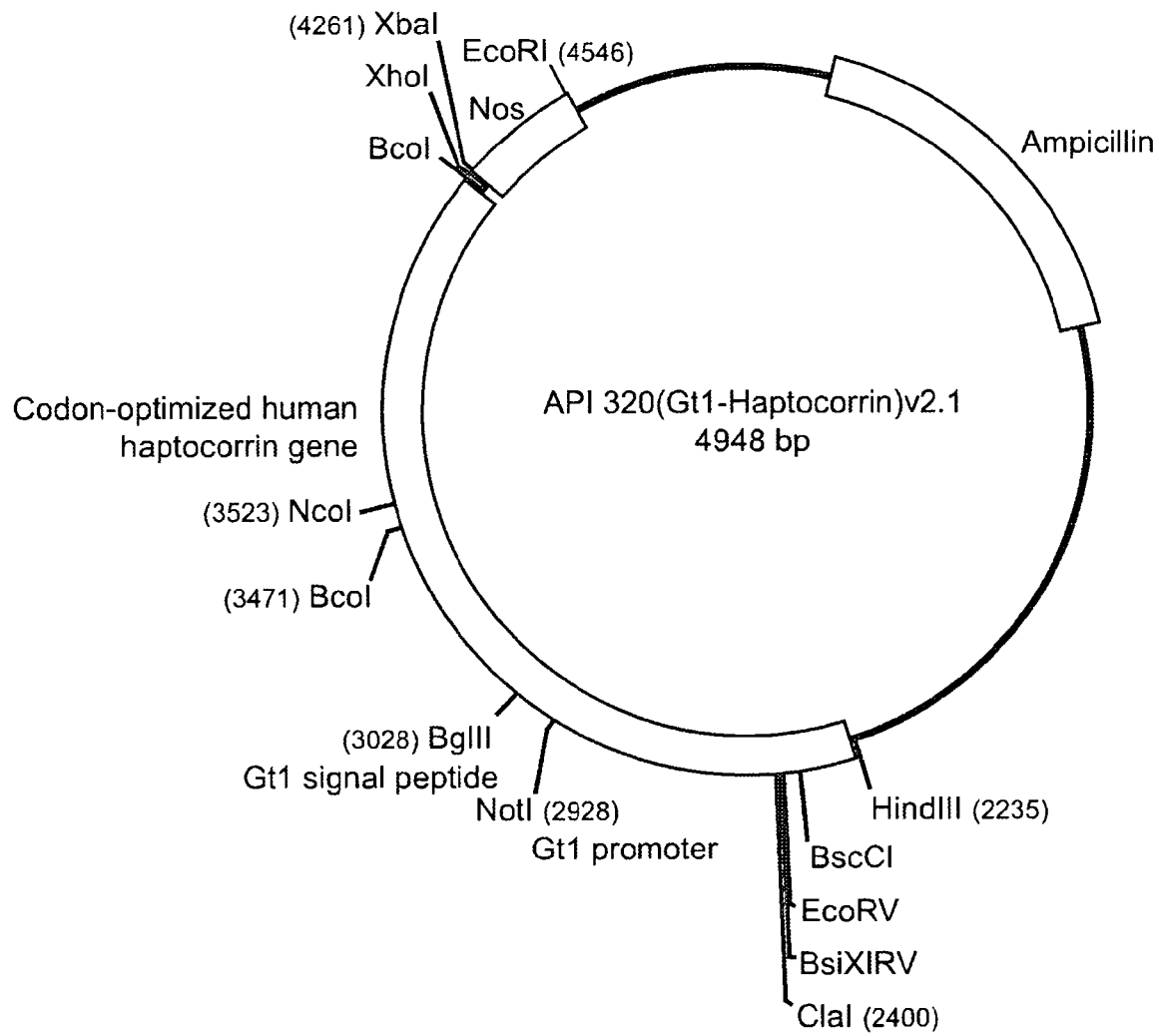

FIG. 22 is a restriction map of the 4948 bp plasmid, API320 (pGt1-Haptocorrin v 2.1), showing an expression cassette for haptocorrin, and containing a Gt1 promoter, a Gt1 signal peptide, codon optimized haptocorrin, a Nos terminator and an ampicillin resistance selectable marker.

Figure 23:
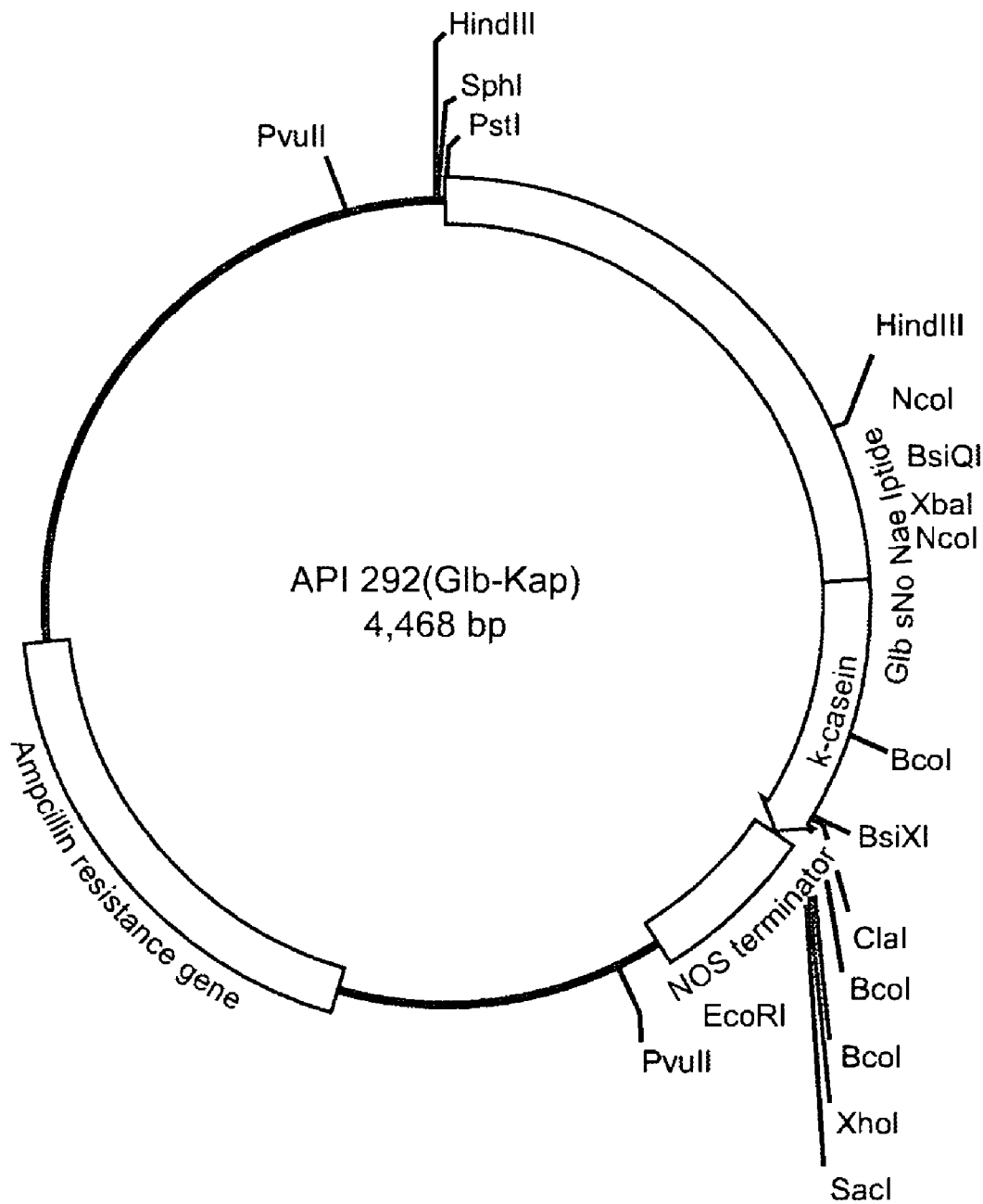

FIG. 23 is a restriction map of the 4468 bp plasmid, API292 (pGlb-kcasein v2.1), showing an expression cassette for kappa-casein ("κ-casein"), and containing a Glb promoter, a Glb signal peptide, a k-casein gene, a Nos terminator and an ampicillin resistance selectable marker.

Figure 24:
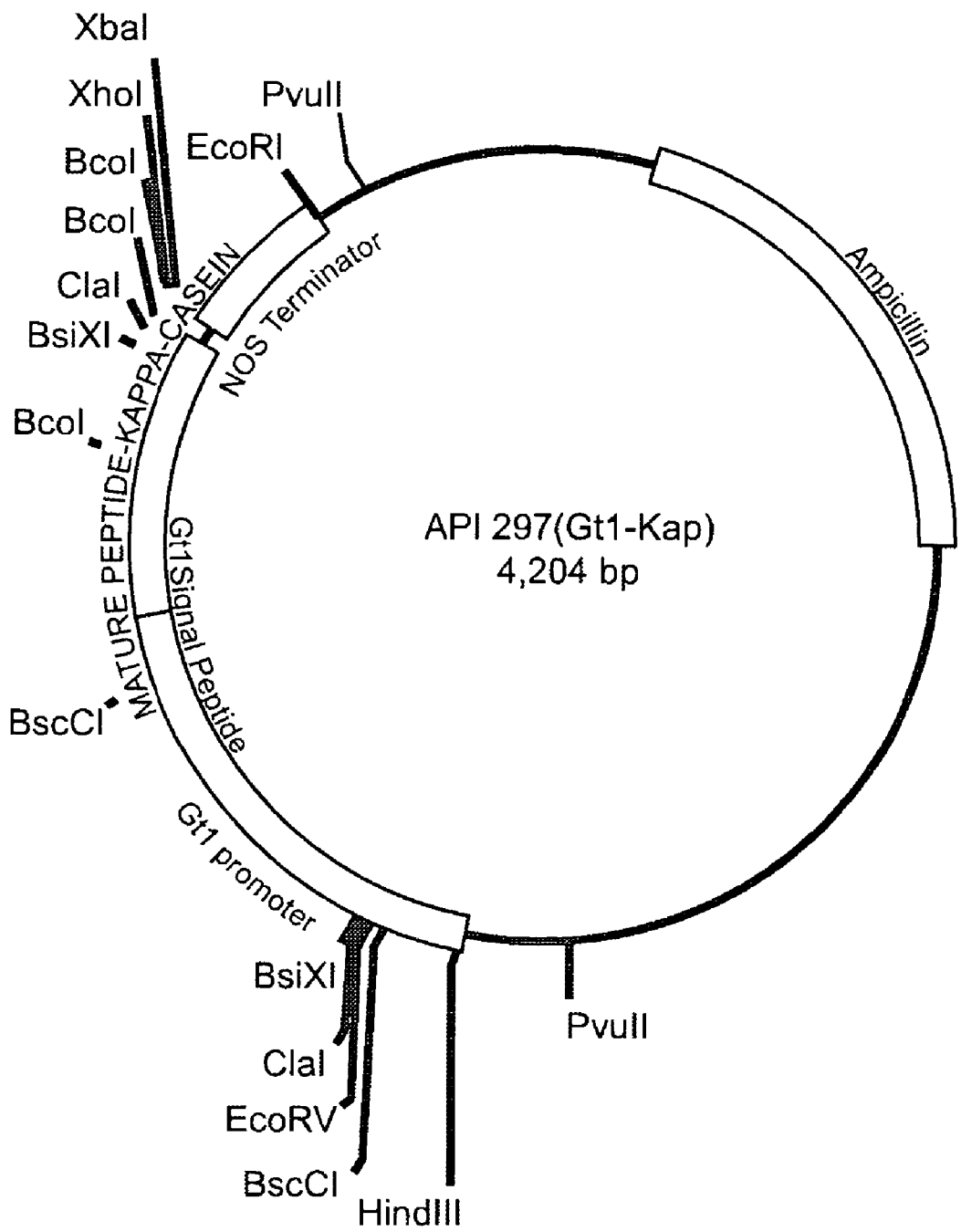

FIG. 24 is a restriction map of the 4204 bp plasmid, API297 (pGT1-kaapa-Casein v2.1), showing an expression cassette for kappa-casein, and containing a Gt1 promoter, a Gt1 signal peptide, mature kappa-casein polypeptide encoding gene, a Nos terminator and an ampicillin resistance selectable marker.

Figure 25:
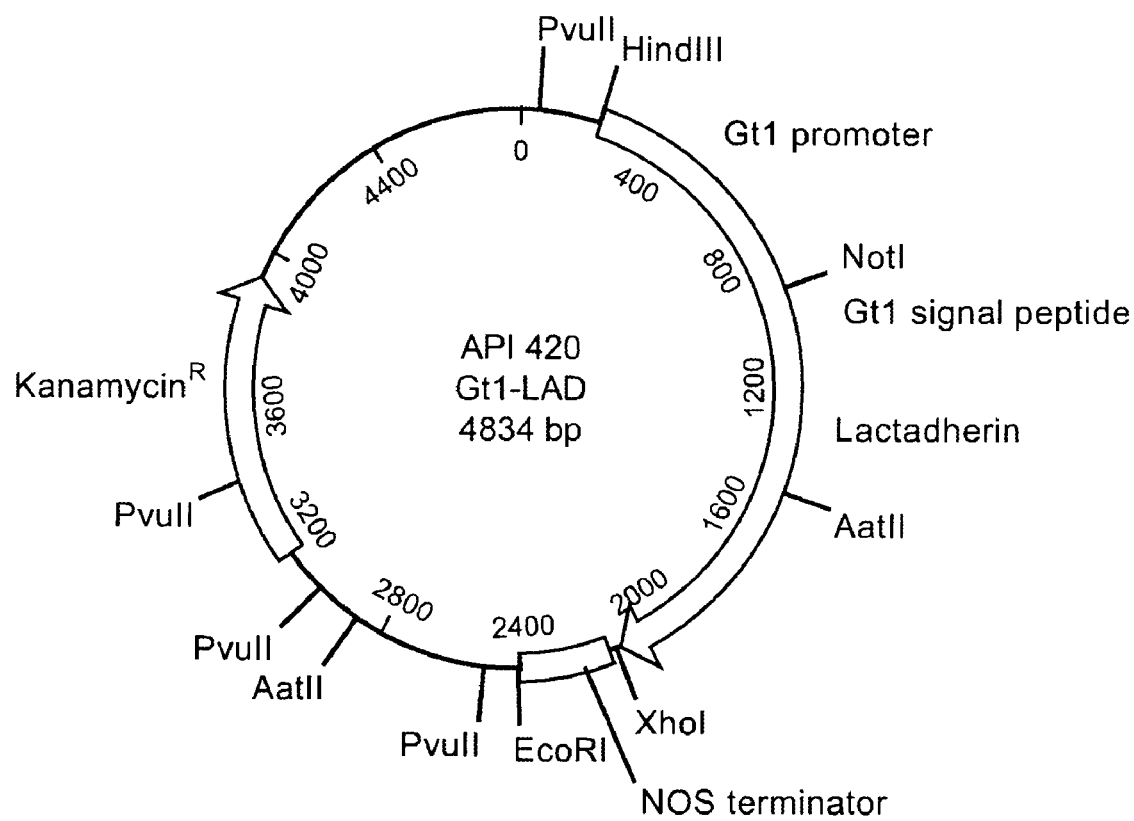

FIG. 25 is a restriction map of the 4834 bp plasmid, API420 (pGt1-LAD), showing an expression cassette for lactadherin, and containing a Gt1 promoter, a Gt1 signal peptide, lactadherin gene, a Nos terminator and a kanamycin resistance selectable marker.

Figure 26:
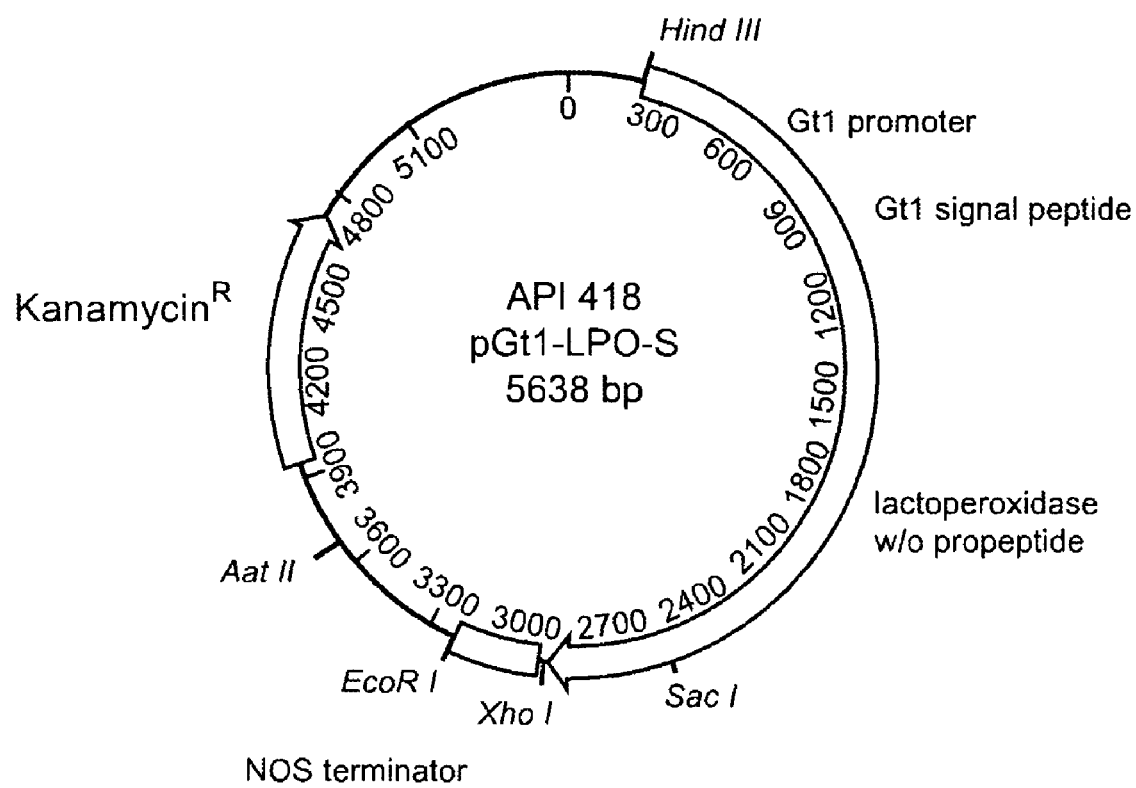

FIG. 26 is a restriction map of the 5638 bp plasmid, API418 (pGT1-LPO-S), showing an expression cassette for lactoperoxidase (minus the propeptide), and containing a Gt1 promoter, a Gt1 signal peptide, lactoperoxidase gene without the propeptide, a Nos terminator and a kanamycin resistance selectable marker.

Figure 27:
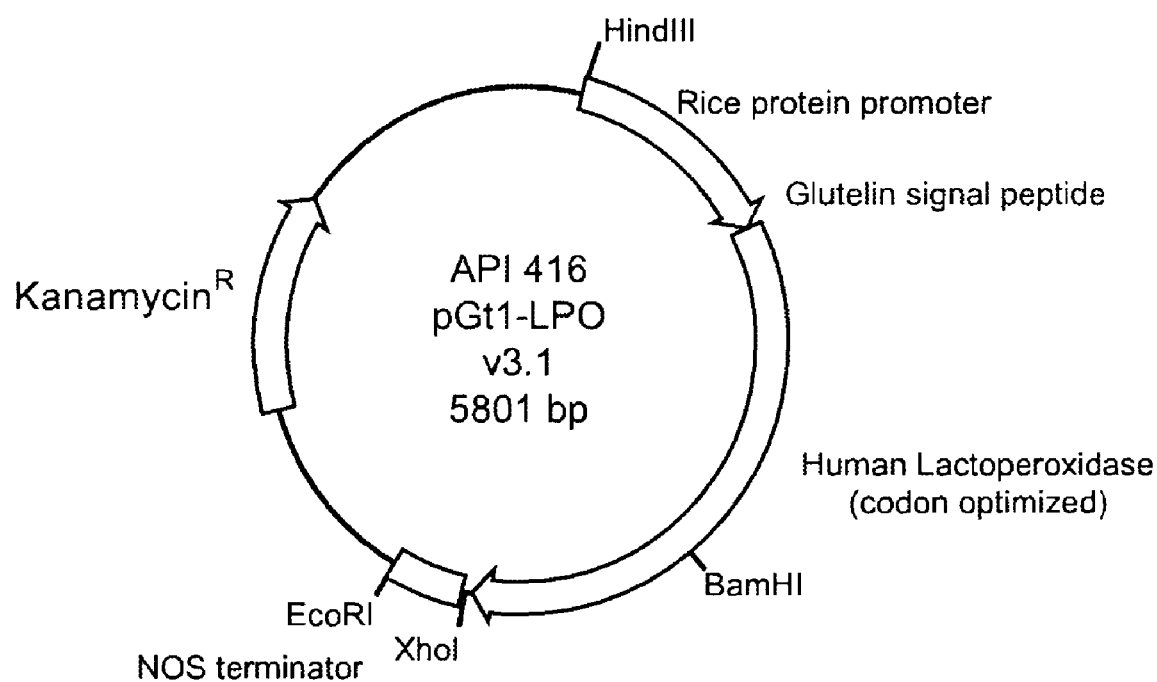

FIG. 27 is a restriction map of the 5801 bp plasmid, API416 (pGt1-lactoperoxidase), showing an expression cassette for codon optimized human lactoperoxidase, and containing a rice Gt1 promoter, a Gt1 signal peptide, codon optimized lactoperoxidase, a Nos terminator and a kanamycin resistance selectable marker.

Figure 28:
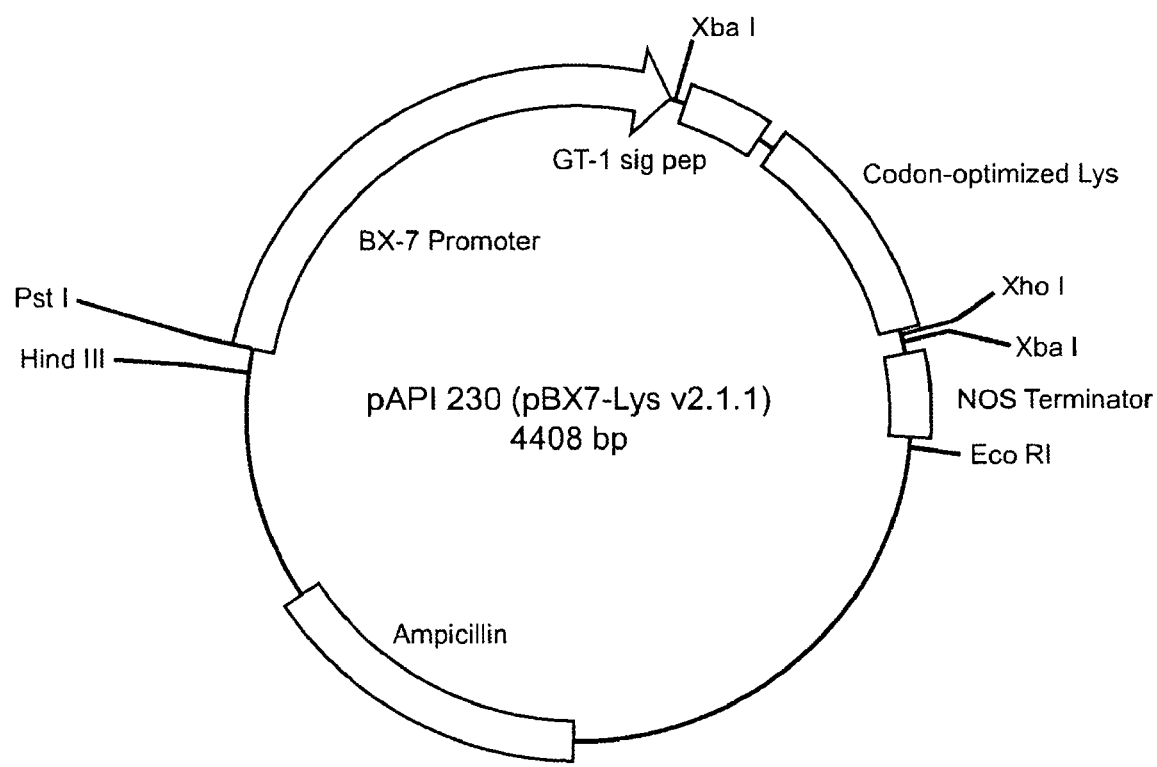

FIG. 28 is a restriction map of the 4408 bp plasmid, API230 (pBX7-Lysozyme v2.1.1), showing an expression cassette for codon optimized lysozyme, and containing a BX-7 promoter, a Gt1 signal peptide, codon optimized lysozyme gene, a Nos terminator and an ampicillin resistance selectable marker.

Figure 29A:
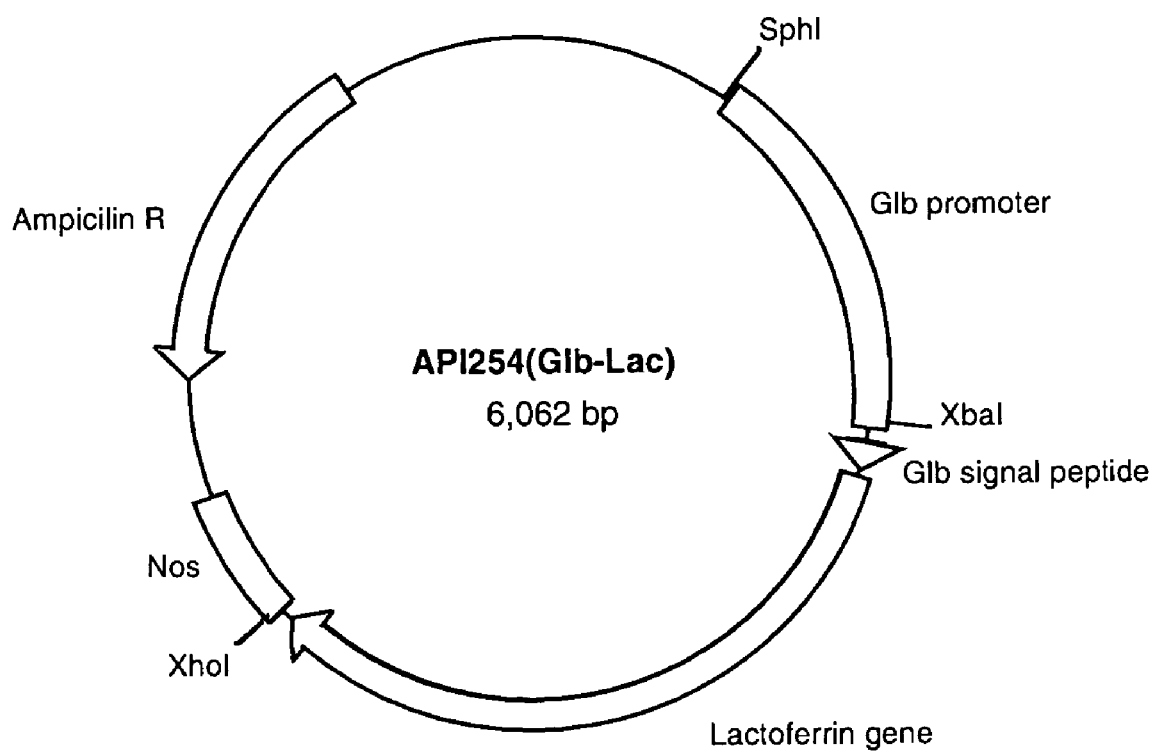
Figure 29B:
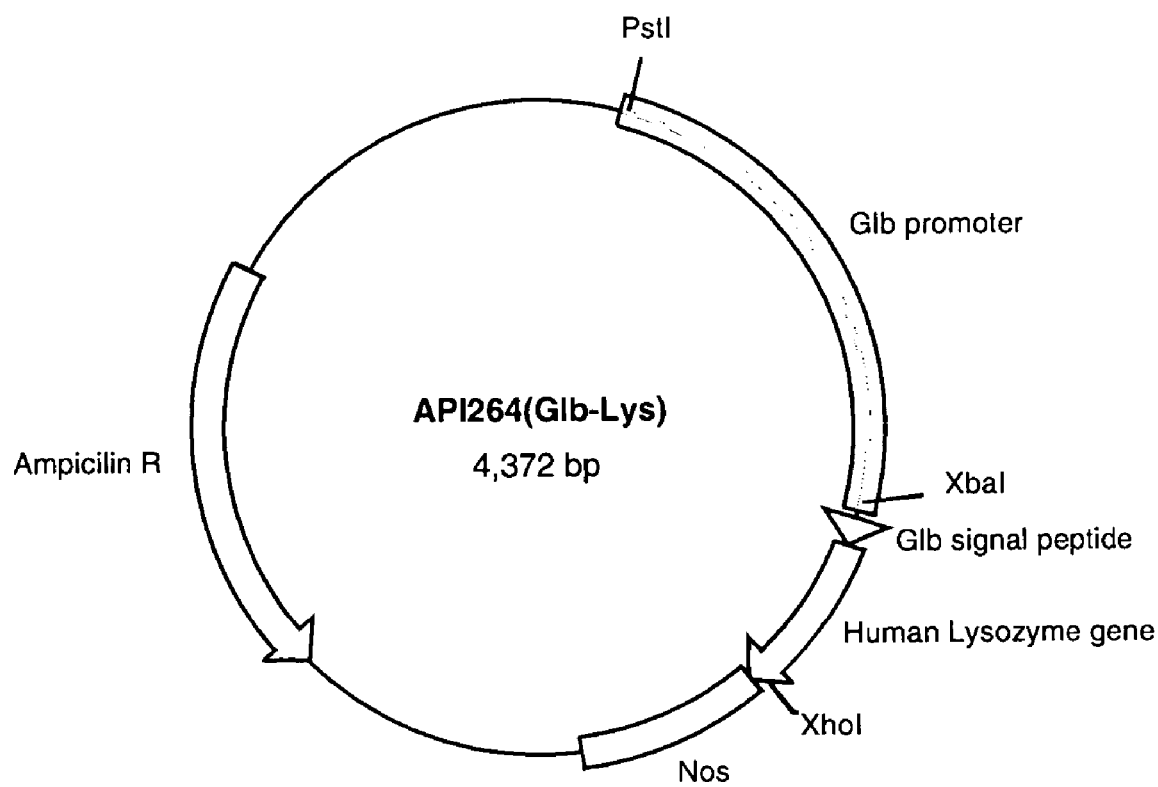

FIGS. 29A-29B represent schematic diagrams of the map of 2 plasmids, API254 (FIG. 29A) and API264 (FIG. 29B) containing heterologous protein coding sequences under the control of the rice endosperm-specific globulin promoter (Glb), the Glb signal peptide, and Nos terminator. API254 contains the lactoferrin coding sequence, and API264 contains the human lysozyme coding sequence.

Figure 30:
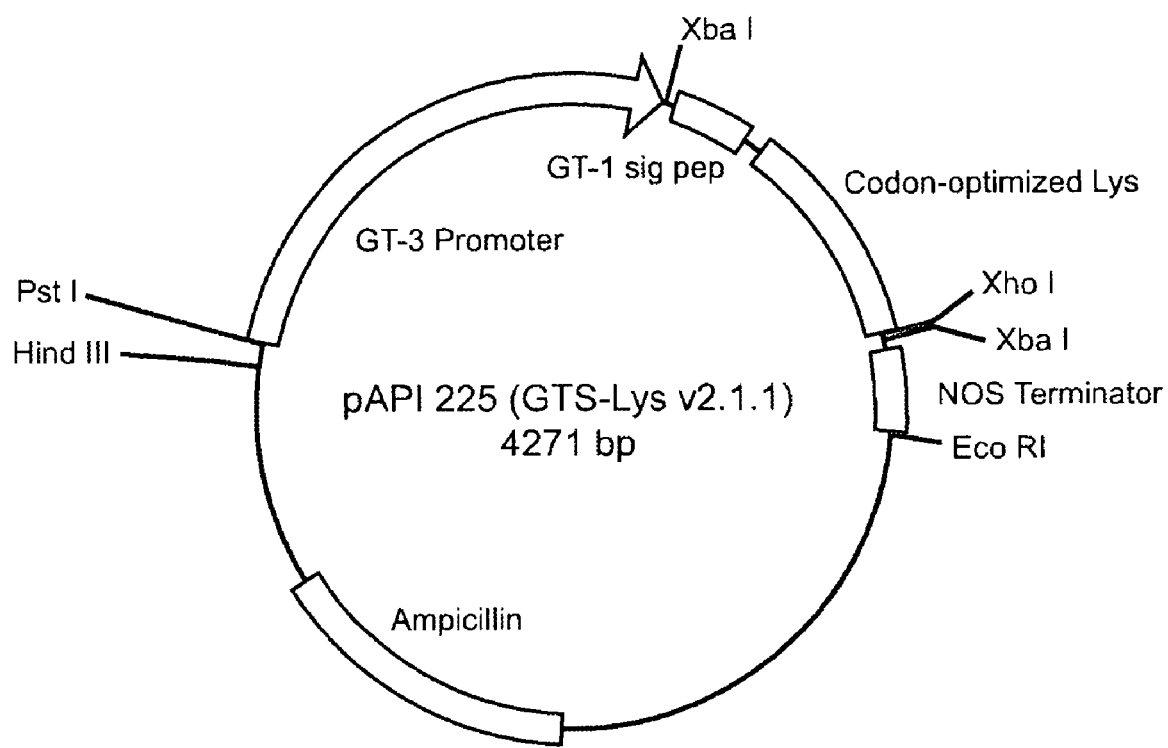

FIG. 30 is a restriction map of the 4271 bp plasmid, API225, showing an expression cassette for codon optimized lysozyme, and containing a GT-3 promoter, a Gt1 signal peptide, codon optimized lysozyme, a Nos terminator and an ampicillin resistance selectable marker.

Figure 31:
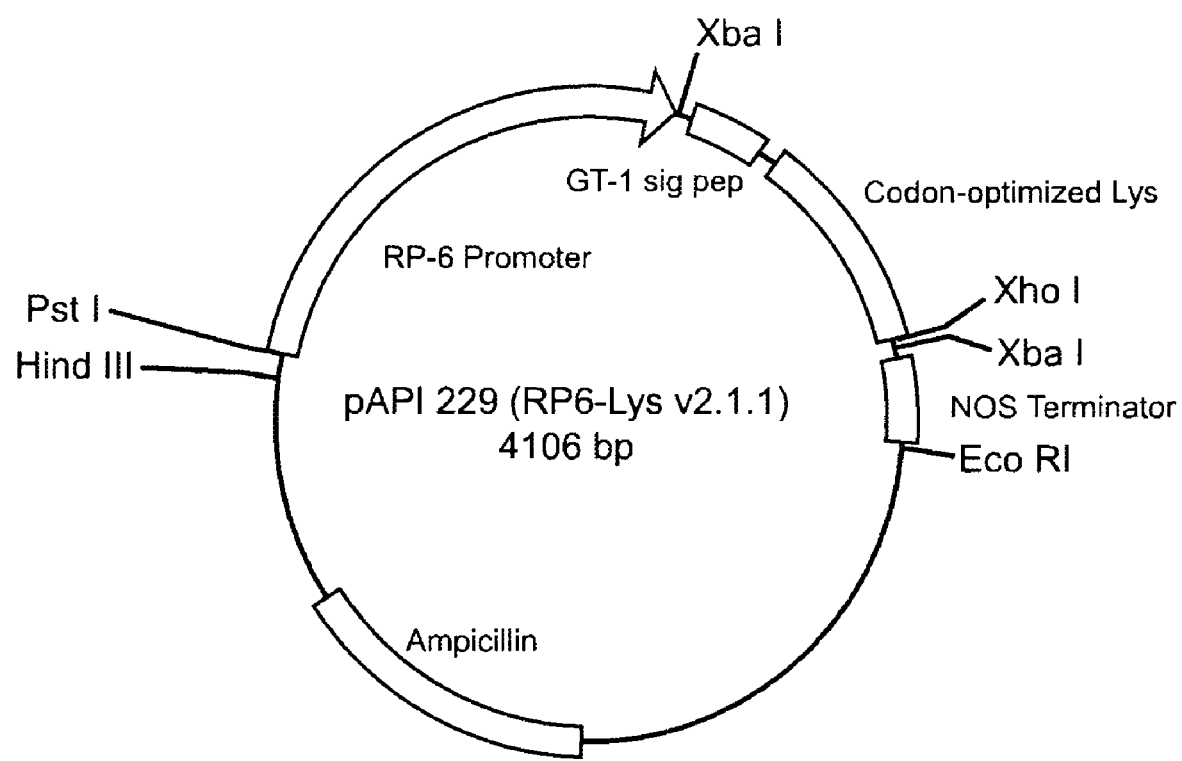

FIG. 31 is a restriction map of the 4106 bp plasmid, API229, showing an expression cassette for codon optimized lysozyme, and containing a RP-6 promoter, a Gt1 signal peptide, codon optimized lysoyme, a Nos terminator and an ampicillin resistance selectable marker.

Figure 32A:
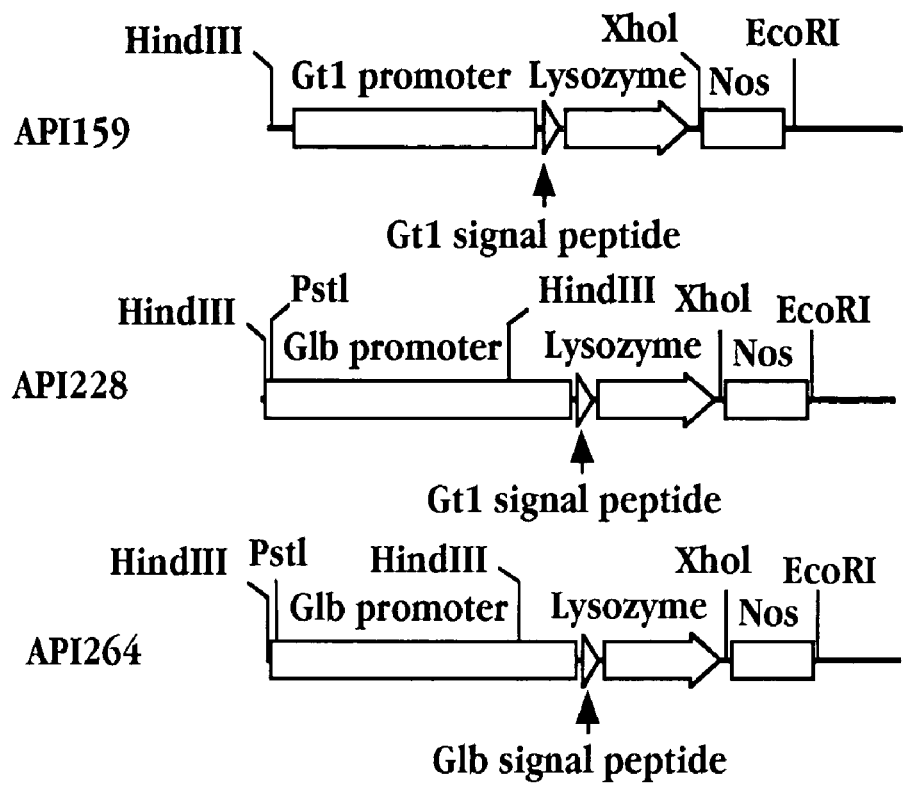
Figure 32B:
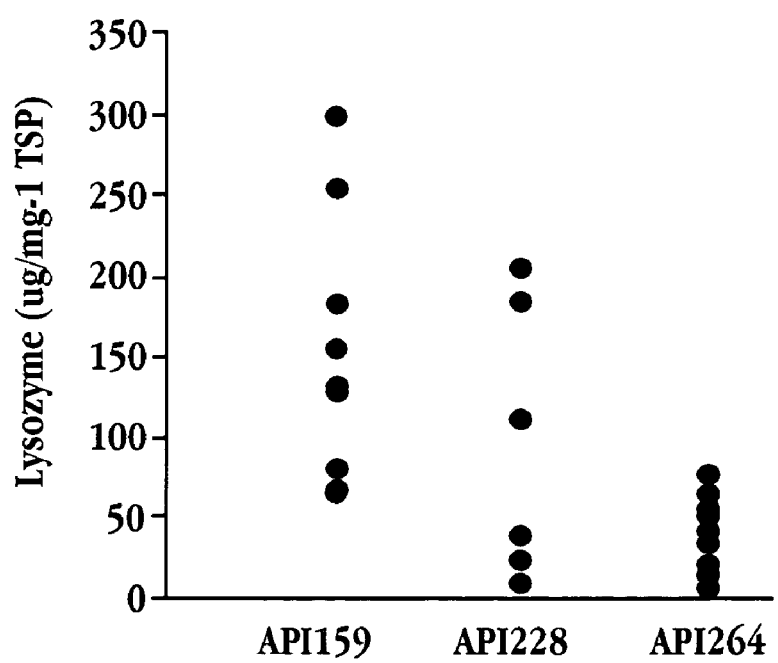

FIGS. 32A-32B are a comparison of the expression of lysozyme under Gt1 or Gib promoter with Gt1 signal peptide or Glb signal peptide. FIG. 32A is a schematic representation of plasmid API159 that contains Gt1 promoter, Gt1 signal peptide, a lysozyme gene and Nos terminator; plasmid API 228 that contains Glb promoter, Gt1 signal peptide, a lysozyme gene and Nos terminator; and plasmid API264 that contains Glb promoter, Glb signal peptide, a lysozyme gene and Nos terminator. FIG. 32B shows the activities of lysozyme in lysozyme-positive seeds produced in transgenic rice plants transformed with API159, API228 and API264. The seeds from multiple lines of each construct were analyzed by the lysozyme activity assay. Individual seeds from each plant were analyzed. Seeds lacking detectable amounts of lysozyme were excluded. The activities of 20-lysozyme-positive seeds per plant, including both heterozygous and homozygous seeds were averaged. The average activities were plotted on the chart.

Figure 33:
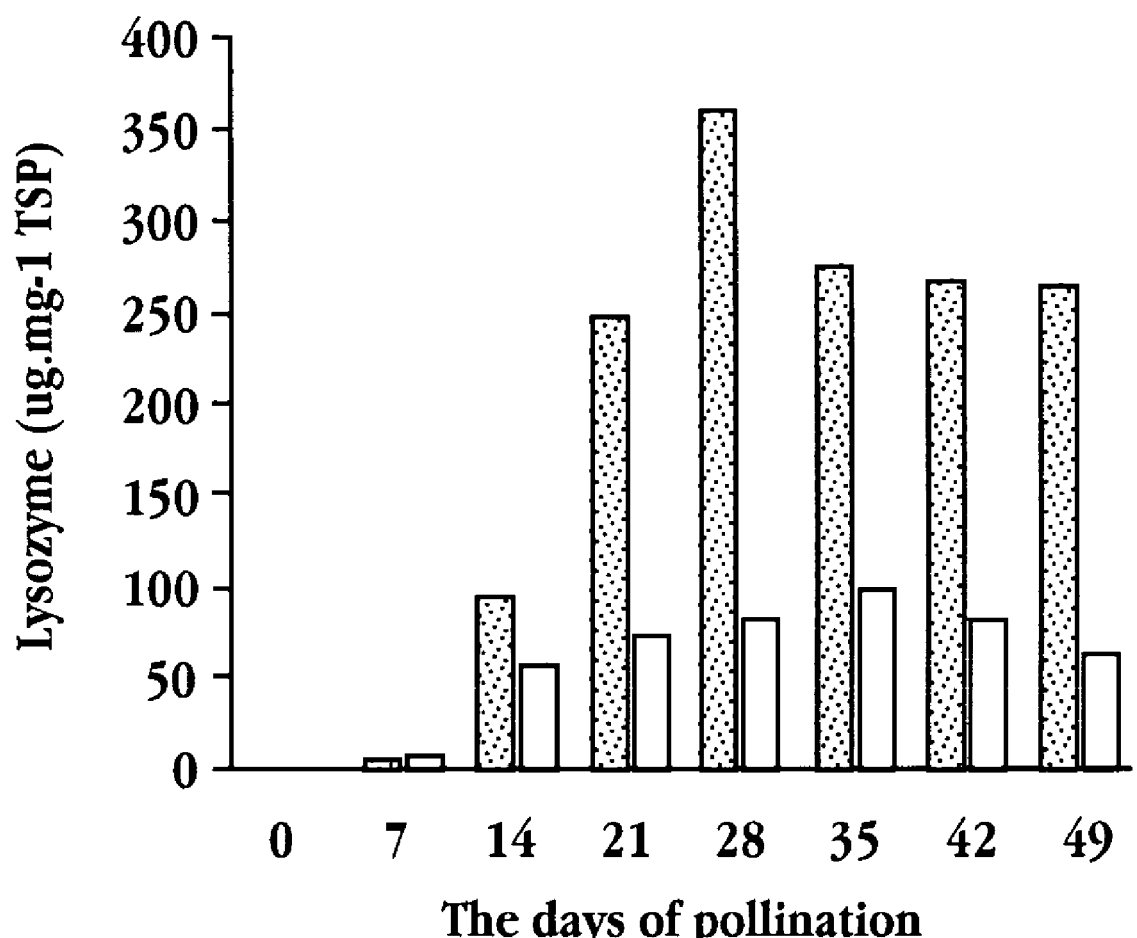

FIG. 33 shows the expression time course of human lysozyme during endosperm development in transgenic line. Ten spikelets were harvested at 7, 14, 21, 28, 35, 42 and 49 days after pollination ("DAP") and analyzed by the lysozyme activity assay. The dark bars were from 159-1-53-16-1. The light bars were from 264-1-92-6-1.

Figure 34:
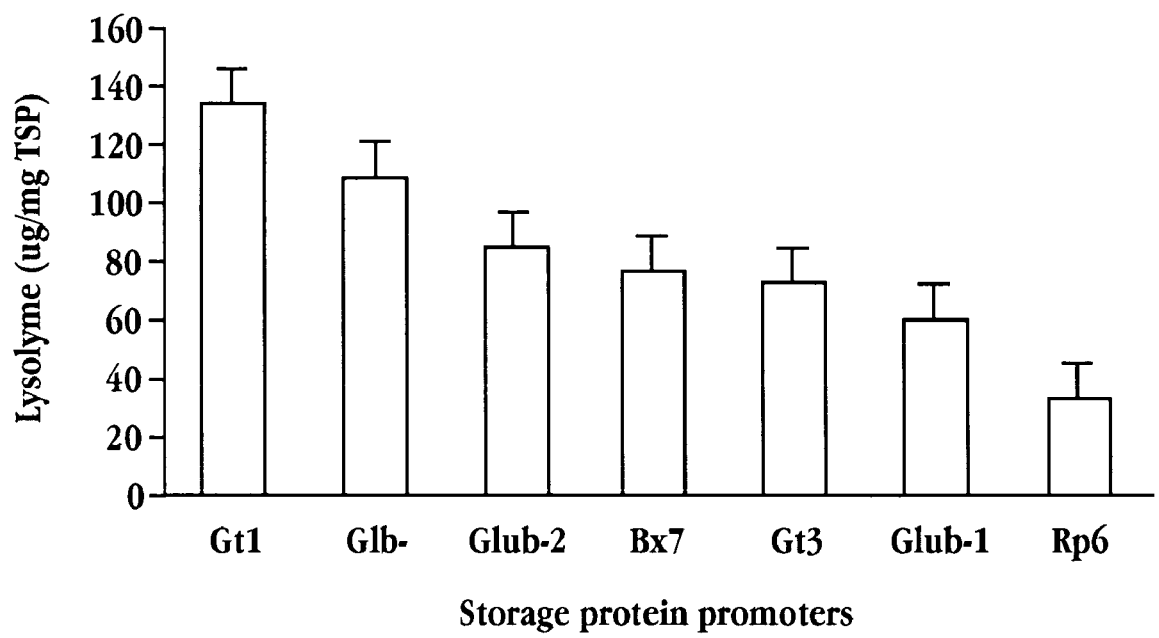

FIG. 34 is a bar graph comparing the level of lysozyme expression in transgenic T1 rice seeds under 7 different promoters: Gt1, Glb, Glub-2, Bx7, Gt3, Glub-1 and Rp6. All constructs contained a Gt1 signal peptide.

DETAILED DESCRIPTION OF THE INVENTION

I. Definitions

Unless otherwise indicated, all terms used herein have the meanings given below, and are generally consistent with same meaning that the terms have to those skilled in the art of the present invention. Practitioners are particularly directed to Sambrook et al. (1989) Molecular Cloning: A Laboratory Manual (Second Edition), Cold Spring Harbor Press, Plainview, N.Y. and Ausubel F M et al. (1993) Current Protocols in Molecular Biology, John Wiley & Sons, New York, N.Y., for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies that might be used in connection with the invention.

The term "polypeptide" refers to a biopolymer compound made up of a single chain of amino acid residues linked by peptide bonds. The term "protein" as used herein may be synonymous with the term "polypeptide" or may refer, in addition, to a complex of two or more polypeptides.

The term "anti-microbial protein" refers to a protein that is anti-bacterial and can include acute phase proteins, cationic anti-microbial peptides and probiotic proteins. Such anti-microbial proteins are capable of inhibiting the growth of one or more of Gram-negative bacteria, Gram-positive bacteria, fungi (including yeast), parasites (including planaria and nematodes) and viruses. Typically, such anti-microbial peptides exhibit selective biological activity against such microbes over eukaryotic cells.

The term "anti-bacterial protein" refers to a protein that is bacteriostatic or bactericidal in nature.

The term "bacteriostatic protein" refers to refers to a protein capable of inhibiting the growth of, but not capable of killing bacteria.

The term "bactericidal protein" refers to a protein capable of killing bacteria.

The term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art. Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

The term "plasmid" refers to a circular double-stranded (ds) DNA construct used as a cloning vector, and which forms an extrachromosomal self-replicating genetic element in many bacteria and some eukaryotes.

The term "selectable marker-encoding nucleotide sequence" refers to a nucleotide sequence capable of expression in plant cells and where expression of the selectable marker confers to plant cells containing the expressed gene the ability to grow in the presence of a selective agent. As used herein, the term "Bar gene" refers to a nucleotide sequence encoding a phosphinothricin acetyltransferase enzyme that upon expression confers resistance to the herbicide glufosinate-ammonium ("Basta").

A "transcription regulatory region" or "promoter" refers to nucleic acid sequences that influence and/or promote initiation of transcription. Promoters are typically considered to include regulatory regions, such as enhancer or inducer elements. The promoter will generally be appropriate to the host cell in which the target gene is being expressed. The promoter, together with other transcriptional and translational regulatory nucleic acid sequences (also termed "control sequences"), is necessary to express any given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a construct which has been introduced into a host and may include parts of different genes of exogenous or autologous origin, including regulatory elements. A chimeric gene construct for plant/seed transformation is typically composed of a transcriptional regulatory region (promoter) operably linked to a heterologous protein coding sequence, or, in a selectable marker heterologous nucleic acid construct, to a selectable marker gene encoding a protein conferring antibiotic resistance to transformed plant cells. A typical chimeric gene of the present invention, includes a transcriptional regulatory region inducible during seed development, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, "operably linked" elements, e.g., enhancers, do not have to be contiguous. Linking is accomplished by ligation at convenient restriction sites. If such sites do not exist, the synthetic oligonucleotide adaptors or linkers are used in accordance with conventional practice.

The term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

The term "sequence identity" means nucleic acid or amino acid sequence identity in two or more aligned sequences, aligned using a sequence alignment program.

The term "% homology" is used interchangeably herein with the term "% identity" and refers to the level of nucleic acid or amino acid sequence identity between two or more aligned sequences, when aligned using a sequence alignment program. For example, 70% homology means the same thing as 70% sequence identity determined by a defined algorithm, and accordingly a homologue of a given sequence has greater than 80% sequence identity over a length of the given sequence. Exemplary levels of sequence identity include, but are not limited to, 80, 85, 90 or 95% or more sequence identity to a given sequence, e.g., the coding sequence for lactoferrin, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at (ncbi.nlm.gov/BLAST/). See, also, Altschul, S. F. et al., 1990 and Altschul, S. F. et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences which have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. [See, Altschul, et al., 1997.]

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm$-5°$ C. ($5°$ below the Tm of the probe); "high stringency" at about $5-10°$ below the Tm; "intermediate stringency" at about $10-20°$ below the Tm of the probe; and "low stringency" at about $20-25°$ below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook et al, 1989, Chapters 9 and 11, and in Ausubel et al., 1993, expressly incorporated by reference herein). An example of high stringency conditions includes hybridization at about $42°$ C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1×SSC and 0.5% SDS at $42°$ C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

A plant cell, tissue, organ, or plant into which a heterologous nucleic acid construct comprising the coding sequence for an anti-microbial protein or peptide has been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of the coding sequence for an anti-microbial protein. Hence, a plant of the invention will include any plant which has a cell containing introduced nucleic acid sequences, regardless of whether the sequence was introduced into the plant directly through transformation means or introduced by generational transfer from a progenitor cell which originally received the construct by direct transformation.

The term "transgenic plant" refers to a plant that has incorporated exogenous nucleic acid sequences, i.e., nucleic acid sequences which are not present in the native ("untransformed") plant or plant cell. Thus a plant having within its cells a heterologous polynucleotide is referred to herein as a "transgenic plant". The heterologous polynucleotide can be either stably integrated into the genome, or can be extra-chromosomal. Preferably, the polynucleotide of the present invention is stably integrated into the genome such that the polynucleotide is passed on to successive generations. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. "Transgenic" is used herein to include any cell, cell line, callus, tissue, plant part or plant, the genotype of which has been altered by the presence of heterologous nucleic acids including those transgenics initially so altered as well as those created by sexual crosses or asexual reproduction of the initial transgenics.

The terms "transformed", "stably transformed" or "transgenic" with reference to a plant cell means the plant cell has a non-native (heterologous) nucleic acid sequence integrated into its genome which is maintained through two or more generations.

The term "expression" with respect to a protein or peptide refers to the process by which the protein or peptide is produced based on the nucleic acid sequence of a gene. The process includes both transcription and translation. The term "expression" may also be used with respect to the generation of RNA from a DNA sequence.

The term "introduced" in the context of inserting a nucleic acid sequence into a cell, means "transfection", or "transformation" or "transduction" and includes the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

By "host cell" is meant a cell which contains a vector and supports the replication, and/or transcription or transcription and translation (expression) of the expression construct. Host cells for use in the present invention can be prokaryotic cells, such as E. coli, or eukaryotic cells such as yeast, plant, insect, amphibian, or mammalian cells. In general, host cells are monocotyledonous or dicotyledonous plant cells.

A "plant cell" refers to any cell derived from a plant, including undifferentiated tissue (e.g., callus) as well as plant seeds, pollen, progagules and embryos.

The term "mature plant" refers to a fully differentiated plant.

The terms "native" and "wild-type" relative to a given plant trait or phenotype refers to the form in which that trait or phenotype is found in the same variety of plant in nature.

The term "plant" includes reference to whole plants, plant organs (for example, leaves, stems, roots, etc.), seeds, and plant cells and progeny of same. Plant cell, as used herein includes, without limitation, seeds, suspension cultures, embryos, meristematic regions, callus tissue, leaves roots shoots, gametophytes, sporophytes, pollen, and microspores. The class of plants that can be used in the methods of the present invention is generally as broad as the class of higher plants amenable to transformation techniques, including both monocotyledonous and dicotyledonous plants.

The term "seed" is meant to encompass all seed components, including, for example, the coleoptile and leaves, radicle and coleorhiza, scutulum, starchy endosperm, aleurone layer, pericarp and/or testa, either during seed maturation and seed germination.

The term "seed in a form for use as a food or food supplement" includes, but is not limited to, seed fractions such as de-hulled whole seed, flour (seed that has been de-hulled by milling and ground into a powder) a seed protein extract (where the protein fraction of the flour has been separated from the carbohydrate fraction) and/or a purified protein fraction derived from the transgenic grain.

The term "therapeutic agent" refers to one or more milk proteins or transgenic seeds expressing one or more milk proteins administered in an amount effective to achieve a therapeutic effect. The milk protein or seed may be administered in a natural, unmodified form, or purified. The milk protein or seed may a source for the purified therapeutic agent. The therapeutic agent may include any necessary excipients or formulations for administration.

The term "purifying" is used interchangeably with the term "isolating" and generally refers to the separation of a particular component from other components of the environment in which it was found or produced. For example, purifying a recombinant protein from plant cells in which it was produced typically means subjecting transgenic protein containing plant material to biochemical purification and/or column chromatography.

The term "active" refers to any biological activity associated with a particular milk protein, such as the enzymatic activity associated with human lysozyme. It follows that the biological activity of a given milk protein refers to any biological activity typically attributed to that factor by those of skill in the art.

The term "human milk protein" or "proteins normally present in human milk" refers to one or more proteins, or biologically active fragments thereof, found in normal human milk, including, without limitation, of lactoferrin, lysozyme, lactoferricin, lactadherin, kappa-casein, haptocorrin, lactoperoxidase, alpha-1-antitrypsin, immunoglobulins, and biologically active fragments thereof.

The term "nutritionally enhanced food" refers to a food, typically a processed food, to which a seed-produced human milk protein has been added, in an amount effective to confer some health benefit, such as improved gut health, resistance to pathogenic bacteria, or iron transport, to a human consuming the food.

"Plant-derived food ingredients" refers to plant-derived food stuff, typically monocot grain, but also including, separately, lectins, gums, sugars, plant-produced proteins and lipids, that may be blended or combined, alone or in combination with one or more plant-derived ingredients, to form an edible food.

"Monocot seed components" refers to carbohydrate, protein, and lipid components extractable from monocot seeds, typically mature monocot seeds.

"Substantially unpurified form", as applied to human milk proteins in a seed extract means that the protein or proteins present in the extract are present in an amount less than 50% by weight, typically between 0.1 and 10 percent by weight.

"Seed maturation" or "grain development" refers to the period starting with fertilization in which metabolizable reserves, e.g., sugars, oligosaccharides, starch, phenolics, amino acids, and proteins, are deposited, with and without vacuole targeting, to various tissues in the seed (grain), e.g., endosperm, testa, aleurone layer, and scutellar epithelium, leading to grain enlargement, grain filling, and ending with grain desiccation.

"Inducible during seed maturation" refers to promoters which are turned on substantially (greater than 25%) during seed maturation.

"Heterologous DNA" or "foreign DNA" refers to DNA which has been introduced into plant cells from another source, or which is from a plant source, including the same plant source, but which is under the control of a promoter or terminator that does not normally regulate expression of the heterologous DNA.

"Heterologous protein" is a protein, including a polypeptide, encoded by a heterologous DNA.

A "signal/targeting/transport sequence" is an N- or C-terminal polypeptide sequence which is effective to localize the polypeptide or protein to which it is attached to a selected intracellular or extracellular region, including an intracellular vacuole or other protein storage body, chloroplast, mitochondria, or endoplasmic reticulum, or extracellular space or seed region, such as the endosperm, following secretion from the cell.

A "product" encoded by a DNA molecule includes, for example, RNA molecules and polypeptides.

A DNA sequence is "derived from" a gene if it corresponds in sequence to a segment or region of that gene. Segments of genes which may be derived from a gene include the promoter region, the 5' untranslated region, and the 3' untranslated region of the gene.

"Alpha-amylase" as used herein refers to an enzyme which principally breaks starch into dextrins.

"Beta-amylase" as used herein refers to an enzyme which converts start and dextrins into maltose.

"Cereal adjuncts" as used herein refers to cereal grains, principally barley, wheat, rye, oats, maize, sorghum and rice, or processed whole or portions thereof, especially the starch fraction, which are added to the barley mash, which allows the barley enzymes to hydrolyze both the barley starch and the starch derived from the cereal adjunct. "Transgenic cereal adjuncts" as used herein refers to transgenic cereal grains, principally barley, wheat, rye, oats, maize, sorghum and rice, and which is expressing a recombinant molecule in a grain part, principally the endosperm (starch) layer.

"Total soluble protein fraction" refers to total protein extracted from ground or milled mature monocot seed after extraction in an aqueous buffer, under the following standard conditions. Mature seed is dry-milled and added to standard phosphate buffered saline (PBS), pH 7.4, at a ratio of 1 g milled seed/10 ml buffer. The mixture is incubated at room temperature with gentle shaking for 1 hr, to extract soluble protein. Following incubation, the mixture is clarified, e.g., by filtration or centrifugation, to remove particulate material.

"At least X % by total soluble protein weight of a human milk protein" means that a "total soluble protein fraction" contains a milk protein (or two or more milk proteins) in an amount, expressed as a weight percentage of total protein in the soluble fraction that is greater than X %. The weight percentage of the milk protein in the total soluble protein can be determined by standard means, such as by fractionating total soluble fraction to isolate or separate milk protein, and determining the weight per known volume of milk protein relative to the total protein weight per same volume in the total soluble protein fraction.

II. Human Milk Proteins

Milk proteins can be grouped into two general categories, casein and whey proteins. Approximately 80% of the proteins present in milk are caseins. There are generally three or four casein proteins present in the milk of most mammalian species. The different caseins are distinct molecules but have similarities in structure. Casein proteins include α-casein, β-casein, and κ-casein, among others. Whey proteins include α-lactoglobulin, β-lactoglobulin, lactoferrin, lysozyme, immunoglobulins, and lactoperoxidase, among others.

Lysozyme and lactoferrin are milk proteins that are an integral part of the immune system of multicellular animals. They are found in epithelial secretions (tears, mucous, gastric juice) and blood plasma of mammals, birds, reptiles, amphibia, and a variety of invertebrates. They are also enriched in mammalian milk and avian eggs, where they serve as primary antimicrobial proteins. Furthermore, lysozyme is a major component of the secretory granules of neutrophils and macrophages and is released at the site of infection in the earliest stages of the immune response. Lactoferrin is found at high concentrations within specific granules of polymorphonuclear leukocytes.

It has previously been demonstrated that lysozyme and lactoferrin are efficacious in promoting resistance to infectious diseases in experimental animals and humans and that they play a role of primary defense proteins on epithelial surfaces in addition to being important determinants in the establishment of a healthy microflora within the digestive tract. It has further been shown in vivo that lactadherin is efficacious in promoting resistance to rotavirus. In vivo studies have shown that the immunoglobulins provide resistance to a variety of viruses including polio, rotavirus, cytomegalovirus, rubella, herpes simplex virus, mumps virus, human immunodeficiency virus, hepatitis C virus, hepatitis B virus, and measles, as well as for influenza.

A. Lysozymes

Human milk lysozyme, called muramidase or peptidoglycan N-acetylmuramoyl-hydrolase (EC 3.2.1.17) contains 130 amino acid residues and is a protein of 14.7 kDa in size. Human lysozyme is non-glycosylated and possesses unusual stability in vitro and in vivo due to its amino acid and secondary structure.

Lysozyme is one of the most abundant proteins present in human milk with a concentration of about 400 μg/ml. The concentration of lysozyme is approximately 0.13 μg/ml in cows milk (almost 3000 times less than found in human milk), 0.25 μg/ml in goat's milk, 0.1 μg/ml in sheep's milk and almost absent in rodent's milk (Chandan R C, 1968). Lysozyme is also found in other mammalian secretions, such as tears and saliva.

The protective role of lysozyme has been observed to include lysis of microbial cell walls, adjuvant activity of the end products peptidoglycan lysis, direct immunomodulating effects on leukocytes, and neutralization of bacterial endotoxins. The bacteriostatic and bactericidal actions of lysozyme were originally discovered by Flemming in 1922 and have been studied in detail. Lysozyme is effective against gram positive and gram negative bacteria, as well as some types of yeasts. The antimicrobial effects of lysozyme often act synergistically with other defense molecules, including immunoglobulin and lactoferrin. Furthermore, structural changes in the cell wall due to lysozyme render bacteria more susceptible to phagocytosis by macrophages and neutrophils.

The hydrolysis of microbial peptidoglycans results in the release of the cleavage product, muramyl dipeptide, which is a potent adjuvant and is the active component of Freund's complete adjuvant. Muramyl dipeptide enhances IgA production, macrophage activation, and rapid clearance of a variety of bacterial pathogens in vivo. Lysozyme itself is also immunomodulatory. It directly interacts with the cell membrane of phagocytes to increase their uptake of bacteria. Lysozyme also augments the proliferative response of mitogen stimulated lymphocytes to interleukin-2 and increases the rate of synthesis of IgG and IgM by more than 5-and 2-fold respectively. Furthermore, the immunomodulatory action of lysozyme is not dependent upon enzymatic activity and is retained following denaturation. When lysozyme is fed to mice, it increases the number of intraepithelial and mesenteric lymph node lymphocytes that display antigens.

Lysozymes act as enzymes that cleave peptidoglycans, and ubiquitous cell wall component of microorganisms, in particular bacteria. Specifically, lysozymes are 1,4-β-acetylmuramidases that hydrolyze the glycoside bond between N-acetylmuramic acid and N-acetylglucosamine. Gram-positive bacteria are highly susceptible to lysozyme due to the polypeptidoglycan on the outside of the cell wall. Gram-negative strains have a single polypeptidoglycan layer covered by lipopolysaccharides and are therefore less susceptible to lysis by lysozyme, however, the sensitivity can be increased by the addition of EDTA (Schütte and Kula, 1990). Lysozyme also exhibits antiviral activity, as exemplified by the significant reduction in recurrent occurrences of genital and labial herpes after oral treatment of patients with lysozyme (Jollès, 1996). More recently, lysozyme from chicken egg whites, human milk and human neutrophils has been shown to inhibit the growth of HIV-1 in an in vitro assay (Lee-Huang et al., 1999). In addition, an anti-fungal activity has been demonstrated for lysozymes using oral isolates of *Candida albicans* (the most common fungal causative agent of oropharyngeal infection in humans; (Samaranayake et al., 1997). In this capacity, lysozyme can function as a broad spectrum antimicrobial agent.

The ability of lysozyme to bind bacterial endotoxins, especially LPS, confers an important anti-microbial property to the molecule. Lysozyme binds electrostatically to the lipid A component of bacterial endotoxins at a 1:3 molar ratio. The resulting conformational change in endotoxin keeps it from interacting with macrophage receptors and dampens the release of pro-inflammatory cytokines such as interleukin-1 (IL-1), interleukin-6 (IL-6), and tumor necrosis factor (TNF). Thus, lysozyme exhibits antiinflammatory activity during pathogen challenges.

The current major commercial source for lysozyme is chicken egg whites. Sequence analysis shows that lysozyme from chicken egg whites exhibits only partial homology (60%) with that synthesized by humans. Chicken and human lysozyme do not cross-react with their respective antibodies (Faure et al., 1970), indicating significant structural differences between these two lysozymes. Human lysozyme has been purified from breast milk (Boesman-Finkelstein et al., 1982; Wang et al., 1984), neutrophills (Lollike et al., 1995), and urine of hemodialysis patients (Takai et al., 1996). Breast milk remains the main source for isolation of human lysozyme, but the supply is limited. Precautions are required for isolation of the enzyme from human sources to avoid contamination with viral and microbial pathogens.

Recombinant human lysozyme has been produced in the mammary gland of transgenic mice. The enzyme retained its antimicrobial activity, but the final concentration in the milk was low (Maga et al., 1998; Maga et al., 1994; Maga et al., 1995). Human lysozyme has been expressed in *Aspergillus oryzae* (*A. oryzae*) (Tsuchiya et al., 1992) yeast (*S. cerevisiae*; Castañón et al., 1988; Jigami et al., 1986; and Yoshimura et al., 1988) and in small amounts in tobacco leaves (Nakajima et al., 1997). However, the expression level of recombinant human lysozyme in these organisms could be very low, and the cost of these forms may be prohibitive for food applications. In addition, human lysozyme produced in microorganisms may require extensive purification before it can be used in foods, particularly for infants and children.

In contrast to many other proteins, lysozyme is highly resistant to digestion in the gastrointestinal tract. In vitro studies have demonstrated that both molecules are resistant to hydrolysis by pepsin in the pH range found in the stomach. Furthermore, partial denaturation of lysozyme increases its bactericidal activity against some types of bacteria, and low pH, such as found in the stomach, increases the bactericidal effects of lysozyme. A proteolytic fragment (amino acids 98-112 of chicken egg white lysozyme) completely lacking enzymatic activity has been found to be the active bactericidal component of lysozyme.

The rice produced human lysozyme of the present invention exhibits acid pH resistance, as well as resistance to pepsin and pancreatin to make it resistant to digestion in the gastrointestinal tract. The excellent thermostability provides the feasibility to pasteurize products that include the recombinant human lysozyme.

B. Lactoferrin

Lactoferrin is an iron-binding protein found in the granules of neutrophils where it apparently exerts an antimicrobial activity by withholding iron from ingested bacteria and fungi; it also occurs in many secretions and exudates (milk, tears, mucus, saliva, bile, etc.). In addition to its role in iron transport, lactoferrin has bacteriostatic and bactericidal activities, in addition to playing a role as an anti-oxidant (Satue-Gracia et al., 2000).

The mature lactoferrin (LF) polypeptide consists of 692 amino acids, consists of a single-chain polypeptide that is relatively resistant to proteolysis, is glycosylated at two sites (N138 and N478) and has a molecular weight of about 80 kD. Human lactoferrin (hLF) is found in human milk at high concentrations (at an average of 1-3 mg/ml), and at lower concentrations (0.1-0.3 mg/ml) in exocrine fluids of glandular epithelium cells such as bile, tears, saliva etc.

The primary functions of lactoferrin have been described as iron regulation, immune modulation and protection from infectious microbes. Lactoferrin can bind two ferric ions and has been shown to have biological activities including bacteriostatic (Bullen et al., 1972), bactericidal (Arnold, et al., 1980) and growth factor activity in vitro. Further, lactoferrin can promote the growth of bacteria that are beneficial to the host organism by releasing iron in their presence. Additional studies have recently shown lactoferrin to have antiviral activity towards cytomegalovirus, herpes simplex virus, rotovirus and HIV both in vitro and in vivo. (See, e.g., Fujihara et al., 1995; Grover et al., 1997; and Harmsen et al., 1995.).

Lactoferrin, like transferrin, has a strong capacity to bind free iron under physiological conditions due to its tertiary structure, which consists of two globular lobes linked by an extended alpha-helix. The ability of lactoferrin to scavenge iron from the physiological environment can effectively inhibit the growth of "more than 90% of all microorganisms" by depriving them of a necessary component of their metabolism, which will inhibit their growth in vivo and in vitro.

Unrelated to iron binding, the bactericidal activity of lactoferrin stems from its ability to destabilize the outer membrane of gram-negative bacteria through the liberation of lipopolysaccaharides that constitute the cell walls of the bacteria. Additionally, lactoferrin has recently been shown to bind to prions, a group of molecules common in *E. coli*, causing permeability changes in the cell wall. Studies in germfree piglets fed lactoferrin before being challenged with *E. coli* show significant decrease in mortality compared to the control group.

In contrast to most other proteins, lactoferrin has also been shown to be resistant to proteolytic degradation in vitro, with trypsin and chymotrypsin remarkably ineffective in digesting lactoferrin, particularly in its iron-saturated form. Some large fragments of lactoferrin were formed, but proteolysis was clearly limited.

Additionally, a fragment of lactoferrin, known as lactoferricin, is formed by limited proteolytic digestion and has been shown to have extremely effective antibacterial activity.

Recombinant LF (rLF) has been produced as a fusion protein in *Aspergillus oryzae* (Ward et al., 1992) and in the baculovirus expression system (Salmon et al., 1997). The *Aspergillus*-produced protein will require a high degree of purification as well as safety and toxicity testing prior to using it as a food additive (Lönnerdal, 1996). Lactoferrin has also been expressed in tobacco (*Nicotiana tabacum* L. cv Bright Yellow) cell culture (Mitra and Zhang, 1994), tobacco plants (Salmon et al., 1998) and potato (*Solanum tuberosum*) plants (Chong and Langridge, 2000). In tobacco cell culture the protein was truncated, whereas in tobacco and potato plants the rLF was processed correctly, but its expression level was very low (0.1% of total soluble protein) (Chong and Langridge, 2000). However, the expression level of recombinant human lactoferrin in these organisms could be very low, and the cost of these forms may be prohibitive for food applications. In addition, human lactoferrin produced in microorganisms may require extensive purification before it can be used in foods, particularly for infants and children.

C. Lactoperoxidase

Lactoperoxidase is an enzyme which catalyzes the conversion of hydrogen peroxide to water. This enzyme is found in human milk, and plays host defensive roles through antimicrobial activity. When hydrogen peroxide and thiocyanate are added to raw milk, the SCN's oxidized by the enzyme-hydrogen peroxide complex producing bactericidal compounds which destroy Gram-negative bacteria (Shin).

D. Kappa-Casein

Caseins are the predominant proteins in the milk of most mammals and the stage and tissue specific expression pattern of casein genes is hormone regulated. This group of proteins are readily digested and account for almost half of the protein content in human milk They are important as nutritional protein for breast-fed infants. It has also been advocated that part of the antimicrobial activity of human milk resides in the caseins, most likely the glycosylated kappa-casein (Aniansson). Human milk casein is represented by two casein species, β and κ, of which kappa-casein represents less than 10% of the casein fraction (Groenen and Van der Poel, 1994). Sequences for the human kappa-casein have been elucidated (Edlund et al, 1996) and a codon-optimized version of the human kappa-casein gene has been synthesized for expression in monocot grains.

E. Alpha-1-antitrypsin ("AAT")

AAT belongs to the class of serpin inhibitors, has a molecular mass of 52 kD, and contains about 15% carbohydrate (Carrell et al, 1983). Concentrations of AAT in human milk range from 0.1 to 0.4 mg/mL (Davidson and Lönnerdal, 1979; McGilligan et al., 1987). While the binding affinity of AAT is highest for human neutrophil elastase, it also has affinity for pancreatic proteases such as chymotrypsin and trypsin (Beatty et al., 1980).

While milk proteins have been expressed in systems such as transgenic cows and *Aspergillus* (Lönnerdal, 1996), transgenic rice provides a more attractive vehicle for the production of recombinant human AAT for food applications. High levels of expression are possible by using the combination of regulatory elements such as promoter, signal peptide, and terminator as disclosed herein. In addition, rice is often one of the first foods introduced to infants because of its nutritional value and low allergenicity. Safety concerns about microbial expression systems (e.g. *Aspergillus*) limit the feasibility of using proteins from such sources as food components in formula (Lönnerdal, 1996). In addition, the cost of producing and purifying proteins from these other systems is often prohibitive for food applications. Thus, expression of recombinant human milk proteins in rice may be a safe and economically viable possibility for supplementing infant formula with such proteins (See also Chowanadisai; Huang; Johnson; Lindberg; and Rudloff).

F. Lactadherin

Lactadherin is a protective glycoprotein present in human milk that helps protect breast-fed infants against infection by microorganisms. Protection against certain virus infections by human milk is also associated with lactadherin. (Newburg, 1999, 1998; Peterson; Hamosh).

G. Alpha-Lactalbumin

α-Lactalbumin is a major whey protein (approximately 13% of the total whey protein) that is a calcium metalloprotein. α-Lactalbumin contains 123 amino acids in most species (122 in rabbit and 140 in rat) and has a molecular weight of 14, 146 Daltons. α-Lactalbumin has been detected in the milk of all mammals. It interacts with galactosyl transferase to form lactose synthetase and has thus been described as a key protein for lactogenesis. Other functional properties have been attributed to this protein such as a cell lytic activity, induction of cell growth inhibition, or apoptosis.

H. Beta-Lactoglobulin

β-lactoglobulin is the major protein in whey, making up about 50-60% of the total whey protein. β-Lactoglobulin contains 162 amino acid residues and has a molecular weight of 18.3 kDa. It exists in milk as a dimer in solution due to electrostatic interaction of Asp and Glu residues of one monomer with corresponding Lys residues of another monomer. At high protein concentrations and low temperatures, β-lactoglobulin exists as an octomer involving ionization of the —COOH groups.

I. Alpha-Casein and Beta-Casein

The caseins, which make up about 80% of the milk proteins, consist of four proteins, two forms of alpha-casein (alpha s1 and alpha s2), beta-casein, and kappa-casein. Most casein proteins are present in structures known as casein micelles, which are important in determining the physical properties of milk. The caseins are involved in the transport of calcium phosphate in milk, which is important for bone development in the infant mammal.

Beta-casein, which is the most abundant milk protein, is involved in binding calcium phosphate and thus controlling milk calcium levels. Recombinant human β-casein has been produced in *Solanum tuberosum* (potato) cells under the control of promoters using *Agrobacterium tumefaciens*-mediated leaf disc transformation methods. However, immunoblot experiments identified approximately only 0.01% of the total soluble protein as β-casein (Chong et al., Transgen Res, 6(4): 289-296 (1997)).

J. Immunoglobulins

Immunoglobulins present in human act to confer resistance to a variety of pathogens to which the mother may have been exposed. (See, for example, Humphreys; Kortt; Larrick; Maynard; and Peeters).

III. Expression Vectors for Generation of Transgenic Plants Expressing Human Milk Proteins Expression vectors for use in the present invention are chimeric nucleic acid constructs (or expression vectors or cassettes), designed for operation in plants, with associated upstream and downstream sequences.

In general, expression vectors for use in practicing the invention include the following operably linked components that constitute a chimeric gene: (i) a transcriptional regulatory region from a monocot gene having a seed maturation-specific promoter, and (ii) a protein-coding sequence encoding a protein normally present in human milk. The expression vector may further include a leader DNA sequence encoding a monocot seed-specific transit sequence capable of targeting a linked polypeptide to an endosperm-cell organelle operably linked to said transcriptional regulatory region. A preferred leader sequence is for targeting to a protein-storage body.

The chimeric gene, in turn, is typically placed in a suitable plant-transformation vector having (i) companion sequences upstream and/or downstream of the chimeric gene which are of plasmid or viral origin and provide necessary characteristics to the vector to permit the vector to move DNA from bacteria to the desired plant host; (ii) a selectable marker sequence; and (iii) a transcriptional termination region generally at the opposite end of the vector from the transcription initiation regulatory region.

Exemplary methods for constructing chimeric genes and transformation vectors carrying the chimeric genes are given in the examples below.

A. Promoters

In one aspect of this embodiment, the expression construct includes a transcription regulatory region (promoter) which exhibits specifically upregulated activity during seed maturation. Examples of such promoters include the maturation-specific promoter region associated with one of the following maturation-specific monocot storage proteins: rice glutelins, globulins, oryzins, and prolamines; barley hordeins; wheat gliadins, glutenins, and purindolines; maize zeins and glutelins; oat glutelins; sorghum kafirins; millet pennisetins; and rye secalins. Exemplary regulatory regions from these genes are exemplified by SEQ ID NOS: 13-21, as identified in the Description of the Sequences. A preferred regulatory region is included within the sequence presented as SEQ ID NO:13.

Of particular interest is the expression of the nucleic acid encoding a human milk protein from a transcription initiation region that is preferentially expressed in plant seed tissue. Examples of such seed preferential transcription initiation sequences include those sequences derived from sequences encoding plant storage protein genes or from genes involved in fatty acid biosynthesis in oilseeds. Exemplary preferred promoters include a glutelin (Gt-1) promoter, as exemplified by SEQ ID NO: 16, which effects gene expression in the outer layer of the endosperm and a globulin (Glb) promoter, as exemplified by SEQ ID NO: 14, which effects gene expression in the center of the endosperm. Promoter sequences for regulating transcription of gene coding sequences operably linked thereto include naturally-occurring promoters, or regions thereof capable of directing seed-specific transcription, and hybrid promoters, which combine elements of more than one promoter. Methods for construction such hybrid promoters are well known in the art.

In some cases, the promoter is derived from the same plant species as the plant cells into which the chimeric nucleic acid construct is to be introduced. Promoters for use in the invention are typically derived from cereals such as rice, barley, wheat, oat, rye, corn, millet, triticale or sorghum.

Alternatively, a seed-specific promoter from one type of monocot may be used regulate transcription of a nucleic acid coding sequence from a different monocot or a non-cereal monocot.

Numerous types of appropriate expression vectors, and suitable regulatory sequences are known in the art for a variety of plant host cells. The transcription regulatory or promoter region is chosen to be regulated in a manner allowing for induction under seed-maturation conditions. Examples of such promoters include those associated with the following monocot storage proteins: rice glutelins, globulins, oryzins, and prolamines, barley hordeins, wheat gliadins, glutelins and purindolines, maize zeins and glutelins, oat glutelins, sorghum kafirins, millet pennisetins, and rye secalins. Exemplary promoter sequences are identified herein as SEQ ID NOS: 13-21. Other promoters suitable for expression in maturing seeds include the barley endosperm-specific B1-hordein promoter (Brandt, A., et al., (1985), Glub-2 promoter, Bx7 promoter, Gt3 promoter, Glub-1 promoter and Rp-6 promoter, particularly if these promoters are used in conjunction with transcription factors. The primary structure of a B1 hordein gene from barley is provided in Carlsberg (*Res. Commun.*, 50, 333-345).

B. Signal/targeting/transport Sequences

In addition to encoding the protein of interest, the expression cassette or heterologous nucleic acid construct may encode a signal/targeting/transport peptide that allows processing and translocation of the protein, as appropriate. Exemplary signal/targeting/transport sequences, particularly for targeting proteins to intracellular bodies, such as vacuoles, are signal/targeting sequences associated with the monocot maturation-specific genes: glutelins, globulins, oryzins, prolamines, hordeins, gliadins, glutenins, purindolines, zeins, kafirins, pennisetins, secalins, albumin, globulin, ADP glucose pyrophosphorylase, starch synthase, branching enzyme, Em, and lea. Exemplary sequences encoding a leader sequence for protein storage body are identified herein as SEQ ID NOS: 22-28.

In one preferred embodiment, the method is directed toward the localization of recombinant milk protein expression in a given subcellular compartment, in particular a protein-storage body, but also including the mitochondrion, endoplasmic reticulum, vacuoles, chloroplast or other plastidic compartment. For example, when recombinant milk protein expression is targeted to plastids, such as chloroplasts, in order for expression to take place the construct also employ the use of sequences to direct the gene to the plastid. Such sequences are referred to herein as chloroplast transit peptides (CTP) or plastid transit peptides (PTP). In this manner, when the gene of interest is not directly inserted into the plastid, the expression construct additionally contains a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al., 1991; Clark et al., 1989; della-Cioppa et al., 1987; Romer et al., 1993; and Shah et al., 1986. Additional transit peptides for the translocation of the protein to the endoplasmic reticulum (ER) (Chrispeels, K., 1991), nuclear localization signals (Raikhel, 1992), or vacuole may also find use in the constructs of the present invention.

Another exemplary class of signal/targeting/transport sequences are sequences effective to promote secretion of heterologous protein from aleurone cells during seed germination, including the signal sequences associated with α-amylase, protease, carboxypeptidase, endoprotease, ribonuclease, DNase/RNase, (1-3)-β-glucanase, (1-3)(1-4)-β-glucanase, esterase, acid phosphatase, pentosamine, endoxylanase, β-xylopyranosidase, arabinofuranosidase, β-glucosidase, (1-6)-β-glucanase, perioxidase, and lysophospholipase.

Since many protein storage proteins are under the control of a maturation-specific promoter, and this promoter is operably linked to a leader sequence for targeting to a protein body, the promoter and leader sequence can be isolated from a single protein-storage gene, then operably linked to a milk-protein storage protein in the chimeric gene construction. One preferred and exemplary promoter-leader sequence is from the rice Gt1 gene, having an exemplary sequence identified by SEQ ID NO:13. Alternatively, the promoter and leader sequence may be derived from different genes. One preferred and exemplary promoter/leader sequence combination is the rice Glb promoter linked to the rice Gt1 leader sequence, as exemplified by SEQ ID NO: 14.

C. Protein Coding Sequences

The construct also includes the nucleic acid coding sequence for a heterologous protein, under the control of a promoter, preferably a seed-specific promoter. In accordance with the present invention, polynucleotide sequences which encode human milk proteins include splice variants, fragments of such human milk proteins, fusion proteins, modified forms or functional equivalents thereof, collectively referred to herein as "human milk protein-encoding nucleic acid sequences".

Such "human milk protein-encoding nucleic acid sequences" may be used in recombinant expression vectors (also termed heterologous nucleic acid constructs), directing the expression of a human milk protein in appropriate host cells.

Due to the inherent degeneracy of the genetic code, a number of nucleic acid sequences which encode substantially the same or a functionally equivalent amino acid sequence may be generated and used to clone and express a given human milk protein, as exemplified herein by the codon optimized coding sequences used to practice the invention (further described below). Thus, for a given human milk protein-encoding nucleic acid sequence, it is appreciated that as a result of the degeneracy of the genetic code, a number of coding sequences can be produced that encode the same human milk protein amino acid sequence. For example, the triplet CGT encodes the amino acid arginine. Arginine is alternatively encoded by CGA, CGC, CGG, AGA, and AGG. Therefore such substitutions in the coding region fall within the range of sequence variants covered by the present invention. Any and all of these sequence variants can be utilized in the same way as described herein for a "reference" human milk protein-encoding nucleic acid sequence.

A "variant" human milk protein-encoding nucleic acid sequence may encode a "variant" human milk protein amino acid sequence which is altered by one or more amino acids from the native milk protein sequence, both of which are included within the scope of the invention. Similarly, the term "modified form of", relative to a given human milk protein, means a derivative or variant form of a native human milk protein or the coding sequence therefor. That is, a "modified form of" a human milk protein has a derivative sequence containing at least one nucleic acid or amino acid substitution, deletion or insertion. The nucleic acid or amino acid substitution, insertion or deletion may occur at any residue within the sequence, as long as the encoded amino acid sequence maintains the biological activity of the native human milk protein, e.g., the bactericidal effect of lysozyme.

A "variant" human milk protein-encoding nucleic acid sequence may encode a "variant" human milk protein sequence which contains amino acid insertions or deletions, or both. Furthermore, a variant human milk protein coding sequence may encode the same polypeptide as the reference polynucleotide or native sequence but, due to the degeneracy of the genetic code, has a nucleic acid coding sequence which is altered by one or more bases from the reference or native nucleotide sequence.

The variant nucleic acid coding sequence may encode a variant amino acid sequence which contains a "conservative" substitution, wherein the substituted amino acid has structural or chemical properties similar to the amino acid which it replaces and physicochemical amino acid side chain properties and high substitution frequencies in homologous proteins found in nature (as determined, e.g., by a standard Dayhoff frequency exchange matrix or BLOSUM matrix). In addition, or alternatively, the variant nucleic acid coding sequence may encode a variant amino acid sequence which contains a "non-conservative" substitution, wherein the substituted amino acid has dissimilar structural or chemical properties to the amino acid which it replaces.

Standard substitution classes include six classes of amino acids based on common side chain properties and highest frequency of substitution in homologous proteins in nature, as is generally known to those of skill in the art and may be employed to develop variant human milk protein-encoding nucleic acid sequences. A "variant" human milk protein-encoding nucleic acid sequence may encode a "variant" human milk protein sequence which contains a combination of any two or three of amino acid insertions, deletions, or substitution.

Human milk protein-encoding nucleotide sequences also include "allelic variants" defined as an alternate form of a polynucleotide sequence which may have a substitution, deletion or addition of one or more nucleotides, which does not substantially alter the function of the encoded polypeptide.

The polynucleotides for use in practicing the invention include sequences which encode human milk proteins and splice variants thereof, sequences complementary to the protein coding sequence, and novel fragments of the polynucleotide. The polynucleotides may be in the form of RNA or in the form of DNA, and include messenger RNA, synthetic RNA and DNA, cDNA, and genomic DNA. The DNA may be double-stranded or single-stranded, and if single-stranded may be the coding strand or the non-coding (anti-sense, complementary) strand.

As will be understood by those of skill in the art, in some cases it may be advantageous to use a human milk protein-encoding nucleotide sequences possessing non-naturally occurring codons. Codons preferred by a particular eukaryotic host (Murray et al., 1989) can be selected, for example, to increase the rate of human milk protein expression or to produce recombinant RNA transcripts having desirable properties, such as a longer half-life, than transcripts produced from naturally occurring sequence. Codon-optimized sequences for use in practicing the invention are further described below.

A human milk protein-encoding nucleotide sequence may be engineered in order to alter the human milk protein coding sequence for a variety of reasons, including but not limited to, alterations which modify the cloning, processing and/or expression of the human milk protein by a cell.

Heterologous nucleic acid constructs may include the coding sequence for a given human milk protein, a variant, fragment or splice variant thereof: (i) in isolation; (ii) in combination with additional coding sequences; such as fusion protein or signal peptide, in which the human milk protein coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the human milk protein coding sequence is a heterologous gene.

Depending upon the intended use, an expression construct may contain the nucleic acid sequence which encodes the entire human milk protein, or a portion thereof. For example, where human milk protein sequences are used in constructs for use as a probe, it may be advantageous to prepare constructs containing only a particular portion of the human milk protein encoding sequence, for example a sequence which is discovered to encode a highly conserved human milk protein region.

In a general embodiment, the human milk protein produced by a mature, transgenic monocot seed with a total soluble protein fraction containing at least 3% by total protein weight of the human milk protein. The total soluble protein fraction may contain at least 5%, 10%, 20%, 30%, 40%, or more by total protein weight of the human milk protein.

In another general embodiment, a human lysozyme amino acid sequence encoded by a human lysozyme-encoding nucleic acid sequence in an expression vector used to practice the invention has at least 70%, preferably 80%, 85%, 90% or 95% or more sequence identity to the human lysozyme amino acid sequence presented as SEQ ID NO:2.

In yet another general embodiment, a human lactoferrin amino acid sequence encoded by a human lactoferrin-encoding nucleic acid sequence in an expression vector used to practice the invention has at least 70%, preferably 80%, 85%, 90% or 95% or more sequence identity to the human lactoferrin amino acid sequence presented as S D. Codon Optimization It has been shown that production of recombinant protein in transgenic barley grain was enhanced by codon optimization of the gene (Horvath et al., 2000; Jensen et al., 1996). The intent of codon optimization was to change an A or T at the third position of the codons of G or C. This arrangement conforms more closely with codon usage in typical rice genes (Huang et al., 1990a).

For example, in order to obtain a high expression level for human lysozyme in rice cells, the coding sequence was codon optimized. The G+C content was thus increased from 46% to 68%. The codon optimized lysozyme coding sequence for use in practicing the invention is presented as SEQ ID NO:1.

Similarly, in order to obtain high level expression level of human lactoferrin (hLF) in rice cells, the native hLF coding sequence was codon optimized. Out of 693 codons used in the lactoferrin gene, 413 codons were changed by one or two nucleotides. The amino acid sequence of LF was unchanged. The codon optimized lactoferrin coding sequence for use in practicing the invention is presented as SEQ ID NO:3.

Exemplary codon optimized sequences for other human milk proteins are given as follows: for lactoferricin, SEQ ID NO: 7; for lactadherin, SEQ ID NO: 8; for kappa-casein, SEQ ID NO: 9; for haptocorrin, SEQ ID NO: 10; for lactoperoxidase, SEQ ID NO: 11; and for alpha-1-antitrypsin, SEQ ID NO: 12.

E. Transcription Factor Coding Sequences

In one embodiment of the invention, the transgenic plant is also transformed with the coding sequence of one or more transcription factors capable of stimulating the expression of a maturation-specific promoter. Specifically, the embodiment involves the use of the maize Opaque 2 (O2) and prolamin box binding factor (PBF) together with the rice endosperm bZip (Reb) protein as transcriptional activators of monocot storage protein genes. Exemplary sequence for these three transcription factors are given identified below as SEQ ID NOS: 29-31. Transcription factor sequences and constructs applicable to the present invention are detailed in co-owned PCT application No. PCT/US01/14234, International Publication number WO 01/83792 A1, published Nov. 8, 2001, which is incorporated herein by reference.

Transcription factors are capable of sequence-specific interaction with a gene sequence or gene regulatory sequence. The interaction may be direct sequence-specific binding in that the transcription factor directly contacts the gene or gene regulatory sequence or indirect sequence-specific binding mediated by interaction of the transcription factor with other proteins. In some cases, the binding and/or effect of a transcription factor is influenced (in an additive, synergistic or inhibitory manner) by another transcription factor. The gene or gene regulatory region and transcription factor may be derived from the same type (e.g., species or genus) of plant or a different type of plant. The binding of a transcription factor to a gene sequence or gene regulatory sequence may be evaluated by a number of assays routinely employed by those of skill in the art, for example, sequence-specific binding may be evaluated directly using a label or through gel shift analysis.

As detailed in the cited PCT application, the transcription factor gene is introduced into the plant in a chimeric gene containing a suitable promoter, preferably a maturation-specific seed promoter operably linked to the transcription factor gene. Plants may be stably transformed with a chimeric gene containing the transcription factor by methods similar to those described with respect to the milk-protein gene(s). Plants stably transformed with both exogenous transcription factor(s) and milk-protein genes may be prepared by co-transforming plant cells or tissue with both gene constructs, selecting plant cells or tissue that have been co-transformed, and regenerating the transformed cells or tissue into plants. Alternatively, different plants may be separately transformed with exogenous transcription factor genes and milk-protein genes, then crossed to produce plant hybrids containing by added genes.

F. Additional Expression Vector Components

Expression vectors or heterologous nucleic acid constructs designed for operation in plants, comprise companion sequences upstream and downstream to the expression cassette. The companion sequences are of plasmid or viral origin and provide necessary characteristics to the vector to permit the vector to move DNA from bacteria to the plant host, such as, sequences containing an origin of replication and a selectable marker. Typical secondary hosts include bacteria and yeast.

In one embodiment, the secondary host is *E. coli*, the origin of replication is a colE1-type, and the selectable marker is a gene encoding ampicillin resistance. Such sequences are well known in the art and are commercially available as well (e.g., Clontech, Palo Alto, Calif.; Stratagene, La Jolla, Calif.).

The transcription termination region may be taken from a gene where it is normally associated with the transcriptional initiation region or may be taken from a different gene. Exemplary transcriptional termination regions include the Nos terminator from *Agrobacterium* Ti plasmid and the rice α-amylase terminator.

Polyadenylation tails (Alber et al., 1982) may also be added to the expression cassette to optimize high levels of transcription and proper transcription termination, respectively. Polyadenylation sequences include, but are not limited to, the *Agrobacterium* octopine synthetase signal (Gielen, et al., 1984) or the nopaline synthase of the same species (Depicker, et al., 1982).

Suitable selectable markers for selection in plant cells include, but are not limited to, antibiotic resistance genes, such as, kanamycin (nptll), G418, bleomycin, hygromycin, chloramphenicol, ampicillin, tetracycline, and the like. Additional selectable markers include a bar gene which codes for bialaphos resistance; a mutant EPSP synthase gene which encodes glyphosate resistance; a mutant acetolactate synthase gene (ALS) which confers imidazolinone or sulphonylurea resistance; and a methotrexate resistant DHFR gene.

The particular marker gene employed is one which allows for selection of transformed cells as compared to cells lacking the DNA which has been introduced. Preferably, the selectable marker gene is one which facilitates selection at the tissue culture stage, e.g., a kanamycin, hygromycin, or ampicillan resistance gene.

The vectors of the present invention may also be modified to include intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens*.

In general, a selected nucleic acid sequence is inserted into an appropriate restriction endonuclease site or sites in the vector. Standard methods for cutting, ligating and *E. coli* transformation, known to those of skill in the art, are used in constructing vectors for use in the present invention. (See generally, Maniatis, et al., MOLECULAR CLONING: A LABORATORY MANUAL, 2d Edition (1989); Ausubel, et al., (c) 1987, 1988, 1989, 1990, 1993, CURRENT PROTOCOLS IN MOLECULAR BIOLOGY, John Wiley & Sons, New York, N.Y.; and Gelvin, S. B., et al., eds. PLANT MOLECULAR BIOLOGY MANUAL, (1990), all three of which are expressly incorporated by reference, herein).

IV. Generation of Transgenic Plants

Plant cells or tissues are transformed with expression constructs (heterologous nucleic acid constructs, e.g., plasmid DNA into which the gene of interest has been inserted) using a variety of standard techniques. Effective introduction of vectors in order to facilitate enhanced plant gene expression is an important aspect of the invention. It is preferred that the vector sequences be stably integrated into the host genome.

The method used for transformation of host plant cells is not critical to the present invention. The transformation of the plant is preferably permanent, i.e. by integration of the introduced expression constructs into the host plant genome, so that the introduced constructs are passed onto successive plant generations. The skilled artisan will recognize that a wide variety of transformation techniques exist in the art, and new techniques are continually becoming available.

Any technique that is suitable for the target host plant may be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to calcium-phosphate-DNA co-precipitation, electroporation, microinjection, *Agrobacterium*-mediated transformation, liposome-mediated transformation, protoplast fusion or microprojectile bombardment. The skilled artisan can refer to the literature for details and select suitable techniques for use in the methods of the present invention. Exemplary methods for plant transformation are given in Example 3.

When *Agrobacterium* is used for plant cell transformation, a vector is introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) is inserted into a broad host range vector capable of replication in *E. coli* and *Agrobacterium*, examples of which are described in the literature, for example pRK2 or derivatives thereof (see, for example, Ditta et al., 1980 and EPA 0 120 515, expressly incorporated by reference herein). Alternatively, one may insert the sequences to be expressed in plant cells into a vector containing separate replication sequences, one of which stabilizes the vector in *E. coli*, and the other in *Agrobacterium* (McBride et al., 1990), wherein the pRiHRI (Jouanin, et al., 1985) origin of replication is utilized and provides for added stability of the plant expression vectors in host *Agrobacterium* cells.

Included with the expression construct and the T-DNA is one or more selectable marker coding sequences which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, with a particular marker preferred depending on the particular host and the manner of construction.

For *Agrobacterium*-mediated transformation of plant cells, explants are incubated with *Agrobacterium* for a time sufficient to result in infection, the bacteria killed, and the plant cells cultured in an appropriate selection medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of the recombinant protein produced by the plants. The seed contains at least 3% by total protein weight of a human milk protein when extracted with an aqueous medium. In exemplary embodiments, the seed contains at least 5%, 10%, 20%, 30%, 40% or more by total protein weight of a human milk protein.

A. Plants

The plants used as hosts in the methods of the present invention include monocotyledonous and dicotyledonous plants. In a preferred embodiment, the plants used in the methods of the present invention are derived from monocots, particularly the members of the taxonomic family known as the Gramineae. This includes all members of the grass family of which the edible varieties are known as cereals. The cereals include a wide variety of species such as wheat (*Triticum* sps.), rice (*Oryza* sps.), barley (*Hordeum* sps.), oats (*Avena* sps.), rye (*Secale* sps.), corn (maize) (*Zea* sps.), and millet (*Pennisettum* sps.). In practicing the present invention, preferred grains are rice, wheat, maize, barley, rye, and triticale. Also preferred are dicots exemplified by soybean (*Glycine* spp.)

In order to produce transgenic plants that express human milk protein, monocot plant cells or tissues derived from them are transformed with an expression vector comprising the coding sequence for a human milk protein. Transgenic plant cells obtained as a result of such transformation express the coding sequence for a human milk protein. The transgenic plant cells are cultured in medium containing the appropriate selection agent to identify and select for plant cells which express the heterologous nucleic acid sequence. After plant cells that express the heterologous nucleic acid sequence are selected, whole plants are regenerated from the selected transgenic plant cells. Techniques for regenerating whole plants from transformed plant cells are generally known in the art.

Transgenic plant lines, e.g., rice, wheat, corn or barely, can be developed and genetic crosses carried out using conventional plant breeding techniques.

Production of recombinant proteins in monocot seeds, e.g., rice (*Oryza sativa* L.) seeds have the advantage that high level expression make it an economically practical strategy for the production of human milk proteins of therapeutic value. Further, rice is a normal part of the diet of infants and children, has good nutritional value and low allergenicity. Thus, the use of rice as the basis for a food supplement is unlikely to introduce any risk and thereby eliminates the need for a high degree of purification when included in an infant formula.

In addition, rice is the staple food crop of more than half the world's population. Recent reports on the production of pro-vitamin A (beta-Carotene) in rice seeds exemplifies the need for value added food crops especially in the developing world (Ye et al., 2000) where rice is used as major food crop.

V. Detecting Expression of Recombinant Human Milk Proteins

Transformed plant cells are screened for the ability to be cultured in selective media having a threshold concentration of a selective agent. Plant cells that grow on or in the selective media are typically transferred to a fresh supply of the same media and cultured again. The explants are then cultured under regeneration conditions to produce regenerated plant shoots. After shoots form, the shoots are transferred to a selective rooting medium to provide a complete plantlet. The plantlet may then be grown to provide seed, cuttings, or the like for propagating the transformed plants. The method provides for efficient transformation of plants with expression of a gene of autologous or heterologous origin and regeneration of transgenic plants, which can produce a recombinant human milk protein.

The expression of the recombinant human milk protein may be confirmed using standard analytical techniques such as Western blot, ELISA, PCR, HPLC, NMR, or mass spectroscopy, together with assays for a biological activity specific to the particular protein being expressed.

Example 2 details a comparison between Gt1 and Glb promoters and signal peptides on the expression of lysozyme in transgenic rice.

Example 4 describes the characterization of human lysozyme produced in the seeds of transgenic rice plants. Analyses used to confirm that recombinant lysozyme produced in transgenic rice is essentially the same as the native form of the protein both in physical characteristics and biological activity included, SDS-PAGE, reverse IEF gel electrophoresis, Western blot analysis, enzyme linked immunosorbant assay (ELISA), enzymatic activity assay and bactericidal activity assay using indicator strains, *Micrococcus luteus* and *E. coli* strain JM109.

Example 5 describes the characterization of human lactoferrin produced in the seeds of transgenic rice plants. Analyses used to confirm that recombinant lactoferrin produced in transgenic rice is essentially the same as the native form of the protein both in physical characteristics and biological activity included, Southern blot, Western blot, ELISA, N-Terminal Amino Acid Sequencing, analysis of glycosylation and determination of sugar content, a determination of the isoelectric point, pH dependent iron release of rLF, bacteriostatic activity assay of rLF using enteropathogenic *E. coli* as the indicator strain.

Example 6 details the characterization of alpha-1-antitrypsin produced by transgenic monocot plant cells. Example 7 details the characterization of other milk proteins also produced by monocot plant transformed with the chimeric genes of the invention.

VI. Seeds and Soluble Protein Extracts

The invention provides a method of producing high levels of recombinant human milk protein in monocot plant seeds. In practicing the method, a monocot plant stably transformed with a chimeric gene, as detailed above, is cultivated under seed-maturation conditions, that is, the transgenic plant is allowed to develop until the plant seeds have largely completed the seed maturation process. The seeds are then harvested from the plant, conventionally, providing a seed source for high levels of human milk protein. In particular, the seeds yield a total soluble protein fraction containing at least 3%, typically 5-20% or more recombinant human milk protein.

The seeds can be stored in seed or milled form and employed directly as a feed or food source, as discussed below. Alternatively, the seeds can be used in forming a milk-protein composition composed of a total soluble protein fraction obtained from the seeds and containing at least 3% by total protein weight of a human milk protein. Methods for producing the milk-protein composition are detailed below. Briefly, ground, dry-milled or wet-milled seeds are added to an aqueous buffer such as PBS and allowed to incubate, i.e., at room temperature, preferably with agitation during a period sufficient to extract the majority of total extractable protein. The mixture can then be treated, e.g., by centrifugation or filtration, to remove particulate matter. The resulting total soluble extraction fraction can then be further processed to further concentrate and/or isolate the milk protein, or dried to form a water-soluble protein extract, or stored in liquid form.

The transgenic seeds or milk protein composition may be used as a food, a food additive, or in the preparation of a food composition. Exemplary food compositions include a flour and/or extract, which can be prepared by any conventional means. Exemplary means are presented in co-owned U.S. application Ser. No. 10/077,381 and corresponding PCT Application No. PCT/US01/14234, now publication no. WO 01/83792, both of which are incorporated by reference herein.

The production of high levels of human milk proteins in grains, exemplified herein by rice provides the distinct advantage that food supplements may be prepared with little or no purification. In a preferred approach, the human milk protein containing transgenic grain is ground (e.g., into flour) and directly added to a food such as infant formula, without additional processing. This flour can also be utilized as a starting material for purification of human milk proteins for therapeutic/pharmaceutical use in humans and animals.

Transgenic seeds are ideal bioreactors, combining low production costs and low or minimal downstream processing costs prior to use. Seed grain proteins can accumulate to 9-19% of grain weight (Lásztitym 1996); the endosperm proteins are synthesized during grain maturation and stored in protein bodies for use in the germination and seedling growth of the next plant generation; grains can be stored for years without loss of functionality, and therefore the downstream processing can be conducted independently of growing seasons.

The human milk protein-containing transgenic grains of the invention may be used directly as food, e.g., rice, corn, wheat, barley, etc. Alternatively, food supplements are prepared from the human milk protein-containing transgenic grain. The composition may be used in dried form as an additive for an ingestible food, feed, or food composition. The milk protein-containing transgenic grain may further be used directly, in a purified form, or in a composition as a therapeutic agent. The results presented herein demonstrate that human milk proteins may be expressed at high levels in the seeds of transgenic plants, e.g., up to 0.25 to 1% of total seed dry weight. A grain composition will typically yield an amount of milk protein that is comparable to that in the mature seed. The production of high levels of human milk proteins in grains, exemplified herein by rice, provides the distinct advantage that food supplements may be prepared with little or no purification. In a preferred approach, the human milk protein containing transgenic grain is ground (e.g., into flour) and directly added to a food, or in the form of an extract or malt, such as for preparing a nutritionally enhanced infant formula, without additional processing. Since the recombinant grain finds utility as a food or food supplement, as a flour, extract or malt, the regulatory requirements for purity are not stringent. Accordingly, human milk protein-containing transgenic grains are ideal bioreactors, combining low production costs and low or minimal downstream processing costs prior to use.

The human milk protein-containing transgenic grains may alternatively be food supplements are prepared from the human milk protein-containing transgenic grain. Where the transgenic seed is rice, the invention provides additional advantages in that rice is consumed by a majority of the population in the world and is generally regarded as safe for human consumption. Rice-based foods are considered hypoallergenic (NIH publication, 1984). In many countries, rice is the first solid food for infants and rice-based infant formulas are commercially available (Bhan et al., 1988; Gasta ñaduy et al, 1990). These make rice attractive as a "protein factory" to produce therapeutics and nutraceuticals for human consumption. The cloning and expression of human proteins, for example, human milk proteins lysozyme and lactoferrin in rice grains has opened a new avenue for the bioproduction of other milk proteins.

All publications, patents and patent applications are herein expressly incorporated by reference in their entirety to the same extent as if each individual publication, patent or patent application was specifically and individually indicated to be incorporated by reference in its entirety.

The following examples illustrate but are not intended in any way to limit the invention.

EXAMPLE 1

Expression Vectors for Generation of Transgenic Plants

In general, expression vectors were constructed using standard molecular biological techniques as described in Ausubel et al., 1987. The vectors contain a heterologous protein coding sequence for lactoferrin or lysozyme under the control of a rice tissue-specific promoter, as further described below.

A. An Expression Vector for Human Lysozyme Expression in Transgenic Rice Cells

The synthesized lysozyme gene was cloned into an API base vector pAPI137 by conventional molecular cloning techniques (Sambrook et al., 1989). Plasmid pAPI137 contains the RAmy3D promoter (Huang et al., 1993), the codons for the RAmy3D signal peptide and the RAmy3D terminator. The RAmy3D promoter, isolated from the rice amylase gene family, is activated in rice calli by sugar starvation (Huang et al., 1993). The human lysozyme gene was placed between the sequences of the RAmy3D signal peptide and the RAmy3D terminator to give plasmid pAPI156 having a size of 4829 bp.

The promoter of the rice Glutelin 1 gene (Gt-1) and the nucleotide sequence of the signal peptide were cloned with two primers based on the published Gt1 gene sequence (Okita et al. J Biol Chem 264: 12573-12581, 1989). The forward primer with HindIII site was named MV-Gt-1-F1; 5'-ATC-GAAGCTTCATGAGTAATGTGTGAGCAT-TATGGGACCACG-3' (SEQ ID NO:5). The reverse primer was named Xba-Gt-1-R1; 5'-CTAGTCTAGACTCGAGC-CACGGCCATGGGGCCGGCTAGGGAGC-CATCGCACAAG AGGAA-3' (SEQ ID NO:6). Genomic DNA was isolated from leaves of rice variety M202 (Dellaporta et al., 1983). The PCR product amplified from the genomic DNA was cloned into pCR 2.1 (Invitrogen, Carlsbad, Calif.). The resulting plasmid was named pCRGt-1 or pAPI134.

To generate a Gt-1 expression plasmid, pAPI134 was digested with HindIII and XbaI. The fragment containing the Gt-1 promoter and Gt-1 signal peptide was cloned into a pUC19 based plasmid containing the nopaline synthase 3' (Nos) terminator. The resulting plasmid was named pAPI141 and contains the rice Gt-1 promoter, the Gt-1 signal peptide, a multiple cloning site and the Nos terminator.

Figure 1:
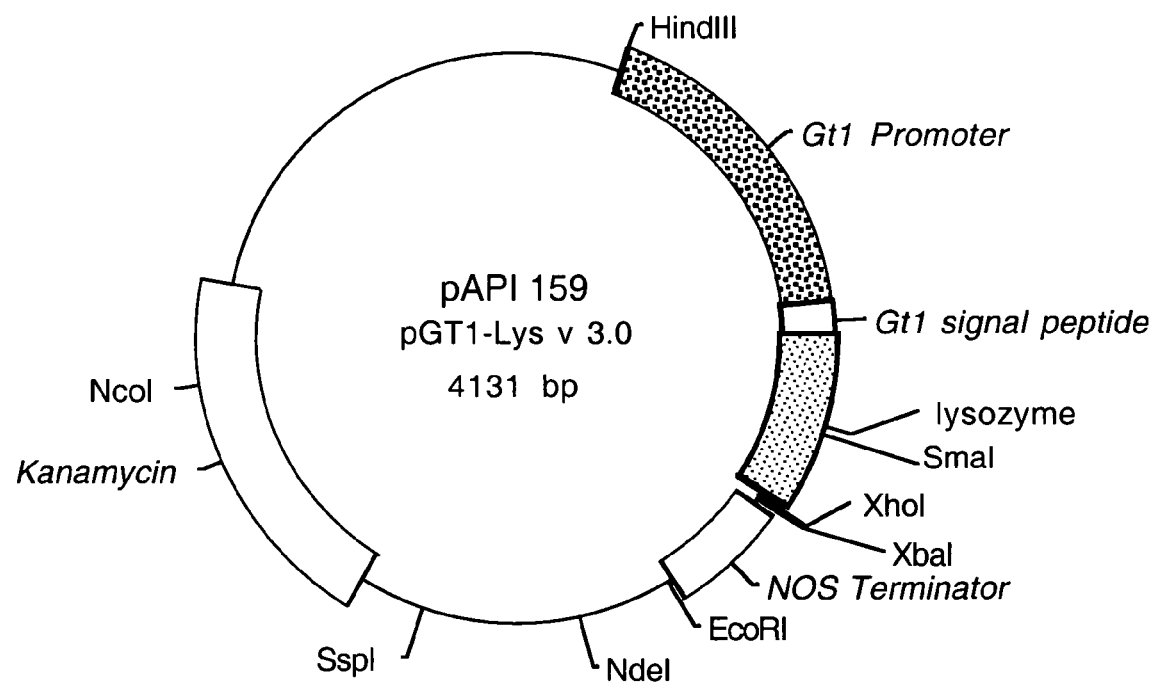
FIG. 1 is a map of the pAPI159 expression construct that contains the human lysozyme coding sequence under the control of a Gt1 promoter and Gt1 signal sequence.

The synthesized human lysozyme gene "lys-ger" (by Operon Technologies, Inc., Alameda, Calif.) that was optimized based on the rice gene codon usage was digested with DraI and XhoI and cloned into pAPI141 digested with NaeI and XhoI according to standard cloning techniques (Sambrook et al., 1989). The resulting plasmid was called pAPI159 (FIG. 1) having a size of 4131 bp.

B. An Expression Vector for Human Lactoferrin Expression in Transgenic Rice

The hLF gene (Rey, M W, 1990) was codon optimized and synthesized by Operon Technologies (CA, USA). The plasmid containing the codon-optimized gene was called Lac-ger. Lac-ger was digested with SmaI/XhoI and the fragment containing the lactoferrin gene was cloned into pAPI141 that was partially digested with NaeI and completely digested with XhoI. The resulting plasmid was named pAPI164. For expression of hLF in rice seeds, the codon-optimized gene was operably linked to the rice endosperm specific glutelin (Gt1) promoter and Nos terminator (FIG. 8).

EXAMPLE 2

Comparison of Promoter Activity in the Expression of Lysozyme in Transgenic Rice A. Comparison Between Gt1 and Glb Promoters and Signal Peptides In earlier studies, inconsistencies were observed between promoter activity of Glb and Gt1 from transient assay data and the protein accumulation level in transgenic plants bearing the same promoters with signal peptides. These unpublished studies suggested that post-translational regulation was involved in recombinant protein expression and accumulation in the endosperm. It was unknown whether the storage protein signal peptide played a role in recombinant protein expression level or whether heterologous proteins could be sent to the protein bodies along the sorting pathways of native storage proteins. In order to improve the expression level of recombinant proteins in cereal crop seed, it is important to understand recombinant protein targeting and trafficking in the endosperm expression system. Hence, comparison was made between the rice storage protein promoters and signal peptides from the Glutelin-1 gene ("Gt1") and the globulin gene ("Glb") showed that both promoters and both signal peptides were capable of effecting expression of lysozyme.

(i). Storage Proteins

Rice endosperm contains four main storage proteins: acid-soluble glutelin, alcohol-soluble prolamin, water-soluble albumin and salt-soluble globulin (Juliano B O), polysaccharides, proteins, and lipids of rice (Am. Assoc. Cereal Chem., St. Paul, Minn. (1985)). They are targeted into two types of protein bodies in rice endosperm. Prolamin aggregates within the endoplasmic reticulum ("ER") lumen into regularly shaped vacuole called protein body type I. The formation of these protein bodies is dependent on the chaperone BiP80 in the ER. Glutelin is deposited into protein storage vacuoles (PSV) via the Golgi apparatus into irregularly shaped vacuole called type II protein body. The components in the protein body type II and its sorting pathway are not well known. The targeting locations and sorting pathway of globulin and albumin also remain unknown. It appears that once the signal sequence is removed in the ER, the sorting and trafficking depend on the targeting information within the polypeptides and chaperones in the ER. The sorting signals are divided into three categories: sequence-specific vacuole sorting signals (ssVSS), C-terminal vacuole sorting signal (ctVSS), and physical structure vacuole sorting signals (psVSS), as described in Frigerio L. et al. (*Plant Physiol.*, 126: 167-175 (2001)); Matsuoka K. et al., (*J. Exp. Botany*, 50:165-174 (1999)) and Vitale A. & Raikhel N. V. (*Trends in Plant Science*, 4:149-155 (1999)).

(ii). Method

Two promoters storage protein genes, Gt1 and Glb, and the corresponding glutelin-1 and globulin signal peptide coding sequences were used to express the human lysozyme protein in developing endosperm. In the three plasmids, pAPI264, pAPI159 and pAPI228, the human lysozyme gene was fused with the nucleotide sequences of the Glb promoter and globulin signal peptide coding sequences, the Gt1 promoter and glutelin signal peptide coding sequences and the combination of the Glb promoter with the glutelin (GT1) signal peptide coding sequences, respectively (FIG. 32A). Lysozyme amounts of T1 seeds were determined for 23 independently transformant lines of pAPI264, 10 lines of pAPI159 and 7 lines of pAPI159. The transgenic lines of pAPI159, which synthesized lysozyme using the Gt1 promoter and the glutelin signal peptide, produced the enzyme in amounts ranging from 34.25 µg to 297.23 µg·mg$^{-1}$ total soluble protein (TSP) with an average of 133.76 µg·mg$^{-1}$ TSP. Plants transformed with pAPI264 carrying the Glb promoter and the globulin signal peptide yielded between 4.09 and 63.64 µg·mg$^{-1}$ TSP lysozyme with an average of 33.96 µg·mg$^{-1}$ TSP, while lines of pAPI228, which combined the Glb promoter and the glutelin signal peptide, yielded between 8.9 and 203.46 µg·mg$^{-1}$ TSP with an average of 87.70 µg·mg$^{-1}$ TSP.

The lysozyme expression amounts achieved with the Gt1 promoter+GT1 signal peptide was 3.94 fold higher than that with the Glb promoter+GLB signal peptide, while the expression amounts of lysozyme obtained with the Glb promoter+GT1 signal peptide was intermediate but increased 2.58 fold over that produced with the GLB signal peptide (FIG. 32B). Apparently the GT1 signal peptide is more efficient than the GLB signal peptide at lysozyme expression and deposition in rice endosperm. This demonstrates the importance of choosing an optimal signal peptide for the production of recombinant proteins in developing rice grains.

(iii). Chimeric Gene Components

Time course of human lysozyme expression during rice endosperm development. We monitored lysozyme accumulation during endosperm development of transgenic lines 159-1-53-16-1 and 264-92-6. Immature spikelets were harvested at 7, 14, 21, 28, 35, 42 and 49 days after pollination ("DAP"). The lysozyme amounts in the endosperms were measured by the activity assay. Lysozyme accumulation in the seeds of transgenic plant 159-1-53-16-1 began at 7 DAP and peaked at 21 DAP. Thereafter lysozyme content decreased until 35 DAP and then stabilized until seed maturity (FIG. 33). Lysozyme accumulation in developing seeds of the transgenic plant 264-92-6 likewise began at 7 DAP, peaked at 28 DAP, after which lysozyme content steadily decreased through seed maturation (FIG. 33). These results show that lysozyme accumulation in the two types of transgenic lines during endosperm development follows the same pattern as that of the native globulin and glutelin storage proteins.

(iv). Subcellular Localization of Human Lysozyme in Transgenic Seeds

In order to determine whether the recombinant lysozyme was targeted to protein bodies in the endosperm, we investigated its subcellular localization by immunofluorescence microscopy. Transgenic plant 264-92-6 synthesizing lysozyme with the Glb promoter and globulin signal peptide and transgenic plant 159-1-53-16-1, producing human lysozyme with the Gt-1 promoter and the glutelin signal peptide were analyzed. Dual localization with either native glutelin or globulin was used to determine the site of lysozyme deposition.

Synthetic peptides derived from the amino acid sequences of rice glutelin and globulin were used to raise antibodies in rabbits. Antibody specificity was confirmed with Western blots of endosperm proteins. No cross-reaction of glutelin and globulin antibodies with other endosperm proteins was detected with the host TP309 or the transgenic lines 264-92-6 and 159-1-53-16-1. The human lysozyme specific antibody detected the 13 kD of lysozyme protein exclusively in the fractionated and total protein extracts.

Immature seeds from two transgenic lines, 159-1-53-16-1 (T4) and 264-92-6(T2) and untransformed control, TP309, were harvested at 14 DAP and fixed and a comparable analysis was conducted. In transgenic line 264-92-6, strong immunofluorescence signals of lysozyme and native proteins were detected with fully overlapping pattern, both when lysozyme and globulin or lysozyme and glutelin were compared (data not shown). Merging the two separately recorded images produces a yellow pseudo color signal. A scan for green and red wavelength emission across the 5 protein bodies along the white line in the not quite perfectly aligned images identifies the co-localization of human lysozyme with globulin. The orange tinge of the protein bodies is due to the stronger emission of red fluorescence than green. The perfect image merger provides a bright yellow color, and the recording of the green and red fluorescence emission along the white line identifies the same five protein bodies. These results demonstrated that lysozyme was colocalized in protein bodies with the native storage proteins. The results also demonstrated that the storage proteins globulin and glutelin are localized in the same cell compartment, substantiating the indication that globulin and glutelin are targeted into the same type II protein bodies in rice endosperm. We conclude that lysozyme contains all sorting information for protein body targeting, at least when co-expressed with rice storage proteins.

The localization patterns of lysozyme and native storage proteins in 159-1-53-16-1 are, however, quite different and more complex than those of transgenic line 264-92-6. In transgenic 159-1-53-16-1, lysozyme does not completely colocalize with the native storage proteins. Globulin localized preferentially in smaller, peripheral protein bodies in the younger cells of the cortical region from 14 DAP endosperm, while lysozyme localized preferentially in irregularly shaped protein bodies. However, lysozyme did colocalize more evenly with globulin in the older cells of the central region from the developing endosperm. Merging the two separately scanned images visualized green fluorescing, lysozyme-rich type II protein bodies and red fluorescing, smaller, globulin-rich protein bodies. Recording of the red and green fluorescence emission along the white scanning line reveals that there is almost twice as much lysozyme in the large type II protein bodies as there is in the small protein bodies, while the globulin signal in the small protein bodies is 2-3 times observed in type II protein bodies. Thus, there appears to be a preferential targeting of the two proteins. In the central region of the endosperm, a more equal co-localization of lysozyme and globulin was observed, especially in the larger type II protein bodies, when judged by the intensity of green and red fluorescence, which provides the yellow color upon merging the two images. This is evident from the merged image scan at the two emission wavelengths. However, there are also small protein bodies containing a dominant portion of globulin or lysozyme in these cells.

Distinct patterns were also found in 159-1-53-16-1 when anti-glutelin antibody was co-incubated with anti-lysozyme antibody in the younger cells of the cortical region from mid-developing endosperm. Like globulin, most of the glutelin localized in the smaller, peripheral protein bodies in younger cells, while lysozyme localized in irregularly shaped protein bodies. Lysozyme partially colocalized with glutelin in the older cells from the center region of mid-developing endosperm. Merging the two images and scanning for fluorescence-intensity at the two wavelengths reveals co-localization of the two proteins in the large and small protein bodies, some being highly enriched in lysozyme and others in glutelin. A comparable distribution is observed in the cells of the central part of the endosperm. The results suggested that lysozyme distorted the native storage protein targeting/sorting when under the control of the Gt1 promoter/GT signal peptide, producing high lysozyme expression, but not when under the control of Glb promoter/GLB signal peptide with lower lysozyme expression.

To determine if native protein accumulation was affected in the endosperm of the transgenic plants, we analyzed the amounts of glutelin, globulin and lysozyme proteins from two transgenic lines and TP309 by Western blotting. The results showed that glutelin protein was reduced in 159-1-53-16-1, but was increased in 264-92-6 in comparison to TP309. Amounts of globulin protein were reduced in both 264-92-6 and 159-1-53-16-1. This change is particularly significant in the transgenic line 159-1-53-16-1 with its higher lysozyme expression level. The results showed that globulin was more affected than glutelin, no matter which signal peptide was used.

Based on the results, we conclude that lysozyme was targeted to the protein bodies and that the signal peptide played an important role in lysozyme expression. The plants with high expression levels of the recombinant protein showed distorted native protein expression and trafficking.

Thus, the combination of the Gt1 promoter and Gt1 signal peptide was more effective than the combination of the Glb promoter and Glb signal peptide, with the combination of Glb promoter and Gt1 signal peptide having intermediate level of activity. Results showed that the high level expression of recombinant protein distorted the trafficking and sorting of the native storage proteins and affected the native storage protein expression. Results also indicated that mature human lysozyme protein contains a determinant recognized in the plant cell for the protein storage vacuole (PSV) sorting following signal peptide cleavage, and that the lysozyme was sorted to Type II protein bodies.

B. Comparison of Seven Promoters and Gt1 Signal Peptide in Regulating the Expression of Lysozyme Plasmids API159 (Gt1 promoter) (FIG. 1), API228 (Glb promoter)(FIG. 32A), API230 (FIG. 28), API229 (RP-6 promoter) (FIG. 31), API225 (GT3 promoter), a plasmid carrying the Glub-2 promoter, and another plasmid carrying the Club-1 promoter, were compared in their ability to effect the expression of lysozyme in transgenic rice T1 seeds. Results shown in FIG. 34 indicate that for expression of lysozyme, Gt1 was the strongest promoter, followed by Glb, Glub-2, Bx7, Gt3, Glub-1 and Rp6, in order of promoter strength.

EXAMPLE 3

Generation of Transgenic Plants Expressing Human Milk Proteins

The procedure of microprojectile-mediated rice transformation (U.S. Pat. No. 6,284,956) was followed. Calli was raised from TP309 mature rice seeds, with calli two to four mm in diameter selected and placed on N6 media supplemented with 0.3 M mannitol and 0.3 M sorbitol for 20 hours before bombardment. Biolistic bombardment was carried out with the biolistic PDC-1000/He system (Bio-Rad, USA). Plasmid carrying milk protein genes and pAPI76, a plasmid carrying hygromycin selectable marker gene were gold-coated and co-bombarded at a ratio of 6:1 with a helium pressure of 1100 psi. Two day old bombarded calli were then transferred to N6 selection media supplemented with 20 mg/l hygromycin B and allowed to grow in the dark at 26° C. for 45 days.

In order to develop transgenic rice plants, the selected calli were transferred to pre-regeneration and regeneration media. When regenerated plants became 1-3 cm in height, the plantlets were transferred to rooting media which consisted of half concentration of MS and 0.05 mg/l NAA. After two weeks, plantlets with developed roots and shoots were transferred to soil and kept under the cover of plastic container for a week. The plants were allowed to grow about 12 cm tall and shifted to the green house where they were grown up to maturity.

A. Generation of Human Lysozyme Expressing Transgenic Rice Plants

The synthetic human lysozyme (hLys) gene under the control of the RAmy3D promoter and terminator in the pAPI156 plasmid (as described in Example 1A) was used to generate sixty independent transformants by particle bombardment-mediated transformation.

Particle bombardment mediated transformation of rice was carried out as described above. Briefly, rice calli derived from TP309 were bombarded with gold particles coated with plasmids pAPI156 and pAPI76 in a ratio of 6:1 using the helium biolistic particle delivery system, PDS 1000 (Bio-Rad, CA). Transformed calli were selected in the presence of hygromycin B (35 mg/L) on N6 (Sigma, MO).

Selected cell lines were maintained in culture media with 3% sucrose (Huang et al., 1993). Lysozyme expression was induced by sugar starvation. Briefly, AA medium (containing 3% sucrose) was removed by aspiration, followed by washing the cells three times with AA minus sucrose (AA-S). The cells were then incubated with AA-S at 40% (v/v) density for three and a half days to obtain the optimal level of lysozyme expression.

Transformants expressing lysozyme were identified by immunoblot analysis, turbidimetric rate determination with *Micrococcus lysodeikticus* or ELISA. Calli were ranked according to the expressed lysozyme level. Suspension cell cultures from the top lines were established following the procedure described previously (Huang et al., 1993). The amount of total protein (Bradford assay) and lysozyme (ELISA) was evaluated in selected calli (Table 1).

TABLE 1

Expression Level Of Human Milk Lysozyme In Transformed Calli

| Cell line | Calli (g) | Total protein (µg) | Lysozyme (µg) | Lysozyme/ protein (%) |
|---|---|---|---|---|
| 156-1 | 0.39 | 2626.5 | 65.7 | 2.5 |
| 156-5 | 0.38 | 5510 | 68.9 | 1.25 |
| 156-16 | 0.4 | 4815 | 120.4 | 2.5 |
| 156-19 | 0.44 | 2440 | 30.5 | 1.25 |
| 156-28 | 0.49 | 4910 | 24.6 | 0.5 |
| 156-43 | 0.56 | 8150 | 101.9 | 1.25 |
| 156-47 | 0.37 | 2472 | 6.2 | 0.25 |

The synthetic human lysozyme (hLys) gene under the control of the Gt1 promoter and Nos terminator in the pAPI159 plasmid (FIG. 1) was used to generate independent transformants by particle bombardment-mediated transformation. Transformed calli were selected as described above, then transferred to pre-regeneration and regeneration media. When regenerated plants became 1-3 cm in height, the plantlets were transferred to rooting media which consisted of half concentration of MS and 0.05 mg/l NAA. After two weeks, plantlets with developed roots and shoots were transferred to soil and kept under the cover of plastic container for a week. The plants were allowed to grow about 12 cm tall and shifted to the green house where they were grown up to maturity (R0 plants).

Screening for R0 plants expressing human lysozyme. Individual rice endosperms or grains were ground with cold phosphate buffered-saline (PBS) with the addition of 0.35 M NaCl. Grinding was conducted with a pre-cooled mortar and pestle at 1 ml buffer/grain. Clear grain homogenate was obtained by subjecting the resulting grain extract to centrifugation at 14,000 rpm for 10 min at 40° C.

Embryos from individual R1 seed (derived from R0 plants) that showed a level of lysozyme expression that was greater than 10 µg/seed were saved and used to generate R1 plants. Briefly, seeds were dissected into embryo and endosperm portions. The endosperm was ground and assayed for lysozyme expression (as further described below). Embryos were sterilized in 50% commercial bleach for 25 minutes and washed with sterile $H_2O$ three times for 5 minutes each. Sterilized embryos were placed in a tissue culture tube that contained MS solid medium. Embryos germinated and plantlets having about three inches shoots and healthy root systems were obtained in two weeks. The plantlets were then transferred to pots to obtain mature plants (R1).

A total of 197 embryos from 12 selected R0 plants were germinated and 157 R1 seedlings planted in the greenhouse for generation of R2 grains. Individual R2 grains (n=1502) from 109 R1 fertile plants were screened for lysozyme expression by lysozyme activity assay in order to identify 42 homozygous plants.

Homozygous R1 plants were identified by analyzing positive expressions of recombinant human lysozyme (rHlys) from a minimum of 20 individual R2 grains. Homozygous lines derived from these plants were planted in a rice field in California. During growth, agronomic characteristics of both transgenic and non-transgenic plants, such as plant height, percentage of fertility, number of effective tillers, filled grains/panicle, non-filled grains/plant, time to maturity and 1000 grain weight were determined and compared. Plants with satisfactory agronomic traits were selected and rHlys expression levels were determined by lysozyme activity assay. Plants that met the criteria for satisfactory agronomic traits and had more than 35 µg of rHlys/grain were advanced to next generations.

SDS-PAGE, electroblotting and Western blot analysis were carried out with 18% precast gel (Invitrogen, Carlsbad, Calif.) as described in Example 4. The primary rabbit polyclonal antibody against human lysozyme was purchased from Dako A/S (Denmark) and used at 1:5000. Lysozyme was quantified by a turbidimetric activity assay with *Micrococcus luteus* (Sigma) on 96-well microtiter plate as described in Example 4. Briefly, 250 µl of 0.015% *M. luteus* cell suspension was incubated with 10 µl of samples containing lysozyme with a concentration less than 2.4 µg/ml. The reaction was followed by the kinetic mode in MICROPLATE MANAGER™ (Bio-Rad, CA) for 5 min at 450 nm. The concentration of lysozyme was then determined in reference to the standard curve.

Figure 2:
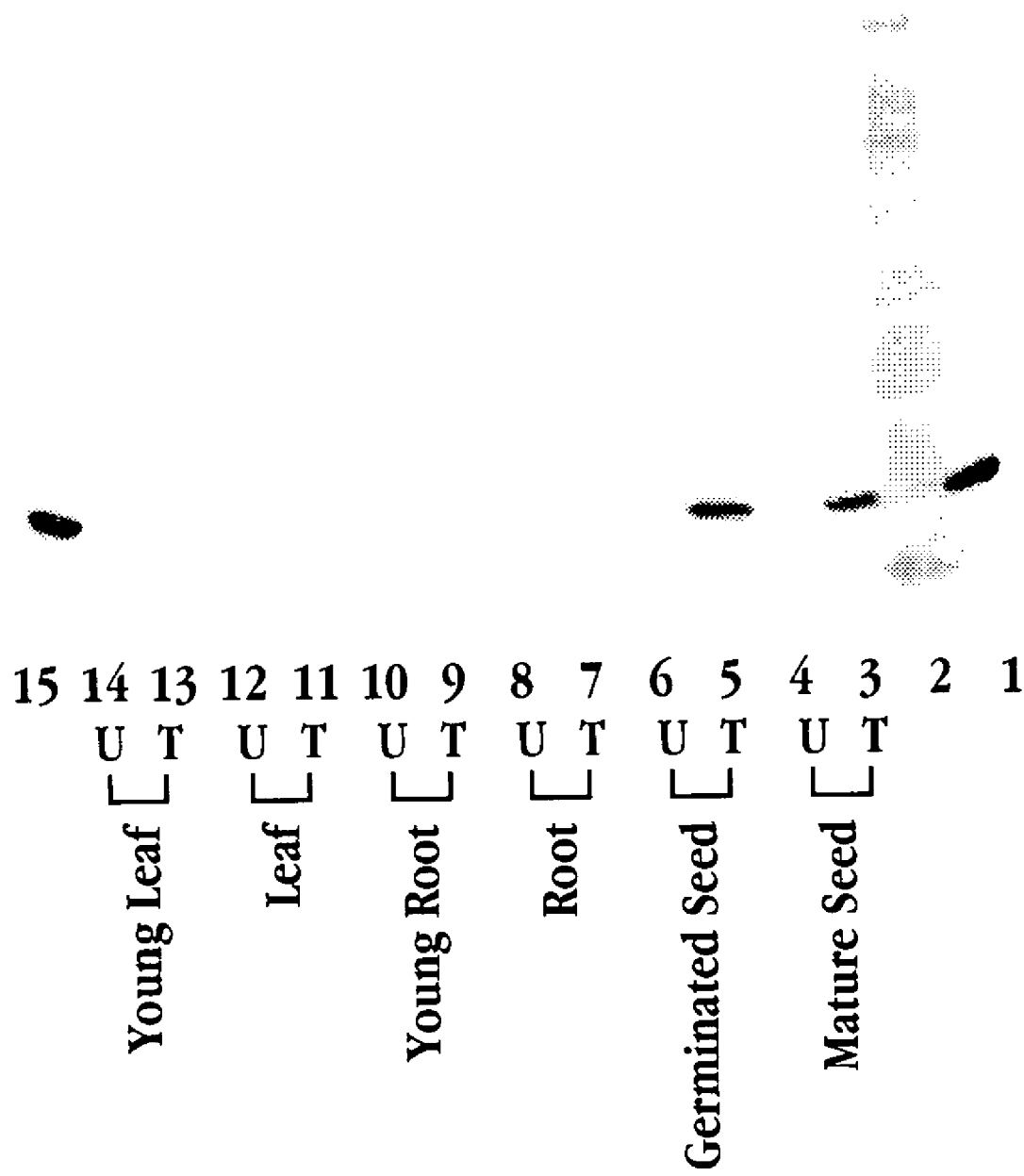
FIG. 2 shows the results of Western blot analysis for the expression of recombinant human lysozyme in various tissues of rice plants, where lanes 1 and 15 are a human milk lysozyme standard; lane 2 is a broad range molecular weight marker from Sigma; lanes 3 and 4 represent mature seed tissue extracts; lanes 5 and 6 represent germinated seed extracts; lanes 7 and 8 represent root tissue extracts; lanes 9 and 10 represent extracts from young root tissue; lanes 11 and 12 represent leaf extracts; and lanes 13 and 14 represent extracts from young leaf; from untransformed ("U") or transgenic ("T") plants, respectively. The total loading protein amount was 40 µg per lane.
Figure 7:
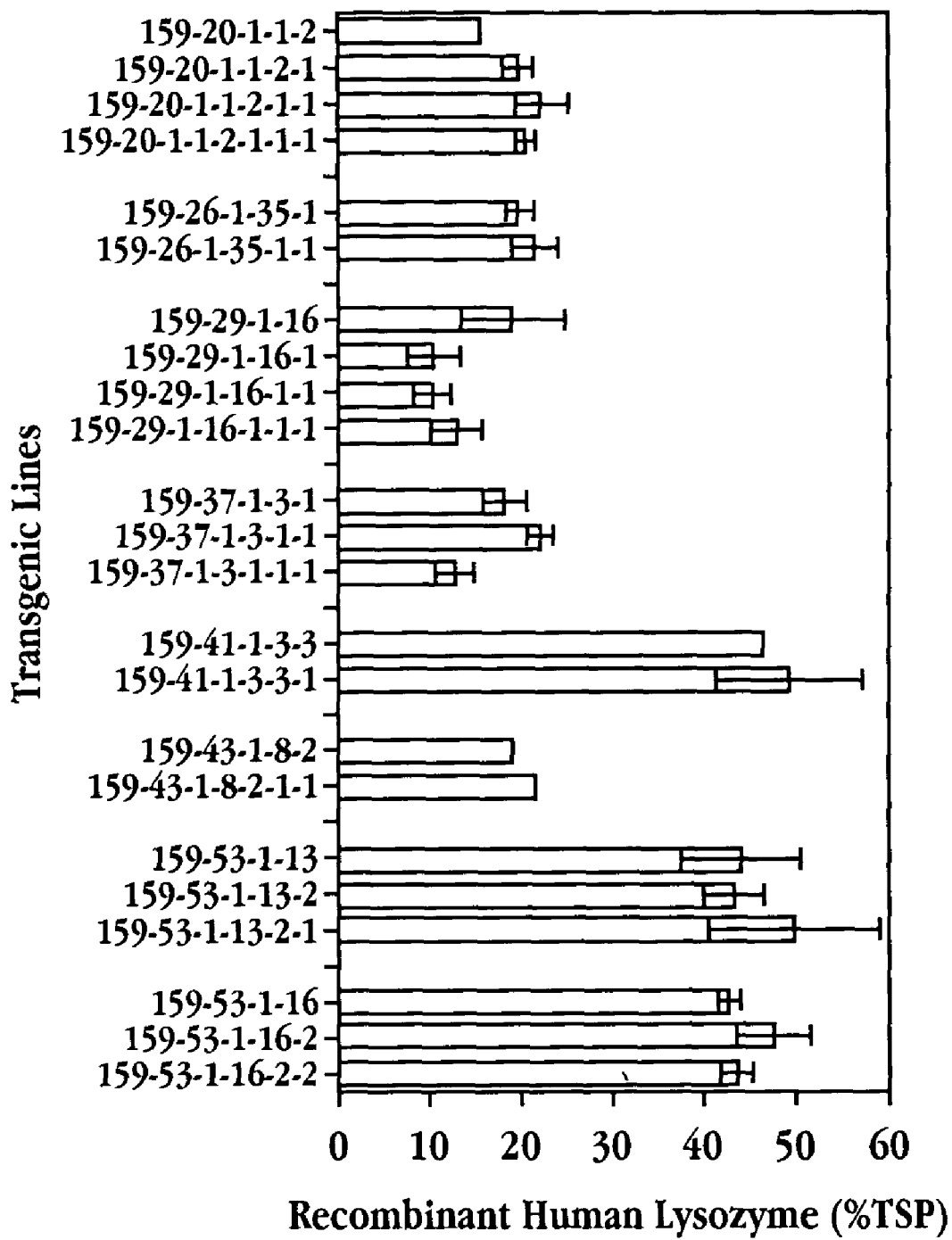
FIG. 7 presents the results of an analysis of lysozyme expression in transgenic rice grains over several generations. Proteins from 1 g of brown rice flour were extracted with 40 ml of extraction buffer containing 0.35 M NaCl in PBS.

The stable expression level of human lysozyme (rHlys) reached at least about 0.6% rHlys per brown rice weight amounting to 45% of the total soluble protein extract from rice grain. FIG. 2 illustrates the seed specific expression of human lysozyme in transgenic plants. rHlys is only found in mature and germinated grain, but not in any other tissues tested. FIG. 7 shows the expression level of human lysozyme in powdered R3 seeds taken from transgenic rice plants B. Generation of Human κ-casein Expressing Transgenic Rice Plants To construct Gt1-kap, pAPI297 (FIG. 24), a plasmid carrying codon-optimized human kappa-casein gene was resynthesized as a SchI and XhoI DNA segment. The fragment was then ligated to pAPI145 that was digested with NaeI and XhoI. The resulting plasmid was called pAPI297 with the expression cassette consisting of the rice Gt1 promoter, Gt1 signal peptide, codon-optimized human kappa-casein and Nos terminator region. To construct a Glb-kap plasmid, pAPI292, (FIG. 23), the SchI and XhoI DNA segment carrying the codon-optimized human kappa-casein gene was ligated to pAPI241 which was digested with NaeI and XhoI. The resulting plasmid was called pAPI292 with the expression cassette of Glb (globulin) promoter, Glb signal peptide, the codon-optimized human kappa-casein and Nos terminator region.

Plasmids pAPI297 and pAPI292 were used to prepare transformed rice plants via particle bombardment as described above. Over 100 independent transgenic rice plants containing the chimeric kappa-casein genes were generated. Mature R1 seeds (single and half seeds) obtained from transgenic rice plants were analyzed via Western blot analysis for expression of recombinant human kappa-casein. A number of independent transgenic plants were found to express κ-casein human milk protein at levels greater then 3% TSP in mature rice seeds (results not shown).

C. Generation of Human Lysozyme-Expressing Transgenic Wheat Plants

To prepare tissues for wheat transformation, two wheat varieties (Bobwhite and Anza) were planted in 6-inch pot at 5 seeds/pot. Wheat plants were grown in a growth chamber in a day/night cycle of 16 hr/8 hr at 18° C./12° C. The relative humidity was kept at approximately 80%. For callus induction, spikelets were harvested 12 to 14 days after anthesis. Caryopses were removed from the spikelets and placed in a 50 ml tube and sterilized by rinsing with 70% ethanol for 1 to 2 min, followed by incubation in a 20% commercial bleach for 45 min with agitation on a shaker at 100 rpm. Sterilized caryopses were then rinsed with sterile water followed by three washes with sterile water, 5 min each. Immature embryos (IEs) were isolated from sterilized caryopses. IEs were young and starchy and 0.8 to 2.0 mm in size. To develop callus, IEs were placed on wheat callus induction medium (Lemaux and Cho, 2001) with scutellum-side down. The IEs were incubated at 26° C. in the dark for 3 days with 80 to 100 embryos/plate. Callus was developed from IEs. To maintain regenerability of the callus, callus was initially cultured and subcultured in D3 medium in dim light (Lemaux and Cho, 2001). Only green callus were carried forward via sub-culturing.

For plasmids involved in wheat transformation, construction of plasmid, pAPI159 (FIG. 1), containing codon-optimized human lysozyme gene, was previously described (Huang et al, 2002). Plasmid pAPI230 (FIG. 28) containing the Bx7 promoter was isolated from a gene encoding wheat high molecular weight glutenin (Marchylo et al, 1992; Hwang et al, 2001). This gene had been shown to be highly expressed in wheat grain and was constructed by replacing GUS gene in pAPI231 (Hwang et al, 2001) with a cassette containing Gt1 signal peptide and a codon-optimized human lysozyme gene, originally derived from pAPI159.

For plant cell transformation and regeneration of transgenic plants, either of two selectable markers were utilized for the wheat transformation protocol. To transform Bobwhite, pAPI159 and pAHC20 (Christensen and Quail, 1996), containing a chimeric gene consisting of the corn ubiquitin promoter hooked to the bar gene, were coated onto gold particles. Sub-cultured green calli were set on DBC3-osmotic medium (Lemaux and Cho, 2001) for 5 to 24 hrs and transformed with plasmid DNAs via particle bombardment. Callus was then placed on DBC3 medium with 5 mg/L bialaphos as a selection. Callus growing on bialaphos selective medium was subcultured every two weeks for 2 months. The transformed callus tissue was placed on regeneration medium to generate transgenic plants, and the transgenic plants were then placed on rooting medium. When the transgenic plants were about 3 inches tall, they were transferred to soil and placed in growth chamber where the transgenic plants were raised to maturity. Transgenic wheat plants were grown in a growth chamber in a day/night cycle of 16 hr/8 hr at 18° C./12° C. with a relative humidity of 80%.

To transform the wheat variety Anza, gold particles were coated with DNA of plasmid API230 along with a selectable marker plasmid carrying rice actin promoter linked to gene encoding hygromycin-B phosphotransferase. After particle bombardment, transformed callus were placed on DBC3 medium (Lemaux and Cho, 2001) with 50 mg/L hygromycin B for selection. Healthy callus was subcultured two times within a 30 day period. After 60 days of selection on DBC3 medium, transgenic callus was placed on regeneration and then rooting medium as described above. Transgenic wheat plants of the Anza variety were raised in a growth chamber under growth conditions as described above. A total of 13 transgenic wheat plants from 8 transgenic events containing pAPI159 were obtained from the wheat variety Bobwhite. Two transgenic plants containing pAPI230 were obtained from the wheat variety Anza. These plants were raised to maturity and all of these plants set seeds.

The expression of recombinant human lysozyme in transgenic wheat grains was analyzed by a lysozyme turbidimetric activity assay, Coomassie stain and Western blot analysis of SDS-PAGE respectively (Example 4). Among the 13 initial transgenic events transformed with plasmid pAPI159, six plants showed expression of recombinant human lysozyme. The expression level ranged up to 84.4 μg lysozyme per mg gram protein or 8.4% TSP wheat protein. This was confirmed by gel analysis. The two transgenic plants carrying pAPI230 were also analyzed and one (line 230-4) of the two plants expressed lysozyme. Individual grain analysis shows that an expression variation among grains, from 3 μg/mg protein to 100 μg/mg protein (data not shown). These results were confirmed by gel analysis. These results indicate that both Gt1 and Bx7 promoter control the expression of the recombinant protein.

For standard gel analysis, individual wheat grains (or half grains) were ground with 1 ml (0.5 ml) of 0.35 M NaCl in phosphate buffered saline (PBS), pH 7.4, using an ice-cold mortar and pestle. The resulting homogenate was centrifuged at 15,000 rpm for 15 min at 4° C. and the supernatant (30 to 50 μg total soluble protein) was loaded onto a 4 to 20% precast gradient polyacrylamide gel (Novex). After electrophoresis, total soluble protein pattern in the gel was stained with 0.1% Coomassie Brilliant Blue R-250.

For Western blot analysis, the gel was electroblotted to a 0.45 μm nitrocellulose membrane. The blot was blocked with 5% non-fat dry milk in phosphate buffered saline (PBS) for 2 hrs followed by three washes with PBS for 10 min each. The primary rabbit polyclonal antibody against hLZ (Dako A/S, Denmark) was used at 1:5000 dilution in PBS.

Lysozyme activity was quantified by a turbidimetric activity assay with *Micrococcus luteus* (Sigma) on 96-well microtiter plate as described in Example 4. Briefly, 250 μl of a 0.015% *M. luteus* cell suspension was incubated with 10 μl of samples containing lysozyme with a concentration less than 2.4 μg/ml. The reaction was followed by the kinetic mode in MICROPLATE MANAGER™ (Bio-Rad, CA) for 5 min at 450 nm. The concentration of lysozyme was then determined in reference to the standard curve.

Based on the analysis of transgenic R1 grains, transgenic line 159-7 (expressing lysozyme from the Gt1 promoter) and line 230-4 (expressing lysozyme from the Bx7 promoter) were selected and progeny plants advanced to the next generation for expression analysis in R2 grains. Expression of recombinant human lysozyme was analyzed with turbidimetric activity assay with the results indicated in Table 2. Most of the R2 lines carrying plasmid API159 expressed recombinant human lysozyme between 7 to 10% total soluble mature seed protein, with one line reaching 13% TSP. Lines carrying plasmid API230 expressed human recombinant lysozyme at 3.3 to 8.4% TSP.

TABLE 2

Expression of recombinant human lysozyme in R2 wheat grains

| R0 Line | LZ % TSP | Std |
| --- | --- | --- |
| 159-7-2 | 13.0 | 6.38 |
| 159-7-3 | 8.8 | 2.84 |
| 159-7-9 | 10.0 | 4.00 |
| 159-7-10 | 9.1 | 4.73 |
| 159-7-11 | 9.8 | 4.63 |
| 159-7-12 | 4.8 | 3.01 |
| 157-7-13 | 4.7 | 3.74 |
| 157-714 | 9.7 | 5.40 |
| 159-7-15 | 7.3 | 2.41 |
| 159-7-16 | 9.0 | 4.71 |
| 230-4-2 | 8.2 | 4.09 |
| 230-4-5 | 4.3 | 2.57 |
| 230-4-8 | 3.3 | 1.58 |

LZ = lysozyme,
TSP = Total soluble protein,
Std = Standard deviation

Figure 3A:
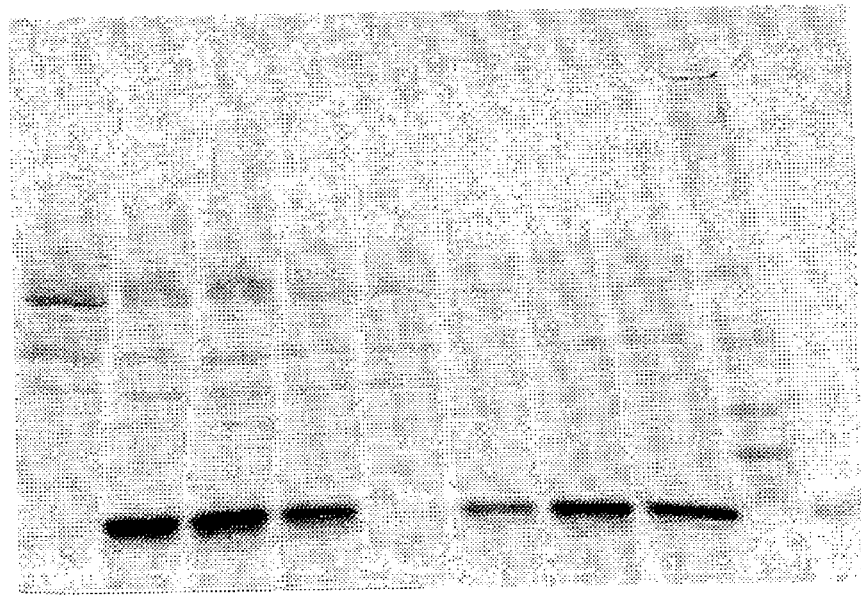
FIGS. 3A and 3B show SDS-PAGE (FIG. 3A) and Western blot (FIG. 3B) analysis of R2 transgenic wheat expressing human recombinant lysozyme. Lane 1 depicts a non-transgenic Bobwhite extract; Lanes 2 through 8 are transgenic soluble protein seed extracts from seven independent transgenic events, 11-5, 11-3, 14-7, 3-5, 9-2, 9-1 and 10-10 respectively; Lane 9 is a molecular weight marker; and Lane 10 is 1 µg of a human lysozyme standard (Sigma). Among the seven lanes with transgenic plant extracts in the gel, six of them expressed a protein having a molecular weight identical to that of native human lysozyme (lane 10).
Figure 3B:
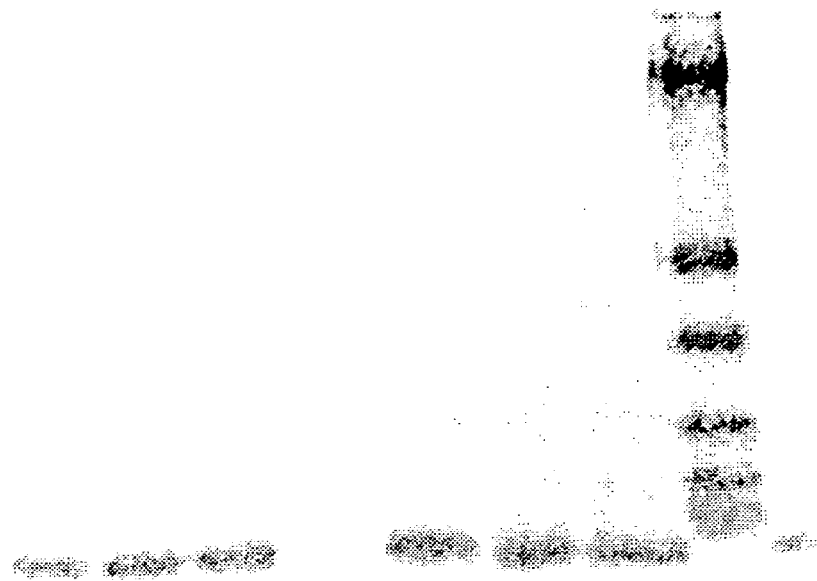

To visualize the expression of recombinant human lysozyme, crude total soluble protein was extracted from R2 generation transgenic wheat grains and analyzed by SDS-PAGE (FIG. 3A) and Western blot analysis (FIG. 3B).

FIG. 3A shows Coomassie brilliant blue staining of aqueous phase extraction of transgenic wheat grains (var. Bobwhite) expressing human recombinant lysozyme. Both non-transformed and transgenic wheat seeds (~10 pooled R2 seed from seven individual transgenic plants originating from the transgenic wheat line 159-7) were ground with PBS pH 7.4 buffer. The resulting extracts were spun at 14,000 rpm at 4° C. for 10 min. Supernatant was collected and ~50 µg of this soluble protein extract was resuspended in sample loading buffer, and loaded onto a precast SDS-PAGE gel. Lane 1 depicts a non-transgenic Bobwhite extract; Lanes 2 through 8 are transgenic soluble protein seed extracts from seven independent transgenic plants, 11-5, 11-3, 14-7, 3-5, 9-2, 9-1 and 10-10 respectively; Lane 9 is a molecular weight marker; and Lane 10 is 1 µg of a human lysozyme standard (Sigma). Among the seven lanes with transgenic plant extracts in the gel, six of them expressed a protein having a molecular weight identical to that of native human lysozyme (lane 10). This protein band was not present in non-transgenic Bobwhite and missing in one of the transgenic lines, possibly due to transgene segregation. The protein band (lysozyme) was the strongest, indicating that recombinant human lysozyme was the most abundant soluble protein in the mature wheat grains. This protein band, same as native human lysozyme, reacted to anti-lysozyme antibody, indicated that this band was authentic recombinant human lysozyme.

FIG. 3B shows the Western blot analysis of the recombinant human lysozyme expressed in the transgenic wheat grains. The R2 pooled seed soluble protein extracts (~5 µg total protein) from seven independent transgenic wheat plants were prepared as described for FIG. 3A above, separated by SDS-PAGE gel and then blotted onto a nitrocellulose filter. The identification of lysozyme expressed in wheat seeds was carried out by Western analysis using anti-lysozyme antibody. Lane designations are identical to those for FIG. 3A, above.

These results confirm that, by utilizing either the Gt1 or Bx7 promoter in transgenic wheat, high-level expression of an active recombinant human milk protein (lysozyme) can be obtained.

Additionally, plasmids API159 (FIG. 1) and API230 (FIG. 28) were used to transform wheat plants substantially in the same manner as in transforming rice plants (Examples 3A-3B). Eight transgenic wheat lines were produced with API159, generating an expression level of about 150 to 300 µg of lysozyme per grain. Two transgenic wheat lines were produced with API230, yielding an expression level of about 50 to 120 µg of lysozyme per grain.

D. Generation of Human AAT-Expressing Transgenic Wheat Plants

The plasmid API282 (FIG. 14) containing the Bx7 promoter, Bx7 signal peptide and AAT gene, Nos terminator and ampicillin resistance gene was used to transform wheat plants, substantially as in the transformation of rice plants. Twenty one transgenic lines were produced. Expression of AAT was determined to be about 5 to 12 µg per grain of wheat seeds.

E. Generation of Human Lysozyme-Expressing Transgenic Barley Plants

The plasmid API159 was also used to transform barley plants substantially as described as for transformation of rice plants. Five transgenic barley lines were produced, yielding about 3.9 to 12.3 µg of lysozyme per grain.

F. Generation of Human Lactoferrin Expressing Transgenic Rice Plants

The synthetic human lactoferrin gene under the control of the Gt1 promoter in the pAPI164 plasmid was used to generate over 100 independent transformants by particle bombardment-mediated transformation.

Particle bombardment mediated transformation of rice was carried out as described above. At least 20 R1 grains from each R0 plant were analyzed for rHLF expression. Individual R1 grains were cut into halves. The endospermic half was subjected to rHLF expression analysis by Western blot or ELISA and the corresponding positive embryonic half was germinated to generate R1 seedlings. The seedlings were transplanted to generate R2 grains. During the screening of R1 grains we observed that all the positive grains were opaque-pinkish in color in comparison to negative or control grains. The opaque-pinkish color in rice grains was then used to identify homozygous lines. A transgenic plant was considered to be homozygous and expressing rHLF if all grains from that plant were opaque-pinkish. Homozygous lines were then confirmed by ELISA analysis. Based on the expression analysis and agronomic characters, selected homozygous R2 lines were advanced to R3 and R6 generations.

EXAMPLE 4

Characterization of Recombinant Human Lysozyme (rLys) Produced by Transgenic Rice Plants A. Southern Blot Analysis About three grams of young leaves were collected and grounded with liquid nitrogen into a fine powder. The genomic DNA was isolated according to the procedure as described in Dellaporta et al., 1983, and purified by phenol-chloroform extraction. Approximately 5 µg of DNA was then with HindIII and EcoRI, separated on a 1% agarose gel, blotted onto a Hybond[+] membrane (Amersham Pharmacia Biotech, Piscataway, N.J.). The blot was probed with gel purified human Hlys gene and developed by ECL™ direct nucleic acid labeling and detection system (Amersham Pharmacia). By comparing to known amounts of the intact 1470 bp human lysozyme (Hlys) gene, the intact copy number of the transgenes, including promoter and Hlys gene, was estimated to vary from about 1 to about 6. No positive correlation between copy number of the rHlys transgene and amount of rHlys synthesized was discernible.

B. SDS-PAGE and Reverse IEF Gel Electrophoresis

Induced calli or harvested cells from suspension cell cultures were ground with cold phosphate buffered-saline (PBS) with a protease inhibitor cocktail (2 µg/ml aprotonin, 0.5 µg/ml leupeptin, 1 mM EDTA and 2 mM Pefabloc). The protease inhibitor cocktail was excluded from the buffer used subsequently during the purification of the enzyme, since the inhibitors did not increase the lysozyme expression yield. Grinding was conducted with a pre-chilled mortar and pestle at approximately 2 ml buffer/g calli or cells. A clear homogenate was obtained by subjecting the resulting extract to centrifugation at 16,000×g for 10 minutes at 4 C.

SDS-PAGE was carried out using an 18% precast gel (Novex, CA). The resulting gel was stained with 0.1% Coomassie brilliant blue R-250 at 45% methanol and 10% glacial acetic acid for three hours. Gel destaining was conducted with 45% methanol and 10% glacial acetic acid until the desired background was reached.

Reverse IEF gel electrophoresis was carried out using a precast Novex pH 3-10 IEF gel according to the manufacturer's instructions (Novex, CA). About 30 µg of lysozyme was loaded onto the gel and electrophoresed at 100 V for 50 minutes followed by application of 200 V for 20 minutes. The gel was then fixed in 136 mM sulphosalicylic acid and 11.5% TCA for 30 minutes and stained in 0.1% Coomassie brilliant blue R-250, 40% ethanol, 10% glacial acetic acid for 30 minutes. The destaining solution contained 25% ethanol and 8% acetic acid.

C. Western Blot Analysis

A SDS-PAGE gel was electroblotted to a 0.45 µm nitrocellulose membrane using a MINI TRANS-BLOT™ Electrophoretic Transfer Cell (Bio-Rad, CA) and subsequently subjected to immuno-blotting analysis. The blot was blocked with 5% non-fat dry milk in PBS, pH 7.4 for at least two hours followed by three washes with PBS, pH 7.4 for 10 minutes each. The primary rabbit polyclonal antibody against human lysozyme (Dako A/S, Denmark) was diluted at 1:2000 in the blocking buffer and the blot was incubated in the solution for at least one hour. The blot was then washed with PBS three times for 10 minutes each. The secondary goat anti-rabbit IgG (H+L)-alkaline phosphatase conjugate (Bio-Rad, CA) was diluted in the blocking buffer at 1:4000. The membrane was then incubated in the secondary antibody solution for one hour and then washed three times. Color development was initiated by adding the substrate system BCIP-NBT (Sigma) and the process was stopped by rinsing the blot with $H_2O$ once the desirable intensity of the bands had been achieved.

D. Enzyme Linked Immunosorbant Assay (ELISA)

An indirect sandwich ELISA was developed to quantify total lysozyme expressed in rice calli or cells and used as an alternative assay to determine the lysozyme expression yield. A direct sandwich ELISA for lysozyme quantification has been previously reported (Lollike et al., 1995, Taylor, 1992), however an alternate assay was developed as a key reagent used in the assay is no longer commercially available.

In carrying out the assay, rabbit anti-human lysozyme antibody (Dako D/K, Denmark) was used to coat a 96 well plate at 1:5000 diluted in PBS overnight at room temperature. After washing with PBS, the plate was blocked with 5% normal donkey serum (Jackson ImmunoResearch Laboratories, PA) in PBS for one hour. The plate was washed again with PBS. Lysozyme samples were diluted in 0.05% TWEEN in PBS and captured by adding to the plate and incubating for one hour. After washing the plate with PBS, sheep anti-human lysozyme at 1:1000 diluted with 0.05% TWEEN in PBS was added and incubated for one hour. The plate was washed again with PBS. Peroxidase-conjugated affinipure donkey anti-sheep IgG (H+L) diluted in 0.05% TWEEN in PBS at 1:10,000 was added and incubated for one hour. After a final wash of the plate with PBS, color was developed by incubating the plate with TMB substrate (Sigma, MO) for 5-15 minutes and the absorbance read at 655 nm.

E. Enzymatic Activity Assay for Lysozyme

A reliable and quantitative method was developed to analyze the expression level of enzymatically active lysozyme. The turbidimetric assay was developed using a 96-well microtiter plate format and based on the standard lysozyme assay that is carried out spectrophotometrically in cuvettes. A microtiter plate based method previously described for the detection of lysozyme release from human neutrophils had a detection range of 1-100 ng/ml (Moreira-Ludewig et al., 1992). The assay conditions were modified to maintain the linearity of detection up to 3.0 µg/ml.

The enzymatic activity of lysozyme was routinely determined by spectrophotometric monitoring of the decrease in turbidity at 450 nm of a suspension of *Micrococcus luteus* (*M. lysodeikticus*) cells (Shugar, 1952). Specifically, 250 µl of a 0.015% (w/v) *Micrococcus leteus* cell suspension was prepared in 66 mM potassium phosphate, pH 6.24 (buffer A). Cell suspensions were equilibrated at room temperature and the reaction was initiated by adding 10 µl samples containing lysozyme with concentrations from 0 to 2.4 µg/ml. Lysozyme activity was determined in a kinetic mode for 5 minutes at 450 nm. The concentration of lysozyme was then calculated by reference to the standard curve constructed with human milk-derived lysozyme.

Figure 5:
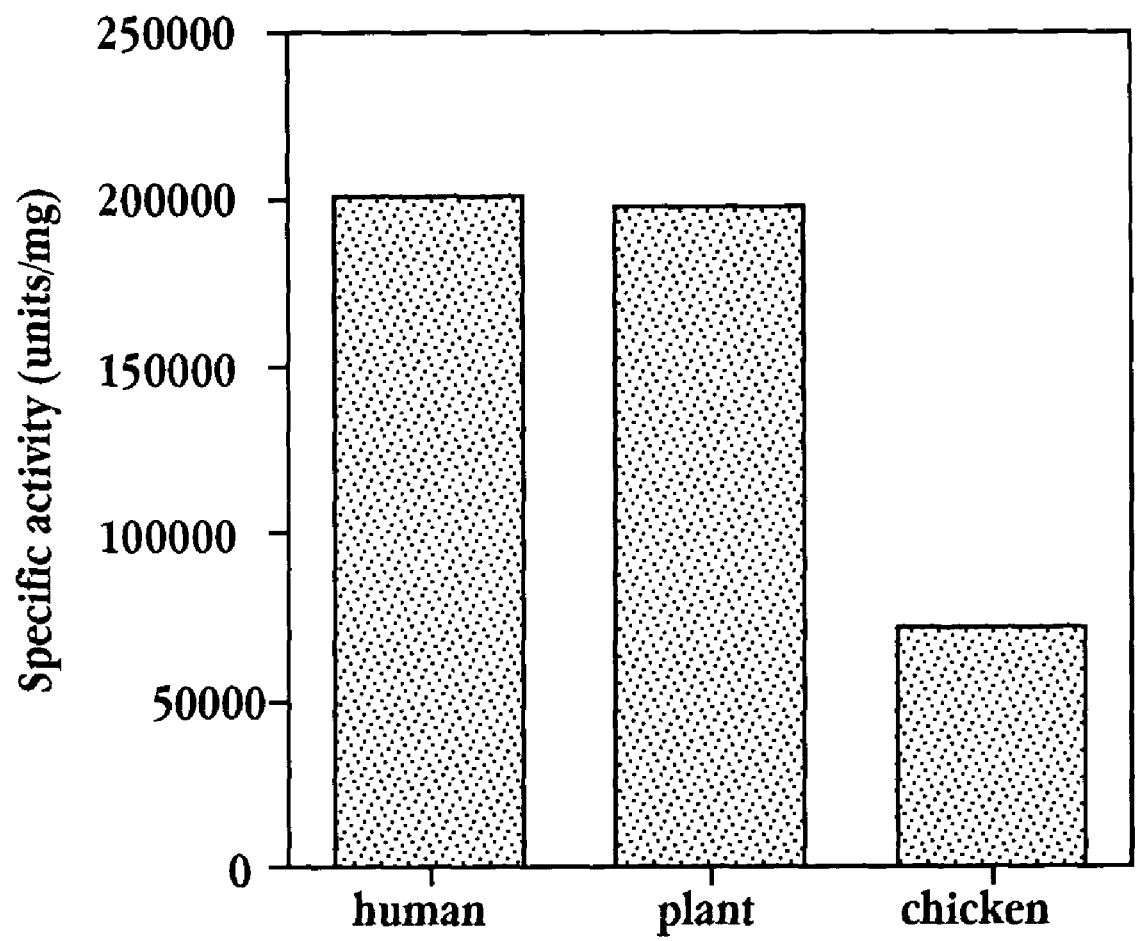
FIG. 5 is a graph showing the specific activity of lysozyme, as determined by incubating an identical concentration of a human lysozyme standard, human lysozyme from transgenic rice (plant) and lysozyme from chicken egg white with a standard amount of M. luteus, followed by evaluation of the reduction in the turbidity due to the activity of lysozyme over five minutes.

The enzymatic activity of human milk lysozyme and the rice cell derived lysozyme of the invention was compared. As shown in FIG. 5, the lysozyme effected reduction of the turbidity of *Micrococcus leteus* cell suspensions at 450 nm was very similar for lysozyme from the two sources, while buffer alone did not have any effect on the reduction of turbidity.

Three selected suspension cell culture lines were induced to express lysozyme and the yield estimated in parallel by ELISA and the enzymatic activity assay described above (results shown in Table 3). T-test analysis showed that there was no significant difference between the lysozyme concentration measured by ELISA and enzymatic activity assay ($p<0.05$). These results demonstrate that active recombinant human milk lysozyme is synthesized and maintained in rice callus cells and can be isolated without losing its activity.

TABLE 3

Comparison of Lysozyme Yields Estimates by Enzymatic Activity Assay and ELISA

| Cell line | Lysozyme yield by enzymatic activity assay (lysozyme/total protein µg/mg) | Lysozyme yield by ELISA (lysozyme/total protein µg/mg) |
|---|---|---|
| 156-5 | 25.8 +/− 6.3 | 30.3 +/− 3.9 |
| 156-16 | 32.1 +/− 5.7 | 32.9 +/− 3.2 |
| 156-31 | 47.0 +/− 6.2 | 42.3 +/− 7.0 |

F. Bacterial Function of Recombinant Human Lysozyme

Figure 4:
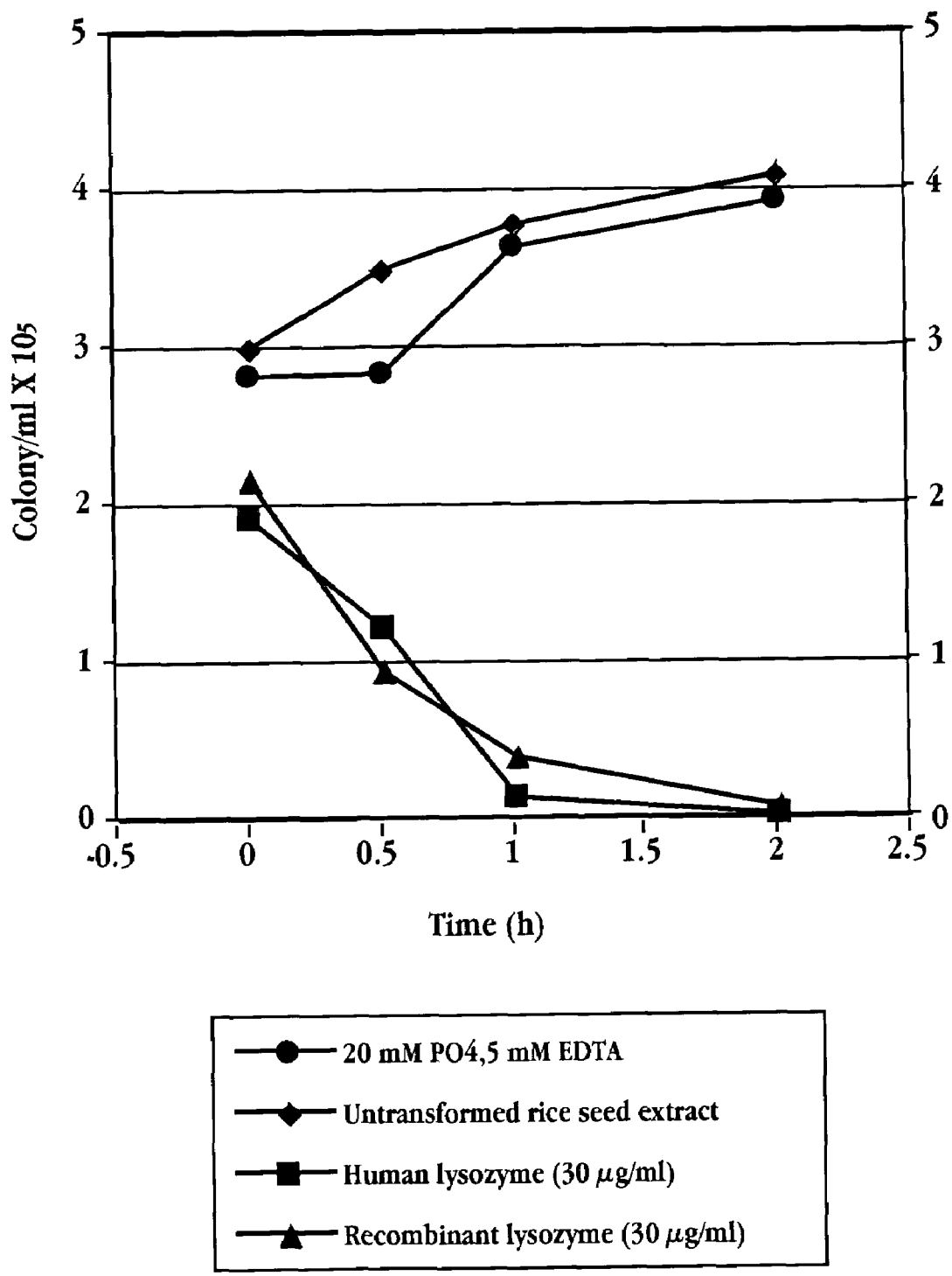
FIG. 4 shows the effect of incubating recombinant human lysozyme from transgenic rice seed, a human lysozyme standard (30 µg/ml), a control (20 mM sodium phosphate, pH 7.0, 5 mM EDTA) or an untransformed rice extract on the growth of E. coli strain JM109. At the end of the incubation (for the time indicated), an aliquot of the mixture was plated on LB plates and colony forming units per ml (CFU/ml) was calculated.

The sensitive lysis of *Micrococcus luteus* cells in a turbidimetric assay (FIG. 5) indicates that recombinant human lysozyme possesses enzymatic activity and functions as a bactericide. To confirm this with a gram-negative bacterium, a bactericidal assay was carried out using an *E. coli* strain (JM109) as a test organism (FIG. 4).

In carrying out the assay, an aliquot of overnight JM109 culture was grown in LB medium until mid log phase. A standard innoculum of mid-log phase JM109 at $2\times10^5$ CFU (colony forming units)/ml was used in the bactericidal assay. Buffer (20 mM Sodium phosphate, pH 7.0, 0.5 mM EDTA) alone, buffer containing human milk lysozyme or rice seed derived lysozyme at about 30 μg/ml were sterilized by filtration. The mixture of cells and lysozyme solution was then incubated at 37 C for the specified length of time. One-fifth of the mixture volume was plated onto the LB agar plates and incubated overnight at 37 C in order to determine the number of colony forming units. At the concentration of 30 μg/ml, recombinant human lysozyme exhibited a similar bactericidal effect as lysozyme from human milk. There was no reduction of colony forming units using an extract from the non-transgenic control.

G. Purification of Lysozyme from Rice Calli, Suspension Cultures and Transgenic Rice Grains Five rice calli lines expressing high levels of lysozyme were propagated and induced by sucrose starvation. The calli or cells were ground by a Tissuemizer in extraction buffer (PBS, 0.35 M NaCl) at 2 ml buffer/g of wet calli. The resulting tissue homogenate was centrifuged at 25,000×g for 30 minutes at 4 C. The supernatant was removed and subjected to filtration through a pre-filter and then through a 0.45 μm nitrocellulose filter.

Approximately 1 liter of filtered supernatant from 500 grams of induced wet calli were then dialyzed against 50 mM sodium phosphate, pH 8.5 at 4 C overnight. The supernatant was loaded onto a 200 ml SP SEPHAROSE™ fast flow column (XK26/40, Pharmacia) equilibrated with the loading buffer (50 mM sodium phosphate, pH 8.5) at a flow rate of four ml/min. The column was then washed with the same buffer until a baseline of A280 was achieved. Lysozyme was eluted by 0.2 M NaCl in the loading buffer and fractions containing lysozyme activity were pooled, concentrated and reapplied to a SEPHACRYL™-100 column equilibrated and run with PBS at a flow rate of one ml/min. Proteins were eluted and separated by using PBS at a flow rate of one ml/min. Pure lysozyme fractions were identified by activity assay and total protein assay (Bradford) and the purity of lysozyme was confirmed by SDS-PAGE.

The five lines with the highest lysozyme expression level were selected and propagated continuously in petri dishes or shake flasks for lysozyme isolation and purification. A crude extract from rice callus contains both recombinant human lysozyme and large amounts of native rice proteins. Since the calculated pI of lysozyme is approximately 11, a strong cation exchange column, SP-SEPHAROSE™ fast flow (Pharmacia), was chosen as the first column to separate the rice proteins from recombinant human lysozyme. Most of the rice proteins did not bind to the column when equilibrated with 50 mM sodium phosphate, pH 8.5. The recombinant human lysozyme, on the other hand, bound to the column and was eluted by 0.2 M NaCl. Rice proteins that co-eluted with recombinant human lysozyme, were separated from lysozyme by gel filtration through a SEPHACRYL™ S-100 column and highly purified recombinant human lysozyme was obtained.

To purify human lysozyme from rice grains, R2 rice seeds from transgenic plants were dehusked and milled to flour using conventional methods. Lysozyme was extracted by mixing the rice flour with 0.35 N NaCl in PBS at 100 grams/liter at room temperature for one hour. The resulting mixture was subjected to filtration through 3 μm of a pleated capsule, then through 1.2 μm of a serum capsule and finally through a SUPORCAP 50 capsule with a 0.8 μm glass filter on top of 0.45 μm filter (Pall, Mich.).

The clear rice extract (1 liter) was then dialyzed against 50 mm sodium phosphate, pH 8.5 at 4° C. overnight and the dialyzed sample was loaded onto a cation exchange resin SP-SEPHAROSE™ (Pharmacia Amersham), which was pre-conditioned with 50 mm sodium phosphate, pH 8.5 before loading. After loading, the column was washed with the same buffer until a base line A280 reading was achieved, then lysozyme was eluted with 0.2 N NaCl in 50 mm sodium phosphate, pH 8.5. Fractions containing lysozyme were pooled and reapplied to a SEPHACRYL™ S-100 column (Bio-Rad; equilibrated and run with PBS). Pure lysozyme was fractions were identified by enzymatic assay and total protein assay (Bradford). Finally the purity of lysozyme was confirmed by SDS-PAGE.

H. Attributes of Recombinant Human Lysozyme Produced in Rice (i). N-Terminal Amino Acid Sequencing Recombinant human lysozyme (rLys) isolated from rice cells as described above, was separated by 18% SDS-PAGE followed by electroblotting to a PVDF membrane (Bio-Rad, CA). The lysozyme band was identified by staining the membrane with 0.1% Coomassie Brilliant Blue R-250 in 40% methanol and 1% glacial acetic acid for 1 minute. The stained PVDF membrane was immediately destained in 50% methanol until the band was clearly visible. After the blot was thoroughly washed with $H_2O$ and air-dried, it was sequenced with a sequencer ABI 477 by Edman degradation chemistry at the Protein Structure Laboratory of the University of California at Davis. The results showed that the rLys produced in transgenic rice seed had an identical N-terminal sequences to the human lysozyme, as follows:

Recombinant Lys - - - Lys Val Phe Glu Arg ( ) Glu Leu Ala Arg Thr (SEQ ID NO: 32)

Human Lys - - - Lys Val Phe Glu Arg Cys Glu Leu Ala Arg Thr (SEQ ID NO: 33)

The blank parenthesis in recombinant lysozyme represents residue Cys which cannot be detected by the machine. This cycle was not defined, and could be due to the un-modified cysteine residue which cannot form a stable derivative in Edman degradation analysis.

Additionally, a number of structural and functional attributes of human lysozyme and recombinant lysozyme produced in rice were found to be the same, including molecular weight, pI, bactericidal effect with *E. coli*, thermal and pH stability and specific activity.

(ii). Thermal and pH Stability of Lysozyme

For biotechnological applications of the recombinant human lysozyme, its thermal and pH stability as well as its resistance to proteases is of decisive importance. A human lysozyme standard and lysozyme from rice were diluted to a final concentration of 50 μg/ml in PBS and subjected to the following thermal treatment in a sequential mode: (1): 62° C. for 15 minutes; (2): 72° C. for 20 seconds; (3): 85° C. for 3 minutes and finally; (4): 100° C. for about 8 to about 20 seconds. Studies were conducted with 100 μl per tube and repeated three times. Aliquots were saved at the end of each treatment and the remaining lysozyme activity was measured by activity assay. The result showed that recombinant lysozyme exhibited the same degree of thermal stability in the temperature range from 62° C. to 100° C. as human lysozyme.

Figure 6A:
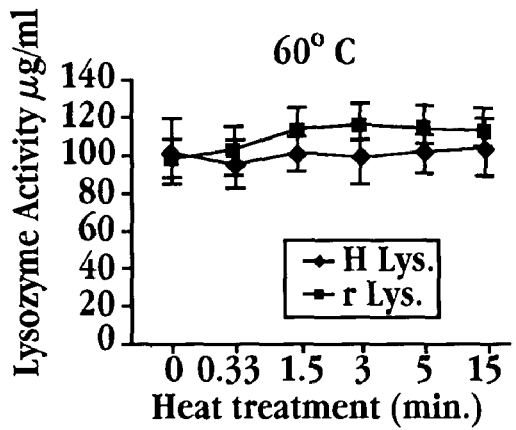
FIGS. 6A-6D show the thermal stability of human lysozyme ("Hlys") and recombinant human lysozyme from transgenic rice ("rHLys"). Lysozyme activity was determined by activity assay after the lysozyme mixtures were subjected to temperatures of 60 C (FIG. 6A), 72 C (FIG. 6B), 85 C (FIG. 6C), and 100 C (FIG. 6D).

In another embodiment, approximately 50 μl of Hlys or rHlys was dissolved in PBS at 100 μg/ml and subjected to heat treatment. Four different temperatures of 65° C., 72° C., 85° C. and 100° C. were tested. With each temperature, 0 min, 0.33 min, 1.5 min, 3 min, 5 min and 15 min were selected to analyze the impact of incubation time on the stability of lysozyme (FIG. 6A).

For studies on pH stability, lysozyme was dissolved in 0.9% NaCl at 100 µg/ml at pH 10, 9, 7.4, 5, 4, and 2. The solutions were incubated at 24° C. for one hour. Experiments were conducted with 200 µl per tube and repeated three times. Remaining lysozyme was detected by lysozyme activity assay.

Figure 6B:
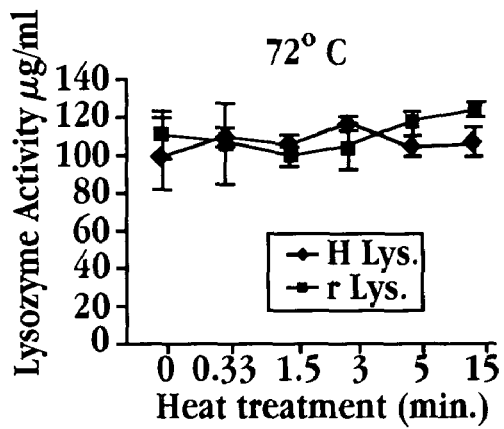
Figure 6C:
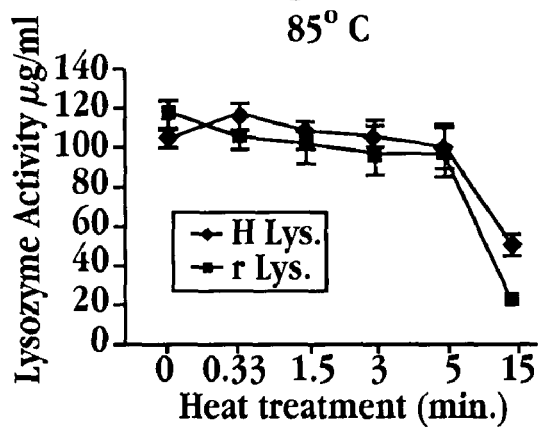
Figure 6D:
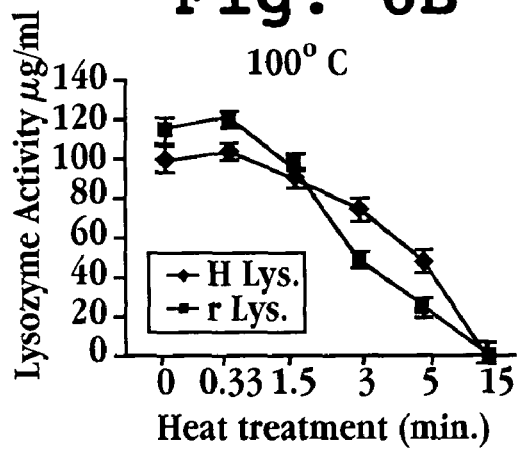
Figure 6E:
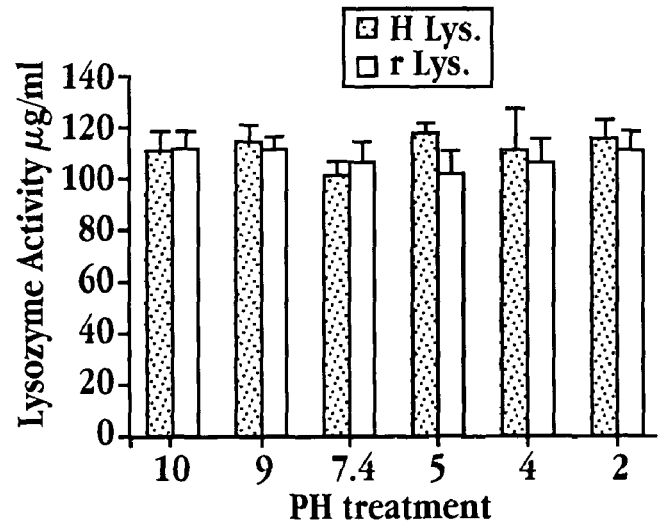
FIG. 6E shows the pH stability of Hlys and rHlys lysozyme activity determined by activity assay.

For pH treatments at pH 2, 4 and 5, Hlys and rHlys was dissolved in PBS adjusted to the corresponding pHs with HCl at 100 µg/ml. For pH 9 and 10, lysozyme was dissolved in TBS and 150 mM sodium carbonate/bicarbonate at 100 µg/ml, respectively. Approximately 100 µl of lysozyme solution was incubated at 37° C. for 30 min. The lysozyme activity was assessed by activity assay (FIG. 6B).

Both Hlys and rHlys displayed similar thermal and pH stability.

(iii). Determination of In Vitro Protease Resistance of Lysozyme

Lysozyme was dissolved in 0.9% NaCl at 100 µg/ml. The pH of the solution was reduced to 3, 4 and 5 with HCl. Pepsin (Sigma, MO) (pepsin:lysozyme=1:22 (w/w)) was added and the solutions were incubated at 37° C. for one hour. Then the pH of all treatments was raised to pH 7 with bicarbonate. Pancreatin (Sigma, MO) (pancreatin:lysozyme=1:110 (w/w)) was added to the neutral solution and incubated at 37 C for two hours. The remaining lysozyme activity was measured by activity assay.

In in vitro digestion experiments with pepsin and pancreatin, the native and recombinant human lysozyme displayed very similar resistance to pepsin and pancraetin digestion. Under these conditions, human albumin was degraded as demonstrated by SDS-PAGE (data not shown).

(iv). Biochemical Characterization of Lysozyme

After recombinant human lysozyme was purified to near homogeneity, several biochemical characterizations were carried out to compare human milk lysozyme with recombinant human milk lysozyme derived from rice cells. The results summarized in Table 4 show that by SDS-PAGE, native human milk lysozyme and recombinant lysozyme migrated to the same position.

Nucleotides encoding the rice Ramy3D signal peptide were attached to the human lysozyme gene in the expression vector pAPI156. Determination of the N-terminal amino acid sequence of the purified recombinant human lysozyme revealed an N-terminal sequence identical with that of native human lysozyme, as detailed above. Rice cells thus cleave the correct peptide bond to remove the RAmy3D signal peptide, when it is attached in the human lysozyme precursor.

The overall charge of recombinant and native human lysozyme were compared by isoelectric-focusing (IEF) gel electrophoresis and pI values determined. Since lysozyme is a basic protein with a calculated pI of 10.20, the pI comparison studies were carried out by reverse IEF gel electrophoresis. Recombinant and native human lysozyme displayed identical pI, indicating the same overall charge (data not shown).

Recombinant human lysozyme derived from transgenic rice had a specific activity similar to the native lysozyme (200,000 units/mg (Sigma, MO), whereas, lysozyme from chicken egg whites had the expected 3-4 fold lower specific activity (Sigma, MO) (FIG. 5).

TABLE 4

Comparison of Biochemical Characteristics of Human Milk Lysozyme and Recombinant Lysozyme

| Lysozyme source | N-terminal sequence | Size (kDa) | Glycosylation | Specific activity (units/mg) | pI |
|---|---|---|---|---|---|
| Human milk | KVFER C ELART (SEQ ID NO: 33) | 14 | No | 201,526 | 10.2 |
| rice | KVFER(−)*ELART (SEQ ID NO: 32) | 14 | No | 198,000 | 10.2 |

*This cycle was not defined, and could be due to the un-modified cysteine residue which cannot form a stable derivative in Edman degradation analysis.

The results described above demonstrate the ability to use rice cells as a production system to express human lysozyme from milk. Over 160 individual transformants were screened by immunoblot, enzymatic activity assay and ELISA. Yields of recombinant human milk lysozyme reached 4% of soluble cell proteins in culture cells and over 40% of soluble proteins in rice grains. Although the mechanism is not part of the invention, the high expression level may be explained by the utilization of the strong RAmy3D promoter (Huang et al., 1993) in culture cell system and Gt1 promoter in grain expression system and the codon-optimized gene.

The plant derived human milk lysozyme obtained by the methods of the present invention was identical to endogenous human lysozyme in electrophoretic mobility, molecular weight, overall surface charges and specific bactericidal activity.

EXAMPLE 5

Characterization of Recombinant Human Lactoferrin (rLF) Produced by Transgenic Rice Plants A. Southern Blot Analysis About three grams of young leaf were collected and ground with liquid nitrogen into a very fine powder. The DNA was isolated according to the procedure as described in Dellaporta et al., 1983, and purified by phenol-chloroform extraction. Approximately 5 µg of ECoRI and HindIII digested DNA from each line was used to make blot for Southern analysis. The ECL™ direct nucleic acid labeling and detection system (Amersham, USA) was used for analysis.

The lactoferrin gene copy number was estimated to be from about 1 to about 10 as determined by Southern blot hybridization using EcoRI and HindIII digested genomic DNA. The API164-12-1 (R0) transgenic plant line was subjected to Southern analysis together with ten Western blot positive, field grown R1 lines. A typical Southern blot shows that there are at least three fragments above the original plasmid derived plant transformation unit (3156 bp). All the LF inserts appear to be inherited from the original R0 transgenic plant event to R5 generation.

B. Protein Isolation and Western Blot

Rice seeds were ground with 1 ml of 0.35 N NaCl in phosphate buffer saline (PBS), pH 7.4 using an ice-cold mortar and pestle and the resulting homogenate was centrifuged at 15000 rpm for 15 min at 4° C. The supernatant was used as a protein extract and about 1/25 or 1/50 of the salt soluble content was loaded onto a 10% pre cast gel (Novex, USA) and electrophoresis was carried according to the manufacturer's instructions. For total protein detection, the polyacrylamide gel was stained with 0.1% Coomassie brilliant blue R-250

(dissolved in 45% methanol and 10% glacial acetic acid) for at least three hours and destained with 45% methanol and 10% glacial acetic acid until the desired background was achieved.

For Western blot analysis, SDS-PAGE gels were electroblotted onto a 0.45 µm nitrocellulose membrane with a MINI TRANS-BLOT™ Electrophoretic Transfer Cell System (Bio-Rad, USA) and subsequently subjected to immuno-blotting analysis. The blot was blocked with 5% non-fat dry milk in PBS for at least two hours followed by three washes with PBS for 10 minutes each. The primary rabbit polyclonal antibody against hLF (Daka A/S, Denmark) was diluted at 1:2500 in the blocking buffer and the blot was incubated in the solution for one hour. The blot was washed with PBS for three times with 10 minutes each. The secondary goat anti-rabbit IgG (H+L)-alkaline phosphatase conjugated (Bio-Rad, USA) was diluted in the blocking buffer at 1:5000 ratio. The membrane was incubated in the secondary antibody solution for one hour and followed by three washes with PBS. Color development was initiated by adding the substrate system BCIP-NBT (Sigma, USA) and the process was stopped by rinsing the blot with H2O once the desirable intensity of the bands was achieved.

One hundred eight (108) R0 plants were grown to maturity, seeds were harvested from 56 fertile plants and individual seeds analyzed by Western blot to detect the expression of rLF. Coomassie blue staining was carried out to compare the mobility of rLF with native human lactoferrin (hLF) (FIG. 9), with 40 µg of total protein loaded onto each lane, along with 40 ng of native purified hLF per lane as the positive control. Estimation of total rLF by ELISA indicated that from 93 µg to 130 µg rLF was expressed in transformed rice seeds. A typical Western blot analysis (FIG. 10) illustrates that both rLF and native hLF migrate at approximately the same rate with the molecular weight about 80 kDa, consistent with that determined by other researchers (Wang et al., 1984).

C. Protein Purification

Rice seeds from R2 homozygous generation were dehusked and milled to flour conventionally. Recombinant lactoferrin was extracted by mixing the rice flour with 0.35 N NaCl in PBS at 100 g/l at room temperature for two hours. The resulting mixture was centrifuged at 15,000 rpm for one hour at 4° C. The collected supernatant was subjected to the following steps of filtration before loading onto a SEPHAROSE™ column. First, the supernatant was run through a few layers of cheesecloth. Then the filtrate was passed sequentially through an 8 µm paper, 1 µm paper and a 0.25 µm nitrocellulose membrane. The clear protein solution was loaded onto a ConA SEPHAROSE™ column (Pharmacia, XK 26) which had been equilibrated with 0.5 N NaCl in 20 mM Tris, pH 7.4 (binding buffer) at a flow rate at 4 ml/min. After the loading was complete, the column was washed with binding buffer until the baseline at A280 nm was achieved. Lactoferrin was eluted with 0.1N mannoside in the binding buffer. Fractions containing lactoferrin were pooled and loaded onto a second column SP-SEPHAROSE™ (Bio-Rad, USA) which has been equilibrated with 0.4 N NaCl in 50 mM sodium phosphate, pH 8.0 (binding buffer B) at the flow rate 4 ml/min. Then the column was washed with the binding buffer B until the baseline at A280 nm was obtained. Lactoferrin was eluted by 1 N NaCl in 50 mM sodium phosphate, pH 8.0 and the fractions containing LF were pooled and dialyzed against PBS. Finally the purity of LF was assessed by SDS-PAGE and stored at −80° C.

In another embodiment, recombinant human lactoferrin (rHLF) was extracted by mixing rice flour with 0.35 M NaCl in PBS at 75 g/L at room temperature for 2.5 hours. The extract was passed through six layers of cheesecloth before centrifugation (10,000 g for 1 hour at 4° C.). The supernatant was recovered and the NaCl concentration was adjusted to 0.4 M (pH 8.0). After a second centrifugation at 10,000 g for 10 minutes at 4° C., the supernatant was collected and filtered through 0.45 µm nitrocellulose membrane. The filtrate was loaded onto a SP-SEPHAROSE™ column (Bio-Rad, Hercules, Calif.) which had been equilibrated with 0.4 M NaCl in 50 mM sodium phosphate, pH 8.0 (binding buffer) at a flow rate of 4 ml/min. The column was washed with the binding buffer until baseline A280 was obtained. Lactoferrin was eluted by a linear gradient and dialyzed against PBS. The purified rHLF was analyzed by SDS-PAGE and stored at −80° C.

D. Enzyme Linked Immunosorbant Assay (ELISA)

ELISA was conducted using seed extracts, isolated as described above, with total protein assayed using the Bradford method (Bradford, M., 1976). The ELISA was based on a typical sandwich format generally known in the art. Briefly, 96 well plates were coated with rabbit anti-human lactoferrin antibody (Daka A/S, Denmark), then rLF and control samples were added to individual wells of the plate and incubated for 1 hour at 35° C. Rabbit anti-human lactoferrin horseradish peroxidase conjugate (Biodesign, USA) was then added to each well and incubated for 1 hour at 35° C., followed by addition of the tetramethylbenzidine substrate (Sigma, USA) and incubation for 3 minutes at room temperature. The reaction was stopped by adding 1N H2SO4 to each well. The plates were read at dual wavelengths of 450 and 650 nm in a Microplate Reader (Bio-Rad, model 3550) and the data was processed by using MICROPLATE MANAGER™ III (Bio-Rad). The results of an analysis of 10 homozygous selected lines showed that from 93 µg to 130 µg rLF was expressed per seed.

E. Selection of Plants for Advance Generations

At least 20-40 seeds from 11 independent lines were analyzed. Individual R1 seeds were cut into half and endospermic halves were subjected to analysis by Western blot with the positive corresponding embryonic halves germinated on 3% sucrose medium with 0.7% agar. The seedlings were transplanted to the field for R1 generation. Out of 11 individual lines, 3 lines were expressed. A total of 38 plants were grown in the field derived from the 3 expressed mother lines. Based on the agronomic character (Table 5) of those 38 plants, 28 plants were selected.

It was observed that all the Western positive R1 seeds were opaque to pinkish in color in comparison to control seeds, so this criterion was applied in screening the R2 seeds. Mature R2 seeds were harvested at maturity and dehusked. The pinkish R2 seeds were confirmed by Western dot blot and ELISA as expressing rLF (data not presented). Finally 10 homozygous R2 lines were selected and grown in the field in order to advance the generation.

TABLE 5

Comparison Of Phenotypic Characteristics Of Native TP-309 And Transformed TP-309 Rice Seeds

| Source | Effective tiller | Blank grain (%) | 1000 seed weight (g) | µg of rLF/seed |
|---|---|---|---|---|
| TP-309 | 43 | 5.0 | 25 | |
| Homozygous transgenic lines | 42 | 19.7 | 20.2 | 125 |

During R2 and R3 generation the percentage of blank seeds was higher in homozygous transgenic lines than in the non-transgenic control. This affected the 1000 seed weight. However, in the R4 generation no significant differences in phenotypic character were observed in homozygous transgenic lines when compared to non-transformed TP309 (Table 5).

F. Attributes of Recombinant Human Lactoferrin Produced in Rice

Physical characterization of the rLF showed there was no significant difference between the rLF and a commercially available purified form of hLF based on N-terminal amino acid sequencing, and physical characteristics of rLF such as molecular weight as determined by MALDI-MS, HPLC profile of which showed a comparable peptide map, pH dependent iron release and bacteriostatic activity, using the analyses described below.

(i). N-Terminal Amino Acid Sequencing

Purified rLF from rice seeds was resolved by 10% SDS-PAGE, followed by electroblotting to PVDF membrane (Bio-Rad, USA). The target band was identified by staining the membrane with 0.1% Coomassie brilliant blue R-250 in 40% methanol and 1% glacial acetic acid for 1 minute. The stained PVDF membrane was immediately destained in 50% methanol until the band is clearly visible. The blot was thoroughly washed with ddH2O and air dried. Finally this sample was sent to the Protein Structure Laboratory in University of California at Davis (CA, USA) for sequencing analysis.

to the manufacturer' instruction. About 30 μg of purified rLF was loaded and the running condition was 100 V for 50 minutes and 200 V for 20 minutes. The gel was then fixed in 136 mM sulphosalicylic acid and 11.5% TCA for 30 minutes, stained in 0.1% Coomassie brilliant blue R-250, 40% ethanol, 10% glacial acetic acid for 30 minutes and destained in a solution containing 25% ethanol and 8% acetic acid.

(iv). Comparison of Physical Characteristics of rLF with Native hLF

The HPLC profile of native and rLF showed a comparable peptide map. This confirmed that LF from the two sources have an identical amino acid sequence (data not presented). Additional comparisons confirm that human lactoferrrin produced in transgenic rice closely resembles native human lactoferrin, as evidenced by (1) the N-terminal sequence of purified rLF from homozygous R2 seeds and hLF (Dakao A/S, Denmark), which were shown to be identical (Table 6); (2) the isoelectric point (pI) of native and rice seed derived LF which is the same, indicating that they have similar surface charges (Table 6); (3) the pH dependent iron release of rLF which was shown to be closely related to that of native hLF (FIG. 12 and see section vii of Example 5); and (4) the bacteriostatic activity of rHLf which was shown to be similar to that of native human lactoferrin (nHLf) on enteropathogenic E. coli (EPEC; FIG. 11) and confirmed the presence of active recombinant LF in extracts derived from transformed rice seeds (see section ix of Example 5).

TABLE 6

Physical characterization data for human (hLF) and rice seed derived recombinant lactoferrin (rLF)

| LF source | Size (kDa) | N-terminal sequence | pI | Glucosy-lated | Sugar content (%) |
|---|---|---|---|---|---|
| hLF | 80.6 | Gly Arg Arg Arg Arg Ser Val Gln Trp Cys Ala (SEQ ID NO: 34) | 8.2 | YES | 5.5 |
| rLF | 78.5 | Gly Arg Arg Arg Arg Ser Val Gln Trp ( ) Ala (SEQ ID NO: 35) | 8.2 | YES | 2.9 |

(ii). Detection of Glycosylation and Determination of Sugar Content

Glycosylation of the recombinant human lactoferrin produced in rice was analyzed by an immunoblot kit for glycoprotein detection (Bio-Rad, USA) per instructions from the manufacturer. An increase of molecular weight of lactoferrin due to carbohydrate content was determined by Matrix Assisted Laser Desorption Ionization-Mass spectrometry (MALDI-MS) (PE Applied Biosystems, Voyager System).

Recombinant lactoferrin produced in rice is glycosylated as evident from the binding to Con A resin, the positive staining by glycoprotein detection kit as well as the larger detected mass as compared to the calculated mass (76.2 kDa) based on the peptide backbone. MALDI-MS showed that seed derived recombinant lactoferrin has molecular weight of 78.5 kD while human milk lactoferrin is 80.6 kDa (Table 6). The difference could be due to the lesser degree of glycosylation in the rice seed-derived lactoferrin. Analysis shows that the purified rHLF contains xylose but lacks sialic acid, which is consistent with plant post-translational modification patterns (Matsumoto et al., 1995).

(iii). Determination of Isoelectric Point of Lactoferrin

Reverse isoelectric focusing (IEF) gel electrophoresis was carried out with a precast Novex IEF gel, pH 3-10 according (v). Iron Content and Nutrient Value Determination of Rice Seeds The iron content of R2 homozygous seeds was determined. Two grams of dry mature seeds from each transformed and non-transformed line were weighed and wet-ashed with HNO3 and H2O2 solution at 110° C. (Goto et al., 1999). The ash was dissolved in 1N HCl solution. The iron content was then measured by absorbance of Fe—O-phenanthrolin at 510 nm, using a Sigma kit (Sigma, USA) per instructions of manufacturer.

The different values of nutrient facts of homozygous transgenic seeds and non transgenic seeds were measured by standard procedure at A & L Western Agricultural Laboratories (Modesto, Calif., USA).

A comparative analysis of transgenic lactoferrrin-expressing rice seeds with non transformed native Teipei-309 showed that there is no significant difference between transformed and non transformed seeds in nutrient value with the exception that the concentration of iron is 50% greater (Table 7). The increased level of iron may be the reason for the opaqueness and pink coloration of the rLF expressing transgenic rice seeds.

In another embodiment, 0.2 grams of dried, dehusked grains expressing rHLF were wet-ashed with concentrated HNO3 for two days and dissolved in 5 ml of DDI H2O. The iron contents of the samples were measured by flame atomic absorption spectrophotometry (Thermo Jarrel Ash SH4000, Franklin, Mass.). NIST liver was analyzed concurrently to verify the accuracy of the standard curve.

The iron content of transgenic rice grains was more than twice that of non-transformed TP309 grains, while there were no significant differences in other tested nutrition factors between transformed and non-transformed grains (Table 8). This suggests that groups ingesting transgenic rice with rHLF will increase the iron intake.

The transgenic grains with increased iron content were opaque-pinkish in color. The opaque-pinkish color was observed inside as well as outside the rice endosperm. This opaque-pinkish color, segregated in Mendelian fashion, was linked with expression of rHLF and was inherited through the R4 generation.

There was no difference noticed during the seed germination of transgenic seeds, the phenotype of R2 R3 and R4 plants was vigorous and the seed yield was similar to that of non-transgenic Taipei-309 control plants (data not shown).

The results showed that iron release was similar for both hLF and rLF. Iron release began around pH 4 and was completed around pH 2 (FIG. 12). The iron binding was reversible since iron-desaturated rLF was re-saturated by raising the pH to 7 (data not shown). The similarity in pH dependent iron release of rLF to that of the hLF standard demonstrated that rLF is able to adapt the appropriate tertiary structure for proper iron binding and release (Salmon, Legrand et al. 1997).

(viii). Binding and Uptake by Caco-2 Cells 50,000 Caco-2 cells/well were seeded and grown in Minimum Essential Medium (GIBCO, Rockville, Md.) containing 10% fetal bovine serum in 24 or 48 well tissue culture plates for 3 weeks. For binding studies, Caco-2 cells were incubated with varying concentrations (0-2 µM) of 125I-HLf in the presence or absence of 100-fold excess of unlabeled nHLf for 2 hours at 4° C. and cells were washed 5 times with ice-cold PBS. Cells were solubilized with 0.5 ml of 0.1% SDS and radioactivity was quantified in a gamma counter. For uptake studies, 0.4 µM of 125I-HLf was incubated with Caco-2 cells for 0 to 24 hours at 37° C. and cells were washed, dissociated

TABLE 7

Comparison of Nutrition Value (in mg) Per 100 Gram of Non Transformed and Transformed Rice Seeds

| Source | Carbohydrate | Protein | Fat | Ca | K | Na | Fe | Water | Calories |
|---|---|---|---|---|---|---|---|---|---|
| TP309 | 76.0 | 8.7 | 2.4 | 9 | 370 | <10 | 0.8 | 11.3 | 369 |
| Homozygous transformed lines | 75.7 | 8.7 | 2.2 | 8 | 330 | <10 | 1.2 | 11.8 | 367 |

TABLE 8

Comparison of Mineral Contents (in µg) Per Gram of rHLF-Transformed and Non-Transformed Rice Grains

| Source | Cu | Fe | Mn | Zn |
|---|---|---|---|---|
| Non-transformed | 2.9 | 8.7 | 33.1 | 20.8 |
| Transformed | 4.7 | 19.2 | 17.7 | 28.7 |

(vi). Tissue Specificity and Stability of rLF

An endosperm specific rice glutelin promoter was used to express recombinant lactoferrin in maturing or matured seeds. To confirm the tissue specificity of the expressed lactoferrin, protein was extracted from root, shoot, leaf beside mature seed and subjected to Western blot and the results indicated that there was no detectable expression of rLF except in the seed/endosperm (FIG. 10). Furthermore, the presence of rLF in 5 day old germinated seeds showed the stability of stored rLF within the plant cell during germination.

(vii). Iron Saturation and pH Dependent Iron Release

Lactoferrin was incubated with 2M excess ferric iron (FeCl3:NTA=1:4) and sodium bicarbonate (Fe:HCO3=1:1) for 2 h at room temperature. Excess free iron was removed by using a PD-10 desalting column (Pharmacia, USA) and the iron saturation level was determined by the A280/A456 ratio. Both native hLF and rLF were completely saturated by iron. Holo hLF was incubated in buffers with a pH between 2 and 7.4, at room temperature for 24 h. Free iron released from hLF was removed and the iron saturation level was determined by A280/A456 ratio.

by the same way as in the binding study. 0.5 ml of 24% TCA solution was added to the dissociated cells and free iodine was removed by the centrifugation. Free and protein-bound $^{125}I$ were quantified separately to evaluate how much of HLf was degraded in the cells. Receptor-binding of rHLf to the human intestinal Caco-2 cell line was saturable and specific, indicating that rHLf bound to the Lf receptor. The binding constant was similar for rHLf and nHLf, but the number of binding sites was slightly higher for rHLf, which may be due to the difference in glycosylation. Uptake of HLf by Caco-2 cells was identical for rHLf and nHLf.

(ix). In Vitro Digestion: Effect on Antimicrobial Activity and Binding/Uptake to Caco-2 Cells Lactoferrin is known to inhibit the growth of a variety of bacterial species based on its iron chelation and direct bactericidal properties. The anti-microbial effect of rLF extracted from rice seeds was tested following treatment using an in vitro digestion model with an enzymatic system containing pepsin (an enzyme active in stomach) and pancreatin (an enzyme active in deodenum).

LF proteins were dissolved in PBS at 1 mg/ml, and either left untreated, pepsin treated (0.08 mg/ml at 37° C. for 30 min), or pepsin/pancreatin treated (0.016 mg/ml at 37° C. for 30 min). LF proteins were sterilized by passing through a membrane filter with a pore size of 0.2 µm [Rudloff, 1992]. The filter sterilized LF (0.5 µg/ml) was incubated with 104 colony forming unit (CFU) enteropathogenic E. coli (EPEC)/ µl in 100 µl sterile synthetic broth (1.7%: AOAC) containing 0.1% dextrose and 0.4 ppm ferrous sulfate at 37° C. for 12 h and colony forming units (CFU) were determined.

Starting with an enteropathogenic E. coli (EPEC) concentration of $10^4$ CFU (colony forming units), the untreated samples of rLF reached up to $10^{6.5}$ CFU after 12 h of incubation at 37° C. in comparison to hLF, which produced up to $10^6$ CFU. An in vitro digestion model using an enzymatic system containing pepsin (enzyme active in stomach) and pancreatin (enzyme active in deodenum) with moderate shaking to imitate the transit of protein through infant gut [Rudloff, 1992] was used. rLf and nHLf were treated with active pepsin and pancreatic enzymes and exposed to $10^4$ CFU EPEC cells for 12 h at 37° C. (FIG. 11). Both the native human lactoferrin standard (nHLf) and the recombinant rice-derived lactoferrin (rLf) remained active in inhibiting growth of enteropathogenic E. coli, indicating that both nHLf and rHLf are resistant to protease digestion.

SDS-PAGE and ELISA revealed that nHLf and rHLf resist digestion by pepsin (at pH 3.8) and pancreatin, whereas human serum albumin is completely digested after in vitro digestion. Western blots revealed that immunoreactivity was also maintained after digestion. Although some smaller molecules were generated during digestion of HLf, most of the immunologically detectable HU retained its intact size. More than 50% of rHLf and nHLf was immunologically detectable by ELISA, but $^{125}$I-HLf was around 40% and $^{59}$Fe-HLf was only 20% detectable, indicating that ELISA detects small peptide fragments of HLf, which are removed by the PD-10 column and that about 50-60% of Fe was released from detectable HLf after in vitro digestion. The iron-holding capacity was not significantly different.

The dissociation constant (Kd) and the number of binding sites for HLf to its receptor were determined from the binding study. Both Kd and the number of binding sites were not significantly different between nHLf and rHLf after in vitro digestion (FIG. 13A and 13B). Digestion did not appear to affect on the Kd but made the number of binding sites much lower. Total Lf uptake was not significantly different between nHLf and rHLf after in vitro digestion (FIG. 13C), though uptake was about one third when compared with undigested nHLf. Total iron uptake from nHLf was twice as high as that from rHLf. Percent degradation of HLf was similar regardless of digestion or not, and the native or recombinant form (FIG. 13D).

(x). Thermal Stability: Effect on Antimicrobial Activity and Binding/Uptake to Caco-2 Cells 1.0 mg/ml of holo-HLf in PBS was treated by the following conditions: (a) 62° C. for 15 minutes, (b) 72° C. for 20 seconds, (c) 85° C. for 3 minutes, or (d) 100° C. for 8 seconds. Survival ratio of HLf determined by ELISA were more than 90% following treatment at 62° C. for 15 minutes, at 72° C. for 20 seconds, or at 85° C. for 3 minutes, but it was considerably lower after 100° C. for 8 seconds. This high temperature precipitated both types of HLf and only 10% of HLf was detectable by ELISA. More than 80% of iron was still bound to both rHLf and nHLf after all thermal treatments with the exception of 100° C. for 8 sec. In 10% of survived HLf after 100° C. for 8 sec, the iron saturation level of nHLf was above 80% whereas that of rHLf was only about 40%.

SDS-PAGE and Western blots revealed no difference in immunoreactivity between nHLf and rHLf at 62° C. for 15 minutes, at 72° C. for 20 seconds, and at 85° C. for 3 minutes, but at 100° C. for 8 seconds, rHLf almost completely lost its immunological activity, whereas nHLf still maintained detectable immunoreactivity.

There was no significant difference in anti-microbial activity between nHLf and rHLf after heat-treatment. Anti-microbial activity of HU was not affected by treatment at either 62° C. for 15 min, 72° C. for 20 sec or 85° C. for 3 min.

The Kd and the number of binding site for nHLf and rHLf were not significantly different at 62° C. and 72° C. though there is a trend that nHLf is somewhat lower Kd and binding sites than rHLf. As the temperature was increased (such as 85° C. and 100° C.), more rHLf bound to Caco-2 cells, most likely by non-specific binding due to more rHLf being denatured than nHLf. Uptake properties were similar for nHLf and rHLf even in the group treated at 100° C. where uptake of both types of HLf was highest among all the thermal treatments. Free iodine levels in the cells were also evaluated since it reflects degradation of HLf. About 20% of HLf was degraded in the untreated sample. There was no significant difference between nHLf and rHLf. Interestingly, samples treated at 100° C. were degraded twice as much as untreated samples of nHLf and rHLf, which may indicate that denaturation of HLf caused by heat treatment will make the protein more susceptible to proteases in the cells.

(xi). pH Stability: Effect on Antimicrobial Activity and Binding/Uptake to Caco-2 Cells 1.0 mg/ml of holo-HLf in PBS was adjusted to pH 2, 4, 6, or 7.4 by the addition of 1 M HCl and incubated for 1 h at room temperature. The pH was then adjusted to 7.0 with 1 M NaHCO3. Free iron released from HLf, was removed by a desalting column.

After low pH treatment, 100% of both nHLf and rHLf survived. The iron-holding capacity was maintained in all samples and the iron saturation level was above 95%. SDS-PAGE and Western blots revealed that there was no difference between nHLf and rHLf for any of the treatments. A slightly smaller immunoreactive molecule (~70 kD) was detected after exposure of nHLf to pH 2 and 4 and of rHLf to pH 2.

Antimicrobial activities of nHLf and rHLf were stable after exposure to low pH in the range of pH 2.0 to 7.4. As the pH was lowered, the activity of rHLf appeared to be higher and constant, whereas nHLf did not show any pH dependency.

Kd and the number of binding sites for nHLf were not significantly different from those for rHLf but a trend was always lower for nHLf within the range of pH 2.0 to 7.4, which is similar to control and thermal treatment samples. The Kd and the number of binding sites for nHLf and rHLf were unaffected by pH treatment down to 2.0 for 1 hour. Uptake properties were similar for nHLf and rHLf in the pH range of 2.0 to 7.4. Degradation of HLf in Caco-2 cells was also evaluated and there was no significant difference between nHLf and rHLf.

EXAMPLE 6

Generation and Characterization of Recombinant Human α-1-Antitrypsin (AAT) Produced by Transgenic Rice Plants A. Construction and Expression of Human AAT in Rice Plants The construction and purification of functional recombinant human AAT were carried out as exemplified in previous examples. Briefly, codon-optimized AAT gene was cloned into an pAPI145 that contains the rice Gt1 promoter, Gt1 signal peptide, and Nos terminator, pAPI241 that contains Glb promoter, Glb signal peptide, and Nos terminator, and API280 that contains Bx7 promoter, Bx7 signal peptide, and Nos terminator, as exemplified in Example 1. The resulting plasmids were named pAPI250, API255 and pAPI282, respectively (FIG. 14). Transgenic plants expressing AAT were generated as above, and plant-generated recombinant AAT was characterized. To express AAT in culture cells, codon-optimized AAT gene was cloned into an expression cassette that contains the rice RAmy3D promoter, signal peptide, and terminator. Recombinant AAT expression was induced and secreted to the culture medium under the sugar starvation condition. Purification of rAAT was achieved through a scheme that consisted of an affinity column (Con A), anion exchange column (DEAE), and a hydrophobic interaction column (Octyl).

B. SDS-Polyacrylamide Gel Electrophoresis (SDS-PAGE)

AAT samples were ground with PBS with mortar and pestle. The resulting extract was spun and 20 microliters of supernatant loaded into a precast SDS-PAGE gel. The AAT protein was clearly visualized with Coomassie brilliant blue staining (FIG. 15).

C. Western Blot Analysis

For immunoblotting analysis, gels were electroblotted to a 0.45 μm nitrocellulose membrane with a MINI TRANS-BLOT™ Electrophoretic Transfer cell (Bio-Rad, USA) and subsequently subjected to immunoblotting analysis. Blots were blocked with 5% non-fat dry milk in PBS, pH 7.4 for at least two hours followed by three washes with PBS, pH 7.4 for 10 minutes each. The primary rabbit polyclonal antibody against human alpha-1-antitrypsin (Dako A/S, Denmark) was diluted to 1:2500 in the blocking buffer and the blot was incubated for at least one hour. The blot was then washed as described previously. The secondary antibody, goat anti-rabbit IgG (H+L)-alkaline phosphatase conjugated (Bio-Rad), was diluted in the blocking buffer at a dilution of 1:4000. The membrane was then incubated in the secondary antibody solution for one hour and followed by the same wash process. Color development was initiated by adding the substrate BCIP/NBT from Sigma.

The western result showed that AAT protein is clearly visualized and confirmed that AAT expressed and deposited in transgenic rice grain, has a molecular weight that is somewhat smaller than that of native AAT (FIG. 16).

D. ELISA

Standards for this assay ranged from 1.25-20 ng/mL of AAT (Athena) diluted in PBST. Nunc Immuno-plate MAX-ISORP™ 96-well plates (Nunc, Denmark) were coated for 16 h at 4° C. by a 1:10,000 dilution of rabbit anti-human AAT in 0.05 M sodium bicarbonate, pH 9.6. The plates were washed 3 times with PBST (PBS, pH=7.4, 0.05% TWEEN-20) and subsequently incubated with sample for 1 h at room temperature while rocking. The plates were washed again 3 times with PBST, followed by incubation with a 1:50,000 dilution of goat anti-human AAT conjugated to HRP for 1 h at room temperature. The plates were washed 3 times with PBST, and bound antibody was detected by the HRP/hydrogen peroxide catalyzed reaction of TMB. The reaction was stopped with 2 M sulfuric acid, and the plates were read on a microtiter plate reader at 450 nm, using 620 nm as a reference filter.

Recombinant AAT is 2.1 times more immunoreactive, when comparing equal concentrations as determined by the Lowry assay.

E. AAT Activity Assay

AAT activity was analyzed using a modified method published by Travis and Johnson (1981). In 96-well microtiter plates, 60 μL samples diluted in Tris buffer, (0.2 M Tris, pH 8.0) were added. In each well, 60 μL of elastase [0.01 mg/mL porcine pancreatic elastase (PPE) in Tris buffer] was also added. The plate was rocked for 5 min at room temperature to allow any available AAT to bind to the elastase. Another 120 μL of substrate solution (10 M N-Succinyl-AAA-p-nitroanilide in DMSO diluted in Tris buffer to give 0.33 M N-Succinyl-AAA-p-nitroanilide) was added, and the plate was rocked for 1-2 min at room temperature. The plate was immediately read on a microtiter plate at 405 nm. The plate was read again after 5 min, and the change in absorbance was calculated. AAT activity was determined using linear regression from a standard curve. The results show that AAT protein produced in rice grain has similar bioactivity as that of native AAT.

F. Band Shift Assay

The unique property of the covalent-linked complex formed between AAT and PPE permits an analysis of the activity of AAT by SDS-PAGE. Briefly, 20 μl of tested samples containing AAT from the screening or purification processes was incubated with 100 ng PPE at 37° C. for 15 minutes. Five μl of SDS-loading dye was added and the reaction mixture boiled for five minutes. The sample was then centrifuged and kept on ice until loaded onto a 10% precast SDS-PAGE gel. The resulting gel was stained with 0.1% Coomassie brilliant blue R-250 as described below. For immunodetection, a western blot analysis was carried as described above. Again the band shift assay indicated that AAT protein produced in rice grain has similar bioactivity as that of native AAT (FIG. 17A and 17B).

G. In vitro digestion. The digestion was carried out using a modified method of Rudloff and Lonnerdal (1992) was used after some modifications. Native and recombinant AAT were diluted in PBS or formula to 0.5 mg/mL. Hydrochloric acid (1 M) was added to all samples to adjust the pH 3, 4, and 5, then 2.5 μL of 2% pepsin in 0.01 M HCl (3,100 U/mg solid) were added and all samples were placed in a shaking incubator for 30 or 60 min at 37° C. The pH was restored by drop-wise addition of 1 M NaHCO3, and 2.5 μL of 0.4% pancreatin in 0.1 M NaHCO3 were added. Samples were incubated for 1 or 2 hours at 37° C., and the reaction was halted by dilution 1:2 in sample buffer and boiling for 3 min. For samples subjected to pepsin digestion only, boiling was unnecessary since the pepsin was inactivated when the pH was raised above pH 6 with NaHCO3 (Piper and Fenton, 1965). The enzyme: substrate ratio was approximately 1:20 for samples in buffer only and about 1:600 for samples in formula.

A significant amount of recombinant and native AAT survived the in vitro digestion, and both forms were more resistant to degradation than human serum albumin. Digestion with pepsin at pH 4 shows that 65% of recombinant AAT is detectable by ELISA after digestion, which is similar to 67% of native AAT surviving. The trypsin assay shows that much of the inhibitory properties of both forms are still intact, and the activity assay reveals that 63% and 59% of the activity of native and recombinant AAT remains, respectively. When exposed to both pepsin and pancreatin in buffer, native AAT resisted degradation when the pH of the pepsin incubation was pH 4 or higher. Under this condition, the recombinant form was less resistant, although a large part remained after pepsin digestion at pH 5 and pancreatin digestion. At pH 4, more of the recombinant protein was degraded, either due to pepsin activity or pH instability. AAT activity could not be determined after digestion by pepsin and pancreatin because of the inactivation of pancreatin by boiling which also inactivates AAT activity. In formula, both forms appeared to be equally resistant to degradation. While both native and recombinant AAT were still present after pepsin digestion at pH 5 followed by pancreatin digestion, bands at about 33 kD (casein) are faint or missing. It is possible that other proteins in formula are preferentially cleaved, reducing the amount of AAT being digested.

H. Thermal Stability of Recombinant Human ATT

Both native and recombinant human AAT were diluted in phosphate buffered saline (PBS) or infant formula (Enfamil with Iron, Mead Johnson, Evansville, Ill.) to a concentration of 0.1 mg/mL. Samples, 100 μL in capped, 10×75 mm glass tubes, were treated as follows: 60° C. for 15 min, 72° C. for 20 sec, 85° C. for 3 min, and 137° C. (temperature of oil bath) for 20 sec. The samples were allowed to cool to room temperature after heat treatment. For formula samples with bile extract added, 2.5 μL of 12% porcine bile extract (Sigma) were added, then vortexed quickly, incubated at 37° C. for 10 min, and vortexed again. All samples were diluted 1:10 in PBS and transferred to 1.5 mL tubes. Formula samples were centrifuged at 15,000 g for 20 min to remove the insoluble fraction, and the supernatant was withdrawn after skimming off the fat. All samples were subsequently transferred to 1.5 mL tubes and analyzed.

The thermal stability of native AAT exceeded that of the recombinant form in buffer, but the recombinant AAT retained significant stability under most conditions. When heated in buffer only, SDS-PAGE and Western blots show that the two forms of AAT have similar structural stability. While the ELISA data show that the recombinant protein is less stable at the higher temperatures, the recombinant protein is similar to the native form under the other conditions. However, the functional stability of the recombinant protein may be affected. The thermal stability assay shows that the recombinant protein lost functional ability at several of the heat conditions, whereas the native protein was functional at all heat conditions except for at 62° C. for 15 minutes. While the elastase-inhibiting properties of native AAT were about 90% after all heat treatments, 62 and 51% of the recombinant protein's activity remained after 85° C., 3 minutes, and 137° C., 20 seconds, respectively.

The heat treatments of native and recombinant AAT in formula affected the detection of the proteins, but the addition of bile extract following heat treatment restored antibody recognition of the recombinant form. While the Western blot data show less detectable protein only at 85° C., 3 min for the native AAT and at 72° C., 20 sec and 137° C., 20 sec for the recombinant AAT, the ELISA data shows less than 20% protein detected for both forms and for all heat conditions. When bile extracts were added to the heated formula samples, the ELISA data for the recombinant form showed that more than 50% was still detectable after heat treatment. The bile extract did affect detection of the native form by ELISA for most of the heat treatments. The Western blots corroborated the ELISA data and showed that the bile extract may dissociate the recombinant AAT from other formula proteins, but it is not effective for native AAT at the higher temperatures.

I. pH Stability of Human ATT

Native and recombinant AAT were diluted in PBS or formula to 0.1 mg/mL. The sample volume was 1 mL, and the pH of each sample was adjusted drop-wise with 1 M HCl. The range of pHs tested was from pH 2 to 8 for the samples in PBS and pH 2 to 7 for samples in formula. After a 1 hour incubation at room temperature, the pH was restored to pH 7 with 1 M NaHCO3. Formula samples were centrifuged as exemplified in above Thermal Stability section.

Both native and recombinant AAT appear resistant to low pH conditions in both PBS and formula. There were no differences between treatment groups and controls for pH 3 through 7, and controls or between the native and recombinant AAT according to SDS-PAGE, Western blots, and trypsin assay. However, the elastase assay and ELISA data show that recombinant AAT is more affected by acidic conditions than the native form. In PBS, native AAT was more than 95% intact, while about 60-80% of the recombinant AAT activity was intact. Infant formula may have a stabilizing effect on the recombinant protein, since it was found to be as stable as the native form according to ELISA and the Western blot.

Native and recombinant AAT can withstand acidic and digestive conditions as assessed by SDS-PAGE, Western blots, ELISA and activity assay. Native AAT regains much of its structural and functional stability after treatment at acidic conditions followed by neutralization, whereas recombinant AAT shows some loss of activity at a wide pH range, which may reflect a different glycosylation pattern. The conditions of the infant-modeled digestion, pH 5 during pepsin treatment, are not ideal for pepsin, which normally possesses full activity at pH 2. AAT has been detected in human infant feces, which supports the notion that it is capable of surviving digestion in vivo, particularly during the first three months of the infant's life. This evidence also supports the validity of the in vitro digestion system. It is likely that AAT possesses enough resistance to acidic and digestive conditions to allow a significant amount to survive and affect the digestion process.

Recombinant AAT remained functionally intact after being exposed to low pH, in vitro digestion, and several types of heat treatment. It is therefore possible that recombinant AAT may be added to infant formula, can tolerate some processing conditions, and remain intact in the gastrointestinal tract of infants. Thus, recombinant AAT may help protect other physiologically active proteins, such as lactoferrin and lysozyme, which also may be added in recombinant forms in the gut of formula-fed infants. In conclusion, addition of recombinant AAT together with other recombinant proteins may enhance their bioactivity and make the formula more similar to human milk.

EXAMPLE 7

Generation and Characterization of Recombinant Proteins Produced by Transgenic Rice Plants A. Generation of Recombinant Antibodies Recombinant antibodies have been expressed in transgenic plants (for examples, see Peeters et al., 2001; Giddings et al., 2000; Larrick et al., 1998). However, expression and production of recombinant antibodies in the seeds of transgenic plants have certain advantages. The production of high levels of antibodies in grains, for example rice grains, provides distinct advantage that food supplements may be prepared with little or no purification, and other advantages that are illustrated herein the patent application.

In one embodiment, an expression vector is constructed as illustrated in Example 1 that includes codon optimized nucleotide sequences encoding functional components of an antibody. For example, the components can be a heavy chain, a light chain, a linker region or a J chain and a secretory component. The expression vector may also include a promoter, a signal/target/transport sequence or sequences and a terminal sequence or sequences. Preferred promoter, signal/target/ transport sequence and terminal sequence are exemplified herein. For example, for expression of each functional component of an antibody in rice seeds, a codon-optimized component gene is operably linked to the rice endosperm specific glutelin (Gt1) promoter, a Gt1 signal peptide and Nos terminator to form a component expression vector.

Each component expression vector is introduced to rice cells and plants to generate antibody component-expressing transgenic rice cells and plants, as exemplified in Example 3. In one embodiment, the expression vectors containing antibody heavy chain, light chain, linker region or J chain, and a secretory component can be introduced individually. The plants expressing each individual component can be crossed to generate plants that express a functional antibody.

In another embodiment, the expression vectors containing functional components of an antibody can be introduced to the plant at the same time, using the transformation methods exemplified in Example 3, such as by co-bombardment. A plant that expresses functional antibody is selected for further propagation.

In another embodiment, the expression vector containing codon optimized nucleotide sequence encoding a single chain antibody is introduced to rice cells and plants to generate antibody expressing transgenic rice cells and plants, as exemplified in Example 3. The nucleotide sequence encoding a single chain antibody can be constructed as conventional in the art, for example Kortt et al., 2001, Maynard and Georgiou, 2000; Humphreys D P and Glover, 2001.

The plant-generated recombinant antibody can be isolated and purified as exemplified in the patent application.

D. Generation of Other Expression Plasmids

Other expression plasmids for use in transforming plants herein for the production of recombinant polypeptides in transgenic plants were made substantially as previously described. These plasmids are shown in FIGS. 21-31 and including API321 (FIG. 21), containing a Glb promoter, a Gt1 signal peptide, codon-optimized haptocorrin gene, Nos terminator, and an amipicillin resistance gene; API320 (FIG. 22) containing a Gt1 promoter, a Gt1 signal peptide, codon-optimized human haptocorrin gene, Nos terminator, and an amipicillin resistance gene; API292 (FIG. 23) containing a Glb promoter, a Glb signal peptide, kappa-casein gene, Nos terminator, and an amipicillin resistance gene; API297 (FIG. 24) containing a Gt1 promoter, a Gt1 signal peptide, a gene encoding mature kappa-casein polypeptide, Nos terminator, and an amipicillin resistance gene; API420 (FIG. 25) containing a Gt1 promoter, a Gt1 signal peptide, lactadherin gene, Nos terminator, and a kanamycin resistance gene; API418 (FIG. 26) containing a Gt1 promoter, a Gt1 signal peptide, lactoperoxidase gene minus the sequence encoding the propeptide, Nos terminator, and a kanamycin resistance gene; API416 (FIG. 27) containing a rice Gt1 promoter, a Gt1 signal peptide, codon-optimized lactoperoxidase gene, Nos terminator, and a kanamycin resistance gene; API230 (FIG. 28) containing a Bx7 promoter, a Gt1 signal peptide, codon-optimized lysozyme gene, Nos terminator, and an amipicillin resistance gene; API254 (FIG. 29A) containing a Glb promoter, a Glb signal peptide, lactoferrin gene, Nos terminator, and an amipicillin resistance gene; API264 (FIG. 29B) containing a Glb promoter, a Glb signal peptide, human lysozyme gene, Nos terminator, and an amipicillin resistance gene; API225 (FIG. 30) containing a GT3 promoter, a Gt1 signal peptide, codon-optimized lysozyme gene, Nos terminator, and an amipicillin resistance gene; and API229 (FIG. 31) containing a RP-6 promoter, a Gt1 signal peptide, codon-optimized lysozyme gene, Nos terminator, and an amipicillin resistance gene.

EXAMPLE 8

Co-transformation of Heterologous Polypeptide and Reb Gene in Transgenic Rice Plants A. Enhanced Lysozyme Expression in Transgenic Rice Seed Co-Transformed with Reb Codon-optimized human lysozyme gene was linked to Glb promoter and Glb signal peptide to generate plasmid Glb-Lys (API264) as shown in FIG. 29B, which was used to transform rice with or without Native-Reb, as previously described and as described in WO 01/83792. Normal plant phenotypes were obtained among transformants containing Glb-Lys alone or with Native-Reb. To determine the presence of Reb gene and Glb-Lys in the transgenic rice genome, one primer designed from vector sequence and another designed from the Reb gene 3' terminator were used to identify these lines. In this case, only the recombinant Reb gene was amplified. PCR analysis confirmed the presence of transgenes in the rice genome. Ten of 11 plants from independent transformation events contained both Reb and the lysozyme transgenes. The REB protein of immature seeds from five randomly selected transgenic lines was detected by Western blotting. The expression level of the REB protein in transgenic lines ranged from 25% to 71% higher than that in untransformed TP309. This demonstrated that the transgenic Reb gene was active in transgenic plants.

Seeds of confirmed transgenic rice plants were harvested at maturity, and the lysozyme activity was analyzed. As shown in FIG. 19, lysozyme expression in the seeds from 30 independent transformation events containing both the Native-Reg and the Glb-Lys ranged from 30.57 to 279.61 µg/mg TSP with an average of 125.75±68.65 µg/mg TSP. Seeds of 17 transgenic events containing the Glb-Lys gene alone expressed lysozyme in amounts ranging from 7 to 76 µg/mg TSP with an average of 33.95±20.55 µg/mg TSP. No lysozyme activity was detected in untransformed rice seeds. The results showed that the expression level of lysozyme increased an average of 3.7-fold when seeds were transgenic for both the Reb gene and Glb-Lys. Statistical analysis (t test) showed that the amount of lysozyme in seeds from the plants transgenic for the Reb gene and Glb-Lys is significantly higher than that in the plants transgenic for Gib-Lys alone ($p<0.001$).

B. Enhanced Human Lysozyme Expression in Transgenic Rice Seed Co-Transformed with Maize Transcriptional Factor, Prolamin-Box Binding Factor (PBF)

Three transcriptional factors were tested; rice endosperm bZIP protein (REB), Opaque2 (O2) and PBF. The transcriptional factors and human lysozyme gene under the control of rice glutelin 1 (Gt1) or globulin (Glb) promoter were co-bombarded into rice callus. Transgenic R1 grains carrying both genes were obtained. The effect of transcriptional factors on the expression of human lysozyme was monitored. Under the control of Glb promoter, REB increased Lys expression by about 3-fold. REB showed no effect on a stronger promoter, Gt1. Transcription factor increased Lys expression, but not significantly. PBF increased Lys expression on average 1.5-fold over Gt1-Lys alone. The highest Lys-expressing lines were selected and advanced to R2 generation in the greenhouse. As shown in Table 8 below, Lys expression level from an R2 line, 265/159-41-5, was about 190 µg per grain and 9.5 mg/gram of brown rice flour (equivalent to 0.8% grain weight). The level of expression was about 1.5-fold higher than that of the highest expression line without the transcription factor. In addition, data showed that PBF not only increased the expression of Lys, but also increased the expression of native storage proteins such as glutelin and globulin, and the protein related to protein trafficking. It implies that PBF can act on the promoters of multiple genes to increase the expression of those proteins in rice endosperm.

TABLE 8

| Line Number | $R_1$* (µg/grain) | $R_2$* (µg/grain) | $R_2$ Lysozyme (mg/g brown rice) | Homozygous |
|---|---|---|---|---|
| 285/159-41 | 150.23 | 190.00 | 9.5 | homozygous |
| 285/159-43 | 114.30 | 155.00 | 9.0 | homozygous |

TABLE 8-continued

| Line Number | $R_1$* (μg/grain) | $R_2$* (μg/grain) | $R_2$ Lysozyme (mg/g brown rice) | Homozygous |
|---|---|---|---|---|
| 285/159-81 | 103.58 | 175.59 | | heterozygous |
| 285/159-286 | 152.07 | 180.00 | | heterozygous |

* The expression data were averaged from 10 seeds in $R_1$ and from 10 lines in $R_2$.

EXAMPLE 9

Production of Rice Extract Containing Recombinant Proteins

A. General Procedure for Production of Rice Extract

Transgenic rice containing heterologous polypeptides can be converted to rice extracts by either a dry milling or wet milling process. In the dry milling process, transgenic paddy rice seeds containing the heterologous polypeptides, such as recombinant human lysozyme or lactoferrin were dehusked with a dehusker. The rice was grounded into a fine flour though a dry milling process, for example, in one experiment, at speed 3 of a model 91 Kitchen Mill from K-TEC. Phosphate buffered saline ("PBS"), containing 0.135 N NaCl, 2.7 mM KCl, 10mM Na2HPO4, 1.7 mM KH2PO4, at pH 7.4, with or without additional NaCl, such as 0.35 N NaCl, was added to the rice flour. In some experiments, approximately 10 ml of extraction buffer was used for each 1 g of flour. In other experiments, the initial flour/buffer ratio varied over a range such as 1 g/40 ml to 1 g/10 ml. The mixture was incubated at room temperature with gentle shaking for 1 hr. In other experiments, the incubation temperature was lower or higher, such as from about 22° C. to about 60° C., and the incubation time was longer or shorter, such as from about 10 minutes to about 24 hr. A Thermolyne VariMix™ platform mixer set at high speed was used to keep the particulates suspended.

In place of PBS, other buffers were used in some experiments, such as ammonium bicarbonate. In one embodiment, 10 liters of 0.5M ammonium bicarbonate was added to 1 kg of rice flour.

The resulting homogenate was clarified either by filtration or centrifugation. For the filtration method, the mixture was allowed to settle for about 30 minutes at room temperature, after which the homogenate was collected and filtered. Filters in three different configurations were purchased from Pall Gemansciences and used. They were: a 3 μm pleated capsule, a 1.2 μm serum capsule and a Suporcap capsule 50 (0.2 μm). For centrifugation, a BECKMAN™ J2-HC centrifuge was used and the mixture was centrifuged at 30,000 g at 40° C. for about 1 hr. The supernatant was kept and the pellet was discarded.

In one embodiment, the filtrate and supernatant were further processed, for example by ultra-filtration or dialysis or both to remove components such as lipids, sugars and salt.

The filtrate from the above filtration procedure, which is also called the clarified extract, was then concentrated using a spiral wound tangential flow filter operated in a batch recirculation mode. In one embodiment, PES (polyethersulfone) 3000-4000 molecular weight cutoff membranes was used for this step. These final concentrated extracts were held overnight in a cold room.

The concentrated extracts were next dried to a powder by lyophilization. During loading of the lyophilizer trays, the extracts were not subjected to a final 0.2 or 0.45 micron depth filtration to minimize loss of target proteins. The lyophilized material was scraped from the lyophilizer trays and combined into a plastic bag. The dry material was compressed by drawing a vacuum on the bag and then the material was blended and the particle size reduced by hand-kneading it through the plastic.

The lyophilized materials were then suitable for use as an extract directly or in admixture with other food. In one experiment, the lyophilized materials were blended with various ingredients to produce control and test infant-formula. The ingredients were blended using a HOBART™ mixer (140 quart size) equipped with a paddle agitator. These final blends were packed in 1 kg double MYLAR™ bags and the headspace was filled with nitrogen before sealing.

Table 10 shows the recovery of recombinant human lactoferrin from 105 kg transgenic rice flour during each extraction step. The amount of recombinant human LF present was determined quantitatively as described in Example 5.

TABLE 10

Recombinant Lactoferrin in Rice Extraction

| Stage of process | Lactoferrin | |
|---|---|---|
| | Lac mass | % of max |
| Baseline extraction yield | 4.0 mg/g flour | |
| Expected maximum | 420 g | 100% |
| Initial extract | 338 g | 80 |
| Clarified extract | 373 g | 89 |
| Concentrated extract | 343 g | 82 |
| Dried extract | 340 g | 81 |

Rice extract can also be produced using a wet milling procedure. Transgenic paddy rice seeds containing recombinant human lysozyme were re-hydrated for a period of 0 to 288 hrs at 30° C. The rehydrated seeds were ground in PBS extraction buffer. The initial seed/buffer ratio varied over a range such as 1 g/40 ml to 1 g/10 ml. Table 11 shows recovery of human lysozyme from rice seeds soaked from 0 to 288 hrs.

TABLE 11

Recovery of human Lysozyme from Soaked Rice Seeds

| Rehydration time (hrs) | Lysozyme (μg/grain) | Recovery (%) |
|---|---|---|
| 0 | 87 | 100 |
| 48 | 69 | 79 |
| 60 | 79 | 91 |
| 168 | 60 | 69 |
| 216 | 56 | 64 |
| 288 | 58 | 67 |

Over 60% human lysozyme was recovered from the wet milling process. The result of the wet milling becomes initial extract which may be stored frozen until use. The processing of initial extract to obtain dried extract was the same as that described for dry milling in this section.

B. Concentration and Diafiltration of Recombinant Lysozyme and Control Rice Extracts.

The conditions used in concentration and diafiltration varied depending on volume, speed, cost, etc. These conditions are all routine in the art based on the description herein. The frozen initial extract was thawed in the coldroom (about 2-8° C.) for six hours. The thawed material were clarified though a 0.45 μm filter and concentrated using a 5000 Nominal Molecular Weight Cutoff membrane of Polyethersultone.

90 ml of the filtrate of control extract was concentrated to 10 ml and additional 10 ml of deionized water was added to the concentrated filtrate. The diluted filtrate was diafiltrated one more time using water. The precipitate started forming at 16 mS and increased as the ionic strength decreased. 1M ammonium bicarbonate was added to the retentate to add ionic strength. The haze decreased although did not disappear completely. The material was diafiltered multiple times, in one embodiment three times, with water and multiple times, in one embodiment three times, with 0.1 M ammonium bicarbonate. It was concentrated to 9 ml and the membrane was rinsed with 0.1 M ammonium bicarbonate. The concentrate was filtered through several 0.2 μm button filters. In one embodiment, 2.3 ml of the filtrate was lyophilized as is; 2.3 ml of the filtrate was diluted to 12 ml with deionized water and lyophilized, and 2.0 ml of the filtrate was diluted to 25 ml with deionized water and lyophilized. All remained clear.

A total of 89 ml of the filtrate of rHLys extract was concentrated to 10 ml, and additional 10 ml of 0.1 M ammonium bicarbonate was added. The resulting mixture was concentrated back to 10 ml and another 10 ml of 0.1 M ammonium bicarbonate was added. The retentate started to haze up. The material was diafiltered multiple times, in one embodiment three times, with 0.1 M ammonium bicarbonate. It was concentrated to 9 ml and the membrane was rinsed with 0.1 M ammonium bicarbonate. The concentrate was filtered through several 0.45 μm button filters. In one embodiment, 2.0 ml of the filtrate was lyophilized as is; 2.0 ml of the filtrate was diluted to 12 ml with deionized water where a haze formed, and lyophilized, and 2.0 ml of the filtrate was diluted to 12 ml with 0.1 M ammonium bicarbonate which remained clear, and lyophilized.

C. Comparison of Trial Extraction of Recombinant Lysozyme Rice with PBS and Ammonium Bicarbonate The conditions used in concentration and diafiltration varied depending on volume, speed, cost, etc. These conditions are all routine in the art based on the description herein. rHlys rice flour was mixed with extraction buffer at about 100 g/L for about 1 hour using a magnetic stir bar. In one 2 liter beaker, the extraction buffer was PBS, pH 7.4 plus 0.35 M NaCl. In another 2 liter beaker, the extraction buffer was 0.5 M ammonium bicarbonate. A 15 cm buchner was pre-coated with about 6 g of Cel-pure C300 before adding another 20 g of Cel-pure C300. The mixture was filtered at about 3-4 Hg. It was then washed twice with about 100 ml of respective extraction buffer. The extracted filtrate was collected and concentrated with ultra-filtration cartridges: 5K Regenerate Cellulose, 5K PES, and 1K Regenerated Cellulose. The concentrates were lyophilized and analyzed for rHlys contents. The ammonium bicarbonate and PBS, pH 7.4 plus 0.35 M NaCl both extracted approximately the same amount of rHlys. There was little loss of lysozyme units in the permeate with any of the ultrafiltration units that were used.

Other extraction buffer can also be used to extract recombinant proteins expressed in transgenic rice grains, for example Tris buffer, ammonium acetate, depending on applications. For example, for using recombinant human LF for iron supplement, iron may be added to the extraction buffer and the buffer is set at a pH so that the apo-LF can pick up iron during the extraction process. Under this condition, LF can become saturated with iron (holo-LF). In another example, a buffer lacking of iron and a pH resulting in iron release from LF is used to produce apo-LF.

D. Production of Rice Extracts Containing Recombinant Proteins

The conditions used in concentration and diafiltration varied depending on volume, speed, cost, etc. These conditions are routine in the art based on the description herein. All equipment was soaked in hot 0.1M NaOH at a starting temperature of about 55° C. Rice flour was added to an about 250-500 gal stainless steel tank containing 0.5M ammonium bicarbonate at about 95-105 g/L. It was mixed for about 60-80 minutes at about 9° C.

12 plates of 36 inch filter press C300 were pre-coated with about 3-6 kg Cel-pure C300. About 19-26 g/L of Cel-pure was added to the extract and mixed thoroughly. The mixture was pressed at a pressure of about 22 psi at a flow rate of about 82 liters/minute. The filtrate was collected into a 250 gallon stainless steel tank and washed with 0.5M ammonium bicarbonate. The press was blown dry. The process was carried out at about 10° C.

The 300 NMW cut-off membranes (Polysulfone) that had been cleaned and stored with 0.1M NaOH after control run were rinsed thoroughly with deionized water. The extract was concentrated and bumped to a 100 gal stainless steel tank. The membrane and the concentration tank were flushed with 0.1M ammonium bicarbonate to recover all of the products. The product were covered with plastic and left in the 100 gal tank overnight at room temperature. The concentrate was filtered through spiral wound 1 μm filter and into 5 gallon poly container. The concentrate was lyophilized. About 81% of lactoferrin and about 58% of lysozyme was recovered from transgenic rice grains, respectively.

E. Blending of Rice Extract Containing Recombinant Proteins into Infant Formula

The three types of lyophilized dry extract that contains rice proteins (control) or rice proteins with lysozyme or lactoferrin were combined with standard infant formula. The blending was done such the final infant formula contained about 1 gram lactoferrin and 0.1 gram lysozyme per liter of infant formula. The ingredients were blended using a Hobart mixer (140 quart size) equipped with a paddle agitator. These final blends were packed in 1 kg double Mylar bags and the headspace was filled with nitrogen before sealing.

Samples of infant formula containing human lysozyme and lactoferrin were quantified using procedures described in Examples 4 and 5.

TABLE 12 human lysozyme and lactoferrin in infant formula

| Infant Formula | Lactoferrin (mg/ml) | Lysozym (mg/ml) |
| --- | --- | --- |
| With control rice extract | 0.0 | 0.0 |
| With transgenic rice extract | 1.03 | 0.13 |

Using extract as a delivery method of recombinant protein has clear advantages over the purified form or in the whole grain. The conventional approach, such as in the whole grain form, has limitations such as protein stability during high temperature and pressure processing. Furthermore, the purification approach is expensive. Therefore the extract approach 1) maintains a low cost compared to purification approach; 2) requires much smaller volume, for example about 1-10% of whole grain weight; 3) increases the concentration of recombinant protein from about 0.05-0.5% in whole grain form to about 10 to 20% in the extract form. Some extract form even reaches 40% depending on the expression level of recombinant protein. Therefore, the extract approach will allow broader application of the recombinant proteins compared to the whole grain approach. In addition, the extract approach removes starch granule, which requires high gelling temperature, for example about 75° C. Consequently, the extract approach provides more flexibility in processing the rice grain and the recombinant proteins into food and diet, and the alike, without worrying about using high temperature to denature starch granule.

Brief Description of the Sequences

| Description | SEQ ID NO |
|---|---|
| Codon optimized lysozyme coding sequence:<br>AAAGTCTTCGAGCGGTGCGAGCTGGCCCGCACGCTCAAGCGGCTCGGCAT<br><br>GGACGGCTACCGGGGCATCAGCCTCGCCAACTGGATGTGCCTCGCCAAGT<br><br>GGGAGTCGGGCTACAACACCCGCGCAACCAACTACAACGCCGGCGACCGC<br><br>TCCACCGACTACGGCATCTTCCAGATCAACTCCCGCTACTGGTGCAACGAC<br><br>GGCAAGACGCCCGGGGCCGTCAACGCCTGCCACCTCTCCTGCTCGGCCCT<br><br>GCTGCAAGACAACATCGCCGACGCCGTCGCGTGCGCGAAGCGCGTCGTCC<br><br>GCGACCCGCAGGGCATCCGGGCCTGGGTGGCCTGGCGCAACCGCTGCCA<br><br>GAACCGGGACGTGCGCCAGTACGTCCAGGGCTGCGGCGTCTGA | 1 |
| Amino acid sequence based on codon optimized lysozyme coding sequence:<br>KVFERCELARTLKRLGMDGYRGISLANWMCLAKWESGYNTRATNYNAGDRST<br><br>DYGIFQINSRYWCNDGKTPGAVNACHLSCSALLQDNIADAVACAKRVVRDPQGI<br><br>RAWVAWRNRCQNRDVRQYVQGCGV | 2 |
| Codon optimized lactoferrin coding<br>sequence: GGGCGGCGGCGGCGCTCGGTGCAGTGGTGCGCCGTGTCCCAGC<br><br>CCGAGGCGACCAAGTGCTTCCAGTGGCAGCGCAACATGCGGAAGGTGCGC<br><br>GGCCCGCCGGTCAGCTGCATCAAGCGGGACTCCCCCATCCAATGCATCCAG<br><br>GCCATCGCGGAGAACCGCGCCGACGCGGTCACCCTGGACGGCGGGTTCAT<br><br>CTACGAGGCGGGGCTCGCCCCGTACAAGCTCCGCCCGGTGGCGGCGGAG<br><br>GTGTACGGCACCGAGCGCCAGCCGCGCACGCACTACTACGCGGTGGCCGT<br><br>CGTCAAGAAGGGCGGGTCCTTCCAGCTCAACGAGCTGCAGGGCCTGAAGT<br><br>CGTGCCACACGGGCCTCCGGCGGACGGCGGGCTGGAACGTGCCCATCGG<br><br>CACCCTGCGCCCCTTCCTGAACTGGACCGGCCCGCCGGAGCCGATCGAGG<br><br>CCGCCGTGGCCCGCTTCTTCAGCGCCTCCTGCGTCCCCGGCGCCGACAAG<br><br>GGCCAGTTCCCGAACCTCTGCCGGCTCTGCGCCGGGACGGGCGAGAACAA<br><br>GTGCGCCTTCTCCTCGCAGGAGCCGTACTTCTCCTACTCGGGCGCGTTCAA<br><br>GTGCCTCCGCGACGGGGCCGGCGACGTGGCGTTCATCCGCGAGTCCACCG<br><br>TGTTCGAGGACCTCTCCGACGAGGCGGAGCGGGACGAGTACGAGCTGCTG<br><br>TGCCCCGACAACACCCGCAAGCCGGTGGACAAGTTCAAGGACTGCCACCTG<br><br>GCGCGGGTGCCCTCGCACGCGGTCGTCGCCCGCAGCGTCAACGGCAAGGA<br><br>GGACGCGATCTGGAACCTCCTCCGCCAGGCCCAGGAGAAGTTCGGCAAGG<br><br>ACAAGTCCCCCAAGTTCCAGCTCTTCGGGAGCCCCAGCGGCCAGAAGGACC<br><br>TCCTCTTCAAGGACTCCGCGATCGGCTTCTCCCGCGTCCCCCCGCGCATCG<br><br>ACTCCGGCCTGTACCTCGGCTCCGGGTACTTCACCGCGATCCAGAACCTCC<br><br>GGAAGAGCGAGGAGGAGGTGGCGGCGCGGCGGGCCCGCGTCGTGTGGTG<br><br>CGCCGTGGGCGAGCAGGAGCTGCGGAAGTGCAACCAGTGGAGCGGCCTGA<br><br>GCGAGGGGTCGGTGACCTGCTCGTCCGCCAGCACCACCGAGGACTGCATC<br><br>GCGCTCGTCCTCAAGGGGGAGGCCGACGCGATGAGCCTCGACGGGGGGTA<br><br>CGTCTACACCGCCGGCAAGTGCGGCCTGGTCCCGGTCCTGGCGGAGAACT | 3 |

-continued

| Description | SEQ ID NO |
|---|---|
| ACAAGTCGCAGCAGTCCAGCGACCCCGACCCGAACTGCGTGGACCGCCCC | |
| GTCGAGGGCTACCTCGCCGTGGCCGTCGTGCGCCGGTCCGACACCTCCCT | |
| GACGTGGAACAGCGTCAAGGGCAAGAAGAGCTGCCACACCGCCGTGGACC | |
| GCACCGCCGGCTGGAACATCCCGATGGGCCTCCTCTTCAACCAGACCGGCT | |
| CCTGCAAGTTCGACGAGTACTTCTCCCAGTCCTGCGCCCCCGGCTCGGACC | |
| CCCGCTCCAACCTGTGCGCCCTCTGCATCGGGGACGAGCAGGGCGAGAAC | |
| AAGTGCGTGCCCAACAGCAACGAGCGGTACTACGGCTACACGGGGGCCTT | |
| CCGCTGCCTGGCGGAGAACGCCGGGGACGTCGCGTTCGTGAAGGACGTGA | |
| CCGTGCTGCAAAACACGGACGGGAACAACAACGAGGCGTGGGCGAAGGAC | |
| CTCAAGCTCGCCGACTTCGCCCTGCTGTGCCTCGACGGCAAGCGCAAGCCC | |
| GTCACCGAGGCGCGGTCCTGCCACCTGGCGATGGCCCCCAACCACGCCGT | |
| CGTCTCCCGCATGGACAAGGTCGAGCGCCTCAAGCAGGTGCTCCTGCACCA | |
| GCAGGCCAAGTTCGGCCGGAACGGCAGCGACTGCCCGGACAAGTTCTGCC | |
| TGTTCCAGTCGGAGACCAAGAACCTCCTCTTCAACGACAACACCGAGTGCCT | |
| GGCGCGCCTCCACGGCAAGACCACCTACGAGAAGTACCTCGGCCCGCAGT | |
| ACGTCGCCGGCATCACCAACCTCAAGAAGTGCTCCACCTCCCCCCTCCTGG | |
| AGGCGTGCGAGTTCCTCCGCAAGTGA | |
| Amino acid sequence based on codon optimized lactoferrin coding sequence: | 4 |
| GRRRRSVQWCAVSQPEATKCFQWQRNMRKVRGPPVSCIKRDSPIQCIQAIAEN | |
| RADAVTLDGGFIYEAGLAPYKLRPVAAEVYGTERQPRTHYYAVAVVKKGGSFQL | |
| NELQGLKSCHTGLRRTAGWNVPIGTLRPFLNWTGPPEPIEAAVARFFSASCVPG | |
| ADKGQFPNLCRLCAGTGENKCAFSSQEPYFSYSGAFKCLRDGAGDVAFIREST | |
| VFEDLSDEAERDEYELLCPDNTRKPVDKFKDCHLARVPSHAVVARSVNGKEDAI | |
| WNLLRQAQEKFGKDKSPKFQLFGSPSGQKDLLFKDSAIGFSRVPPRIDSGLYLG | |
| SGYFTAIQNLRKSEEEVAARRARVVWCAVGEQELRKCNQWSGLSEGSVTCSS | |
| ASTTEDCIALVLKGEADAMSLDGGYVYTAGKCGLVPVLAENYKSQQSSDPDPN | |
| CVDRPVEGYLAVAVVRRSDTSLTWNSVKGKKSCHTAVDRTAGWNIPMGLLFNQ | |
| TGSCKFDEYFSQSCAPGSDPRSNLCALCIGDEQGENKCVPNSNERYYGYTGAF | |
| RCLAENAGDVAFVKDVTVLQNTDGNNNEAWAKDLKLADFALLCLDGKRKPVTE | |
| ARSCHLAMAPNHAVVSRMDKVERLKQVLLHQQAKFGRNGSDCPDKFCLFQSE | |
| TKNLLFNDNTECLARLHGKTTYEKYLGPQYVAGITNLKKCSTSPLLEACEFLRK | |
| MV-Gt1-F1 primer:<br>5'ATC GAA GCT TCA TGA GTA ATG TGT GAG CAT TAT GGG ACC ACG 3' | 5 |
| Xba-Gt1-R1 primer: 5'CTA GTC TAG ACT CGA GCC ATG GGG CCG GCT AGG GAG CCA TCG CAC AAG AGG AA 3' | 6 |
| Codon optimized lactoferricin coding sequence<br>ACCAAGTGCTTCCAGTGGCAGCGCAACATGCGGAAGGTGCGCGGCCCGCC<br>GGTCAGCTGCATCAAGCGGGAC | 7 |
| Codon optimized lactadherin coding sequence<br>CTGGACATCTGCTCGAAGAACCCGTGCCACAACGGCGGGCTCTGCGAGGA | 8 |

-continued

| Description | SEQ ID NO |
|---|---|
| GATCAGCCAGGAGGTGCGGGCGACGTGTTCCCCTCGTACACCTGCACCT | |
| GCCTGAAGGGCTACGCCGGGAACCACTGCGAGACGAAGTGCGTGGAGCCC | |
| CTGGGGATGGAGAACGGCAACATCGCCAACTCCCAGATCGCCGCCTCCTCC | |
| GTGCGGGTGACCTTCCTCGGCCTCCAGCACTGGGTCCCGGAGCTGGCCCG | |
| GCTCAACCGGGCGGGCATGGTGAACGCGTGGACCCCCTCGTCCAACGACG | |
| ACAACCCGTGGATCCAAGTGAACCTGCTCCGCCGCATGTGGGTCACCGGCG | |
| TGGTCACCCAAGGCGCCAGCCGCCTGGCCAGCCACGAGTACCTCAAGGCC | |
| TTCAAGGTCGCCTACAGCCTCAACGGCCACGAGTTCGACTTCATCCACGAC | |
| GTCAACAAGAAGCACAAGGAGTTCGTGGGCAACTGGAACAAGAACGCGGTC | |
| CACGTGAACCTCTTCGAGACCCCCGTCGAGGCCCAGTACGTCCGCCTCTAC | |
| CCCACGAGCTGCCACACCGCCTGCACGCTCCGCTTCGAGCTGCTGGGGTG | |
| CGAGCTGAACGGGTGCGCGAACCCGCTGGGGCTCAAGAACAACAGCATCC | |
| CCGACAAGCAGATCACGGCCTCGTCGTCGTACAAGACCTGGGGCCTGCACC | |
| TCTTCTCGTGGAACCCGAGCTACGCCCGGCTGGACAAGCAGGGCAACTTCA | |
| ACGCCTGGGTCGCCGGGAGCTACGGGAACGACCAGTGGCTCCAGGTGGAC | |
| CTCGGCAGCTCCAAGGAGGTCACCGGCATCATCACGCAGGGGGCCCGCAA | |
| CTTCGGCTCCGTGCAGTTCGTGGCCTCCTACAAGGTGGCCTACTCGAACGA | |
| CAGCGCCAACTGGACCGAGTACCAGGACCCGCGCACCGGGTCCAGCAAGA | |
| TCTTCCCCGGCAACTGGGACAACCACAGCCACAAGAAGAACCTGTTCGAGA | |
| CCCCCATCCTCGCCCGGTACGTCCGCATCCTCCCCGTCGCTTGGCACAACC | |
| GGATCGCGCTCCGGCTGGAGCTCCTCGGCTGCTGA | |
| Codon optimized kappa-casein coding sequence<br>GAGGTCCAAAACCAGAAGCAGCCCCGCCTGCCACGAGAACGACGAGCGCCC | 9 |
| CTTCTACCAGAAGACCGCACCCTACGTCCCGATGTACTACGTCCCGAACAG | |
| CTACCCCTACTACGGTACGAACCTGTACCAGCGCCGCCCGGCCATCGCTAT | |
| CAACAACCCCTACGTCCCCCGGACCTACTACGCGAACCCGGCCGTGGTGC | |
| GGCCCCACGCGCAGATCCCGCAGCGGCAGTACCTGCCAAACAGCCACCCC | |
| CCCACCGTGGTGCGGCGGCCCAACCTCCACCCGAGCTTCATCGCTATCCCC | |
| CCCAAGAAGATCCAGGACAAGATCATCATCCCGACCATCAACACCATCGCCA | |
| CCGTGGAGCCGACGCCAGCCCCGCGACCGAGCCCACGGTGGACAGCGT | |
| CGTGACCCCAGAGGCGTTCTCCGAATCGATCATCACCTCCACCCCCGAGAC | |
| CACCACGGTGGCCGTCACGCCGCCGACGGCATGA | |
| Codon optimized haptocorrin coding sequence<br>GAGATCTGCGAGGTCTCCGAGGAGAACTACATCCGCCTCAAGCCCCTCCTG | 10 |
| AACACCATGATCCAGAGCAACTACAACCGGGGCACGTCGGCCGTGAACGTC | |
| GTGCTCTCCCTGAAGCTCGTGGGCATCCAGATCCAGACCCTCATGCAGAAG | |
| ATGATCCAGCAGATCAAGTACAACGTGAAGAGCCGCCTCTCGGACGTGTCC | |
| AGCGGCGAGCTGGCGCTCATCATCCTCGCGCTCGGCGTGTGCCGGAACGC | |
| GGAGGAGAACCTCATCTACGACTACCACCTCACGGACAAGCTGGAGAACAA |

-continued

| Description | SEQ ID NO |
|---|---|
| GTTCCAGGCCGAGATCGAGAACATGGAGGCCCACAACGGCACCCCGCTGA | |
| CCAACTACTACCAGCTCAGCCTGGACGTCCTCGCGCTCTGCCTGTTCAACG | |
| GGAACTACTCCACCGCCGAGGTGGTCAACCACTTCACCCCCGAGAACAAGA | |
| ACTACTACTTCGGCTCGCAGTTCTCCGTGGACACCGGGGCCATGGCCGTCC | |
| TGGCCCTCACCTGCGTGAAGAAGTCCCTCATCAACGGCCAGATCAAGGCCG | |
| ACGAGGGCTCCCTGAAGAACATCTCGATCTACACCAAGAGCCTCGTGGAGA | |
| AGATCCTCAGCGAGAAGAAGGAGAACGGGCTGATCGGCAACACCTTCTCGA | |
| CCGGCGAGGCGATGCAGGCCCTGTTCGTGAGCAGCGACTACTACAACGAG | |
| AACGACTGGAACTGCCAGCAGACCCTCAACACGGTCCTGACCGAGATCAGC | |
| CAGGGCGCGTTCAGCAACCCCAACGCCGCCGCCCAGGTCCTGCCGGCCCT | |
| GATGGGCAAGACCTTCCTCGACATCAACAAGGACAGCTCCTGCGTGTCCGC | |
| GAGCGGCAACTTCAACATCTCCGCCGACGAGCCGATCACGGTGACGCCGC | |
| CCGACAGCCAGTCGTACATCTCCGTGAACTACAGCGTGCGGATCAACGAGA | |
| CCTACTTCACGAACGTGACGGTCCTCAACGGCTCGGTCTTCCTGAGCGTGA | |
| TGGAGAAGGCGCAGAAGATGAACGACACGATCTTCGGCTTCACGATGGAGG | |
| AGCGCAGCTGGGCCCCTACATCACCTGCATCCAGGGCCTCTGCGCCAACA | |
| ACAACGACCGCACCTACTGGGAGCTGCTGAGCGGCGGCGAGCCGCTGAGC | |
| CAGGGGGCCGGCAGCTACGTGGTCCGCAACGGCGAGAACCTGGAGGTCCG | |
| GTGGAGCAAGTACTGA | |
| Codon optimized lactoperoxidase coding sequence<br>CAAACGACCCGGACGTCGGCGATCTCCGACACGGTCTCGCAGGCCAAGGT | 11 |
| GCAAGTCAACAAGGCATTCCTGGATTCGCGCACGCGGCTGAAGACCGCGAT | |
| GTCGTCCGAGACCCCGACGAGCCGGCAGCTGAGCGAGTACCTCAAGCACG | |
| CGAAGGGGCGGACGCGCACCGCCATCCGCAATGGCCAAGTGTGGGAGGAA | |
| TCCCTGAAGCGGCTGCGGCAGAAGGCGTCGCTCACCAACGTGACCGACCC | |
| GTCCCTCGACCTGACCAGCCTCTCCCTGGAGGTCGGCTGCGGCGCCCCGG | |
| CGCCCGTCGTGCGCTGCGACCCCTGCTCGCCATACCGCACGATCACGGGC | |
| GACTGCAACAACCGGCGGAAGCCGGCACTGGGGGCTGCGAACCGCGCCCT | |
| CGCGCGCTGGCTCCCCGCCGAGTACGAGGACGGCCTCAGCCTCCCCTTCG | |
| GTTGGACCCCCGGCAAGACGCGCAACGGCTTCCCGCTCCCGCTCGCTCGC | |
| GAGGTCAGCAACAAGATCGTCGGTTACCTGAACGAGGAGGGGGTCCTCGAC | |
| CAAAACCGCTCCCTCCTCTTCATGCAGTGGGGGCAGATCGTGGACCACGAC | |
| CTGGACTTCGCCCCGGACACGGAGCTGGGCTCCAGCGAGTACAGCAAGAC | |
| CCAGTGCGACGAATACTGCATCCAGGGCGACAACTGCTTCCCGATCATGTT | |
| CCCCCCGAACGACCCGAAGGCGGGCACCCAGGGCAAGTGCATGCCGTTCT | |
| TCCGGGCAGGCTTCGTCTGCCCGACCCCCCCGTACAAGTCCCTCGCGCGC | |
| GAGCAGATCAACGCGCTCACGTCCTTCCTCGACGCCAGCTTCGTCTACAGC | |
| AGCGAGCCGTCCCTCGCCAGCCGCCTCCGCAACCTCAGCAGCCCCCTCGG | |
| CCTCATGGCGGTCAACCAGGAGGTGTCGGACCACGGCCTCCCATACCTGCC | |

| Description | SEQ ID NO |
|---|---|
| GTACGACAGCAAGAAGCCGTCCCCCTGCGAGTTCATCAACACCACCGCGCG | |
| CGTCCCGTGCTTCCTCGCCGGCGATTCGCGGGCGAGCGAGCACATCCTCC | |
| TCGCCACGAGCCACACCCTGTTCCTCCGCGAGCACAACCGCCTCGCCCGG | |
| GAGCTGAAGCGCCTCAACCCGCAGTGGGACGGCGAGAAGCTCTACCAGGA | |
| GGCCCGGAAGATCCTCGGCGCTTTCGTCCAGATCATCACCTTCCGGGACTA | |
| CCTCCCCATCCTGCTCGGTGACCACATGCAGAAGTGGATCCCCCCCTACCA | |
| AGGCTACTCCGAGAGCGTGGACCCGCGCATCTCCAACGTCTTCACGTTCGC | |
| GTTCCGCTTCGGGCACCTGGAGGTGCCGTCGTCGATGTTCCGCCTCGACGA | |
| GAACTACCAGCCCTGGGGCCCAGAGCCGGAGCTGCCGCTCCACACCCTGT | |
| TCTTCAACACCTGGCGGATGGTCAAGGACGGCGGCATCGACCCGCTCGTGC | |
| GCGGGCTCCTGGCTAAGAAGTCGAAGCTCATGAAGCAGAACAAGATGATGA | |
| CCGGCGAGCTGCGCAACAAGCTGTTCCAGCCCACCCACCGCATCCACGGG | |
| TTCGACCTGGCTGCAATCAACACCCAGCGGTGCCGCGACCACGGCCAGCC | |
| CGGCTACAACTCGTGGCGCGCGTTCTGCGACCTCTCCCAGCCACAGACGCT | |
| GGAGGAGCTCAACACCGTGCTCAAGAGCAAGATGCTCGCCAAGAAGCTGCT | |
| CGGGCTCTACGGCACGCCCGACAACATCGACATCTGGATCGGGGCCATCG | |
| CGGAGCCGCTCGTGGAGCGCGGGCGCGTCGGCCCGCTGCTCGCGTGCCT | |
| CCTGGGCAAGCAATTCCAACAGATCCGCGACGGGGACCGGTTCTGGTGGG | |
| AGAACCCCGGCGTGTTCACCAACGAGCAGAAGGATTCGCTCCAAAAGATGA | |
| GCTTCTCCCGCCTGGTGTGCGACAACACCCGCATCACCAAGGTCCCGCGCG | |
| ACCCATTCTGGGCCAACTCCTACCCGTACGACTTCGTGGACTGCTCCGCCA | |
| TCGACAAGCTCGACCTGTCCCCCTGGGCATCGGTGAAGAACTGA | |
| Codon optimized alpha-1-antitrypsin coding sequence<br>GAGGACCCGCAGGGCGACGCCGCCCAGAAGACCGACACCAGCCACCACGA | 12 |
| CCAGGACCACCCGACGTTCAACAAGATCACCCCGAATTTGGCCGAATTCGC | |
| CTTCAGCCTGTACCGCCAGCTCGCGCACCAGTCCAACTCCACCAACATCTTC | |
| TTCAGCCCGGTGAGCATCGCCACCGCCTTCGCCATGCTGTCCCTGGGTACC | |
| AAGGCGGACACCCACGACGAGATCCTCGAAGGGCTGAACTTCAACCTGACG | |
| GAGATCCCGGAGGCGCAGATCCACGAGGGCTTCCAGGAGCTGCTCAGGAC | |
| GCTCAACCAGCCGGACTCCCAGCTCCAGCTCACCACCGGCAACGGGCTCTT | |
| CCTGTCCGAGGGCCTCAAGCTCGTCGATAAGTTCCTGGAGGACGTGAAGAA | |
| GCTCTACCACTCCGAGGCGTTCACCGTCAACTTCGGGGACACCGAGGAGGC | |
| CAAGAAGCAGATCAACGACTACGTCGAGAAGGGGACCCAGGGCAAGATCGT | |
| GGACCTGGTCAAGGAATTGGACAGGGACACCGTCTTCGCGCTCGTCAACTA | |
| CATCTTCTTCAAGGGCAAGTGGGAGCGCCCGTVCGAGGTGAAGGACACCGA | |
| GGAGGAGGACTTCCACGTCGACCAGGTCACCACCGTCAAGGTCCCGATGAT | |
| GAAGAGGCTCGGCATGTrCAACATCCAGCACTGCAAGAAGCTCTCCAGCTG | |
| GGTGCTCCTCATGAAGTACCTGGGGAACGCCACCGCCATCTTCTTCCTGCC | |
| GGACGAGGGCAAGCTCCAGCACCTGGAGAACGAGCTGACGCACGACATCA | |

| Description | SEQ ID NO |
|---|---|
| TCACGAAGTTCCTGGAGAACGAGGACAGGCGCTCCGCTAGCCTCCACCTCC | |
| CGAAGCTGAGCATCACCGGCACGTACGACCTGAAGAGCGTGCTGGGCCAG | |
| CTGGGCATCACGAAGGTCTTCAGCAACGGCGCGGACCTCTCCGGCGTGAC | |
| GGAGGAGGCCCCCCTGAAGCTCTCCAAGGCCGTGCACAAGGCGGTGCTCA | |
| CGATCGACGAGAAGGGGACGGAAGCTGCCGGGGCCATGTTCCTGGAGGCC | |
| ATCCCCGTGTCCATCCCGCCCGAGGTCAAGFVCAACAAGCCCTTCGTCTTCC | |
| TGATGATCGAGCAGAACACGAAGAGCCCCCTCTTCATGGGGAAGGTCGTCA | |
| ACCCCACGCAGAAGTGA | |
| Codon optimized immunoglobulin-A coding sequence | |
| Rice Gt1 promoter and Gt1 leader coding sequence<br>CATGAGTAATGTGTGAGCATTATGGGACCACGAAATAAAAAGAACATTTTGAT | 13 |
| GAGTCGTGTATCCTCGATGAGCCTCAAAAGTVCTCTCACCCCGGATAAGAAA | |
| CCCTTAAGCAATGTGCAAAGTTTGCATTCTCCACTGACATAATGCAAAATAAG | |
| ATATCATCGATGACATAGCAACTCATGCATCATATCATGCCTCTCTCAACCTA | |
| TTCATTCCTACTCATCTACATAAGTATCTVCAGCTAAATGTTAGAACATAAACC | |
| CATAAGTCACGTTTGATGAGTATTAGGCGTGACACATGACAAATCACAGACT | |
| CAAGCAAGATAAAGCAAAATGATGTGTACATAAAACTCCAGAGCTATATGTCA | |
| TATTGCAAAAGAGGAGAGCTTATAAGACAAGGCATGACTCACAAAAATTCA | |
| CTTGCCTTTCGTGTCAAAAAGAGGAGGGCTTTACATTATCCATGTCATATTGC | |
| AAAAGAAAGAGAGAAAGAACAACACAATGCTGCGTCAATTATACATATCTGTA | |
| TGTCCATCATTATTCATCCACCTTTCGTGTACCACACTVCATATATCATAAGA | |
| GTCACTTCACGTCTGGACATTAACAAACTCTATCTTAACATTTAGATGCAAGA | |
| GCCTTTATCTCACTATAAATGCACGATGATTTCTCATTGTTTCTCACAAAAAG | |
| CGGCCGCTTCATTAGTCCTACAACAACATGGCATCCATAAATCGCCCCATAG | |
| TTTTCTTCACAGTTTGCTTGTTCCTCTTGTGCGATGGCTCCCTAGCC | |
| Codon optimized alpha-1-antitrypsin coding sequence | |
| Rice Glb promoter and Gt1 leader coding sequence<br>CTGCAGGGAGGAGAGGGGAGAGATGGTGAGAGAGGAGGAAGAAGAGGAG | 14 |
| GGGTGACAATGATATGTGGGGCATGTGGGCACCCAATTTTTTAATTCATTCT | |
| TTTGTTGAAACTGACATGTGGGTCCCATGAGATTTATTATTTTTCGGATCGAA | |
| TCGCCACGTAAGCGCTACGTCAATGCTACGTCAGATGAAGACCGAGTCAAAT | |
| TAGCCACGTAAGCGCCACGTCAGCCAAAACCACCATCCAAACCGCCGAGGG | |
| ACCTCATCTGCACTGGTTTTGATAGTTGAGGGACCCGTTGTATCTGGTTTTTC | |
| GATTGAAGGACGAAAATCAAATTTGTTGACAAGTTAAGGGACCTTAAATGAA | |
| CTTATTCCATTTCAAAATATTCTGTGAGCCATATATACCGTGGGCTTCCAATC | |
| CTCCTCAAATTAAAGGGCCTTTTTAAAATAGATAATTGCCTTCTTTCAGTCAC | |
| CCATAAAAGTACAAAACTACTACCAACAAGCAACATGCGCAGTTACACACATT | |
| TTCTGCACATTTCCGCCACGTCACAAAGAGCTAAGAGTTATCCCTAGGACAA | |
| TCTCATTAGTGTAGATACATCCATTAATCTTTTATCAGAGGCAAACGTAAAGC | |
| CGCTCTTTATGACAAAAATAGGTGACACAAAAGTGTTATCTGCCACATACATA |

| Description | SEQ ID NO |
|---|---|
| ACTTCAGAAATTACCCAACACCAAGAGAAAAATAAAAAAAAATCTTTTTGCAA | |
| GCTCCAAATCTTGGAAACCTTTTTCACTCTTTGCAGCATTGTACTCTTGCTCT | |
| TTTTCCAACCGATCCATGTCACCCTCAAGCTTCTACTTGATCTACACGAAGCT | |
| CACCGTGCACACAACCATGGCCACAAAAACCCTATAAAACCCCATCCGATCG | |
| CCATCATCTCATCATCAGTTCATTACCAACAAACAAAGAGGAAAAAAAACAT | |
| ATACACTTCTAGTGATTGTCTGATTGATCATCAATCTAGAGGCGGCCGCATG | |
| GCTAGCAAGGTCGTCTTCTTCGCGGCGGCGCTCATGGCGGCCATGGTGGC | |
| CATCTCCGGC | |
| Rice Gt1 promoter and Gt1 leader coding sequence<br>Other monocot maturation specific promoter sequences | 15-21 |
| Seq #15 Bx7 promoter seq<br>CTGCAGGCCAGGGAAAGACAATGGACATGCAAAGAGGTAGGGGCAGGGAA | |
| GAAACACTTGGAGATCATAGAAGAACATAAGAGGTTAAACATAGGAGGGCAT | |
| AATGGACAATTAAATCTACATTAATTGAACTCATTTGGGAAGTAAACAAATC | |
| CATATTCTGGTGTAAATCAAACTATTTGACGCGGATTTACTAAGATCCTATGT | |
| TAATTTTAGACATGACTGGCCAAAGGTTTCAGTTAGTTCATTTGTCACGGAAA | |
| GGTGTTTTCATAAGTCCAAAACTCTACCAACTTTTTTGCACGTCATAGCATAG | |
| ATAGATGTTGTGAGTCATTGGATAGATATTGTGAGTCAGCATGGATTTGTGTT | |
| GCCTGGAAATCCAACTAAATGACAAGCAACAAAACCTGAAATGGGCTTTAGG | |
| AGAGATGGTTTATCAATTTACATGTTCCATGCAGGCTACCTTCCACTACTCGA | |
| CATGGTTAGAAGTTTTGAGTGCCGCATATTTGCGGAAGCAATGGCACTACTC | |
| GACATGGTTAGAAGTTTTGAGTGCCGCATATTTGCGGAAGCAATGGCTAACA | |
| GATACATATTCTGCCAAACCCCAAGAAGGATAATCACTCCTCTTAGATAAAAA | |
| GAACAGACCAATGTACAAACATCCACACTTCTGCAAACAATACACCAGAACT | |
| AGGATTAAGCCCATTACGTGGCTTTAGCAGACCGTCCAAAAATCTGTTTTGC | |
| AAGCACCAATTGCTCCTTACTTATCCAGCTTCTTTTGTGTTGGCAAACTGCCC | |
| TTTTCCAACCGATTTTGTTTCTTCTCACGCTTTCTTCATAGGCTAAACTAACCT | |
| CGGCGTGCACACAACCATGTCCTGAACCTTCACCTCGTCCCTATAAAGCCC | |
| ATCCAACCTTACAATCTCATCATCACCCACAACACCGAGCACCCCAATCTAC | |
| AGATCAATTCACTGACAGTTCACTGATCTAGA | |
| Seq #16 Glub-2 promoter seq<br>CTGCAGTAATGGATACCTAGTAGCAAGCTAGCTTAAACAAATCTAAATTCCAA | |
| TCTGTTCGTAAACGTTTTCTCGATCGCAATTTTGATCAAAACTATTGAAAACC | |
| TCAATTAAACCATTCAAAATTTTTAATATACCCAACAAGAGCGTCCAAACCAA | |
| ATATGTAAATATGGATGTCATGATAATTGACTTATGACAATGTGATTATTTCAT | |
| CAAGTCTTTAAATCATTAATTCTAGTTGAAGGTTTATGTTTTCTTATGCTAAAG | |
| GGTTATGTTTATATAAGAATATTAAAGAGCAAATTGCAATAGATCAACACAAC | |
| AAATTTGAATGTTTCCAGATGTGTAAAAATATCCAATTAATTGTTTTAAAATA | |
| GTTTTAAGAAGGATCTGATATGCAAGTTTGATAGTTAGTAAACTGCAAAAGGG | |
| CTTATTACATGGAAAATTCCTTATTGAATATGTTTCATTGACTGGTTTATTTTA | |
| CATGACAACAAAGTTACTAGTATGTCAATAAAAAAATACAAGGTTACTTGTCA | |

| Description | SEQ ID NO |
|---|---|

ATTGTATTGTGCCAAGTAAAGATGACAACAAACATACAAATTTATTTGTTCTTT

TATAGAAACACCTAACTTATCAAGGATAGTTGGCCACGCAAAAATGACAACAT

ACTTTACAATTGTATCATCATAAAGATCTTATCAAGTATAAGAACTTTATGGTG

ACATAAAAAATAATCACAAGGGCAAGACACATACTAAAAGTATGGACAGAAAT

TTCTTAACAAACTCCATTTGTTTTGTATCCAAAAGCATAAGAAATGAGTCATG

GCTGAGTCATGATATGTAGTTCAATCTTGCAAAATTGCCTTTTTGTTAAGTATT

GTTTTAACACTACAAGTCACATATTGTCTATACTTGCAACAAACACTATTACC

GTGTATCCCAAGTGGCCTTTTCATTGCTATATAAACTAGCTTGATCGGTCTTT

CAACTCACATCAATTAGCTTAAGTTTCCATTAGCAACTGCTAATAGCT

Seq #17 Gt3 promoter seq
CTGCAGTGTAAGTGTAGCTTCTTATAGCTTAGTGCTTTACTATCTTCACAAGC

ACATGCTATAGTATTGTTCCAAGATGAAAGAATAATTCATCCTTGCTACCAAC

TTGCATGATATTATATTTGTGAATATCCTATCTCTTGGCTTATAATGAAATGTG

CTGCTGGGTTATTCTGACCATGGTATTTGAGAGCCTTTGTATAGCTGAAACC

AACGTATATCGAGCATGGAACAGAGAACAAAATGCAAGGATTTTTTTATTCTG

GTTCATGCCCTGGATGGGTTAATATCGTGATCATCAAAAAGATATGCATAAA

ATTAAAGTAATAAATTTGCTCATAAGAAACCAAAACCAAAAGCACATATGTCC

TAAACAAACTGCATTTTGTTTGTCATGTAGCAATACAAGAGATAATATATGAC

GTGGTTATGACTTATTCACTTTTTGTGACTCCAAAATGTAGTAGGTCTAACTG

ATTGTTTAAAGTGATGTCTTACTGTAGAAGTTTCATCCCAAAAGCAATCACTA

AAGCAACACACACGTATAGTCCACCTTCACGTAATTCTTTGTGGAAGATAACA

AGAAGGCTCACTGAAAAATAAAAGCAAAGAAAAGGATATCAAACAGACCATT

GTGCATCCCATTGATCCTTGTATGTCTATTTATCTATCCTCCTTTTGTGTACCT

TACTTCTATCTAGTGAGTCACTTCATATGTGGACATTAACAAACTCTATCTTAA

CATCTAGTCGATCACTACTTTACTTCACTATAAAAGGACCAACATATATCATC

CATTTCTCACAAAAGCATTGAGTTCAGTCCCACAAAATCTAGA

Seq #18 Glub-1 promoter seq
CTGCAGAGATATGGATTTTCTAAGATTAATTGATTCTCTGTCTAAAGAAAAAA

AGTATTATTGAATTAAATGGAAAAAGAAAAAGGAAAAAGGGGATGGCTTCTG

CTTTTTGGGCTGAAGGCGGCGTGTGGCCAGCGTGCTGCGTGCGGACAGCG

AGCGAACACACGACGGAGCAGCTACGACGAACGGGGACCGAGTGGACCG

GACGAGGATGTGGCCTAGGACGAGTGCACAAGGCTAGTGGACTCGGTCCC

CGCGCGGTATCCCGAGTGGTCCACTGTCTGCAAACACGATTCACATAGAGC

GGGCAGACGCGGGAGCCGTCCTAGGTGCACCGGAAGCAAATCCGTCGCCT

GGGTGGATTTGAGTGACACGGCCCACGTGTAGCCTCACAGCTCTCCGTGGT

CAGATGTGTAAAATTATCATAATATGTGTTTTTCAAATAGTTAAATAATATATAT

AGGCAAGTTATATGGGTCAATAAGCAGTAAAAAGGCTTATGACATGGTAAAA

TTACTTACACCAATATGCCTTACTGTCTGATATATTTTACATGACAACAAAGTT

ACAAGTACGTCATTTAAAAATACAAGTTACTTATCAATTGTAGTGTATCAAGTA

| Description | SEQ ID NO |
|---|---|

AATGACAACAAACCTACAAATTTGCTATTTTGAAGGAACACTTAAAAAAATCA

ATAGGCAAGTTATATAGTCAATAAACTGCAAGAAGGCTTATGACATGGAAAAA

TTACATACACCAATATGCTTTATTGTCCGGTATATTTTACAAGACAACAAAGTT

ATAAGTATGTCATTTAAAAATACAAGTTACTTATCAATTGTCAAGTAAATGAAA

ACAAACCTACAAATTTGTTATTTTGAAGGAACACCTAAATTATCAAATATAGCT

TGCTACGCAAAATGACAACATGCTTACAAGTTATTATCATCTTAAAGTTAGAC

TCATCTTCTCAAGCATAAGAGCTTTATGGTGCAAAAACAAATATAATGACAAG

GCAAAGATACATACATATTAAGAGTATGGACAGACATTTCTTTAACAAACTCC

ATTTGTATTACTCCAAAAGCACCAGAAGTTTGTCATGGCTGAGTCATGAAATG

TATAGTTCAATCTTGCAAAGTTGCCTTTCCTTTTGTACTGTGTTTTAACACTAC

AAGCCATATATTGTCTGTACGTGCAACAAACTATATCACCATGTATCCCAAGA

TGCTTTTTTATTGCTATATAAACTAGCTTGGTCTGTCTTTGAACTCACATCAAT

TAGCTTAAGTTTCCATAAGCAAGTACAAATAGCTCTAGA

Seq #19 Rice prolamin promoter seq
CTGCAGCATCGGCTTAGGTGTAGCAACACGACTTTATTATTATTATTATTATT

ATTATTATTATTTTACAAAAATATAAAATAGATCAGTCCCTCACCACAAGTAGA

GCAAGTTGGTGAGTTATTGTAAAGTTCTACAAAGCTAATTTAAAAGTTATTGC

ATTAACTTATTTCATATTACAAACAAGAGTGTCAATGGAACAATGAAAACCAT

ATGACATACTATAATTTTGTTTTTATTATTGAAATTATATAATTCAAAGAGAATA

AATCCACATAGCCGTAAAGTTCTACATGTGGTGCATTACCAAAATATATATAG

CTTACAAAACATGACAAGCTTAGTTTGAAAAATTGCAATCCTTATCACATTGA

CACATAAAGTGAGTGATGAGTCATAATATTATTTTTCTTGCTACCCATCATGT

ATATATGATAGCCACAAAGTTACTTTGATGATGATATCAAAGAACATTTTTAG

GTGCACCTAACAGAATATCCAAATAATATGACTCACTTAGATCATAATAGAGC

ATCAAGTAAAACTAACACTCTAAAGCAACCGATGGGAAAGCATCTATAAATAG

ACAAGCACAATGAAAATCCTCATCATCCTTCACCACAATTCAAATATTATAGT

TGAAGCATAGTAGTAGAATCCAACAACAATCTAGAG

Seq #20 Rice cysteine peptidase promoter seq
CCAGGCTTCATCCTAACCAUACAGGCAAGATGTrGTATGAAGAAGGGCGAA

CATGCAGATTGTTAAACTGACACGTGATGGACAAGAATGACCGATTGGTGAC

CGGTCTGACAATGGTCATGTCGTCAGCAGACAGCCATCTCCCACGTCGCGC

CTGCTTCCGGTGAAAGTGGAGGTAGGTATGGGCCGTCCCGTCAGAAGGTGA

TTCGGATGGCAGCGATACAAATCTCCGTCCATTAATGAAGAGAAGTCAAGTT

GAAAGAAAGGGAGGGAGAGATGGTGCATGTGGGATCCCCTTGGGATATAAA

AGGAGGACCTTGCCCACTTAGAAAGGAGAGGAGAAAGCAATCCCAGAAGAA

TCGGGGGCTGACTGGCACTTTGTAGCTTCTTCATACGCGAATCCACCAAAAC

ACAGGAGTAGGGTATTACGCTTCTCAGCGGCCCGAACCTGTATACATCGCC

CGTGTCTTGTGTGTTTCCGCTCTTGCGAACCTTCCACAGATTGGGAGCTTAG

AACCTCACCCAGGGCCCCCGGCCGAACTGGCAAAGGGGGCCTGCGCGGT

CTCCCGGTGAGGAGCCCCACGCTCCGTCAGTTCTAAATTACCCGATGAGAA

| Description | SEQ ID NO |
|---|---|

AGGGAGGGGGGGGGGGGAAATCTGCCTTGTTTATTTACGATCCAACGGATT

TGGTCGACACCGATGAGGTGTCTTACCAGTTACCACGAGCTAGATTATAGTA

CTAATTACTTGAGGATTCGGTTCCTAATTTTTTACCCGATCGACTTCGCCATG

GAAAATTTTTATTCGGGGAGAATATCCACCCTGTTTCGCTCCTAATTAAGA

TAGGAATTGTTACGATTAGCAACCTAATTCAGATCAGAATTGTTAGTTAGCGG

CGTTGGATCCCTCACCTCATCCCATCCCAATTCCCAAACCCAAACTCCTCTT

CCAGTCGCCGACCCAAACACGCATCCGCCGCCTATAAATCCCACCCGCATC

GAGCCTATCAAGCCCAAAAAACCACAAACCAAACGAAGAAGGAAAAAAAAAG

GAGGAAAAGAAAGAGGAGGAAAGCGAAGAGGTTGGAGAGAGACGCTCGT

CTCCACGTCGCCGCC

Seq #21 Barley D-Hordein promoter
CTTCGAGTGCCCGCCGATTTGCCAGCAATGGCTAACAGACACATATTCTGCC

AAAACCCCAGAACAATAATCACTTCTCGTAGATGAAGAGAACAGACCAAGAT

ACAAACGTCCACGCTTCAGCAAACAGTACCCCAGAACTAGGATTAAGCCGAT

TACGCGGCTTTAGCAGACCGTCCAAAAAAACTGTTTTGCAAAGCTCCAATTC

CTCCTTGCTTATCCAATTTCTTTTGTGTTGGCAAACTGCACTTGTCCAACCGA

TTTTGTTCTTCCCGTGTTTCTTCTTAGGCTAACTAACACAGCCGTGCACATAG

CCATGGTCCGGAATCTTCACCTCGTCCCTATAAAAGCCCAGCCAATCTCCAC

AATCTCATCATCACCGAGAACACCGAGAACCACAAAACTAGAGATCAATTCA

TTGACAGTCCACCG

| Rice Glb promoter and Gt1 leader coding sequence<br>Other storage body leader sequences<br>Bx7 #22 bx7 signal peptide seq<br>ATGGCTAAGCGCCTGGTCCTCTTTGCGGCAGTAGTCGTCGCCCTCGTGGCT | 22-28 |

CTCACCGCC

Seq #23 Glub-2 signal peptide seq
ATGGCAACTACCATTTTCTCTCGTTTTTCTATATACTTTTGTGCTATGCTATTA

TGCCAGGGTTCTATGGCC

Seq #24 GT3 signal peptide seq
ATGTGGACATTAACAAACTCTATCTTAACATCTAGTCGATCACTACTTTACTTC

ACTATAAAAGGACCAACATATATCATCCATT

Seq #25 Glub-1 signal peptide seq
ATGGCGAGTTCCGTTTTCTCTCGGTITTCTATATACTTTTGTGTTCTTCTATTA

TGCCATGGTTCTATGGCC

Seq #26 prolamin signal peptide seq
ATGAAGATCATTTTCGTATTTGCTCTCCTTGCTATTGTTGCATGCAACGCTTC

TGCACGGTTTGATGCT

Seq #27 Rice cysteine peptidase signal peptide seq
ATGGCCGCCCGCGCCGCCGCCGCCGCGTTCCTGCTGCTGCTCATCGTCGT

TGGTCACCGCGCC

Seq #28 D-Hordein signal peptide
ATGGCTAAGCGGCTGGTCCTCTTTGTGGCGGTAATCGTCGCCCTCGTGGCT CTCACCACCGCC Other monocot maturation specific -continued

| Description | SEQ ID NO |
|---|---|
| promoter sequences | |
| O2 transcription factor sequence | 29 |

ATGGAGCACGTCATCTCAATGGAGGAGATCCTCGGGCCCTTCTGGGAGCTG

CTACCACCGCCAGCGCCAGAGCCAGAGCGAGAGCAGCCTCCGGTAACCGG

CATCGTCGTCGGCAGTGTCATAGACGTTGCTGCTGCTGGTCATGGTGACGG

GGACATGATGGATCAGCAGCACGCCACAGAGTGGACCTTTGAGAGGTTACT

AGAAGAGGAGGCTCTGACGACAAGCACACCGCCGCCGGTGGTGGTGGTGC

CGAACTCTTGTTGCTCAGGCGCCCTAAATGCTGACCGGCCGCCGGTGATGG

AAGAGGCGGTAACTATGGCGCCTGCGGCGGTGAGTAGTGCCGTAGTAGGT

GACCCCATGGAGTACAATGCCATACTGAGGAGGAAGCTGGAGGAGGACCTC

GAGGCCTTCAAAATGTGGAGGGCGGCCTCCAGTGTTGTGACCTCAGATCAA

CGTTCTCAAGGCTCAAACAATCACACTGGAGGTAGCAGCATCAGGAATAATC

CAGTGCAGAACAAGCTGATGAACGGCGAAGATCCAATCAACAATAACCACG

CTCAAACTGCAGGCCTTGGCGTGAGGCTTGCTACTAGCTCTTCCTCGAGAG

ATCCTTCACCATCAGACGAAGACATGGACGGAGAAGTAGAGATTCTGGGGT

TCAAGATGCCTACCGAGGAAAGAGTGAGGAAAAGAAAGGAATCCAATAGAG

AATCAGCCAGACGCTCGAGATACAGGAAAGCCGCTCACCTGAAAGAACTGG

AAGACCAGGTAGCACAGCTAAAAGCCGAGAATTCTTGCCTGCTGAGGCGCA

TTGCCGCTCTGAACCAGAAGTACAACGACGCTAACGTCGACAACAGGGTGC

TGAGAGCGGACATGGAGACCCTAAGAGCTAAGGTGAAGATGGGAGAGGACT

CTCTGAAGCGGGTGATAGAGATGAGCTCATCAGTGCCGTCGTCCATGCCCA

TCTCGGCGCCGACCCCAGCTCCGACGCTCCAGTGCCGCCGCCGCCTATC

CGAGACAGCATCGTCGGCTACTTCTCCGCCACAGCCGCAGACGACGATGCT

TCGGTCGGCAACGGTTTCTTGCGACTGCAAGCTCATCAAGAGCCTGCATCC

ATGGTCGTCGGTGGAACTCTGAGCGCCACAGAGATGAACCGAGTAGCAGCA

GCCACGCATTGCGCGGGGGCCATGGAGCACATCCAGACGGCGATGGGATC

CATGCCGCCGACCTCCGCCTCCGGATCTACACCGCCGCCGCAGGATTATGA

GCTGCTGGGTCCAAATGGGGCCATACACATGGACATGTATTAG

| PBF transcription factor sequence | 30 |

ATGGACATGATCTCCGGCAGCACTGCAGCAACATCAACACCCCACAACAAC

CAACAGGCGGTGATGTTGTCATCCCCCATTATAAAGGAGGAAGCTAGGGAC

CCAAAGCAGACACGAGCCATGCCCCAAATAGGTGGCAGTGGGGAGCGTAA

GCCGAGGCCGCAACTACCTGAGGCGCTCAAGTGCCCACGCTGCGACTCCA

ACAACACCAAGTTTTGCTACTACAACAATTATAGCATGTCACAACCACGCTAC

TTTTGCAAGGCTTGCCGCCGCTATTGGACACATGGTGGTACCCTCCGCAAT

GTCCCCATTGGTGGTGGGTGTCGCAAGAACAAACATGCCTCTAGATTTGTCT

TGGGCTCTCACACCTCATCGTCCTCATCTGCTACCTATGCACCATTATCCCC

TAGCACCAACGCTAGCTCTAGCAATATGAGCATCAACAAACATATGATGATG

GTGCCTAACATGACGATGCCTACCCCAACGACAATGGGCTTATTCCCTAATG

TGCTCCCAACACTTATGCCGACAGGTGGAGGCGGGGGCTTTGACTTCACTA

| Description | SEQ ID NO |
|---|---|

TGGACAACCAACATAGATCATTGTCCTTCACACCAATGTCTCTACCTAGCCA

GGGGCCAGTGCCTATGCTGGCTGCAGGAGGGAGTGAGGCAACACCGTCTT

TCCTAGAGATGCTGAGAGGAGGGATTTTTCATGGTAGTAGTAGCTATAACAC

AAGTCTCACGATGAGTGGTGGCAACAATGGAATGGACAAGCCATTTTCGCTG

CCATCATATGGTGCAATGTGCACAAATGGGTTGAGTGGCTCAACCACTAATG

ATGCCAGACAACTGGTGGGGCCTCAGCAGGATAACAAGGCCATCATGAAGA

GCAGTAATAACAACAATGGTGTATCATTGTTGAACCTCTACTGGAACAAGCA

CAACAACAACAACAACAACAACAACAACAACAACAACAACAACAACAACAAG

GGACAATAA

| Reb transcription factor sequence | 31 |
|---|---|

ATGGAGCGGGTGTTCTCCGTGGAGGAGATCTCCGACCCATTCTGGGTCCCG

CCTCCGCCGCCGCAGTCGGCGGCGGCGGCCCAGCAGCAGGGCGGCGGCG

GCGTGGCTTCGGGAGGTGGTGGTGGTGTAGCGGGGGGCGGCGGCGGCGG

GAACGCGATGAACCGGTGCCCGTCGGAGTGGTACTTCCAGAAGTTTCTGGA

GGAGGCGGTGCTCGATAGCCCCGTCCCGAACCCTAGCCCGAGGGCCGAAG

CGGGAGGGATCAGGGGCGCAGGAGGGGTGGTGCCGGTCGATGTTAAGCA

GCCGCAGCTCTCGGCGGCGGCGACGACGAGCGCGGTGGTGGACCCCGTG

GAGTACAACGCGATGCTGAAGCAGAAGCTGGAGAAGGACCTCGCCGCGGT

CGCCATGTGGAGGGTACAGCCATTCTCCCCCCCTCTAGTACTCGAGAGCTT

ACTGAGATCGGCAATGCTAGCTACTGTTTGCATCGAATGTTTATAGGTATTTA

GATCGGGCATTTCTATAGACCAATGGCGTCCATGGTCTTGCAATGCGCTCTG

TTGAGTGTCGGTGGTTGGTTCGACTCATAGTATGTAGGGTTGTGCGTATGTA

CAAACGGAAGCTTCATAGACCTCGGTATTGAGATTGCGATATCGATGCAACC

TGCGAATTGGCGATGTAATCAGTCATATTCTTACTAAACTGCGAGACAGTGG

TTTGTTTGCAATTGCAATATTTTTGTATGGGGCTGCTTAAACTGTCATTGCCT

TTTTAGATTGGCAATATGTGACTTTATGCAAGTATTTGATTGGGCGGATCCAG

GAACAAAAAGTTGGGGGGATTCAACATACCGAGTACACTGGCATAAACACAT

CATCTCAGTATTAAACTATGCTAAAATGCTATTAAGAGACCTTTAGCACCTCT

TATCTTATCAACCATGGTGAAAAAATTGAAGGGGGGACTCAGGGGGGTATCC

ATGGGTCCGATGGGTGCAGGGGGGACTGAGTCCCCCCTGCACCCACGTTG

AATCCGCCCTGGCATGCGTATAAGCTGTCACAGCCATTTCTAGGTGCTTGTG

CTTAGTTGGGTGATGTCAGCTTAATTTGTCTTTTCTATGTCGTCATCGATTTT

CTAAGAAACGAAAAATAGCCTATTTATGTGCTCCAGAATTTGATGATCCCTGG

CCCTTCATTTGCTGAAATTAGCCTATTTGTTGGTTGCCCTTCAGTTTTTTCCC

AGCTTATGTTGTTGCAATGTGTGGCTATGCCTCGTTTTGTGCCCTATAATTTA

TTATTTGCAATTCATTTTTGTACATGACTTAAAATGACACTAGAGCAACATGCA

CTGATTGGTTATCCTATAATCATTTATGTAGTTCTGTTCATTTTATCATGCTAG

CTCATGTCATTTTCATCTTCAGGCCTCTGGCACAGTTCCACCTGAGCGTCCT

GGAGCTGGTTCATCCTTGCTGAATGCAGATGTTTCACACATAGGCGCTCCTA

| Description | SEQ ID NO |
|---|---|

```
ATTCCATCGGAGGTACTTATCTTATCTGGTTACATTTTCAGATTGTTATGAAA

CTACCCAAATATCCTGCACAATTGCATGGGATTAAATTTTAGTTTCTTTGAAAT

AGAAGTAGAGTTGTATTGCTGTCACGTCATCAAATAGTTCTGAAGCTATGAAT

AAATAAGTTCCGCATTTGTTAGTGATTCTTTGAACATTAGAATTGTTATGCTTA

AGTAGATAGGGTTATGTTTGTTTGGAGTTCCCTTAAATCATTTCATTGCTGAC

TGCCAGCTGGCAGGAGCATTTGTTGTTGCCTTGACCATGAATGAAGACCTTC

CTGTTCTGAGTGCTCACAAGAAAACATATTTTGATTAATGCACCTTGAATCCT

TAGGATCTTGCAAAGATGGGCACTTAGCTTTAGAATTGAGTAGTACTTAAATA

GCTGTTGTTATCATGATTTGTCCTGTAGTGAAATGTCGACAAAACAGGAATG

CTACTTTTGACTTCTGATATTTCATGCCTGGCTTTACTTATGCTCTGTTTGGAA

CATGGGCACATATCAGGCAATGCTACTCCAGTTCAAAACATGCTAAGTGGCC

CAAGTGGGGATCGGGCTCACAGTTGGTACAGAATGTTGATGTCCTTGTAAA

GCAGCCCACCAGCTCTTCATCAAGGGAGCAGTCAGATGATGATGACATGAA

GGGAGAAGCTGAGACCACTGGAACTGCAAGACCTGCTGATCAAAGATTACA

ACGAAGGTGATCATTCATTGCTTCCTTGTAATATAGATTCTGTACATAATTAA

CCTACCTCGTCATGCATGCATGTGTCCTATTTTCACCTTAGCCCTTTCAGTTG

GATTTCCACTTTCATCCGGTAGCCTTTCAGTTTCCTATTGCATCGCATATATG

ATCTTTTACCTACCATATTAGTTCTCTGTGTGCCATACTCAGTGCTTAGTGTC

TCGAGCAAGAGAGGAATTTGTATGGCTATTACACGTAGCACTTTGCTCTCTA

CTTGTTTATTGACATAAGCAATTTGGGATGAATTAAATCTGAGTTCACATCAT

ATTCCTTATGTCACAAGTTTCTGAAACCGATTGTATCTAGTATCTGGTTGATG

CACCCCCATCTTGGATTTGCAAATCAAAGTTATACTCCCTAGAGAGCTTTACC

TTTCATAAAGCAATTACCCCAATAAACCACGGATTTGATAGCTATTGACTATG

ATTACCAGAATTCATTTGGCAGCTATTTTCTCAATTTAAGTTTGGTATTAGTCT

CAGTTGGCTGTAAAATAATGTCACGGTAGGGTACATGTATGTGCAGCATACA

AGGTATGGGTGAGTTATGATATGGACAGTGTGTACACCCCACATTTGCTCAC

TAAAATCAAAATATTCAAACGTCACGTGATGATATGGTGGATTGCATTATACC

TTGTATTGTTTATTATGTTACTTGTGCTAGACAATAATATAGGCTGTTCTTTTG

GGTGATTTTGTATGAAGATGTTGAGCAAGCACTTCTCGATATAATGCTAGTTT

TGTTGACCTGTTCCAGGAAGCAATCCAATCGGGAGTCAGCCAGGCGCTCAA

GAAGCAGAAAGGCAGCTCACTTGAATGAGCTGGAGGCACAGGTGTGATAGT

TCACATAGTTATTTTCGATAAGACATAAAATCCTAAATTACTGGCTACTGACTT

CAGTTATGGATTTACTTGTTACAGGTATCGCAATTAAGAGTCGAGAACTCCTC

GCTGTTAAGGCGTCTTGCTGATGTTAACCAGAAGTACAATGATGCTGCTGTT

GACAATAGAGTGCTAAAAGCAGATGTTGAGACCTTGAGAGCAAAGGTATGCT

ATATATGCCTTTTGCAATATGCATCCCATGGATTGCTACTTTGGCTTGTTTCA

AACTTTCAACGTGACTTGTGTACCCTGTTATTAGAAGAATAATCCCGCCTACC

ATTATACTCTATAAATCACCATTTGGCCAGTCCAAACATGATTATTAAATCAG
```

-continued

| Description | SEQ ID NO |
|---|---|
| GTCAATCTGAACATTGAAATGTATCAAAAATTCGCAGGTGAAGATGGCAGAG | |
| GACTCGGTGAAGCGGGTGACAGGCATGAACGCGTTGTTTCCCGCCGCTTCT | |
| GATATGTCATCCCTCAGCATGCCATTCAACAGCTCCCCATCTGAAGCAACGT | |
| CAGACGCTGCTGTTCCCATCCAAGATGACCCGAACAATTACTTCGCTACTAA | |
| CAACGACATCGGAGGTAACAACAACTACATGCCCGACATACCTTCTTCGGCT | |
| CAGGAGGACGAGGACTTCGTCAATGGCGCTCTGGCTGCCGGCAAGATTGG | |
| CCGGCCAGCCTCGCTGCAGCGGGTGGCGAGCCTGGAGCATCTCCAGAAGA | |
| GGATGTGCGGTGGGCCGGCTTCGTCTGGGTCGACGTCCTGA | |
| KVFER( )ELART | 32 |
| KVFERCELART | 33 |
| GRRRRSVQWCA | 34 |
| GRRRRSVQWCA | 35 |

What is claimed is:

1. A method of producing a recombinant milk protein in monocot plant seeds comprising the steps:
   (a) obtaining a monocot plant stably transformed with a chimeric gene having (i) a seed maturation-specific promoter, (ii) operably linked to said promoter, a leader DNA sequence encoding a monocot seed-specific transit sequence capable of targeting a linked polypeptide to an endosperm-cell organelle, wherein the promoter operably linked to the leader sequence comprises either SEQ ID NO:13 or SEQ ID NO:14 and (iii) a protein-coding sequence encoding a protein normally present in human milk,
   (b) cultivating the plant under seed-maturation conditions, and
   (c) harvesting the seeds from the plant, wherein the milk protein constitutes at least 3% of the total soluble protein contained in the harvested seeds.

2. The method of claim 1, wherein the leader sequence in the chimeric gene is selected from the group of leader sequences of genes encoding rice glutelins, globulins, oryzins and prolamines, barley hordeins, wheat gliadins, glutenins and purindolines, maize zeins and glutelins, oat glutelins, sorghum kafirins, millet pennisetins, and rye secalins.

3. The method of claim 1, wherein the transformed monocot plant is a rice plant, and the promoter operably linked to the leader sequence comprises SEQ ID NO:13.

4. The method of claim 1, wherein the transformed monocot plant is a rice plant, and the promoter operably linked to the leader sequence comprises SEQ ID NO: 14. is SEQ ID NO:14.

5. The method of claim 1, wherein the transformed monocot plant further comprises a nucleic acid that encodes at least one transcription factor selected from the group consisting of Reb, O2 and PBF.

6. The method of claim 5, wherein the transcription factor is O2 and/or PBF.

7. The method of claim 1, wherein the protein-coding sequence is a coding sequence for a milk protein selected from the group consisting of lactoferrin, lysozyme, lactoferricin, lactadherin, kappa-casein, haptocorrin, lactoperoxidase, alpha-lactalbumin, beta-lactoglobulin, alpha-casein, beta-casein alpha-1-antitrypsin, and immunoglobulins.

8. The method of claim 7, wherein the protein-coding sequence is selected from the group of codon-optimized sequences identified by SEQ ID NOS: 1, 3, and 7-12.

9. A method of producing a recombinant milk protein in monocot plant seeds comprising the steps of:
   (a) obtaining a monocot plant stably transformed with a chimeric gene having (i) a seed maturation-specific promoter, (ii) operably linked to said promoter, a leader DNA sequence encoding a monocot seed-specific transit sequence capable of targeting a linked polypeptide to an endosperm-cell organelle, and (iii) the protein-coding sequence comprising of SEQ ID NO:1,
   (b) cultivating the plant under seed-maturation conditions, and
   (c) harvesting the seeds from the plant, wherein the milk protein constitutes at least 3% of the total soluble protein contained in the harvested seeds.

10. The method of claim 9, wherein the promoter in the chimeric gene is the promoter of a gene selected from the group of genes encoding rice glutelins, globulins, oryzins, and prolamines, barley hordeins, wheat gliadins, glutenins and purindolines, maize zeins and glutelins, oat glutelins, sorghum kafirins, millet pennisetins, and rye secalins.

11. The method of claim 9, wherein the leader sequence in the chimeric gene is selected from the group of leader sequences of genes encoding rice glutelins, globulins, oryzins and prolamines, barley hordeins, wheat gliadins, glutenins and purindolines, maize zeins and glutelins, oat glutelins, sorghum kafirins, millet pennisetins, and rye secalins.

12. The method of claim 9, wherein the transformed monocot plant is a rice plant, the promoter in the chimeric gene is a rice glutelin Gt1 promoter, and the leader DNA sequence encodes a rice glutelin Gt1 signal sequence capable of targeting a linked polypeptide to a protein storage body.

13. The method of claim 12, wherein glutelin Gt1 promoter and glutelin Gt1 leader DNA sequence are included within the sequence identified by SEQ ID NO:13.

14. The method of claim 9, wherein the transformed monocot plant is a rice plant, the promoter in the chimeric gene is a rice globulin Glb promoter, and the leader DNA sequence encodes a rice glutelin Gt1 signal sequence capable of targeting a linked polypeptide to a protein storage body.

15. The method of claim 14, wherein the globulin Glb promoter and glutelin Gt1 leader DNA sequence are included within the sequence identified by SEQ ID NO:14.

16. The method of claim 9, wherein the transformed monocot plant further comprises a nucleic acid that encodes at least one transcription factor selected from the group consisting of Reb, O2 and PBF.

17. The method of claim 16, wherein the transcription factor is O2 and/or PBF.

* * * * *

SEQUENCE LISTING

<160> NUMBER OF SEQ ID NOS: 35

<210> SEQ ID NO 1
<211> LENGTH: 393
<212> TYPE: DNA
<213> ORGANISM: Homo sapiens

<400> SEQUENCE: 1

```
aaagtcttcg agcggtgcga gctggcccgc acgctcaagc ggctcggcat ggacggctac      60
cggggcatca gcctcgccaa ctggatgtgc ctcgccaagt gggagtcggg ctacaacacc     120
cgcgcaacca actacaacgc cggcgaccgc tccaccgact acggcatctt ccagatcaac     180
tcccgctact ggtgcaacga cggcaagacg cccggggccg tcaacgcctg ccacctctcc     240
tgctcggccc tgctgcaaga caacatcgcc gacgccgtcg cgtgcgcgaa gcgcgtcgtc     300
cgcgacccgc agggcatccg ggcctgggtg gcctggcgca accgctgcca gaaccgggac     360
gtgcgccagt acgtccaggg ctgcggcgtc tga                                   393
```

<210> SEQ ID NO 2
<211> LENGTH: 130
<212> TYPE: PRT
<213> ORGANISM: Homo sapiens

<400> SEQUENCE: 2

```
Lys Val Phe Glu Arg Cys Glu Leu Ala Arg Thr Leu Lys Arg Leu Gly
  1               5                  10                  15
Met Asp Gly Tyr Arg Gly Ile Ser Leu Ala Asn Trp Met Cys Leu Ala
             20                  25                  30
Lys Trp Glu Ser Gly Tyr Asn Thr Arg Ala Thr Asn Tyr Asn Ala Gly
         35                  40                  45
Asp Arg Ser Thr Asp Tyr Gly Ile Phe Gln Ile Asn Ser Arg Tyr Trp
     50                  55                  60
Cys Asn Asp Gly Lys Thr Pro Gly Ala Val Asn Ala Cys His Leu Ser
 65                  70                  75                  80
```

```
Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130

<210> SEQ ID NO 3
<211> LENGTH: 2079
<212> TYPE: DNA
<213> ORGANISM: Homo sapiens

<400> SEQUENCE: 3
```

| | | | | | |
|---|---|---|---|---|---|
| gggcggcggc | ggcgctcggt | gcagtggtgc | gccgtgtccc | agcccgaggc | gaccaagtgc | 60 |
| ttccagtggc | agcgcaacat | gcggaaggtg | cgcggcccgc | cggtcagctg | catcaagcgg | 120 |
| gactcccca | tccaatgcat | ccaggccatc | gcggagaacc | gcgccgacgc | ggtcaccctg | 180 |
| gacggcgggt | tcatctacga | gcggggctc | gccccgtaca | agctccgccc | ggtggcggcg | 240 |
| gaggtgtacg | gcaccgagcg | ccagccgcgc | acgcactact | acgcggtggc | cgtcgtcaag | 300 |
| aagggcgggt | ccttccagct | caacgagctg | cagggcctga | gtcgtgcca | cacgggcctc | 360 |
| cggcggacgg | cgggctggaa | cgtgcccatc | ggcaccctgc | gccccttcct | gaactggacc | 420 |
| ggcccgccgg | agccgatcga | ggccgccgtg | gcccgcttct | tcagcgcctc | ctgcgtcccc | 480 |
| ggcgccgaca | agggccagtt | cccgaacctc | tgccggctct | gccgcgggac | gggcgagaac | 540 |
| aagtgcgcct | tctcctcgca | ggagccgtac | ttctcctact | cgggcgcgtt | caagtgcctc | 600 |
| cgcgacgggg | ccggcgacgt | ggcgttcatc | cgcgagtcca | ccgtgttcga | ggacctctcc | 660 |
| gacgaggcgg | agcgggacga | gtacgagctg | ctgtgccccg | acaacacccg | caagccggtg | 720 |
| gacaagttca | aggactgcca | cctggcgcgg | gtgccctcgc | acgcggtcgt | cgcccgcagc | 780 |
| gtcaacggca | aggaggacgc | gatctggaac | ctcctccgcc | aggcccagga | gaagttcggc | 840 |
| aaggacaagt | cccccaagtt | ccagctcttc | gggagcccca | gcggccagaa | ggacctcctc | 900 |
| ttcaaggact | ccgcgatcgg | cttctcccgc | gtcccccgc | gcatcgactc | cggcctgtac | 960 |
| tcggctccg | ggtacttcac | cgcgatccag | aacctccgga | gagcgagga | ggaggtggcg | 1020 |
| gcgcggcggg | cccgcgtcgt | gtggtgcgcc | gtgggcgagc | aggagctgcg | gaagtgcaac | 1080 |
| cagtggagcg | gcctgagcga | ggggtcggtg | acctgctcgt | ccgccagcac | caccgaggac | 1140 |
| tgcatcgcgc | tcgtcctcaa | gggggaggcc | gacgcgatga | gcctcgacgg | ggggtacgtc | 1200 |
| tacaccgccg | gcaagtgcgg | cctggtcccg | gtcctggcgg | agaactacaa | gtcgcagcag | 1260 |
| tccagcgacc | ccgaccccga | actgcgtggac | cgccccgtcg | agggctacct | cgccgtggcc | 1320 |
| gtcgtgcgcc | ggtccgacac | ctcccctgacg | tggaacagcg | tcaagggcaa | gaagagctgc | 1380 |
| cacaccgccg | tggaccgcac | cgccggctgg | aacatcccga | tgggcctcct | cttcaaccag | 1440 |
| accggctcct | gcaagttcga | cgagtacttc | tcccagtcct | gcgcccccgg | ctcggacccc | 1500 |
| cgctccaacc | tgtgcgccct | ctgcatcggg | gacgagcagg | gcgagaacaa | gtgcgtgccc | 1560 |
| aacagcaacg | agcggtacta | cggctacacg | ggggccttcc | gctgcctggc | ggagaacgcc | 1620 |
| ggggacgtcg | cgttcgtgaa | ggacgtgacc | gtgctgcaaa | acacgacgg | gaacaacaac | 1680 |
| gaggcgtggg | cgaaggacct | caagctcgcc | gacttcgccc | tgctgtgcct | cgacggcaag | 1740 |

```
cgcaagcccg tcaccgaggc gcggtcctgc cacctggcga tggcccccaa ccacgccgtc   1800
gtctcccgca tggacaaggt cgagcgcctc aagcaggtgc tcctgcacca gcaggccaag   1860
ttcggccgga acggcagcga ctgcccggac aagttctgcc tgttccagtc ggagaccaag   1920
aacctcctct tcaacgacaa caccgagtgc ctggcgcgcc tccacggcaa gaccacctac   1980
gagaagtacc tcggcccgca gtacgtcgcc ggcatcacca acctcaagaa gtgctccacc   2040
tcccccctcc tggaggcgtg cgagttcctc cgcaagtga                          2079
```

<210> SEQ ID NO 4
<211> LENGTH: 690
<212> TYPE: PRT
<213> ORGANISM: Homo sapiens

<400> SEQUENCE: 4

```
Gly Arg Arg Arg Ser Val Gln Trp Cys Ala Val Ser Gln Pro Glu
 1               5                  10                  15

Ala Thr Lys Cys Phe Gln Trp Gln Arg Asn Met Arg Lys Val Arg Gly
             20                  25                  30

Pro Pro Val Ser Cys Ile Lys Arg Asp Ser Pro Ile Gln Cys Ile Gln
         35                  40                  45

Ala Ile Ala Glu Asn Arg Ala Asp Ala Val Thr Leu Asp Gly Gly Phe
     50                  55                  60

Ile Tyr Glu Ala Gly Leu Ala Pro Tyr Lys Leu Arg Pro Val Ala Ala
 65                  70                  75                  80

Glu Val Tyr Gly Thr Glu Arg Gln Pro Arg Thr His Tyr Tyr Ala Val
                 85                  90                  95

Ala Val Val Lys Lys Gly Gly Ser Phe Gln Leu Asn Glu Leu Gln Gly
            100                 105                 110

Leu Lys Ser Cys His Thr Gly Leu Arg Arg Thr Ala Gly Trp Asn Val
        115                 120                 125

Pro Ile Gly Thr Leu Arg Pro Phe Leu Asn Trp Thr Gly Pro Pro Glu
    130                 135                 140

Pro Ile Glu Ala Ala Val Ala Arg Phe Phe Ser Ala Ser Cys Val Pro
145                 150                 155                 160

Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
            180                 185                 190

Tyr Ser Gly Ala Phe Lys Cys Leu Arg Asp Gly Ala Gly Asp Val Ala
        195                 200                 205

Phe Ile Arg Glu Ser Thr Val Phe Glu Asp Leu Ser Asp Glu Ala Glu
    210                 215                 220

Arg Asp Glu Tyr Glu Leu Leu Cys Pro Asp Asn Thr Arg Lys Pro Val
225                 230                 235                 240

Asp Lys Phe Lys Asp Cys His Leu Ala Arg Val Pro Ser His Ala Val
                245                 250                 255

Val Ala Arg Ser Val Asn Gly Lys Glu Asp Ala Ile Trp Asn Leu Leu
            260                 265                 270

Arg Gln Ala Gln Glu Lys Phe Gly Lys Asp Lys Ser Pro Lys Phe Gln
        275                 280                 285

Leu Phe Gly Ser Pro Ser Gly Gln Lys Asp Leu Leu Phe Lys Asp Ser
    290                 295                 300

Ala Ile Gly Phe Ser Arg Val Pro Pro Arg Ile Asp Ser Gly Leu Gly
305                 310                 315                 320
```

```
Ser Gly Tyr Phe Thr Ala Ile Gln Asn Leu Arg Lys Ser Glu Glu
            325                 330                 335

Val Ala Ala Arg Arg Ala Arg Val Val Trp Cys Ala Val Gly Glu Gln
            340                 345                 350

Glu Leu Arg Lys Cys Asn Gln Trp Ser Gly Leu Ser Glu Gly Ser Val
            355                 360                 365

Thr Cys Ser Ser Ala Ser Thr Thr Glu Asp Cys Ile Ala Leu Val Leu
            370                 375                 380

Lys Gly Glu Ala Asp Ala Met Ser Leu Asp Gly Gly Tyr Val Tyr Thr
385                 390                 395                 400

Ala Gly Lys Cys Gly Leu Val Pro Val Leu Ala Glu Asn Tyr Lys Ser
            405                 410                 415

Gln Gln Ser Ser Asp Pro Asp Pro Asn Cys Val Asp Arg Pro Val Glu
            420                 425                 430

Gly Tyr Leu Ala Val Ala Val Val Arg Arg Ser Asp Thr Ser Leu Thr
            435                 440                 445

Trp Asn Ser Val Lys Gly Lys Lys Ser Cys His Thr Ala Val Asp Arg
450                 455                 460

Thr Ala Gly Trp Asn Ile Pro Met Gly Leu Leu Phe Asn Gln Thr Gly
465                 470                 475                 480

Ser Cys Lys Phe Asp Glu Tyr Phe Ser Gln Ser Cys Ala Pro Gly Ser
            485                 490                 495

Asp Pro Arg Ser Asn Leu Cys Ala Leu Cys Ile Gly Asp Glu Gln Gly
            500                 505                 510

Glu Asn Lys Cys Val Pro Asn Ser Asn Glu Arg Tyr Tyr Gly Tyr Thr
            515                 520                 525

Gly Ala Phe Arg Cys Leu Ala Glu Asn Ala Gly Asp Val Ala Phe Val
            530                 535                 540

Lys Asp Val Thr Val Leu Gln Asn Thr Asp Gly Asn Asn Asn Glu Ala
545                 550                 555                 560

Trp Ala Lys Asp Leu Lys Leu Ala Asp Phe Ala Leu Leu Cys Leu Asp
            565                 570                 575

Gly Lys Arg Lys Pro Val Thr Glu Ala Arg Ser Cys His Leu Ala Met
            580                 585                 590

Ala Pro Asn His Ala Val Val Ser Arg Met Asp Lys Val Glu Arg Leu
            595                 600                 605

Lys Gln Val Leu Leu His Gln Gln Ala Lys Phe Gly Arg Asn Gly Ser
            610                 615                 620

Asp Cys Pro Asp Lys Phe Cys Leu Phe Gln Ser Glu Thr Lys Asn Leu
625                 630                 635                 640

Leu Phe Asn Asp Asn Thr Glu Cys Leu Ala Arg Leu His Gly Lys Thr
            645                 650                 655

Thr Tyr Glu Lys Tyr Leu Gly Pro Gln Tyr Val Ala Gly Ile Thr Asn
            660                 665                 670

Leu Lys Lys Cys Ser Thr Ser Pro Leu Leu Glu Ala Cys Glu Phe Leu
            675                 680                 685

Arg Lys
690

<210> SEQ ID NO 5
<211> LENGTH: 42
<212> TYPE: DNA
<213> ORGANISM: Artificial Sequence
<220> FEATURE:
```

```
<223> OTHER INFORMATION: primer

<400> SEQUENCE: 5
atcgaagctt catgagtaat gtgtgagcat tatgggacca cg                          42

<210> SEQ ID NO 6
<211> LENGTH: 53
<212> TYPE: DNA
<213> ORGANISM: Artificial Sequence
<220> FEATURE:
<223> OTHER INFORMATION: primer

<400> SEQUENCE: 6
ctagtctaga ctcgagccat ggggccggct agggagccat cgcacaagag gaa             53

<210> SEQ ID NO 7
<211> LENGTH: 72
<212> TYPE: DNA
<213> ORGANISM: Artificial Sequence
<220> FEATURE:
<223> OTHER INFORMATION: codon optimized lactoferricin coding sequence
      based on Homo sapiens sequence

<400> SEQUENCE: 7
accaagtgct tccagtggca gcgcaacatg cggaaggtgc gcggcccgcc ggtcagctgc      60
atcaagcggg ac                                                          72

<210> SEQ ID NO 8
<211> LENGTH: 1095
<212> TYPE: DNA
<213> ORGANISM: Artificial Sequence
<220> FEATURE:
<223> OTHER INFORMATION: codon optimized lactadherin coding sequence
      based on Homo sapiens sequence

<400> SEQUENCE: 8
ctggacatct gctcgaagaa cccgtgccac aacggcgggc tctgcgagga gatcagccag      60
gaggtgcggg gcgacgtgtt cccctcgtac acctgcacct gctgaaggg ctacgccggg      120
aaccactgcg agacgaagtg cgtggagccc ctggggatgg agaacggcaa catcgccaac     180
tcccagatcg ccgcctcctc cgtgcgggtg accttcctcg gcctccagca ctgggtcccg     240
gagctggccc ggctcaaccg ggcgggcatg gtgaacgcgt ggaccccctc gtccaacgac     300
gacaacccgt ggatccaagt gaacctgctc cgccgcatgt gggtcaccgg cgtggtcacc     360
caaggcgcca gccgcctggc cagccacgag tacctcaagg ccttcaaggt cgcctacagc     420
ctcaacggcc acgagttcga cttcatccac gacgtcaaca agaagcacaa ggagttcgtg     480
ggcaactgga caagaacgc ggtccacgtg aacctcttcg accccgt cgaggcccag          540
tacgtccgcc tctaccccac gagctgccac accgcctgca cgctccgctt cgagctgctg     600
gggtgcgagc tgaacgggtg cgcgaacccg ctggggctca gaacaacag catccccgac      660
aagcagatca cggcctcgtc gtcgtacaag acctggggcc tgcacctctt ctcgtggaac     720
ccgagctacg cccggctgga caagcagggc aacttcaacg cctgggtcgc cgggagctac     780
gggaacgacc agtggctcca ggtggacctc ggcagctcca aggaggtcac cggcatcatc     840
acgcagggg cccgcaactt cggctccgtg cagttcgtgg cctcctacaa ggtggcctac     900
tcgaacgaca cgccaactg gaccgagtac caggacccgc gcaccgggtc cagcaagatc      960
ttccccggca actgggacaa ccacagccac aagaagaacc tgttcgagac ccccatcctc     1020
gcccggtacg tccgcatcct ccccgtcgct tggcacaacc ggatcgcgct ccggctggag     1080
ctcctcggct gctga                                                      1095
```

<210> SEQ ID NO 9
<211> LENGTH: 489
<212> TYPE: DNA
<213> ORGANISM: Artificial Sequence
<220> FEATURE:
<223> OTHER INFORMATION: codon optimized kappa-casein coding sequence
      based on Homo sapiens sequence

<400> SEQUENCE: 9

```
gaggtccaaa accagaagca gcccgcctgc cacgagaacg acgagcgccc cttctaccag      60
aagaccgcac cctacgtccc gatgtactac gtcccgaaca gctaccccta ctacggtacg     120
aacctgtacc agcgccgccc ggccatcgct atcaacaacc cctacgtccc ccggacctac     180
tacgcgaacc cggccgtggt gcggccccac gcgcagatcc cgcagcggca gtacctgcca     240
aacagccacc cccccaccgt ggtgcggcgg cccaacctcc acccgagctt catcgctatc     300
cccccaaga  agatccagga caagatcatc atcccgacca tcaacaccat cgccaccgtg     360
gagccgacgc cagcccccgc gaccgagccc acggtggaca cgtcgtgac  cccagaggcg     420
ttctccgaat cgatcatcac ctccaccccc gagaccacca cggtggccgt cacgccgccg     480
acggcatga                                                             489
```

<210> SEQ ID NO 10
<211> LENGTH: 1233
<212> TYPE: DNA
<213> ORGANISM: Artificial Sequence
<220> FEATURE:
<223> OTHER INFORMATION: codon optimized haptocorrin coding sequence
      based on Homo sapiens sequence
<400> SEQUENCE: 10

```
gagatctgcg aggtctccga ggagaactac atccgcctca gcccctcct  gaacaccatg      60
atccagagca actacaaccg gggcacgtcg gccgtgaacg tcgtgctctc cctgaagctc     120
gtgggcatcc agatccagac cctcatgcag aagatgatcc agcagatcaa gtacaacgtg     180
aagagccgcc tctcggacgt gtccagcggc gagctggcgc tcatcatcct cgcgctcggc     240
gtgtgccgga acgcggagga gaacctcatc tacgactacc acctcacgga caagctggag     300
aacaagttcc aggccgagat cgagaacatg gaggcccaca acggcacccc gctgaccaac     360
tactaccagc tcagcctgga cgtcctcgcg ctctgcctgt tcaacgggaa ctactccacc     420
gccgaggtgg tcaaccactt cacccccgag aacaagaact actacttcgg ctcgcagttc     480
tccgtggaca ccggggccat ggccgtcctg gccctcacct gcgtgaagaa gtccctcatc     540
aacggccaga tcaaggccga cgagggctcc ctgaagaaca tctcgatcta caccaagagc     600
ctcgtggaga agatcctcag cgagaagaag gagaacgggc tgatcggcaa caccttctcg     660
accggcgagg cgatgcaggc cctgttcgtg agcagcgact actacaacga gaacgactgg     720
aactgccagc agaccctcaa cacggtcctg accgagatca gccagggcgc gttcagcaac     780
cccaacgccg ccgcccaggt cctgccggcc ctgatgggca agaccttcct cgacatcaac     840
aaggacagct cctgcgtgtc cgcgagcggc aacttcaaca tctccgccga cgagccgatc     900
acggtgacgc cgcccgacag ccagtcgtac atctccgtga actacagcgt gcggatcaac     960
gagacctact tcacgaacgt gacggtcctc aacggctcgg tcttcctgag cgtgatggag    1020
aaggcgcaga agatgaacga cacgatcttc ggcttcacga tggaggagcg cagctgggc    1080
ccctacatca cctgcatcca gggcctctgc gccaacaaca acgaccgcac ctactgggag    1140
ctgctgagcg cggcgagcc gctgagccag ggggccggca gctacgtggt ccgcaacggc    1200
```
gagaacctgg aggtccggtg gagcaagtac tga        1233

<210> SEQ ID NO 11
<211> LENGTH: 2061
<212> TYPE: DNA
<213> ORGANISM: Artificial Sequence
<220> FEATURE:
<223> OTHER INFORMATION: codon optimized lactoperoxidase coding sequence based on Homo sapiens sequence

<400> SEQUENCE: 11

```
caaacgaccc ggacgtcggc gatctccgac acggtctcgc aggccaaggt gcaagtcaac     60
aaggcattcc tggattcgcg cacgcggctg aagaccgcga tgtcgtccga gaccccgacg    120
agccggcagc tgagcgagta cctcaagcac gcgaaggggc ggacgcgcac cgccatccgc    180
aatggccaag tgtgggagga atccctgaag cggctgcggc agaaggcgtc gctcaccaac    240
gtgaccgacc cgtccctcga cctgaccagc ctctccctgg aggtcggctg cggcgccccg    300
gcgcccgtcg tgcgctgcga cccctgctcg ccataccgca cgatcacggg cgactgcaac    360
aaccggcgga agccggcact gggggctgcg aaccgcgccc tcgcgcgctg gctccccgcc    420
gagtacgagg acggcctcag cctcccctcc ggttggaccc ccgcaagac gcgcaacggc    480
ttcccgctcc cgctcgctcg cgaggtcagc aacaagatcg tcggttacct gaacgaggag    540
ggggtcctcg accaaaaccg ctccctcctc ttcatgcagt gggggcagat cgtggaccac    600
gacctggact cgccccggga cacggagctg ggctccagcg agtacagcaa gacccagtgc    660
gacgaatact gcatccaggg cgacaactgc ttcccgatca tgttcccccc gaacgacccg    720
aaggcgggca cccagggcaa gtgcatgccg ttcttccggg caggcttcgt ctgcccgacc    780
cccccgtaca agtccctcgc gcgcgagcag atcaacgcgc tcacgtcctt cctcgacgcc    840
agcttcgtct acagcagcga gccgtccctc gccagccgcc tccgcaacct cagcagcccc    900
ctcggcctca tggcggtcaa ccaggaggtg tcggaccacg gctcccata cctgccgtac    960
gacagcaaga agccgtcccc ctgcgagttc atcaacacca ccgcgcgcgt cccgtgcttc   1020
ctcgccggcg attcgcgggc gagcgagcac atcctcctcg ccacgagcca caccctgttc   1080
ctccgcgagc acaaccgcct cgcccgggag ctgaagcgcc tcaacccgca gtgggacggc   1140
gagaagctct accaggaggc ccggaagatc ctcggcgctt tcgtccagat catcaccttc   1200
cgggactacc tccccatcct gctcggtgac acatgcaga agtggatccc ccctaccaa    1260
ggctactccg agagcgtgga cccgcgcatc tccaacgtct tcacgttcgc gttccgcttc   1320
gggcacctgg aggtgccgtc gtcgatgttc cgcctcgacg agaactacca gccctggggc   1380
ccagagccgg agctgccgct ccacaccctg ttcttcaaca cctggcggat ggtcaaggac   1440
ggcggcatcg acccgctcgt gcgcgggctc ctggctaaga agtcgaagct catgaagcag   1500
aacaagatga tgaccggcga gctgcgcaac aagctgttcc agcccaccca ccgcatccac   1560
gggttcgacc tggctgcaat caacacccag cggtgccgcg accacggcca gccggctac    1620
aactcgtggc gcgcgttctg cgacctctcc cagccacaga cgctggagga gctcaacacc   1680
gtgctcaaga gcaagatgct cgccaagaag ctgctcgggc tctacggcac gcccgacaac   1740
atcgacatct ggatcgggc catcgcggag ccgctcgtgg agcgcgggcg cgtcggcccg   1800
ctgctcgcgt gcctcctggg caagcaattc aacagatcc gcgacgggga ccggttctgg   1860
tgggagaacc ccggcgtgtt caccaacgag cagaaggatt cgctccaaaa gatgagcttc   1920
tcccgcctgg tgtgcgacaa caccccgcatc accaaggtcc gcgcgacccc attctgggc    1980
```

```
aactcctacc cgtacgactt cgtggactgc tccgccatcg acaagctcga cctgtccccc      2040
tgggcatcgg tgaagaactg a                                                2061
```

<210> SEQ ID NO 12
<211> LENGTH: 1185
<212> TYPE: DNA
<213> ORGANISM: Artificial Sequence
<220> FEATURE:
<223> OTHER INFORMATION: codon optimized alpha-1-antitrypsin coding sequence-
 based on Homo sapiens sequence

<400> SEQUENCE: 12

```
gaggacccgc agggcgacgc cgcccagaag accgacacca gccaccacga ccaggaccac       60
ccgacgttca acaagatcac cccgaatttg gccgaattcg ccttcagcct gtaccgccag      120
ctcgcgcacc agtccaactc caccaacatc ttcttcagcc cggtgagcat cgccaccgcc      180
ttcgccatgc tgtccctggg taccaaggcg acacccacg acgagatcct cgaagggctg       240
aacttcaacc tgacggagat cccggaggcg cagatccacg agggcttcca ggagctgctc      300
aggacgctca accagccgga ctcccagctc agctcacca ccggcaacgg gctcttcctg       360
tccgagggcc tcaagctcgt cgataagttc ctggaggacg tgaagaagct ctaccactcc      420
gaggcgttca ccgtcaactt cggggacacc gaggaggcca agaagcagat caacgactac      480
gtcgagaagg ggacccaggg caagatcgtg gacctggtca aggaattgga cagggacacc      540
gtcttcgcgc tcgtcaacta catcttcttc aagggcaagt gggagcgccc gttcgaggtg      600
aaggacaccg aggaggagga cttccacgtc gaccaggtca ccaccgtcaa ggtcccgatg      660
atgaagaggc tcggcatgtt caacatccag cactgcaaga agctctccag ctgggtgctc      720
ctcatgaagt acctggggaa cgccaccgcc atcttcttcc tgccggacga gggcaagctc      780
cagcacctgg agaacgagct gacgcacgac atcatcacga agttcctgga gaacgaggac      840
aggcgctccg ctagcctcca cctcccgaag ctgagcatca ccggcacgta cgacctgaag      900
agcgtgctgg gccagctggg catcacgaag gtcttcagca acggcgcgga cctctccggc      960
gtgacggagg aggcccccct gaagctctcc aaggccgtgc acaaggcggt gctcacgatc     1020
gacgagaagg ggacggaagc tgccggggcc atgttcctgg aggccatccc cgtgtccatc     1080
ccgcccgagg tcaagttcaa caagcccttc gtcttcctga tgatcgagca gaacacgaag     1140
agccccctct tcatggggaa ggtcgtcaac cccacgcaga gtga                      1185
```

<210> SEQ ID NO 13
<211> LENGTH: 786
<212> TYPE: DNA
<213> ORGANISM: Artificial Sequence
<220> FEATURE:
<223> OTHER INFORMATION: Rice Gt1 promoter and Gt1 leader coding sequence

<400> SEQUENCE: 13

```
catgagtaat gtgtgagcat tatgggacca cgaaataaaa agaacatttt gatgagtcgt       60
gtatcctcga tgagcctcaa aagttctctc accccggata agaaacccctt aagcaatgtg     120 caaagtttgc attctccact gacataatgc aaaataagat atcatcgatg acatagcaac      180
tcatgcatca tatcatgcct ctctcaacct attcattcct actcatctac ataagtatct      240
tcagctaaat gttagaacat aaacccataa gtcacgtttg atgagtatta ggcgtgacac      300
atgacaaatc acagactcaa gcaagataaa gcaaaatgat gtgtacataa aactccagag      360
ctatatgtca tattgcaaaa agaggagagc ttataagaca aggcatgact cacaaaaatt      420
```

```
cacttgcctt tcgtgtcaaa aagaggaggg ctttacatta tccatgtcat attgcaaaag    480
aaagagagaa agaacaacac aatgctgcgt caattataca tatctgtatg tccatcatta    540
ttcatccacc tttcgtgtac cacacttcat atatcataag agtcacttca cgtctggaca    600
ttaacaaact ctatcttaac atttagatgc aagagccttt atctcactat aaatgcacga    660
tgatttctca ttgtttctca caaaaagcgg ccgcttcatt agtcctacaa caacatggca    720
tccataaatc gccccatagt tttcttcaca gtttgcttgt tcctcttgtg cgatggctcc    780
ctagcc                                                               786

<210> SEQ ID NO 14
<211> LENGTH: 1055
<212> TYPE: DNA
<213> ORGANISM: Artificial Sequence
<220> FEATURE:
<223> OTHER INFORMATION: Rice Glb promoter and Gt1 leader coding sequence

<400> SEQUENCE: 14 ctgcaggag gagaggggag agatggtgag agaggaggaa gaagaggagg ggtgacaatg      60
atatgtgggg catgtgggca cccaattttt taattcattc ttttgttgaa actgacatgt   120
gggtcccatg agatttatta tttttcggat cgaatcgcca cgtaagcgct acgtcaatgc   180
tacgtcagat gaagaccgag tcaaattagc cacgtaagcg ccacgtcagc caaaaccacc   240
atccaaaccg ccgagggacc tcatctgcac tggttttgat agttgaggga cccgttgtat   300
ctggtttttc gattgaagga cgaaaatcaa atttgttgac aagttaaggg accttaaatg   360
aacttattcc atttcaaaat attctgtgag ccatatatac cgtgggcttc caatcctcct   420
caaattaaag ggccttttta aaatagataa ttgccttctt tcagtcaccc ataaaagtac   480
aaaactacta ccaacaagca acatgcgcag ttacacacat tttctgcaca tttccgccac   540
gtcacaaaga gctaagagtt atccctagga caatctcatt agtgtagata catccattaa   600
tcttttatca gaggcaaacg taaagccgct ctttatgaca aaaataggtg acacaaaagt   660
gttatctgcc acatacataa cttcagaaat tacccaacac caagagaaaa ataaaaaaaa   720 atcttttgc aagctccaaa tcttggaaac cttttttcact ctttgcagca ttgtactctt   780
gctctttttc caaccgatcc atgtcaccct caagcttcta cttgatctac acgaagctca   840
ccgtgcacac aaccatggcc acaaaaaccc tataaaaccc catccgatcg ccatcatctc   900
atcatcagtt cattaccaac aaacaaaaga ggaaaaaaaa catatacact tctagtgatt   960
gtctgattga tcatcaatct agaggcggcc gcatggctag caaggtcgtc ttcttcgcgg  1020
cggcgctcat ggcggccatg gtggccatct ccggc                             1055

<210> SEQ ID NO 15
<211> LENGTH: 976
<212> TYPE: DNA
<213> ORGANISM: Artificial Sequence
<220> FEATURE:
<223> OTHER INFORMATION: Bx7 promoter

<400> SEQUENCE: 15
ctgcaggcca gggaaagaca atggacatgc aaagaggtag gggcagggaa gaaacacttg     60
gagatcatag aagaacataa gaggttaaac ataggagggc ataatggaca attaaatcta   120
cattaattga actcatttgg gaagtaaaca aaatccatat tctggtgtaa atcaaactat   180
ttgacgcgga tttactaaga tcctatgtta atttttagaca tgactggcca aaggtttcag   240
ttagttcatt tgtcacggaa aggtgttttc ataagtccaa aactctacca acttttttgc   300
```

```
acgtcatagc atagatagat gttgtgagtc attggataga tatttgtgagt cagcatggat    360 ttgtgttgcc tggaaatcca actaaatgac aagcaacaaa acctgaaatg ggctttagga    420
gagatggttt atcaatttac atgttccatg caggctacct tccactactc gacatggtta    480
gaagttttga gtgccgcata tttgcggaag caatggcact actcgacatg gttagaagtt    540
ttgagtgccg catatttgcg gaagcaatgg ctaacagata catattctgc caaaccccaa    600
gaaggataat cactcctctt agataaaaag aacagaccaa tgtacaaaca tccacacttc    660
tgcaaacaat acaccagaac taggattaag cccattacgt ggctttagca gaccgtccaa    720
aaatctgttt tgcaagcacc aattgctcct tacttatcca gcttcttttg tgttggcaaa    780 ctgcccttt ccaaccgatt ttgtttcttc tcacgctttc ttcataggct aaactaacct    840
cggcgtgcac acaaccatgt cctgaacctt cacctcgtcc ctataaaagc ccatccaacc    900
ttacaatctc atcatcaccc acaacaccga gcaccccaat ctacagatca attcactgac    960
agttcactga tctaga                                                    976
```

```
<210> SEQ ID NO 16
<211> LENGTH: 1009
<212> TYPE: DNA
<213> ORGANISM: Artificial Sequence
<220> FEATURE:
<223> OTHER INFORMATION: Glub-2 promoter

<400> SEQUENCE: 16
ctgcagtaat ggatacctag tagcaagcta gcttaaacaa atctaaattc caatctgttc     60
gtaaacgttt tctcgatcgc aattttgatc aaaactattg aaaacctcaa ttaaaccatt    120
caaaattttt aatataccca acaagagcgt ccaaaccaaa tatgtaaata tggatgtcat    180
gataattgac ttatgacaat gtgattattt catcaagtct ttaaatcatt aattctagtt    240
gaaggtttat gttttcttat gctaaagggt tatgtttata taagaatatt aaagagcaaa    300
ttgcaataga tcaacacaac aaatttgaat gtttccagat gtgtaaaaat atccaaatta    360
attgttttaa aatagttta agaaggatct gatatgcaag tttgatagtt agtaaactgc     420
aaaagggctt attcatgga aaattcctta ttgaatatgt ttcattgact ggtttatttt     480
acatgacaac aaagttacta gtatgtcaat aaaaaaatac aaggttactt gtcaattgta    540
ttgtgccaag taaagatgac aacaaacata caaatttatt tgttctttta tagaaacacc    600
taacttatca aggatagttg gccacgcaaa aatgacaaca tacttacaa ttgtatcatc     660 ataaagatct tatcaagtat aagaaccttta tggtgacata aaaataatc acaagggcaa    720 gacacatact aaaagtatgg acagaaattt cttaacaaac tccatttgtt ttgtatccaa    780
aagcataaga aatgagtcat ggctgagtca tgatatgtag ttcaatcttg caaaattgcc    840 ttttgttaa gtattgtttt aacactacaa gtcacatatt gtctatactt gcaacaaaca     900
ctattaccgt gtatcccaag tggccttttc attgctatat aaactagctt gatcggtctt    960
tcaactcaca tcaattagct taagtttcca ttagcaactg ctaatagct                1009
```

```
<210> SEQ ID NO 17
<211> LENGTH: 839
<212> TYPE: DNA
<213> ORGANISM: Artificial Sequence
<220> FEATURE:
<223> OTHER INFORMATION: Gt3 promoter

<400> SEQUENCE: 17
```

```
ctgcagtgta agtgtagctt cttatagctt agtgctttac tatcttcaca agcacatgct      60
atagtattgt tccaagatga aagaataatt catccttgct accaacttgc atgatattat     120
atttgtgaat atcctatctc ttggcttata atgaaatgtg ctgctgggtt attctgacca     180
tggtatttga gagcctttgt atagctgaaa ccaacgtata tcgagcatgg aacagagaac     240
aaaatgcaag gatttttta ttctggttca tgccctggat gggttaatat cgtgatcatc      300
aaaaaagata tgcataaaat taaagtaata aatttgctca taagaaacca aaaccaaaag     360
cacatatgtc ctaaacaaac tgcattttgt ttgtcatgta gcaatacaag agataatata     420
tgacgtggtt atgacttatt cacttttgt gactccaaaa tgtagtaggt ctaactgatt      480
gtttaaagtg atgtcttact gtagaagttt catcccaaaa gcaatcacta aagcaacaca     540
cacgtatagt ccaccttcac gtaattcttt gtggaagata acaagaaggc tcactgaaaa     600
ataaaagcaa agaaaggat atcaaacaga ccattgtgca tcccattgat ccttgtatgt      660
ctatttatct atcctccttt tgtgtacctt acttctatct agtgagtcac ttcatatgtg     720
gacattaaca aactctatct taacatctag tcgatcacta ctttacttca ctataaaagg     780
accaacatat atcatccatt tctcacaaaa gcattgagtt cagtcccaca aaatctaga    839

<210> SEQ ID NO 18
<211> LENGTH: 1302
<212> TYPE: DNA
<213> ORGANISM: Artificial Sequence
<220> FEATURE:
<223> OTHER INFORMATION: Glub-1 promoter

<400> SEQUENCE: 18
ctgcagagat atggattttc taagattaat tgattctctg tctaaagaaa aaagtattta     60
ttgaattaaa tggaaaaaga aaaggaaaa aggggatggc ttctgctttt tgggctgaag     120
gcggcgtgtg gccagcgtgc tgcgtgcgga cagcgagcga acacacgacg gagcagctac    180
gacgaacggg ggaccgagtg gaccggacga ggatgtggcc taggacgagt gcacaaggct    240
agtggactcg gtccccgcgc ggtatcccga gtggtccact gtctgcaaac acgattcaca    300
tagagcgggc agacgcggga gccgtcctag gtgcaccgga agcaaatccg tcgcctgggt    360
ggatttgagt gacacggccc acgtgtagcc tcacagctct ccgtggtcag atgtgtaaaa    420
ttatcataat atgtgttttt caaatagtta ataatatat ataggcaagt tatatgggtc     480
aataagcagt aaaaaggctt atgacatggt aaaattactt acaccaatat gccttactgt    540
ctgatatatt ttcatgaca acaaagttac aagtacgtca tttaaaaata caagttactt     600
atcaattgta gtgtatcaag taaatgcaa caaacctaca aatttgctat tttgaaggaa      660 cacttaaaa aatcaatagg caagttatat agtcaataaa ctgcaagaag cttatgaca      720 tggaaaaatt acatacacca atatgcttta ttgtccggta tattttacaa gacaacaaag    780
ttataagtat gtcatttaaa aatacaagtt acttatcaat tgtcaagtaa atgaaaacaa    840
acctacaaat tgttatttt gaaggaacac ctaaattatc aaatatagct tgctacgcaa     900
aatgacaaca tgcttacaag ttattatcat cttaaagtta gactcatctt ctcaagcata    960
agagctttat ggtgcaaaaa caaatataat gacaaggcaa agatacatac atattaagag   1020
tatgggcaga catttcttta acaaactcca ttttgttatac tccaaaagca ccagaagttt   1080
gtcatggctg agtcatgaaa tgtatagttc aatcttgcaa agttgccttt ccttttgtac   1140
tgtgttttaa cactacaagc catatattgt ctgtacgtgc aacaaactat atcaccatgt   1200
atcccaagat gcttttttat tgctatataa actagcttgg tctgtctttg aactcacatc   1260
```

```
aattagctta agtttccata agcaagtaca aatagctcta ga                1302

<210> SEQ ID NO 19
<211> LENGTH: 675
<212> TYPE: DNA
<213> ORGANISM: Artificial Sequence
<220> FEATURE:
<223> OTHER INFORMATION: Rice prolamin promoter

<400> SEQUENCE: 19
ctgcagcatc ggcttaggtg tagcaacacg actttattat tattattatt attattatta    60
ttattttaca aaatataaa  atagatcagt ccctcaccac aagtagagca agttggtgag   120
ttattgtaaa gttctacaaa gctaatttaa aagttattgc attaacttat ttcatattac   180
aaacaagagt gtcaatggaa caatgaaaac catatgacat actataattt tgttttatt    240 attgaaatta tataattcaa agagaataaa tccacatagc cgtaaagttc tacatgtggt   300
gcattaccaa aatatatata gcttacaaaa catgacaagc ttagtttgaa aaattgcaat   360
ccttatcaca ttgacacata aagtgagtga tgagtcataa tattatttttt cttgctaccc  420 atcatgtata tatgatagcc acaaagttac tttgatgatg atatcaaaga acatttttag   480
gtgcacctaa cagaatatcc aaataatatg actcacttag atcataatag agcatcaagt   540
aaaactaaca ctctaaagca accgatggga aagcatctat aaatagacaa gcacaatgaa   600
aatcctcatc atccttcacc acaattcaaa tattatagtt gaagcatagt agtagaatcc   660
aacaacaatc tagag                                                   675

<210> SEQ ID NO 20
<211> LENGTH: 1098
<212> TYPE: DNA
<213> ORGANISM: Artificial Sequence
<220> FEATURE:
<223> OTHER INFORMATION: Rice cysteine peptidase promoter

<400> SEQUENCE: 20
ccaggcttca tcctaaccat tacaggcaag atgttgtatg aagaagggcg aacatgcaga    60
ttgttaaact gacacgtgat ggacaagaat gaccgattgg tgaccggtct gacaatggtc   120
atgtcgtcag cagacagcca tctcccacgt cgcgcctgct tccggtgaaa gtggaggtag   180
gtatgggccg tcccgtcaga aggtgattcg gatggcagcg atacaaatct ccgtccatta   240
atgaagagaa gtcaagttga agaaaggga  gggagagatg gtgcatgtgg gatcccttg    300 ggatataaaa ggaggaccctt gcccacttag aaaggagagg agaaagcaat cccagaagaa   360 tcggggctg  actggcactt tgtagcttct tcatacgcga atccaccaaa acacaggagt   420
agggtattac gcttctcagc ggcccgaacc tgtatacatc gcccgtgtct tgtgtgtttc   480
cgctcttgcg aaccttccac agattgggag cttagaacct cacccagggc ccccggccga   540
actggcaaag gggggcctgc gcggtctccc ggtgaggagc cccacgctcc gtcagttcta   600
aattacccga tgagaaaggg agggggggggg gggaaatctg ccttgtttat ttacgatcca   660
acggatttgg tcgacaccga tgaggtgtct taccagttac cacgagctag attatagtac   720
taattacttg aggattcggt tcctaatttt ttacccgatc gacttcgcca tggaaaattt   780
tttattcggg ggagaatatc caccctgttt cgctcctaat taagatagga attgttacga   840
ttagcaacct aattcagatc agaattgtta gttagcggcg ttggatccct cacctcatcc   900
catcccaatt cccaaaccca aactcctctt ccagtcgccg acccaaacac gcatccgccg   960
```

```
cctataaatc ccacccgcat cgagcctatc aagcccaaaa aaccacaaac caaacgaaga    1020
aggaaaaaaa aaggaggaaa agaaaagagg aggaaagcga agaggttgga gagagacgct    1080
cgtctccacg tcgccgcc                                                  1098
```

```
<210> SEQ ID NO 21
<211> LENGTH: 432
<212> TYPE: DNA
<213> ORGANISM: Artificial Sequence
<220> FEATURE:
<223> OTHER INFORMATION: Barley D-Hordein promoter

<400> SEQUENCE: 21
cttcgagtgc ccgccgattt gccagcaatg gctaacagac acatattctg ccaaaacccc     60
agaacaataa tcacttctcg tagatgaaga gaacagacca agatacaaac gtccacgctt    120
cagcaaaacag taccccagaa ctaggattaa gccgattacg cggctttagc agaccgtcca   180
aaaaactgt tttgcaaagc tccaattcct ccttgcttat ccaatttctt ttgtgttggc     240
aaactgcact tgtccaaccg attttgttct tcccgtgttt cttcttaaag taactaacac    300
agccgtgcac atagccatgg tccggaatct tcacctcgtc cctataaaag cccagccaat    360
ctccacaatc tcatcatcac cgagaacacc gagaaccaca aaactagaga tcaattcatt    420
gacagtccac cg                                                        432
```

```
<210> SEQ ID NO 22
<211> LENGTH: 60
<212> TYPE: DNA
<213> ORGANISM: Artificial Sequence
<220> FEATURE:
<223> OTHER INFORMATION: bx7 signal peptide sequence

<400> SEQUENCE: 22
atggctaagc gcctggtcct ctttgcggca gtagtcgtcg ccctcgtggc tctcaccgcc     60
```

```
<210> SEQ ID NO 23
<211> LENGTH: 72
<212> TYPE: DNA
<213> ORGANISM: Artificial Sequence
<220> FEATURE:
<223> OTHER INFORMATION: Glub-2 signal peptide sequence

<400> SEQUENCE: 23
atggcaacta ccattttctc tcgttttttct atatactttt gtgctatgct attatgccag     60
ggttctatgg cc                                                         72
```

```
<210> SEQ ID NO 24
<211> LENGTH: 85
<212> TYPE: DNA
<213> ORGANISM: Artificial Sequence
<220> FEATURE:
<223> OTHER INFORMATION: Gt3 signal peptide sequence

<400> SEQUENCE: 24
atgtggacat taacaaactc tatcttaaca tctagtcgat cactacttta cttcactata     60
aaaggaccaa catatatcat ccatt                                           85
```

```
<210> SEQ ID NO 25
<211> LENGTH: 72
<212> TYPE: DNA
<213> ORGANISM: Artificial Sequence
<220> FEATURE:
<223> OTHER INFORMATION: Glub-2 signal peptide sequence

<400> SEQUENCE: 25
atggcgagtt ccgttttctc tcggttttct atatactttt gtgttcttct attatgccat     60
ggttctatgg cc                                                         72
```

```
<210> SEQ ID NO 26
<211> LENGTH: 69
```

```
<212> TYPE: DNA
<213> ORGANISM: Artificial Sequence
<220> FEATURE:
<223> OTHER INFORMATION: prolamin signal peptide sequence

<400> SEQUENCE: 26
atgaagatca ttttcgtatt tgctctcctt gctattgttg catgcaacgc ttctgcacgg     60
tttgatgct                                                             69

<210> SEQ ID NO 27
<211> LENGTH: 63
<212> TYPE: DNA
<213> ORGANISM: Artificial Sequence
<220> FEATURE:
<223> OTHER INFORMATION: Rice cysteine peptidase signal peptide sequence

<400> SEQUENCE: 27
atggccgccc gcgccgccgc cgccgcgttc ctgctgctgc tcatcgtcgt tggtcaccgc     60
gcc                                                                   63

<210> SEQ ID NO 28
<211> LENGTH: 63
<212> TYPE: DNA
<213> ORGANISM: Artificial Sequence
<220> FEATURE:
<223> OTHER INFORMATION: D-Hordein signal peptide sequence

<400> SEQUENCE: 28
atggctaagc ggctggtcct ctttgtggcg gtaatcgtcg ccctcgtggc tctcaccacc     60
gcc                                                                   63

<210> SEQ ID NO 29
<211> LENGTH: 1314
<212> TYPE: DNA
<213> ORGANISM: Artificial Sequence
<220> FEATURE:
<223> OTHER INFORMATION: O2 transcription factor sequence

<400> SEQUENCE: 29
atggagcacg tcatctcaat ggaggagatc ctcgggccct tctgggagct gctaccaccg     60
ccagcgccag agccagagcg agagcagcct ccggtaaccg gcatcgtcgt cggcagtgtc    120
atagacgttg ctgctgctgg tcatggtgac ggggacatga tggatcagca gcacgccaca    180
gagtggacct ttgagaggtt actagaagag gaggctctga cgacaagcac accgccgccg    240
gtggtggtgg tgccgaactc ttgttgctca ggcgccctaa atgctgaccg gccgccggtg    300
atggaagagg cggtaactat ggcgcctgcg gcggtgagta gtgccgtagt aggtgacccc    360
atggagtaca atgccatact gaggaggaag ctgaggagg acctcgaggc cttcaaaatg    420
tggagggcgg cctccagtgt tgtgacctca gatcaacgtt ctcaaggctc aaacaatcac    480
actggaggta gcagcatcag gaataatcca gtgcagaaca agctgatgaa cggcgaagat    540
ccaatcaaca ataaccacgc tcaaactgca ggccttggcg tgaggcttgc tactagctct    600
tcctcgagag atccttcacc atcagacgaa gacatggacg agaagtagaa gattctgggg    660
ttcaagatgc ctaccgagga aagagtgagg aaaagaaagg aatccaatag agaatcagcc    720
agacgctcga gatacaggaa agccgctcac ctgaaagaac tggaagacca ggtagcacag    780
ctaaaagccg agaattcttg cctgctgagg cgcattgccg ctctgaacca gaagtacaac    840
gacgctaacg tcgacaacag ggtgctgaga gcggacatgg agaccctaag agctaaggtg    900
aagatgggag aggactctct gaagcgggtg atagagatga gctcatcagt gccgtcgtcc    960
atgcccatct cggcgccgac ccccagctcc gacgctccag tgccgccgcc gcctatccga   1020
```

```
gacagcatcg tcggctactt ctccgccaca gccgcagacg acgatgcttc ggtcggcaac    1080
ggtttcttgc gactgcaagc tcatcaagag cctgcatcca tggtcgtcgg tggaactctg    1140
agcgccacag agatgaaccg agtagcagca gccacgcatt gcgcggggc catggagcac     1200 atccagacgg cgatgggatc catgccgccg acctccgcct ccggatctac accgccgccg    1260
caggattatg agctgctggg tccaaatggg gccatacaca tggacatgta ttag          1314

<210> SEQ ID NO 30
<211> LENGTH: 987
<212> TYPE: DNA
<213> ORGANISM: Artificial Sequence
<220> FEATURE:
<223> OTHER INFORMATION: PBF transcription factor sequence

<400> SEQUENCE: 30
atggacatga tctccggcag cactgcagca acatcaacac cccacaacaa ccaacaggcg     60
gtgatgttgt catcccccat tataaggag gaagctaggg acccaaagca gacacgagcc    120 atgcccaaa taggtggcag tggggagcgt aagccgaggc cgcaactacc tgaggcgctc     180
aagtgcccac gctgcgactc caacaacacc aagttttgct actacaacaa ttatagcatg    240
tcacaaccac gctacttttg caaggcttgc cgccgctatt ggacacatgg tggtaccctc    300
cgcaatgtcc ccattggtgg tgggtgtcgc aagaacaaac atgcctctag atttgtcttg    360
ggctctcaca cctcatcgtc ctcatctgct acctatgcac cattatcccc tagcaccaac    420
gctagctcta gcaatatgag catcaacaaa catatgatga tggtgcctaa catgacgatg    480
cctaccccaa cgacaatggg cttattccct aatgtgctcc caacacttat gccgacaggt    540
ggaggcgggg gctttgactt cactatggac aaccaacata gatcattgtc cttcacacca    600
atgtctctac ctagccaggg gccagtgcct atgctggctg caggagggag tgaggcaaca    660
ccgtctttcc tagagatgct gagaggaggg atttttcatg gtagtagtag ctataacaca    720
agtctcacga tgagtggtgg caacaatgga atggacaagc cattttcgct gccatcatat    780
ggtgcaatgt gcacaaatgg gttgagtggc tcaaccacta atgatgccag acaactggtg    840
gggcctcagc aggataacaa ggccatcatg aagagcagta ataacaacaa tggtgtatca    900
ttgttgaacc tctactggaa caagcacaac aacaacaaca acaacaacaa caacaacaac    960
aacaacaaca caacaaggg acaataa                                         987

<210> SEQ ID NO 31
<211> LENGTH: 3902
<212> TYPE: DNA
<213> ORGANISM: Artificial Sequence
<220> FEATURE:
<223> OTHER INFORMATION: Reb transcription factor sequence

<400> SEQUENCE: 31
atggagcggg tgttctccgt ggaggagatc tccgacccat tctgggtccc gcctccgccg     60
ccgcagtcgg cggcggcggc ccagcagcag ggcggcggcg gcgtggcttc gggaggtggt    120
ggtggtgtag cggggggcgg cggcggcggg aacgcgatga accggtgccc gtcggagtgg    180
tacttccaga agtttctgga ggaggcggtg ctcgatagcc ccgtcccgaa ccctagcccg    240
agggccgaag cgggagggat caggggcgca ggaggggtgg tgccggtcga tgttaagcag    300
ccgcagctct cggcggcggc gacgacgagc gcggtggtgg accccgtgga gtacaacgcg    360
atgctgaagc agaagctgga gaaggacctc gccgcggtcg ccatgtggag ggtacagcca    420
```

-continued

```
ttctccccc ctctagtact cgagagctta ctgagatcgg caatgctagc tactgtttgc    480
atcgaatgtt tataggtatt tagatcgggc atttctatag accaatggcg tccatggtct    540
tgcaatgcgc tctgttgagt gtcggtggtt ggttcgactc atagtatgta gggttgtgcg    600
tatgtacaaa cggaagcttc atagacctcg gtattgagat tgcgatatcg atgcaacctg    660
cgaattggcg atgtaatcag tcatattctt actaaactgc gagacagtgg tttgtttgca    720
attgcaatat ttttgtatgg ggctgcttaa actgtcattg ccttttttaga ttggcaatat   780
gtgactttat gcaagtattt gattgggcgg atccaggaac aaaaagttgg ggggattcaa    840
cataccgagt acactggcat aaacacatca tctcagtatt aaactatgct aaaatgctat    900
taagagacct ttagcacctc ttatcttatc aaccatggtg aaaaaattga agggggact     960
cagggggta tccatgggtc cgatgggtgc aggggggact gagtccccc tgcacccacg     1020
ttgaatccgc cctggcatgc gtataagctg tcacagccat ttctaggtgc ttgtgcttag  1080
ttgggtgatg tcagcttaat ttgtcttttc tatgtcgtca tcgatttttct aagaaacgaa  1140
aaatagccta tttatgtgct ccagaatttg atgatccctg gcccttcatt tgctgaaatt   1200
agcctatttg ttggttgccc ttcagttttt tcccagctta tgttgttgca atgtgtggct   1260
atgcctcgtt ttgtgcccta taatttatta tttgcaattc attttttgtac atgacttaaa  1320
atgacactag agcaacatgc actgattggt tatcctataa tcatttatgt agttctgttc   1380
attttatcat gctagctcat gtcattttca tcttcaggcc tctggcacag ttccacctga  1440
gcgtcctgga gctggttcat ccttgctgaa tgcagatgtt tcacacatag gcgctcctaa    1500
ttccatcgga ggtacttatc ttatctggtt acattttcag attgttatga aactacccaa   1560
atatcctgca caattgcatg ggattaaatt ttagtttctt tgaaatagaa gtagagttgt    1620
attgctgtca cgtcatcaaa tagttctgaa gctatgaata aataagttcc gcatttgtta   1680
gtgattcttt gaacattaga attgttatgc ttaagtagat agggtatgt ttgtttggag    1740
ttcccttaaa tcatttcatt gctgactgcc agctggcagg agcatttgtt gttgccttga   1800
ccatgaatga agaccttcct gttctgagtg ctcacaagaa aacatatttt gattaatgca   1860
ccttgaatcc ttaggatctt gcaaagatgg gcacttagct ttagaattga gtagtactta   1920
aatagctgtt gttatcatga tttgtcctgt agtgaaatgt cgacaaaaca ggaatgctac   1980
ttttgacttc tgatatttca tgcctggctt tacttatgct ctgtttggaa catgggcaca   2040
tatcaggcaa tgctactcca gttcaaaaca tgctaagtgg cccaagtggg ggatcgggct   2100
cacagttggt acagaatgtt gatgtccttg taaagcagcc caccagctct tcatcaaggg   2160
agcagtcaga tgatgatgac atgaagggag aagctgagac cactggaact gcaagacctg   2220
ctgatcaaag attacaacga aggtgatcat tcattgcttc cttgtaatat agattctgta   2280
cataattaac ctacctcgtc atgcatgcat gtgtcctatt ttcaccttag ccctttcagt   2340
tggatttcca ctttcatccg gtagcctttc agtttcctat tgcatcgcat atatgatctt   2400
ttacctacca tattagttct ctgtgtgcca tactcagtgc ttagtgtctc gagcaagaga   2460
ggaatttgta tggctattac acgtagcact ttgctctcta cttgtttatt gacataagca   2520
atttgggatg aattaaatct gagttcacat catattcctt atgtcacaag tttctgaaac   2580
cgattgtatc tagtatctgg ttgatgcacc cccatcttgg atttgcaaat caagttata    2640
ctccctagag agctttacct ttcataaagc aattaccccca ataaaccacg gatttgatag  2700
ctattgacta tgattaccag aattcatttg gcagctattt tctcaattta agtttggtat   2760
```

```
tagtctcagt tggctgtaaa ataatgtcac ggtagggtac atgtatgtgc agcatacaag    2820
gtatgggtga gttatgatat ggacagtgtg tacaccccac atttgctcac taaaatcaaa    2880
atattcaaac gtcacgtgat gatatggtgg attgcattat accttgtatt gtttattatg    2940
ttacttgtgc tagacaataa tataggctgt tcttttgggt gattttgtat gaagatgttg    3000
agcaagcact tctcgatata atgctagttt tgttgacctg ttccaggaag caatccaatc    3060
gggagtcagc caggcgctca agaagcagaa aggcagctca cttgaatgag ctggaggcac    3120
aggtgtgata gttcacatag ttattttcga taagacataa aatcctaaat tactggctac    3180
tgacttcagt tatggattta cttgttacag gtatcgcaat taagagtcga gaactcctcg    3240
ctgttaaggc gtcttgctga tgttaaccag aagtacaatg atgctgctgt tgacaataga    3300
gtgctaaaag cagatgttga gaccttgaga gcaaaggtat gctatatatg ccttttgcaa    3360
tatgcatccc atggattgct actttggctt gtttcaaact ttcaacgtga cttgtgtacc    3420
ctgttattag aagaataatc ccgcctacca ttatactcta taaatcacca tttggccagt    3480
ccaaacatga ttattaaatc aggtcaatct gaacattgaa atgtatcaaa aattcgcagg    3540
tgaagatggc agaggactcg gtgaagcggg tgacaggcat gaacgcgttg tttcccgccg    3600
cttctgatat gtcatccctc agcatgccat tcaacagctc cccatctgaa gcaacgtcag    3660
acgctgctgt tccatccaa gatgacccga acaattactt cgctactaac aacgacatcg    3720
gaggtaacaa caactacatg cccgacatac cttcttcggc tcaggaggac gaggacttcg    3780 tcaatgcgc tctggctgcc ggcaagattg gccggccagc ctcgctgcag cgggtggcga    3840
gcctggagca tctccagaag aggatgtgcg gtgggccggc ttcgtctggg tcgacgtcct    3900
ga                                                                    3902
```

<210> SEQ ID NO 32
<211> LENGTH: 11
<212> TYPE: PRT
<213> ORGANISM: Oryza sativa
<220> FEATURE:
<221> NAME/KEY: VARIANT
<222> LOCATION: (1)...(11)
<223> OTHER INFORMATION: Xaa = Any Amino Acid

<400> SEQUENCE: 32

Lys Val Phe Glu Arg Xaa Glu Leu Ala Arg Thr
1               5                   10

<210> SEQ ID NO 33
<211> LENGTH: 11
<212> TYPE: PRT
<213> ORGANISM: Homo sapiens

<400> SEQUENCE: 33

Lys Val Phe Glu Arg Cys Glu Leu Ala Arg Thr
1               5                   10

<210> SEQ ID NO 34
<211> LENGTH: 11
<212> TYPE: PRT
<213> ORGANISM: Homo sapiens

<400> SEQUENCE: 34

Gly Arg Arg Arg Arg Ser Val Gln Trp Cys Ala
1               5                   10

<210> SEQ ID NO 35

```
<211> LENGTH: 11
<212> TYPE: PRT
<213> ORGANISM: Artificial Sequence
<220> FEATURE:
<223> OTHER INFORMATION: N-terminal sequence based on human lactoferrin
      sequence
<220> FEATURE:
<221> NAME/KEY: VARIANT
<222> LOCATION: (1)...(11)
<223> OTHER INFORMATION: Xaa = Any Amino Acid

<400> SEQUENCE: 35

Gly Arg Arg Arg Arg Ser Val Gln Trp Xaa Ala
 1               5                   10
```